United States Patent
Lynch et al.

(10) Patent No.: US 8,785,457 B2
(45) Date of Patent: Jul. 22, 2014

(54) PYRIMIDINE DERIVATIVES AS MTOR INHIBITORS

(75) Inventors: Rosemary Lynch, Cambridge (GB); Andrew David Cansfield, Harston (GB); Helen Sarah Niblock, Dalkeith (GB); Daniel Hardy, Stevenage (GB); Jane Elizabeth Scanlon, Cambridge (GB); Rita Adrego, Suffolk (GB); Nigel Ramsden, Herts (GB)

(73) Assignee: Cellzome Limited, Cambridge (GB)

( * ) Notice: Subject to any disclaimer, the term of this patent is extended or adjusted under 35 U.S.C. 154(b) by 181 days.

(21) Appl. No.: 13/256,345

(22) PCT Filed: Mar. 12, 2010

(86) PCT No.: PCT/EP2010/053165
§ 371 (c)(1),
(2), (4) Date: Nov. 23, 2011

(87) PCT Pub. No.: WO2010/103094
PCT Pub. Date: Sep. 16, 2010

(65) Prior Publication Data
US 2012/0065202 A1 Mar. 15, 2012

Related U.S. Application Data

(60) Provisional application No. 61/303,252, filed on Feb. 10, 2010.

(30) Foreign Application Priority Data

Mar. 13, 2009 (EP) .................................... 09155143

(51) Int. Cl.
*A61K 31/5377* (2006.01)
*C07D 413/04* (2006.01)

(52) U.S. Cl.
CPC .......... *A61K 31/5377* (2013.01); *C07D 413/04* (2013.01)
USPC ........................................ 514/264.1; 544/279

(58) Field of Classification Search
CPC .......................... A61K 31/5377; C07D 413/04
USPC ........................................ 544/279; 514/264.1
See application file for complete search history.

(56) References Cited

U.S. PATENT DOCUMENTS

| 8,163,763 B2 * | 4/2012 | Bergeron et al. .......... 514/264.1 |
| 2004/0191836 A1 | 9/2004 | Abraham |

FOREIGN PATENT DOCUMENTS

| WO | 9835985 | 8/1998 |
| WO | 9902166 | 1/1999 |
| WO | 0047212 | 8/2000 |
| WO | 0132651 | 5/2001 |
| WO | 0160814 | 8/2001 |
| WO | 2006134056 | 12/2006 |
| WO | 2008015013 | 2/2008 |
| WO | 2008023159 | 2/2008 |
| WO | 2008115974 | 9/2008 |
| WO | 2008116129 | 9/2008 |
| WO | 2009007748 | 1/2009 |
| WO | 2009007749 | 1/2009 |
| WO | 2009007750 | 1/2009 |
| WO | 2009007751 | 1/2009 |
| WO | 2009008992 | 1/2009 |
| WO | 2009049242 | 4/2009 |
| WO | 2010014939 | 2/2010 |

OTHER PUBLICATIONS

Fura, A. DDT, 2006, 11, pp. 133-142.*
Anari et al., DDT, 2005, 10, pp. 711-717.*
Nedderman, A. N. R. Biopharm. Drug Dispos. 2009, 30, pp. 153-162.*
Tsang, K.T., et al., "Targeting mammalian target of rapamycin (mTOR) for health and diseases," 2007, Drug Discovery Today 12, pp. 112-124.
Schmelzle, Tobias and Hall, Michael N., "TOR, a Central Controller of Cell Growth," Cell, vol. 103, Oct. 13, 2000, pp. 253-262.
Sarbassov, D.D., et al., "Prolonged Rapamycin Treatment Inhibits mTORC2 Assembly and Akt/PKB," Molecular Cell 22, Apr. 21, 2006, pp. 159-168.
Faivre, S., et al., "Current development of mTOR inhibitors as anti-cancer agents," Nat. Rev. Drug. Disc., vol. 5, Aug. 2006, pp. 671-688.
Thoreen, C.C., et al., "An ATP-competitive Mammalian Target of Rapamycin Inhibitor Reveals Rapamycin-resistant Functions of mTORC1," Journal of Biological Chemistry, vol. 284, No. 12, Mar. 20, 2009, pp. 8023-8032.
Knight, Z.A., et al., "Isoform-specific phosphoninositide 3-kinase inhibitors from an arylmorpholine scaffold," Bioorganic & Medicinal Chemistry, 12 (2004), pp. 4749-4759.

(Continued)

*Primary Examiner* — Rebecca Anderson
(74) *Attorney, Agent, or Firm* — Margaret M. Tomaska; Edward R. Gimmi

(57) ABSTRACT

The invention relates to compounds of formula (I)

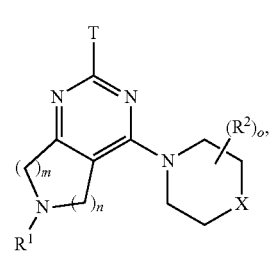

wherein X, $R^1$, $R^2$, T, m, n, o have the meaning as cited in the description and the claims. The compounds of formula (I) are useful as inhibitors of mTOR for the treatment or prophylaxis of mTOR related diseases and disorders. The invention also relates to pharmaceutical compositions including said compounds, the preparation of such compounds as well as the use as medicaments.

8 Claims, 2 Drawing Sheets

(56) References Cited

OTHER PUBLICATIONS

Custer L.L., et al., "The Role of Genetic Toxicology in Drug Discovery and Optimization," Current Drug Metabolosim, 2008, 9, pp. 978-985.

Mortelmans, K., et al., "The Ames Salmonella/microsome mutagenicity assay," Mutation Research 455 (2000), pp. 29-60.

Firestein, Gary S., "Evolving concepts of rheumatoid arthritis," Nature, vol. 423, May 15, 2003, pp. 356-361.

Asakura et al., "Recent advances in basic and clinical aspects of inflammatory bowel disease: Which steps in the mucosal inflammation should we block for the treatment of inflammatory bowel disease?," World Journal of Gastroenterology, Apr. 21, 2007, 13(15), pp. 2145-2149.

Schon, M.P., et al., "Psoriasis," New England Journal of Medicine, May 5, 2005, 352: pp. 1899-1912.

D'Cruz, D.P., et al., "Systemic lupus erythematosus," Lancet, Feb. 17, 2007, vol. 369, pp. 587-596.

Hemmer, B., et al., "New Concepts in The Immunopathogenesis of Multiple Sclerosis," Nature Reviews, Neuroscience vol. 3, Apr. 2002, pp. 291-301.

Hanahan, Douglas and Weinberg, Robert A., "The Hallmarks of Cancer," Cell, vol. 100, Jan. 7, 2000, pp. 57-70.

Garcia-Echeverria, C., et al., "Drug discovery approaches targeting the PI3K/Akt pathway in cancer," Oncogene, 2008, 27, pp. 5511-5526.

Xue, et al., "Palomid 529, a Novel Small-Molecule Drug, is a TORC1/TORC2 Inhibitor That Reduces Tumor Growth, Tumor Angiogenesis, and Vascular Permeability," Cancer Research, Nov. 14, 2008, 68(22), pp. 9551-9557.

Rosner, M., et al., "The mTOR pathway and its role in human genetic diseases," Mutation Research 659 (2008), pp. 284-292.

Serruys, P.W., et al., "Coronary-Artery Stents," New England Journal of Medicine, Feb. 2, 2006, 354:5, pp. 483-495.

Shah, O.J., et al., "Inappropriate Activation of the TSC/Rheb/mTOR/S6K Cassette Induces IRS1/2 Depletion, Insulin Resistance, and Cell Survival Deficiencies," Current Biology, vol. 14, Sep. 21, 2004, pp. 1650-1656.

Yeh, W.C., et al., "Rapamycin inhibits clonal expansion and adipogenic differentiation of 3T3-L1 cells," Proc. Natl. Acad. Sci. USA, vol. 92, Nov. 1995, Biochemistry, pp. 11086-11090.

Ravikumar, B., et al., "Inhibition of mTOR induces autophagy and reduces toxicity of polyglutamine expansions in fly and mouse models of Huntington disease," Nature Genetics, vol. 36, No. 6, Jun. 2004, pp. 585-595.

Berger, Z., et al., "Rapamycin alleviates toxicity of different aggregate-prone proteins," Human Molecular Genetics, 2006, vol. 15, No. 3, pp. 433-442.

Pan, T., et al., "Neuroprotection of rapamycin in lactacystin-induced neurodegeneration via autophagy enhancement," Neurobiology of Disease, 32 (2008), pp. 16-25.

Kizushima, N., et al., "Autophagy fights disease through cellular self-digestion," Nature, vol. 451, Feb. 28, 2008, pp. 1069-1075.

\* cited by examiner

PYRIMIDINE DERIVATIVES AS MTOR INHIBITORS

The present application is a National Stage Application claiming the priority of PCT Application No. PCT/EP2010/053165 filed Mar. 12, 2010, which in turn, claims priority from European Patent Application No. 09155143.2 filed Mar. 13, 2009, and U.S. Provisional Application Ser. No. 61/303,252, filed Feb. 10, 2010. Applicants claim the benefits of 35 U.S.C. §120 as to the PCT application and priority under 35 U.S.C. §119 as to the said European Patent application, and the U.S. Provisional application.

The present invention relates to a novel class of kinase inhibitors, including pharmaceutically acceptable salts, prodrugs and metabolites thereof, which are useful for modulating protein kinase activity for modulating cellular activities such as signal transduction, proliferation, and cytokine secretion. More specifically the invention provides compounds which inhibit, regulate and/or modulate kinase activity, in particular mTOR activity, and signal transduction pathways relating to cellular activities as mentioned above. Furthermore, the present invention relates to pharmaceutical compositions comprising said compounds, e.g. for the treatment of diseases such as immunological, inflammatory, autoimmune, allergic disorders, or proliferative diseases such as cancer and processes for preparing said compounds.

Kinases catalyze the phosphorylation of proteins, lipids, sugars, nucleosides and other cellular metabolites and play key roles in all aspects of eukaryotic cell physiology. Especially, protein kinases and lipid kinases participate in the signaling events which control the activation, growth, differentiation and survival of cells in response to extracellular mediators or stimuli such as growth factors, cytokines or chemokines. In general, protein kinases are classified in two groups, those that preferentially phosphorylate tyrosine residues and those that preferentially phosphorylate serine and/or threonine residues.

Inappropriately high protein kinase activity is involved in many diseases including cancer, metabolic diseases and autoimmune/inflammatory disorders. This can be caused either directly or indirectly by the failure of control mechanisms due to mutation, overexpression or inappropriate activation of the enzyme. In all of these instances, selective inhibition of the kinase is expected to have a beneficial effect.

mTOR ("mammalian target of rapamycin", also known as FRAP or RAFT1) has become a recent focus of drug discovery efforts (Tsang et al., 2007, Drug Discovery Today 12, 112-124). It was discovered that the mTOR protein is the drug target for the immunosuppressive effect of rapamycin, a drug that is used to prevent transplant rejection. Rapamycin works through a gain-of-function mechanism by binding to the intracellular protein "FK-506-binding protein of 12 kDA" (FKBP12) to generate a drug-receptor complex that then binds to and inhibits mTOR. Thus, rapamycin induces the formation of the ternary complex consisting of rapamycin and the two proteins FKBP12 and mTOR.

The mTOR protein is a large kinase of 289 kDA which occurs in all eukaryotic organisms sequenced so far (Schmelzle and Hall, 2000, Cell 103, 253-262). The sequence of the carboxy-terminal "phosphatidylinositol 3-kinase (PI3K)-related kinase" (PIKK) domain is highly conserved between species and exhibits serine and threonine kinase activity but no detectable lipid kinase activity. The intact PIKK domain is required for all known functions of mTOR. The FKBP12-rapamycin-binding (FRB) domain is located close to the PIKK domain and forms a hydrophobic pocket that binds to the rapamycin bound to FKBP12. The FRB domain does not appear to inhibit the enzymatic activity of the kinase domain directly. One explanation is that FKBP12-rapamycin prevents the interaction of mTOR with its substrates due to steric hindrance. The N-terminus of mTOR consists of approximately 20 tandem repeats of 37 to 43 amino acids termed HEAT repeats. The HEAT repeats interact with protein binding partners such as Raptor.

mTOR can form at least two distinct proteins complexes, mTORC1 and mTORC2. In the mTORC1 protein complex mTOR interacts with the proteins Raptor and mLST8/GβL and regulates cell growth by phosphorylating effectors such as p70S6K and 4E-BP1 to promote mRNA translation and protein synthesis. The mTORC1 complex is responsible for sensing nutrient signals (for example the availibility of amino acids) in conjunction with insulin signaling. The activity of mTOR in mTORC1 can be inhibited by rapamycin.

The second protein complex, mTORC2, consists of the proteins mTOR, Rictor, mLST8/GβL and Sin1 and is involved in the organization of actin. The mTORC2 was originally described as rapamycin insensitive. A recent publication demonstrated that rapamycin affects the function of mTORC2 after prolonged treatment through an indirect mechanism by interfering with the assembly of the mTORC2 protein complex (Sarbassov et al., 2006, Molecular Cell 22, 159-168).

The biological function of mTOR is that of a central regulator of various extracellular and intracellular signals, including growth factors, nutrients, energy and stress. Growth factor and hormone (e.g. insulin) induced mTOR activation is mediated by PI3 kinases, Akt, and the tuberous sclerosis protein complex (TSC). For example, mTOR acts as a central regulator of cell proliferation, angiogenesis, and cell metabolism (Tsang et al., 2007, Drug Discovery Today 12, 112-124)). In addition to its immunosuppresive effects rapamycin (Sirolimus) is a potent inhibitor of the proliferation of vascular smooth muscle cells and was approved by the FDA as an anti-restenosis drug used in coronary stents. In addition, it was observed that rapamycin displays anti-tumour activity in several in vitro and animal models (Faivre et al., 2006. Nat. Rev. Drug. Discov. 5(8):671-688).

Because of the therapeutic potential of rapamycin several pharmaceutical companies started to develop rapamycin analogs to improve the pharmacokinetic properties of the molecule (Tsang et al., 2007, Drug Discovery Today 12, 112-124). For example, CCI779 (temsirolimus) represents a more water-soluble ester derivative of rapamycin for intravenous and oral formulation. CCI779 has antitumor activity either alone or in combination with cytotoxic agents in cell lines. RAD001 (everolimus) is a hydroxyethyl ether derivative of rapamycin that is developed for oral administration. AP23573 (deferolimus) is developed for either oral or intravenous administration.

In general, the rapamycin derivatives act through the same molecular mechanism, the induction of the ternary rapamycin-FKBP12-mTOR complex. It is conceivable that the function of mTOR could be equally or even more effectively inhibited by inhibitors of the kinase function. For example, this could be achieved by identifying compounds that interact with the ATP-binding pocket of the mTOR kinase domain. For example Torin1 is a potent and selective ATP-competitive mTOR inhibitor that directly binds to both mTOR complexes and impairs cell growth and proliferation more efficiently than rapamycin (Thoreen et al., 2009. J Biol. Chem. 2009 Jan. 15. [Epub ahead of print]; PMID: 19150980; Feldman et al., 2009. PLOSBiology 7(2):e38).

Diseases and disorders associated with mTOR inhibition are further described, e.g. in WO-A 2008/116129, WO-A 2008/115974, WO-A 2008/023159, WO-A 2009/007748, WO-A 2009/007749, WO-A 2009/007750, WO-A 2009/007751.

Several mTOR inhibitors have been reported in the literature which may be useful in the medical field, for example as anticancer agents (Faivre et al., 2006. Nat. Rev. Drug. Discov. 5(8):671-688). In WO-A 2008/116129 imidazolopyrimidine analogs are described as mixed mTOR and PI3K kinase inhibitors. Pyrazolopyrimidine analogs are described as mixed mTOR and PI3K kinase inhibitors in WO-A 2008/115974. Further pyrimidine derivatives as mTOR kinase and/or PI3K enzyme active compounds are disclosed in WO-A 2008/023159, WO-A 2009/007748, WO-A 2009/007749, WO-A 2009/007750, WO-A 2009/007751, WO-A 2010/014939.

Even though mTOR inhibitors are known in the art there is a need for providing additional mTOR inhibitors having at least partially more effective pharmaceutically relevant properties, like activity, selectivity, and ADMET properties.

Accordingly, the present invention provides compounds of formula (I)

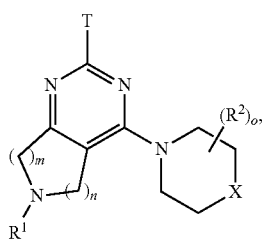

(I)

or a pharmaceutically acceptable salt, prodrug or metabolite thereof, wherein

X is O; or S;

m is 1; 2; or 3;

n is 1; 2; or 3;

$R^1$ is H; $C(O)R^3$; $C(O)OR^3$; $C(O)N(R^3R^{3a})$; $S(O)_2N(R^3R^{3a})$; $S(O)N(R^3R^{3a})$; $S(O)_2R^3$; $S(O)R^3$; $T^1$; or $C_{1-6}$ alkyl, wherein $C_{1-6}$ alkyl is optionally substituted with one or more $R^4$, which are the same or different;

$R^3$, $R^{3a}$ are independently selected from the group consisting of H; $T^1$; and $C_{1-6}$ alkyl, wherein $C_{1-6}$ alkyl is optionally substituted with one or more $R^4$, which are the same or different;

$R^4$ is halogen; CN; $C(O)OR^5$; $OR^5$; $C(O)R^5$; $C(O)N(R^5R^{5a})$; $S(O)_2N(R^5R^{5a})$; $S(O)N(R^5R^{5a})$; $S(O)_2R^5$; $S(O)R^5$; $N(R^5)S(O)_2N(R^{5a}R^{5b})$; $N(R^5)S(O)N(R^{5a}R^{5b})$; $SR^5$; $N(R^5R^{5a})$; $NO_2$; $OC(O)R^5$; $N(R^5)C(O)R^{5a}$; $N(R^5)S(O)_2R^{5a}$; $N(R^5)S(O)R^{5a}$; $N(R^5)C(O)N(R^{5a}R^{5b})$; $N(R^5)C(O)OR^{5a}$; $OC(O)N(R^5R^{5a})$; or $T^1$;

$R^5$, $R^{5a}$, $R^{5b}$ are independently selected from the group consisting of H; and $C_{1-6}$ alkyl, wherein $C_{1-6}$ alkyl is optionally substituted with one or more halogen, which are the same or different;

$T^1$ is $C_{3-7}$ cycloalkyl; 4 to 7 membered heterocyclyl; 8 to 11 membered heterobicyclyl; phenyl; naphthyl; indenyl; or indanyl, wherein $T^1$ is optionally substituted with one or more $R^6$, which are the same or different;

$R^6$ is halogen; CN; $C(O)OR^7$; $OR^7$; oxo (=O), where the ring is at least partially saturated; $C(O)R^7$; $C(O)N(R^7R^{7a})$; $S(O)_2N(R^7R^{7a})$; $S(O)N(R^7R^{7a})$; $S(O)_2R^7$; $S(O)R^7$; $N(R^7)S(O)_2N(R^{7a}R^{7b})$; $N(R^7)S(O)N(R^{7a}R^{7b})$; $SR^7$; $N(R^7R^{7a})$; $NO_2$; $OC(O)R^7$; $N(R^7)C(O)R^{7a}$; $N(R^7)S(O)_2R^{7a}$; $N(R^7)S(O)R^{7a}$; $N(R^7)C(O)N(R^{7a}R^{7b})$; $N(R^7)C(O)OR^{7a}$; $OC(O)N(R^7R^{7a})$; or $C_{1-6}$ alkyl, wherein $C_{1-6}$ alkyl is optionally substituted with one or more $R^8$, which are the same or different;

$R^7$, $R^{7a}$, $R^{7b}$ are independently selected from the group consisting of H; $C_{1-6}$ alkyl, wherein $C_{1-6}$ alkyl is optionally substituted with one or more halogen, which are the same or different;

$R^8$ is halogen; CN; $C(O)OR^9$; $OR^9$; $C(O)R^9$; $C(O)N(R^9R^{9a})$; $S(O)_2N(R^9R^{9a})$; $S(O)N(R^9R^{9a})$; $S(O)_2R^9$; $S(O)R^9$; $N(R^9)S(O)_2N(R^{9a}R^{9b})$; $N(R^9)S(O)N(R^{9a}R^{9b})$; $SR^9$; $N(R^9R^{9a})$; $NO_2$; $OC(O)R^9$; $N(R^9)C(O)R^{9a}$; $N(R^9)S(O)_2R^{9a}$; $N(R^9)S(O)R^{9a}$; $N(R^9)C(O)N(R^{9a}R^{9b})$; $N(R^9)C(O)OR^{9a}$; or $OC(O)N(R^9R^{9a})$;

$R^9$, $R^{9a}$, $R^{9b}$ are independently selected from the group consisting of H; and $C_{1-6}$ alkyl, wherein $C_{1-6}$ alkyl is optionally substituted with one or more halogen, which are the same or different;

o is 1; 2; 3; or 4;

Each $R^2$ is independently selected from the group consisting of H; halogen; CN; $C(O)OR^{10}$; $OR^{10a}$; oxo (=O); $C(O)R^{10}$; $C(O)N(R^{10}R^{10a})$; $S(O)_2N(R^{10}R^{10a})$; $S(O)N(R^{10}R^{10a})$; $S(O)_2R^{10}$; $S(O)R^{10}$; $N(R^{10})S(O)_2N(R^{10a}R^{10b})$; $N(R^{10})S(O)N(R^{10a}R^{10b})$; $SR^{10}$; $N(R^{10}R^{10a})$; $NO_2$; $OC(O)R^{10}$; $N(R^{10})C(O)R^{10a}$; $N(R^{10})S(O)_2R^{10a}$; $N(R^{10})S(O)R^{10a}$; $N(R^{10})C(O)N(R^{10a}R^{10b})$; $N(R^{10})C(O)OR^{10a}$; $OC(O)N(R^{10}R^{10a})$ and $C_{1-6}$ alkyl, wherein $C_{1-6}$ alkyl is optionally substituted with one or more $R^{11}$, which are the same or different;

$R^{10}$; $R^{10a}$; $R^{10b}$ are independently selected from the group consisting of H; $C_{1-6}$ alkyl, wherein $C_{1-6}$ alkyl is optionally substituted with one or more halogen, which are the same or different;

$R^{11}$ is halogen; CN; $C(O)OR^{12}$; $OR^{12}$; $C(O)R^{12}$; $C(O)N(R^{12}R^{12a})$; $S(O)_2N(R^{12}R^{12a})$; $S(O)N(R^{12}R^{12a})$; $S(O)_2R^{12}$; $S(O)R^{12}$; $N(R^{12})S(O)_2N(R^{12a}R^{12b})$; $N(R^{12})S(O)N(R^{12a}R^{12b})$; $SR^{12}$; $N(R^{12}R^{12a})$; $NO_2$; $OC(O)R^{12}$; $N(R^{12})C(O)R^{12a}$; $N(R^{12})S(O)_2R^{12a}$; $N(R^{12})S(O)R^{12a}$; $N(R^{12})C(O)N(R^{12a}R^{12b})$; $N(R^{12})C(O)OR^{12a}$; or $OC(O)N(R^{12}R^{12a})$;

$R^{12}$, $R^{12a}$, $R^{12b}$ are independently selected from the group consisting of H; and $C_{1-6}$ alkyl, wherein $C_{1-6}$ alkyl is optionally substituted with one or more halogen, which are the same or different;

T is phenyl; or 5 to 6 membered aromatic heterocycle, wherein T is substituted with $N(R^{13a})C(O)N(R^{13b}R^{13})$ and optionally further substituted with one or more $R^{14}$, which are the same or different;

$R^{14}$ is halogen; CN; $C(O)OR^{15}$; $OR^{15}$; $C(O)R^{15}$; $C(O)N(R^{15}R^{15a})$; $S(O)_2N(R^{15}R^{15a})$; $S(O)N(R^{15}R^{15a})$; $S(O)_2R^{15}$; $S(O)R^{15}$; $N(R^{15})S(O)_2N(R^{15a}R^{15b})$; $N(R^{15})S(O)N(R^{15a}R^{15b})$; $SR^{15}$; $N(R^{15}R^{15a})$; $NO_2$; $OC(O)R^{15}$; $N(R^{15})C(O)R^{15a}$; $N(R^{15})S(O)_2R^{15a}$; $N(R^{15})S(O)R^{15a}$; $N(R^{15})C(O)N(R^{15a}R^{15b})$; $N(R^{15})C(O)OR^{15a}$; $OC(O)N(R^{15}R^{15a})$; or $C_{1-6}$ alkyl, wherein $C_{1-6}$ alkyl is optionally substituted with one or more halogen, which are the same or different;

$R^{13a}$; $R^{13b}$; $R^{15}$; $R^{15a}$; $R^{15b}$ are independently selected from the group consisting of H; $C_{1-6}$ alkyl, wherein $C_{1-6}$ alkyl is optionally substituted with one or more halogen, which are the same or different;

$R^{13}$ is H; $T^2$; and $C_{1-6}$ alkyl, wherein $C_{1-6}$ alkyl is optionally substituted with one or more $R^{16}$, which are the same or different;

$R^{16}$ is halogen; CN; $C(O)OR^{17}$; $OR^{17}$; $C(O)R^{17}$; $C(O)N(R^{17}R^{17a})$; $S(O)_2N(R^{17}R^{17a})$; $S(O)N(R^{17}R^{17a})$; $S(O)_2R^{17}$; $S(O)R^{17}$; $N(R^{17})S(O)_2N(R^{17a}R^{17})$; $N(R^{17})S(O)N(R^{17a}R^{17})$; $SR^{17}$; $N(R^{17}R^{17a})$; $NO_2$; $OC(O)R^{17}$; $N(R^{17})C$ (O)R$^{17a}$; N(R$^{17}$)S(O)$_2$R$^{17a}$; N(R$^{17}$)S(O)R$^{17a}$; N(R$^{17}$)C(O)N(R$^{17a}$R$^{17}$); N(R$^{17}$)C(O)OR$^{17a}$; OC(O)N(R$^{17}$R$^{17a}$); or T$^2$;

R$^{17}$, R$^{17a}$, R$^{17b}$ are independently selected from the group consisting of H; and C$_{1-6}$ alkyl, wherein C$_{1-6}$ alkyl is optionally substituted with one or more halogen, which are the same or different;

Optionally R$^{13}$, R$^{13b}$ are joined together with the nitrogen atom to which they are attached to form an at least the nitrogen atom as ring heteroatom containing 4 to 7 membered heterocyclyl ring; or 8 to 11 membered heterobicyclyl ring, wherein the 4 to 7 membered heterocyclyl ring; and the 8 to 11 membered heterobicyclyl ring are optionally substituted with one or more R$^{18}$, which are the same or different;

T$^2$ is C$_{3-7}$ cycloalkyl; 4 to 7 membered heterocyclyl; 8 to 11 membered heterobicyclyl; phenyl; naphthyl; indenyl; or indanyl, wherein T$^2$ is optionally substituted with one or more R$^{18}$, which are the same or different;

R$^{18}$ is halogen; CN; C(O)OR$^{19}$; OR$^{19}$; oxo (=O), where the ring is at least partially saturated; C(O)R$^{19}$; C(O)N(R$^{19}$R$^{19a}$); S(O)$_2$N(R$^{19}$R$^{19a}$); S(O)N(R$^{19}$R$^{19a}$); S(O)$_2$R$^{19}$; S(O)R$^{19}$; N(R$^{19}$)S(O)$_2$N(R$^{19a}$R$^{19b}$); N(R$^{19}$)S(O)N(R$^{19a}$R$^{19b}$); SR$^{19}$; N(R$^{19}$R$^{19a}$); NO$_2$; OC(O)R$^{19}$; N(R$^{19}$)C(O)R$^{19a}$; N(R$^{19}$)S(O)$_2$R$^{19a}$; N(R$^{19}$)S(O)R$^{19a}$; N(R$^{19}$)C(O)N(R$^{19a}$R$^{19b}$); N(R$^{19}$)C(O)OR$^{19a}$; OC(O)N(R$^{19}$R$^{19a}$); or C$_{1-6}$ alkyl, wherein C$_{1-6}$ alkyl is optionally substituted with one or more R$^{20}$, which are the same or different;

R$^{19}$, R$^{19a}$, R$^{19b}$ are independently selected from the group consisting of H; C$_{1-6}$ alkyl, wherein C$_{1-6}$ alkyl is optionally substituted with one or more halogen, which are the same or different;

R$^{20}$ is halogen; CN; C(O)OR$^{21}$; OR$^{21}$; C(O)R$^{21}$; C(O)N(R$^{21}$R$^{21a}$); S(O)$_2$N(R$^{21}$R$^{21a}$); S(O)N(R$^{21}$R$^{21a}$); S(O)$_2$R$^{21}$; S(O)R$^{21}$; N(R$^{21}$)S(O)$_2$N(R$^{21a}$R$^{21b}$); N(R$^{21}$)S(O)N(R$^{21a}$R$^{21b}$); SR$^{21}$; N(R$^{21}$R$^{21a}$); NO$_2$; OC(O)R$^{21}$; N(R$^{21}$)C(O)R$^{21a}$; N(R$^{21}$)S(O)$_2$R$^{21a}$; N(R$^{21}$)S(O)R$^{21a}$; N(R$^{21}$)C(O)N(R$^{21a}$R$^{21b}$); N(R$^{21}$)C(O)OR$^{21a}$; or OC(O)N(R$^{21}$R$^{21a}$);

R$^{21}$, R$^{21a}$, R$^{21b}$ are independently selected from the group consisting of H; and C$_{1-6}$ alkyl, wherein C$_{1-6}$ alkyl is optionally substituted with one or more halogen, which are the same or different.

In case a variable or substituent can be selected from a group of different variants and such variable or substituent occurs more than once the respective variants can be the same or different.

The compounds of the present invention show in general good pharmaceutically relevant properties. Surprisingly it was found that preferred compounds of formula (I), wherein T is phenyl and having an F-substitution of the phenyl ring in the meta position relative to the urea group are expected not to have genotoxic issues even though it is generally known in the art that compounds containing a phenyl urea group may form genotoxic metabolites.

Within the meaning of the present invention the terms are used as follows:

"Alkyl" means a straight-chain or branched carbon chain. Each hydrogen of an alkyl carbon may be replaced by a substituent.

"C$_{1-4}$ alkyl" means an alkyl chain having 1-4 carbon atoms, e.g. if present at the end of a molecule: methyl, ethyl, n-propyl, isopropyl, n-butyl, isobutyl, sec-butyl tert-butyl, or e.g. —CH$_2$—, —CH$_2$—CH$_2$—, —CH(CH$_3$)—, —C(CH$_2$)—, —CH$_2$—CH$_2$—CH$_2$—, —CH(C$_2$H$_5$)—, —C(CH$_3$)$_2$—, when two moieties of a molecule are linked by the alkyl group. Each hydrogen of a C$_{1-4}$ alkyl carbon may be replaced by a substituent.

"C$_{1-6}$ alkyl" means an alkyl chain having 1-6 carbon atoms, e.g. if present at the end of a molecule: C$_{1-4}$ alkyl, methyl, ethyl, n-propyl, isopropyl, n-butyl, isobutyl, sec-butyl; tert-butyl, n-pentyl, n-hexyl, or e.g. —CH$_2$—, —CH$_2$—CH$_2$—, —CH(CH$_3$)—, —CH$_2$—CH$_2$—CH$_2$—, —CH(C$_2$H$_5$)—, —C(CH$_3$)$_2$—, when two moieties of a molecule are linked by the alkyl group. Each hydrogen of a C$_{1-6}$ alkyl carbon may be replaced by a substituent.

"C$_{3-7}$ cycloalkyl" or "C$_{3-7}$ cycloalkyl ring" means a cyclic alkyl chain having 3-7 carbon atoms, e.g. cyclopropyl, cyclobutyl, cyclopentyl, cyclohexyl, cyclohexenyl, cycloheptyl. Each hydrogen of a cycloalkyl carbon may be replaced by a substituent.

"Halogen" means fluoro, chloro, bromo or iodo. It is generally preferred that halogen is fluoro or chloro.

"4 to 7 membered heterocyclyl" or "4 to 7 membered heterocycle" means a ring with 4, 5, 6 or 7 ring atoms that may contain up to the maximum number of double bonds (aromatic or non-aromatic ring which is fully, partially or un-saturated) wherein at least one ring atom up to 4 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for a 4 to 7 membered heterocycles are azetidine, oxetane, thietane, furan, thiophene, pyrrole, pyrroline, imidazole, imidazo line, pyrazole, pyrazoline, oxazole, oxazoline, isoxazole, isoxazoline, thiazole, thiazoline, isothiazole, isothiazoline, thiadiazole, thiadiazoline, tetrahydropyran, tetrahydrothiophene, pyrrolidine, imidazolidine, pyrazolidine, oxazolidine, isoxazolidine, thiazolidine, isothiazolidine, thiadiazolidine, sulfo lane, pyran, dihydropyran, tetrahydropyran, imidazolidine, pyridine, pyridazine, pyrazine, pyrimidine, piperazine, piperidine, morpholine, tetrazole, triazole, triazolidine, tetrazolidine, diazepane, azepine or homopiperazine.

"8 to 11 membered heterobicyclyl" or "8 to 11 membered heterobicycle" means a heterocyclic system of two rings with 8 to 11 ring atoms, where at least one ring atom is shared by both rings and that may contain up to the maximum number of double bonds (aromatic or non-aromatic ring which is fully, partially or un-saturated) wherein at least one ring atom up to 6 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for a 8 to 11 membered heterobicycle are indole, indoline, benzofuran, benzothiophene, benzoxazole, benzisoxazole, benzothiazole, benzisothiazole, benzimidazole, benzimidazo line, quinoline, quinazoline, dihydroquinazoline, quinoline, dihydroquinoline, tetrahydroquinoline, decahydroquinoline, isoquino line, decahydroisoquinoline, tetrahydroisoquinoline, dihydroisoquinoline, benzazepine, purine or pteridine. The term 8 to 11 membered heterobicycle also includes spiro structures of two rings like 1,4-dioxa-8-azaspiro[4.5]decane or bridged heterocycles like 8-aza-bicyclo[3.2.1]octane.

"5 to 6 membered aromatic heterocyclyl" or "5 to 6 membered aromatic heterocycle" means a heterocycle derived from cyclopentadienyl or benzene, where at least one carbon atom is replaced by a heteroatom selected from the group consisting of sulfur (including —S(O)—, —S(O)$_2$—), oxygen and nitrogen (including =N(O)—). Examples for such heterocycles are furan, thiophene, pyrrole, imidazole, pyrazole, oxazole, isoxazole, thiazole, isothiazole, thiadiazole, pyranium, pyridine, pyridazine, pyrimidine, triazole, tetrazole.

Preferred compounds of formula (I) are those compounds in which one or more of the residues contained therein have the meanings given below, with all combinations of preferred substituent definitions being a subject of the present invention. With respect to all preferred compounds of the formula (I) the present invention also includes all tautomeric and stereoisomeric forms and mixtures thereof in all ratios, and their pharmaceutically acceptable salts.

In preferred embodiments of the present invention, the substituents mentioned below independently have the following meaning. Hence, one or more of these substituents can have the preferred or more preferred meanings given below.

Preferably, X is O.

Preferably, m and n are independently 1 or 2.

Preferably, m+n=2 or 3.

Preferably, o is 1 or 2. More preferably, o is 1.

Preferably, T is phenyl; pyridine; pyrimidine; pyridazine; or pyrazine (more preferably, phenyl; or pyridine; even more preferably, phenyl), wherein T is substituted with $N(R^{13a})C(O)N(R^{13b}R^{13})$ and optionally further substituted with one or more $R^{14}$, which are the same or different.

Preferably, $R^{13a}$, $R^{13b}$ are H.

Preferably, T is only substituted with $N(R^{13a})C(O)N(R^{13b}R^{13})$. In a further preferred embodiment T is additionally substituted with one or two $R^{14}$, which are the same or different, more preferably one $R^{14}$. In case T is substituted with one or two (preferably one) $R^{14}$ it is preferred that at least one $R^{14}$ is meta substituted relative to the group $N(R^{13a})C(O)N(R^{13b}R^{13})$.

Preferably, $R^{14}$ is a fluoro substituent.

Preferred compounds of formula (I) are those, where X, m, n, o, T are selected to give formula (Ia), (Ib) or (Ic)

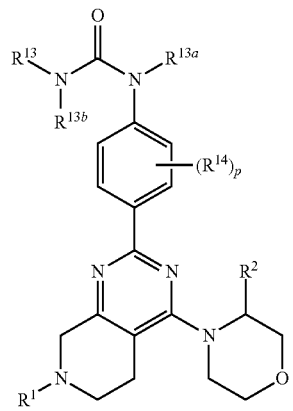
(Ib)

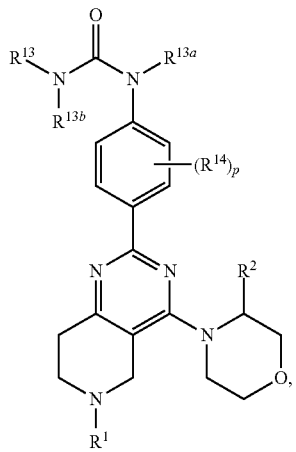
(Ic)

wherein p is 0, 1, or 2.

Even more preferred are compounds of formula (Ia).

In one preferred embodiment p is 0. In another preferred embodiment p is 1 or 2, more preferably 1.

Even more preferred compounds of formula (I) are those, where X, m, n, o, T, $R^{14}$ are selected to give formula (Id), (Ie) or (If)

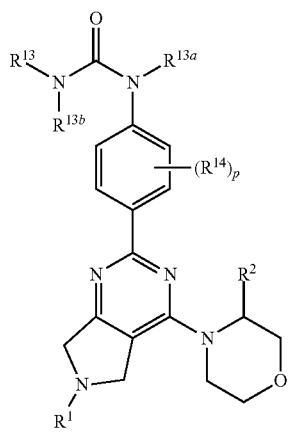
(Ia)

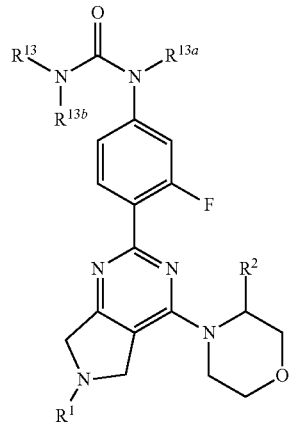
(Id)

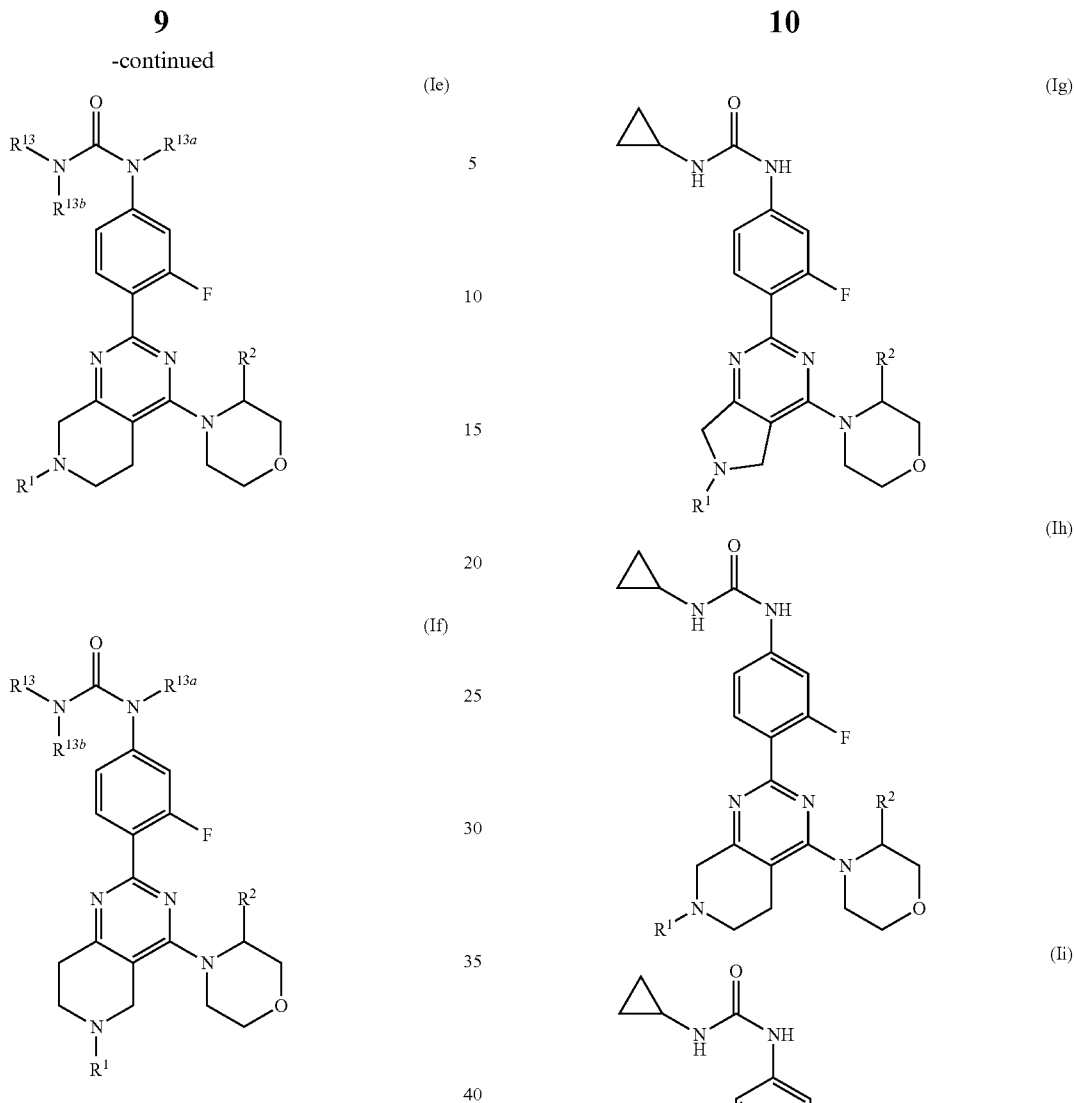

Even more preferred are compounds of formula (Id).

Preferably, $R^1$ is H; $C(O)R^3$; $S(O)_2R^3$; optionally substituted $C_{1-6}$ alkyl; $C(O)OR^3$; $C(O)NHR^3$; optionally substituted $T^1$; or optionally substituted $CH_2$-$T^1$. More preferably, $R^1$ is H; $C(O)R^3$; $S(O)_2R^3$; unsubstituted $C_{1-6}$ alkyl; $C(O)OR^3$; optionally substituted $T^1$; or optionally substituted $CH_2$-$T^1$.

$R^3$ is preferably H; optionally substituted $C_{1-6}$ alkyl; optionally substituted $T^1$; or optionally substituted $CH_2$-$T^1$.

Preferably, $T^1$ is phenyl; or $C_{3-7}$ cycloalkyl and wherein $T^1$ is optionally substituted with one or more $R^6$, which are the same or different.

Preferably, $R^2$ is methyl or hydrogen.

Preferably, $R^{13}$ is H; optionally substituted $C_{1-6}$ alkyl; optionally substituted $T^1$; or optionally substituted $CH_2$-$T^1$. More preferably, is $R^{13}$ H; optionally substituted $C_{1-6}$ alkyl; or optionally substituted $T^1$. Even more preferably, $R^{13}$ is H; unsubstituted $C_{1-6}$ alkyl; cyclopropyl; or $CH_2$-cyclopropyl. Even more preferably, $R^{13}$ is H; unsubstituted $C_{1-6}$ alkyl; or cyclopropyl. Even more preferably, $R^{13}$ is cyclopropyl; ethyl; fluoroethyl; or hydroxyethyl. Even more preferably, $R^{13}$ is cyclopropyl.

Even more preferred compounds of formula (I) are those, where X, m, n, o, T, $R^{13}$, $R^{13a}$, $R^{13b}$, $R^{14}$ are selected to give formula (Ig), (Ih) or (Ii)

Even more preferred are compounds of formula (Ig).

Compounds of formula (I) in which some or all of the above-mentioned groups have the preferred meanings are also an object of the present invention.

Further preferred compounds of the present invention are selected from the group consisting of
(S)-1-(4-(6-formyl-4-(3-methylmorpholino)-6,7-dihydro-5H-pyrrolo[3,4-d]pyrimidin-2-yl)phenyl)urea;
(S)-1-methyl-3-(4-(4-(3-methylmorpholino)-6,7-dihydro-5H-pyrrolo[3,4-d]pyrimidin-2-yl)phenyl)urea;
(S)-1-cyclopropyl-3-(4-(4-(3-methylmorpholino)-6,7-dihydro-5H-pyrrolo[3,4-d]pyrimidin-2-yl)phenyl)urea;
(S)-1-(4-(4-(3-methylmorpholino)-6,7-dihydro-5H-pyrrolo[3,4-d]pyrimidin-2-yl)phenyl)urea;

(S)-1-ethyl-3-(4-(6-formyl-4-(3-methylmorpholino)-6,7-dihydro-5H-pyrrolo[3,4-d]pyrimidin-2-yl)phenyl)urea;

(S)-1-ethyl-3-(4-(4-(3-methylmorpholino)-6-(methylsulfonyl)-6,7-dihydro-5H-pyrrolo[3,4-d]pyrimidin-2-yl)phenyl)urea;

(S)-1-(4-(6-acetyl-4-(3-methylmorpholino)-6,7-dihydro-5H-pyrrolo[3,4-d]pyrimidin-2-yl)phenyl)-3-ethylurea;

(S)-1-ethyl-3-(4-(6-methyl-4-(3-methylmorpholino)-6,7-dihydro-5H-pyrrolo[3,4-d]pyrimidin-2-yl)phenyl)urea;

(S)-1-ethyl-3-(4-(4-(3-methylmorpholino)-6,7-dihydro-5H-pyrrolo[3,4-d]pyrimidin-2-yl)phenyl)urea;

(R)-1-cyclopropyl-3-(4-(4-(3-methylmorpholino)-6,7-dihydro-5H-pyrrolo[3,4-d]pyrimidin-2-yl)phenyl)urea;

(S)-1-cyclopropyl-3-(4-(4-(3-methylmorpholino)-5,6,7,8-tetrahydropyrido[4,3-d]pyrimidin-2-yl)phenyl)urea;

(S)-tert-butyl 2-(4-(3-ethylureido)phenyl)-4-(3-methylmorpholino)-7,8-dihydropyrido[4,3-d]pyrimidine-6(5H)-carboxylate;

(S)-1-methyl-3-(4-(4-(3-methylmorpholino)-5,6,7,8-tetrahydropyrido[4,3-d]pyrimidin-2-yl)phenyl)urea;

(S)-1-ethyl-3-(4-(4-(3-methylmorpholino)-5,6,7,8-tetrahydropyrido[4,3-d]pyrimidin-2-yl)phenyl)urea;

(S)-1-ethyl-3-(4-(4-(3-methylmorpholino)-5,6,7,8-tetrahydropyrido[3,4-d]pyrimidin-2-yl)phenyl)urea;

(S)-1-cyclopropyl-3-(4-(4-(3-methylmorpholino)-5,6,7,8-tetrahydropyrido[3,4-d]pyrimidin-2-yl)phenyl)urea;

(S)-1-methyl-3-(4-(4-(3-methylmorpholino)-5,6,7,8-tetrahydropyrido[3,4-d]pyrimidin-2-yl)phenyl)urea;

(S)-tert-butyl 2-(4-(3-ethylureido)phenyl)-4-(3-methylmorpholino)-5H-pyrrolo[3,4-d]pyrimidine-6(7H)-carboxylate;

(S)-1-ethyl-3-(4-(6-(4-fluorobenzyl)-4-(3-methylmorpholino)-6,7-dihydro-5H-pyrrolo[3,4-d]pyrimidin-2-yl)phenyl)urea;

1-ethyl-3-(4-(4-morpholino-6,7-dihydro-5H-pyrrolo[3,4-d]pyrimidin-2-yl)phenyl)urea;

(S)-1-ethyl-3-(4-(6-(4-fluorobenzoyl)-4-(3-methylmorpholino)-6,7-dihydro-5H-pyrrolo[3,4-d]pyrimidin-2-yl)phenyl)urea;

(S)-1-ethyl-3-(4-(7-ethyl-4-(3-methylmorpholino)-5,6,7,8-tetrahydropyrido[3,4-d]pyrimidin-2-yl)phenyl)urea;

(S)-1-ethyl-3-(4-(7-(4-fluorobenzyl)-4-(3-methylmorpholino)-5,6,7,8-tetrahydropyrido[3,4-d]pyrimidin-2-yl)phenyl)urea;

(S)-1-ethyl-3-(4-(7-(4-fluorobenzoyl)-4-(3-methylmorpholino)-5,6,7,8-tetrahydropyrido[3,4-d]pyrimidin-2-yl)phenyl)urea;

(S)-1-(4-(6-acetyl-4-(3-methylmorpholino)-6,7-dihydro-5H-pyrrolo[3,4-d]pyrimidin-2-yl)phenyl)-3-cyclopropylurea;

(S)-1-ethyl-3-(4-(6-isobutyryl-4-(3-methylmorpholino)-6,7-dihydro-5H-pyrrolo[3,4-d]pyrimidin-2-yl)phenyl)urea;

(S)-1-ethyl-3-(4-(4-(3-methylmorpholino)-6-pivaloyl-6,7-dihydro-5H-pyrrolo[3,4-d]pyrimidin-2-yl)phenyl)urea;

(S)-1-(4-(6-(cyclopropanecarbonyl)-4-(3-methylmorpholino)-6,7-dihydro-5H-pyrrolo[3,4-d]pyrimidin-2-yl)phenyl)-3-ethylurea;

(S)-1-(4-(6-(cyclopropylmethyl)-4-(3-methylmorpholino)-6,7-dihydro-5H-pyrrolo[3,4-d]pyrimidin-2-yl)phenyl)-3-ethylurea;

(S)-2-(4-(3-cyclopropylureido)phenyl)-N-ethyl-4-(3-methylmorpholino)-5H-pyrrolo[3,4-d]pyrimidine-6(7H)-carboxamide;

(S)-ethyl 2-(4-(3-cyclopropylureido)phenyl)-4-(3-methylmorpholino)-5H-pyrrolo[3,4-d]pyrimidine-6(7H)-carboxylate;

(S)-1-(4-(6-(cyclopropanecarbonyl)-4-(3-methylmorpholino)-6,7-dihydro-5H-pyrrolo[3,4-d]pyrimidin-2-yl)phenyl)-3-cyclopropylurea;

(S)-1-cyclopropyl-3-(4-(6-(cyclopropylmethyl)-4-(3-methylmorpholino)-6,7-dihydro-5H-pyrrolo[3,4-d]pyrimidin-2-yl)phenyl)urea;

(S)-1-cyclopropyl-3-(4-(4-(3-methylmorpholino)-6-neopentyl-6,7-dihydro-5H-pyrrolo[3,4-d]pyrimidin-2-yl)phenyl)urea;

(S)-1-ethyl-3-(4-(7-methyl-4-(3-methylmorpholino)-5,6,7,8-tetrahydropyrido[3,4-d]pyrimidin-2-yl)phenyl)urea;

(S)-1-cyclopropyl-3-(4-(6-ethyl-4-(3-methylmorpholino)-6,7-dihydro-5H-pyrrolo[3,4-d]pyrimidin-2-yl)phenyl)urea;

(S)-1-(4-(7-(cyclopropylmethyl)-4-(3-methylmorpholino)-5,6,7,8-tetrahydropyrido[3,4-d]pyrimidin-2-yl)phenyl)-3-ethylurea;

(S)-1-cyclopropyl-3-(4-(6-methyl-4-(3-methylmorpholino)-6,7-dihydro-5H-pyrrolo[3,4-d]pyrimidin-2-yl)phenyl)urea;

(S)-1-ethyl-3-(4-(6-ethyl-4-(3-methylmorpholino)-6,7-dihydro-5H-pyrrolo[3,4-d]pyrimidin-2-yl)phenyl)urea;

(S)-1-cyclopropyl-3-(4-(7-(cyclopropylmethyl)-4-(3-methylmorpholino)-5,6,7,8-tetrahydropyrido[3,4-d]pyrimidin-2-yl)phenyl)urea;

(S)-1-cyclopropyl-3-(4-(4-(3-methylmorpholino)-7-neopentyl-5,6,7,8-tetrahydropyrido[3,4-d]pyrimidin-2-yl)phenyl)urea;

(S)-1-cyclopropyl-3-(4-(7-isobutyl-4-(3-methylmorpholino)-5,6,7,8-tetrahydropyrido[3,4-d]pyrimidin-2-yl)phenyl)urea;

(S)-1-cyclopropyl-3-(4-(7-isopropyl-4-(3-methylmorpholino)-5,6,7,8-tetrahydropyrido[3,4-d]pyrimidin-2-yl)phenyl)urea;

(S)-1-cyclopropyl-3-(4-(6-isobutyryl-4-(3-methylmorpholino)-6,7-dihydro-5H-pyrrolo[3,4-d]pyrimidin-2-yl)phenyl)urea;

(S)-1-cyclopropyl-3-(4-(4-(3-methylmorpholino)-6-pivaloyl-6,7-dihydro-5H-pyrrolo[3,4-d]pyrimidin-2-yl)phenyl)urea;

(S)-1-cyclopropyl-3-(4-(6-isopropyl-4-(3-methylmorpholino)-6,7-dihydro-5H-pyrrolo[3,4-d]pyrimidin-2-yl)phenyl)urea;

(S)-1-(4-(6-(cyclopropylmethyl)-4-(3-methylmorpholino)-6,7-dihydro-5H-pyrrolo[3,4-d]pyrimidin-2-yl)phenyl)-3-methylurea;

(S)-1-(4-(6-(cyclopropylmethyl)-4-(3-methylmorpholino)-6,7-dihydro-5H-pyrrolo[3,4-d]pyrimidin-2-yl)phenyl)urea;

(S)-1-(4-(6-(cyclopropylmethyl)-4-(3-methylmorpholino)-6,7-dihydro-5H-pyrrolo[3,4-d]pyrimidin-2-yl)phenyl)-3-propylurea;

(S)-1-(4-(6-(cyclopropylmethyl)-4-(3-methylmorpholino)-6,7-dihydro-5H-pyrrolo[3,4-d]pyrimidin-2-yl)phenyl)-3-isopropylurea;

(S)-1-(3-hydroxypropyl)-3-(4-(6-methyl-4-(3-methylmorpholino)-6,7-dihydro-5H-pyrrolo[3,4-d]pyrimidin-2-yl)phenyl)urea;

(S)-1-(4-fluorophenyl)-3-(4-(6-methyl-4-(3-methylmorpholino)-6,7-dihydro-5H-pyrrolo[3,4-d]pyrimidin-2-yl)phenyl)urea;

(S)-1-(3-methoxypropyl)-3-(4-(6-methyl-4-(3-methylmorpholino)-6,7-dihydro-5H-pyrrolo[3,4-d]pyrimidin-2-yl)phenyl)urea;

(S)-1-(2-(dimethylamino)ethyl)-3-(4-(6-methyl-4-(3-methylmorpholino)-6,7-dihydro-5H-pyrrolo[3,4-d]pyrimidin-2-yl)phenyl)urea;

(S)-1-cyclobutyl-3-(4-(6-methyl-4-(3-methylmorpholino)-6,7-dihydro-5H-pyrrolo[3,4-d]pyrimidin-2-yl)phenyl)urea;

(S)-1-(4-(7-(cyclopropanecarbonyl)-4-(3-methylmorpholino)-5,6,7,8-tetrahydropyrido[3,4-d]pyrimidin-2-yl)phenyl)-3-ethylurea;

(S)-1-ethyl-3-(4-(7-isobutyryl-4-(3-methylmorpholino)-5,6,7,8-tetrahydropyrido[3,4-d]pyrimidin-2-yl)phenyl)urea;

(S)-1-ethyl-3-(4-(4-(3-methylmorpholino)-7-pivaloyl-5,6,7,8-tetrahydropyrido[3,4-d]pyrimidin-2-yl)phenyl)urea;

(S)-1-(4-(7-acetyl-4-(3-methylmorpholino)-5,6,7,8-tetrahydropyrido[3,4-d]pyrimidin-2-yl)phenyl)-3-ethylurea;

(S)-1-(4-(7-(cyclopropanecarbonyl)-4-(3-methylmorpholino)-5,6,7,8-tetrahydropyrido[3,4-d]pyrimidin-2-yl)phenyl)-3-cyclopropylurea;

(S)-1-cyclopropyl-3-(4-(7-isobutyryl-4-(3-methylmorpholino)-5,6,7,8-tetrahydropyrido[3,4-d]pyrimidin-2-yl)phenyl)urea;

(S)-1-(4-(7-acetyl-4-(3-methylmorpholino)-5,6,7,8-tetrahydropyrido[3,4-d]pyrimidin-2-yl)phenyl)-3-cyclopropylurea;

tert-butyl 2-(4-(3-ethylureido)phenyl)-4-morpholino-5H-pyrrolo[3,4-d]pyrimidine-6(7H)-carboxylate;

(S)-1-cyclopropyl-3-(4-(4-(3-methylmorpholino)-7-pivaloyl-5,6,7,8-tetrahydropyrido[3,4-d]pyrimidin-2-yl)phenyl)urea;

(S)-1-cyclopropyl-3-(4-(6-isobutyl-4-(3-methylmorpholino)-6,7-dihydro-5H-pyrrolo[3,4-d]pyrimidin-2-yl)phenyl)urea;

(S)-1-ethyl-3-(4-(6-isobutyl-4-(3-methylmorpholino)-6,7-dihydro-5H-pyrrolo[3,4-d]pyrimidin-2-yl)phenyl)urea;

(S)-1-ethyl-3-(4-(4-(3-methylmorpholino)-6-neopentyl-6,7-dihydro-5H-pyrrolo[3,4-d]pyrimidin-2-yl)phenyl)urea;

(S)-1-ethyl-3-(4-(4-(3-methylmorpholino)-6-(2,2,2-trifluoroethyl)-6,7-dihydro-5H-pyrrolo[3,4-d]pyrimidin-2-yl)phenyl)urea;

1-ethyl-3-(4-(6-methyl-4-morpholino-6,7-dihydro-5H-pyrrolo[3,4-d]pyrimidin-2-yl)phenyl)urea;

ethyl 2-(4-(3-ethylureido)phenyl)-4-morpholino-5H-pyrrolo[3,4-d]pyrimidine-6(7H)-carboxylate;

(S)-1-(4-(6-methyl-4-(3-methylmorpholino)-6,7-dihydro-5H-pyrrolo[3,4-d]pyrimidin-2-yl)phenyl)urea;

(S)-1-(4-(6-methyl-4-(3-methylmorpholino)-6,7-dihydro-5H-pyrrolo[3,4-d]pyrimidin-2-yl)phenyl)-3-(5-methylisoxazol-3-yl)urea;

(S)-1-(2-hydroxyethyl)-3-(4-(6-methyl-4-(3-methylmorpholino)-6,7-dihydro-5H-pyrrolo[3,4-d]pyrimidin-2-yl)phenyl)urea;

(S)-1-ethyl-3-(4-(6-isopropyl-4-(3-methylmorpholino)-6,7-dihydro-5H-pyrrolo[3,4-d]pyrimidin-2-yl)phenyl)urea;

(S)-1-ethyl-3-(4-(7-isopropyl-4-(3-methylmorpholino)-5,6,7,8-tetrahydropyrido[3,4-d]pyrimidin-2-yl)phenyl)urea;

(S)-1-ethyl-3-(4-(7-isobutyl-4-(3-methylmorpholino)-5,6,7,8-tetrahydropyrido[3,4-d]pyrimidin-2-yl)phenyl)urea;

(S)-ethyl 2-(4-(3-ethylureido)phenyl)-4-(3-methylmorpholino)-5,6-dihydropyrido[3,4-d]pyrimidine-7(8H)-carboxylate;

(S)-ethyl 2-(4-(3-cyclopropylureido)phenyl)-4-(3-methylmorpholino)-5,6-dihydropyrido[3,4-d]pyrimidine-7(8H)-carboxylate;

N-ethyl-2-(4-(3-ethylureido)phenyl)-4-morpholino-5H-pyrrolo[3,4-d]pyrimidine-6(7H)-carboxamide;

(S)-1-(6-hydroxypyridin-2-yl)-3-(4-(6-methyl-4-(3-methylmorpholino)-6,7-dihydro-5H-pyrrolo[3,4-d]pyrimidin-2-yl)phenyl)urea;

(S)-methyl 2-(4-(3-ethylureido)phenyl)-4-(3-methylmorpholino)-5,6-dihydropyrido[3,4-d]pyrimidine-7(8H)-carboxylate;

1-ethyl-3-(4-(4-morpholino-5,6,7,8-tetrahydropyrido[3,4-d]pyrimidin-2-yl)phenyl)urea;

(S)-methyl 2-(4-(3-cyclopropylureido)phenyl)-4-(3-methylmorpholino)-5,6-dihydropyrido[3,4-d]pyrimidine-7(8H)-carboxylate;

(S)-1-(1-methyl-1H-pyrazol-4-yl)-3-(4-(6-methyl-4-(3-methylmorpholino)-6,7-dihydro-5H-pyrrolo[3,4-d]pyrimidin-2-yl)phenyl)urea;

(S)-1-ethyl-3-(2-fluoro-4-(6-methyl-4-(3-methylmorpholino)-6,7-dihydro-5H-pyrrolo[3,4-d]pyrimidin-2-yl)phenyl)urea;

(S)-methyl 2-(4-(3-cyclopropylureido)phenyl)-4-(3-methylmorpholino)-5H-pyrrolo[3,4-d]pyrimidine-6(7H)-carboxylate;

(S)—N-ethyl-2-(4-(3-ethylureido)phenyl)-4-(3-methylmorpholino)-5,6-dihydropyrido[3,4-d]pyrimidine-7(8H)-carboxamide;

(S)-2-(4-(3-cyclopropylureido)phenyl)-N-ethyl-4-(3-methylmorpholino)-5,6-dihydropyrido[3,4-d]pyrimidine-7(8H)-carboxamide;

(S)-methyl 2-(4-(3-ethylureido)phenyl)-4-(3-methylmorpholino)-5H-pyrrolo[3,4-d]pyrimidine-6(7H)-carboxylate;

(S)-ethyl 2-(4-(3-ethylureido)phenyl)-4-(3-methylmorpholino)-5H-pyrrolo[3,4-d]pyrimidine-6(7H)-carboxylate;

(S)-1-ethyl-3-(4-(4-(3-methylmorpholino)-7-(2-(pyridin-3-yl)acetyl)-5,6,7,8-tetrahydropyrido[3,4-d]pyrimidin-2-yl)phenyl)urea;

(S)-1-(4-(6-(3-(dimethylamino)propanoyl)-4-(3-methylmorpholino)-5,6,7,8-tetrahydropyrido[4,3-d]pyrimidin-2-yl)phenyl)-3-ethylurea;

1-ethyl-3-(4-(7-methyl-4-morpholino-5,6,7,8-tetrahydropyrido[3,4-d]pyrimidin-2-yl)phenyl)urea;

N-ethyl-2-(4-(3-ethylureido)phenyl)-4-morpholino-5,6-dihydropyrido[3,4-d]pyrimidine-7(8H)-carboxamide;

methyl 2-(4-(3-ethylureido)phenyl)-4-morpholino-5,6-dihydropyrido[3,4-d]pyrimidine-7(8H)-carboxylate;

ethyl 2-(4-(3-ethylureido)phenyl)-4-morpholino-5,6-dihydropyrido[3,4-d]pyrimidine-7(8H)-carboxylate;

1-(4-(7-acetyl-4-morpholino-5,6,7,8-tetrahydropyrido[3,4-d]pyrimidin-2-yl)phenyl)-3-ethylurea;

1-ethyl-3-(4-(4-morpholino-7-pivaloyl-5,6,7,8-tetrahydropyrido[3,4-d]pyrimidin-2-yl)phenyl)urea;

1-(4-(6-acetyl-4-morpholino-6,7-dihydro-5H-pyrrolo[3,4-d]pyrimidin-2-yl)phenyl)-3-ethylurea;

1-ethyl-3-(4-(4-morpholino-6-pivaloyl-6,7-dihydro-5H-pyrrolo[3,4-d]pyrimidin-2-yl)phenyl)urea;

(S)-1-cyclopropyl-3-(4-(4-(3-methylmorpholino)-6-(2,2,2-trifluoroethyl)-6,7-dihydro-5H-pyrrolo[3,4-d]pyrimidin-2-yl)phenyl)urea;

(S)-1-ethyl-3-(4-(7-(2-hydroxyacetyl)-4-(3-methylmorpholino)-5,6,7,8-tetrahydropyrido[3,4-d]pyrimidin-2-yl)phenyl)urea;

(S)-ethyl 2-(4-(3-ethylureido)-3-fluorophenyl)-4-(3-methylmorpholino)-5H-pyrrolo[3,4-d]pyrimidine-6(7H)-carboxylate;

(S)-ethyl 2-(3-fluoro-4-(3-(2-hydroxyethyl)ureido)phenyl)-4-(3-methylmorpholino)-5H-pyrrolo[3,4-d]pyrimidine-6(7H)-carboxylate;

(S)-ethyl 2-(4-(3-cyclopropylureido)-3-fluorophenyl)-4-(3-methylmorpholino)-5H-pyrrolo[3,4-d]pyrimidine-6(7H)-carboxylate;

(S)-1-ethyl-3-(5-(7-methyl-4-(3-methylmorpholino)-5,6,7,8-tetrahydropyrido[3,4-d]pyrimidin-2-yl)thiazol-2-yl)urea;

(S)-ethyl 2-(4-(3-ethylureido)phenyl)-4-(3-methylmorpholino)-7,8-dihydropyrido[4,3-d]pyrimidine-6(5H)-carboxylate;

(S)-1-(2,5-difluoro-4-(7-methyl-4-(3-methylmorpholino)-5,6,7,8-tetrahydropyrido[3,4-d]pyrimidin-2-yl)phenyl)-3-ethylurea;

(S)-1-ethyl-3-(3-methyl-4-(7-methyl-4-(3-methylmorpholino)-5,6,7,8-tetrahydropyrido[3,4-d]pyrimidin-2-yl)phenyl)urea;

(S)-1-ethyl-3-(3-fluoro-4-(7-methyl-4-(3-methylmorpholino)-5,6,7,8-tetrahydropyrido[3,4-d]pyrimidin-2-yl)phenyl)urea;

(S)-ethyl 2-(4-(3-(3-hydroxyphenyl)ureido)phenyl)-4-(3-methylmorpholino)-5H-pyrrolo[3,4-d]pyrimidine-6(7H)-carboxylate;

(S)-ethyl 2-(4-(3-(2-aminoethyl)ureido)phenyl)-4-(3-methylmorpholino)-5H-pyrrolo[3,4-d]pyrimidine-6(7H)-carboxylate;

(S)-ethyl 2-(4-(3-ethylureido)-2-fluorophenyl)-4-(3-methylmorpholino)-5H-pyrrolo[3,4-d]pyrimidine-6(7H)-carboxylate;

(S)-ethyl 2-(4-(3-(2-amino-2-oxoethyl)ureido)phenyl)-4-(3-methylmorpholino)-5H-pyrrolo[3,4-d]pyrimidine-6(7H)-carboxylate;

(S)-2-(3-(4-(6-(ethoxycarbonyl)-4-(3-methylmorpholino)-6,7-dihydro-5H-pyrrolo[3,4-d]pyrimidin-2-yl)phenyl)ureido)acetic acid;

(S)-ethyl 2-(5-(3-ethylureido)pyrazin-2-yl)-4-(3-methylmorpholino)-5H-pyrrolo[3,4-d]pyrimidine-6(7H)-carboxylate;

(S)-1-(4-(6-(1-acetylpiperidin-4-yl)-4-(3-methylmorpholino)-6,7-dihydro-5H-pyrrolo[3,4-d]pyrimidin-2-yl)-2-fluorophenyl)-3-ethylurea;

(S)-ethyl 4-(3-methylmorpholino)-2-(4-(3-(pyridin-3-yl)ureido)phenyl)-5H-pyrrolo[3,4-d]pyrimidine-6(7H)-carboxylate;

(S)-ethyl 2-(4-(3-(4-(hydroxymethyl)phenyl)ureido)phenyl)-4-(3-methylmorpholino)-5H-pyrrolo[3,4-d]pyrimidine-6(7H)-carboxylate;

(S)-ethyl 2-(4-(3-(2-fluoroethyl)ureido)phenyl)-4-(3-methylmorpholino)-5H-pyrrolo[3,4-d]pyrimidine-6(7H)-carboxylate;

(S)-ethyl 4-(3-methylmorpholino)-2-(4-(3-(pyridin-4-yl)ureido)phenyl)-5H-pyrrolo[3,4-d]pyrimidine-6(7H)-carboxylate;

(S)-methyl 4-(2-(4-(3-ethylureido)-3-fluorophenyl)-4-(3-methylmorpholino)-5H-pyrrolo[3,4-d]pyrimidin-6(7H)-yl)piperidine-1-carboxylate;

(S)-1-(4-(6-(1-acetylpiperidine-4-carbonyl)-4-(3-methylmorpholino)-6,7-dihydro-5H-pyrrolo[3,4-d]pyrimidin-2-yl)-2-fluorophenyl)-3-ethylurea;

(S)-ethyl 2-(4-(3-(2-acetamidoethyl)ureido)phenyl)-4-(3-methylmorpholino)-5H-pyrrolo[3,4-d]pyrimidine-6(7H)-carboxylate;

(S)-ethyl 2-(4-(3-(2-(methylamino)-2-oxoethyl)ureido)phenyl)-4-(3-methylmorpholino)-5H-pyrrolo[3,4-d]pyrimidine-6(7H)-carboxylate;

(S)-1-ethyl-3-(2-fluoro-4-(4-(3-methylmorpholino)-6-(piperidine-4-carbonyl)-6,7-dihydro-5H-pyrrolo[3,4-d]pyrimidin-2-yl)phenyl)urea;

(S)-4-(2-(4-(3-cyclopropylureido)phenyl)-4-(3-methylmorpholino)-5H-pyrrolo[3,4-d]pyrimidin-6(7H)-yl)-4-oxobutanamide;

(S)-tert-butyl 4-((2-(4-(3-cyclopropylureido)phenyl)-4-(3-methylmorpholino)-5H-pyrrolo[3,4-d]pyrimidin-6(7H)-yl)methyl)piperidine-1-carboxylate;

(S)-1-cyclopropyl-3-(4-(4-(3-methylmorpholino)-6-(tetrahydro-2H-pyran-4-carbonyl)-6,7-dihydro-5H-pyrrolo[3,4-d]pyrimidin-2-yl)phenyl)urea;

(S)-1-cyclopropyl-3-(4-(4-(3-methylmorpholino)-6-(piperidin-4-ylmethyl)-6,7-dihydro-5H-pyrrolo[3,4-d]pyrimidin-2-yl)phenyl)urea;

(S)-ethyl 2-(4-(3-cyclopropylureido)-2-fluorophenyl)-4-(3-methylmorpholino)-5H-pyrrolo[3,4-d]pyrimidine-6(7H)-carboxylate;

(S)-1-cyclopropyl-3-(4-(4-(3-methylmorpholino)-6-(3-(2-oxopyrrolidin-1-yl)propanoyl)-6,7-dihydro-5H-pyrrolo[3,4-d]pyrimidin-2-yl)phenyl)urea;

(S)—N-(4-(2-(4-(3-cyclopropylureido)phenyl)-4-(3-methylmorpholino)-5H-pyrrolo[3,4-d]pyrimidin-6(7H)-yl)-4-oxobutyl)acetamide;

(S)-4-(2-(4-(3-cyclopropylureido)phenyl)-4-(3-methylmorpholino)-5H-pyrrolo[3,4-d]pyrimidin-6(7H)-yl)butanoic acid;

(S)—N-(3-(2-(4-(3-cyclopropylureido)phenyl)-4-(3-methylmorpholino)-5H-pyrrolo[3,4-d]pyrimidin-6(7H)-yl)-3-oxopropyl)-N-methylacetamide;

(S)-1-cyclopropyl-3-(4-(4-(3-methylmorpholino)-6-(3-ureidopropanoyl)-6,7-dihydro-5H-pyrrolo[3,4-d]pyrimidin-2-yl)phenyl)urea;

(S)-1-(2,6-difluoro-4-(6-methyl-4-(3-methylmorpholino)-6,7-dihydro-5H-pyrrolo[3,4-d]pyrimidin-2-yl)phenyl)-3-ethylurea;

(S)-1-(2,3-difluoro-4-(6-methyl-4-(3-methylmorpholino)-6,7-dihydro-5H-pyrrolo[3,4-d]pyrimidin-2-yl)phenyl)-3-ethylurea;

(S)-ethyl 2-(4-(3-ethylureido)-2,5-difluorophenyl)-4-(3-methylmorpholino)-5H-pyrrolo[3,4-d]pyrimidine-6(7H)-carboxylate;

(S)-ethyl 2-(4-(3-ethylureido)-2,6-difluorophenyl)-4-(3-methylmorpholino)-5H-pyrrolo[3,4-d]pyrimidine-6(7H)-carboxylate;

tert-butyl 2-(4-(3-cyclopropylureido)-2-fluorophenyl)-4-morpholino-5H-pyrrolo[3,4-d]pyrimidine-6(7H)-carboxylate;

(S)-tert-butyl 2-(4-(3-cyclopropylureido)-2-fluorophenyl)-4-(3-methylmorpholino)-5H-pyrrolo[3,4-d]pyrimidine-6(7H)-carboxylate;

tert-butyl 2-(4-(3-ethylureido)-2-fluorophenyl)-4-morpholino-5H-pyrrolo[3,4-d]pyrimidine-6(7H)-carboxylate;

(S)-methyl 2-(4-(3-cyclopropylureido)-2-fluorophenyl)-4-(3-methylmorpholino)-5H-pyrrolo[3,4-d]pyrimidine-6(7H)-carboxylate;

(S)-1-cyclopropyl-3-(3-fluoro-4-(6-methyl-4-(3-methylmorpholino)-6,7-dihydro-5H-pyrrolo[3,4-d]pyrimidin-2-yl)phenyl)urea;

1-cyclopropyl-3-(3-fluoro-4-(4-morpholino-6,7-dihydro-5H-pyrrolo[3,4-d]pyrimidin-2-yl)phenyl)urea;

(S)-1-cyclopropyl-3-(3-fluoro-4-(4-(3-methylmorpholino)-6,7-dihydro-5H-pyrrolo[3,4-d]pyrimidin-2-yl)phenyl)urea;

1-ethyl-3-(3-fluoro-4-(4-morpholino-6,7-dihydro-5H-pyrrolo[3,4-d]pyrimidin-2-yl)phenyl)urea;

ethyl 2-(4-(3-ethylureido)-2-fluorophenyl)-4-morpholino-5H-pyrrolo[3,4-d]pyrimidine-6(7H)-carboxylate;

(S)-methyl 2-(4-(3-ethylureido)-2-fluorophenyl)-4-(3-methylmorpholino)-5H-pyrrolo[3,4-d]pyrimidine-6(7H)-carboxylate;

(S)-tert-butyl 2-(4-(3-ethylureido)-2-fluorophenyl)-4-(3-methylmorpholino)-5H-pyrrolo[3,4-d]pyrimidine-6(7H)-carboxylate;

1-ethyl-3-(3-fluoro-4-(6-methyl-4-morpholino-6,7-dihydro-5H-pyrrolo[3,4-d]pyrimidin-2-yl)phenyl)urea;

(S)-1-(4-(6-acetyl-4-(3-methylmorpholino)-6,7-dihydro-5H-pyrrolo[3,4-d]pyrimidin-2-yl)-3-fluorophenyl)-3-cyclopropylurea;

ethyl 2-(4-(3-cyclopropylureido)-2-fluorophenyl)-4-morpholino-5H-pyrrolo[3,4-d]pyrimidine-6(7H)-carboxylate;

(S)-1-(4-(6-acetyl-4-(3-methylmorpholino)-6,7-dihydro-5H-pyrrolo[3,4-d]pyrimidin-2-yl)-3-fluorophenyl)-3-ethylurea;

(S)-1-ethyl-3-(3-fluoro-4-(4-(3-methylmorpholino)-6,7-dihydro-5H-pyrrolo[3,4-d]pyrimidin-2-yl)phenyl)urea;

1-cyclopropyl-3-(3-fluoro-4-(6-methyl-4-morpholino-6,7-dihydro-5H-pyrrolo[3,4-d]pyrimidin-2-yl)phenyl)urea;

(S)-1-ethyl-3-(3-fluoro-4-(6-methyl-4-(3-methylmorpholino)-6,7-dihydro-5H-pyrrolo[3,4-d]pyrimidin-2-yl)phenyl)urea;

1-(4-(6-acetyl-4-morpholino-6,7-dihydro-5H-pyrrolo[3,4-d]pyrimidin-2-yl)-3-fluorophenyl)-3-ethylurea;

methyl 2-(4-(3-ethylureido)-2-fluorophenyl)-4-morpholino-5H-pyrrolo[3,4-d]pyrimidine-6(7H)-carboxylate;

(S)-1-cyclopropyl-3-(3-fluoro-4-(4-(3-methylmorpholino)-5,6,7,8-tetrahydropyrido[3,4-d]pyrimidin-2-yl)phenyl)urea;

(S)-1-ethyl-3-(3-fluoro-4-(4-(3-methylmorpholino)-5,6,7,8-tetrahydropyrido[3,4-d]pyrimidin-2-yl)phenyl)urea;

(S)-2-(4-(3-cyclopropylureido)-2-fluorophenyl)-N,N-dimethyl-4-(3-methylmorpholino)-5,6-dihydropyrido[3,4-d]pyrimidine-7(8H)-carboxamide;

1-(4-(6-acetyl-4-morpholino-6,7-dihydro-5H-pyrrolo[3,4-d]pyrimidin-2-yl)-3-fluorophenyl)-3-cyclopropylurea;

(S)-ethyl 2-(2-fluoro-4-(3-(2-hydroxyethyl)ureido)phenyl)-4-(3-methylmorpholino)-5H-pyrrolo[3,4-d]pyrimidine-6(7H)-carboxylate;

(S)-ethyl 2-(2-fluoro-4-(3-(2-fluoroethyl)ureido)phenyl)-4-(3-methylmorpholino)-5H-pyrrolo[3,4-d]pyrimidine-6(7H)-carboxylate;

methyl 2-(2-fluoro-4-(3-(2-fluoroethyl)ureido)phenyl)-4-morpholino-5H-pyrrolo[3,4-d]pyrimidine-6(7H)-carboxylate;

ethyl 2-(2-fluoro-4-(3-(2-fluoroethyl)ureido)phenyl)-4-morpholino-5H-pyrrolo[3,4-d]pyrimidine-6(7H)-carboxylate;

ethyl 2-(2-fluoro-4-(3-(2-hydroxyethyl)ureido)phenyl)-4-morpholino-5H-pyrrolo[3,4-d]pyrimidine-6(7H)-carboxylate;

(S)-1-cyclopropyl-3-(3-fluoro-4-(6-isopropyl-4-(3-methylmorpholino)-6,7-dihydro-5H-pyrrolo[3,4-d]pyrimidin-2-yl)phenyl)urea;

methyl 2-(4-(3-cyclopropylureido)-2-fluorophenyl)-4-morpholino-5H-pyrrolo[3,4-d]pyrimidine-6(7H)-carboxylate;

(S)-1-cyclopropyl-3-(3-fluoro-4-(6-isobutyryl-4-(3-methylmorpholino)-6,7-dihydro-5H-pyrrolo[3,4-d]pyrimidin-2-yl)phenyl)urea;

methyl 2-(2-fluoro-4-(3-(2-hydroxyethyl)ureido)phenyl)-4-morpholino-5H-pyrrolo[3,4-d]pyrimidine-6(7H)-carboxylate;

(S)-2-(4-(3-ethylureido)-2-fluorophenyl)-N,N-dimethyl-4-(3-methylmorpholino)-5,6-dihydropyrido[3,4-d]pyrimidine-7(8H)-carboxamide;

(S)-1-cyclopropyl-3-(3-fluoro-4-(4-(3-methylmorpholino)-6-(methylsulfonyl)-6,7-dihydro-5H-pyrrolo[3,4-d]pyrimidin-2-yl)phenyl)urea;

(S)-2-(4-(3-cyclopropylureido)-2-fluorophenyl)-N,N-dimethyl-4-(3-methylmorpholino)-5H-pyrrolo[3,4-d]pyrimidine-6(7H)-carboxamide;

(R)-ethyl 2-(4-(3-cyclopropylureido)-2-fluorophenyl)-4-(3-methylmorpholino)-5H-pyrrolo[3,4-d]pyrimidine-6(7H)-carboxylate;

(R)-methyl 2-(4-(3-cyclopropylureido)-2-fluorophenyl)-4-(3-methylmorpholino)-5H-pyrrolo[3,4-d]pyrimidine-6(7H)-carboxylate;

(S)-methyl 2-(2-fluoro-4-(3-(2-hydroxyethyl)ureido)phenyl)-4-(3-methylmorpholino)-5H-pyrrolo[3,4-d]pyrimidine-6(7H)-carboxylate;

(R)-tert-butyl 2-(4-(3-cyclopropylureido)-2-fluorophenyl)-4-(3-methylmorpholino)-5H-pyrrolo[3,4-d]pyrimidine-6(7H)-carboxylate;

(S)-methyl 2-(2-fluoro-4-(3-(2-fluoroethyl)ureido)phenyl)-4-(3-methylmorpholino)-5H-pyrrolo[3,4-d]pyrimidine-6(7H)-carboxylate;

1-(3-fluoro-4-(6-isopropyl-4-morpholino-6,7-dihydro-5H-pyrrolo[3,4-d]pyrimidin-2-yl)phenyl)-3-(2-hydroxyethyl)urea;

1-(3-fluoro-4-(6-isopropyl-4-morpholino-6,7-dihydro-5H-pyrrolo[3,4-d]pyrimidin-2-yl)phenyl)-3-(2-fluoroethyl)urea;

(S)-1-(3-fluoro-4-(6-isopropyl-4-(3-methylmorpholino)-6,7-dihydro-5H-pyrrolo[3,4-d]pyrimidin-2-yl)phenyl)-3-(2-fluoroethyl)urea;

(S)-1-(3-fluoro-4-(6-isopropyl-4-(3-methylmorpholino)-6,7-dihydro-5H-pyrrolo[3,4-d]pyrimidin-2-yl)phenyl)-3-(2-hydroxyethyl)urea;

(R)-1-(4-(6-(cyclopropanecarbonyl)-4-(3-methylmorpholino)-6,7-dihydro-5H-pyrrolo[3,4-d]pyrimidin-2-yl)-3-fluorophenyl)-3-cyclopropylurea;

(S)-2-(4-(3-cyclopropylureido)-2-fluorophenyl)-N-isopropyl-4-(3-methylmorpholino)-5,6-dihydropyrido[3,4-d]pyrimidine-7(8H)-carboxamide;

(R)-1-cyclopropyl-3-(3-fluoro-4-(6-formyl-4-(3-methylmorpholino)-6,7-dihydro-5H-pyrrolo[3,4-d]pyrimidin-2-yl)phenyl)urea;

(R)-1-cyclopropyl-3-(3-fluoro-4-(4-(3-methylmorpholino)-6-(methylsulfonyl)-6,7-dihydro-5H-pyrrolo[3,4-d]pyrimidin-2-yl)phenyl)urea; and pharmaceutically acceptable salts, prodrugs and metabolites thereof.

Prodrugs of the compounds of the present invention are also within the scope of the present invention.

"Prodrug" means a derivative that is converted into a compound according to the present invention by a reaction with an enzyme, gastric acid or the like under a physiological condition in the living body, e.g. by oxidation, reduction, hydrolysis or the like, each of which is carried out enzymatically. Examples of a prodrug are compounds, wherein the amino group in a compound of the present invention is acylated, alkylated or phosphorylated to form, e.g., eicosanoylamino, alanylamino, pivaloyloxymethylamino or wherein the hydroxyl group is acylated, alkylated, phosphorylated or converted into the borate, e.g. acetyloxy, palmitoyloxy, pivaloyloxy, succinyloxy, fumaryloxy, alanyloxy or wherein the carboxyl group is esterified or amidated. These compounds can be produced from compounds of the present invention according to well-known methods.

Metabolites of compounds of formula (I) are also within the scope of the present invention.

The term "metabolites" refers to all molecules derived from any of the compounds according to the present invention in a cell or organism, preferably mammal.

Preferably the term relates to molecules which differ from any molecule which is present in any such cell or organism under physiological conditions The structure of the metabolites of the compounds according to the present invention will be obvious to any person skilled in the art, using the various appropriate methods.

Where tautomerism, like e.g. keto-enol tautomerism, of compounds of general formula (I) may occur, the individual forms, like e.g. the keto and enol form, are comprised separately and together as mixtures in any ratio. The same applies for stereoisomers, like e.g. enantiomers, cis/trans isomers, conformers and the like.

Especially, compounds of formula (I), wherein the morpholino or thiomorpholino ring is substituted with one $R^2$ in 3-position are encompassed by the present invention as isomers or enantiomers or mixtures thereof concerning the respective chiral carbon center.

If desired, isomers can be separated by methods well known in the art, e.g. by liquid chromatography. The same applies for enantiomers by using e.g. chiral stationary phases. Additionally, enantiomers may be isolated by converting them into diastereomers, i.e. coupling with an enantiomerically pure auxiliary compound, subsequent separation of the resulting diastereomers and cleavage of the auxiliary residue. Alternatively, any enantiomer of a compound of formula (I) may be obtained from stereoselective synthesis using optically pure starting materials.

The compounds of formula (I) may exist in crystalline or amorphous form. Furthermore, some of the crystalline forms of the compounds of formula (I) may exist as polymorphs, which are included within the scope of the present invention. Polymorphic forms of compounds of formula (I) may be characterized and differentiated using a number of conventional analytical techniques, including, but not limited to, X-ray powder diffraction (XRPD) patterns, infrared (IR) spectra, Raman spectra, differential scanning calorimetry (DSC), thermogravimetric analysis (TGA) and solid state nuclear magnetic resonance (ssNMR).

In case the compounds according to formula (I) contain one or more acidic or basic groups, the invention also comprises their corresponding pharmaceutically or toxicologically acceptable salts, in particular their pharmaceutically utilizable salts. Thus, the compounds of the formula (I) which contain acidic groups can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Compounds of the formula (I) which contain one or more basic groups, i.e. groups which can be protonated, can be present and can be used according to the invention in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the formula (I) simultaneously contain acidic and basic groups in the molecule, the invention also includes, in addition to the salt forms mentioned, inner salts or betaines (zwitterions). The respective salts according to the formula (I) can be obtained by customary methods which are known to the person skilled in the art like, for example by contacting these with an organic or inorganic acid or base in a solvent or dispersant, or by anion exchange or cation exchange with other salts. The present invention also includes all salts of the compounds of the formula (I) which, owing to low physiological compatibility, are not directly suitable for use in pharmaceuticals but which can be used, for example, as intermediates for chemical reactions or for the preparation of pharmaceutically acceptable salts.

Throughout the invention, the term "pharmaceutically acceptable" means that the corresponding compound, carrier or molecule is suitable for administration to humans. Preferably, this term means approved by a regulatory agency such as the EMEA (Europe) and/or the FDA (US) and/or any other national regulatory agency for use in animals, preferably in humans.

The present invention furthermore includes all solvates of the compounds according to the invention.

If desired, the effects of the claimed compounds on mTOR activity may e.g. be tested using transiently expressed epitope-tagged mTOR in a mammalian cell line such as HEK293 that is immunoprecipitated with a monoclonal antibody directed against the epitope tag (Knight et al. 2004, Bioorganic and Medicinal Chemistry 12, 4749-4759). Another assay employs mTOR protein enriched from cells or tissue lysates using conventional protein purification methods. In this assay a GST-fusion protein of the P70 S6 kinase is used as a substrate. The phosphorylation of P70 S6 is detected using a primary phospho-specific antibody (directed against phosphorylated threonine 389) and an enzyme linked secondary anti-body in an ELISA assay (US-A 2004/0191836).

According to the present invention, the expression "mTOR" or "mTOR kinase" means the mTOR protein (Tsang et al., 2007, Drug Discovery Today 12, 112-124). The gene encoding mTOR is located on human chromosome map locus 1p36.2 and it is widely expressed in human tissues.

As shown in the examples, compounds of the invention were tested for their selectivity for mTOR over other kinases. As shown, all tested compounds bind mTOR more selectively than the kinases PI3 Kd or DNA-PK (see table 4 below). Consequently, the compounds of the present invention are considered to be useful for the prevention or treatment of diseases and disorders associated with mTOR, e.g. immunological, inflammatory, autoimmune, or allergic disorders, or proliferative diseases, transplant rejection, Graft-versus-Host-Disease, cardiovascular diseases, metabolic diseases or neurodegenerative diseases.

Furthermore, preferred compounds of the present invention of formula (I), wherein T is phenyl and having an F-substitution of the phenyl ring in the meta position relative to the urea group are expected not to have genotoxic issues.

Genetic toxicology data is used as a surrogate for long-term carcinogenicity data during early development. The aim of genotoxicity testing is to identify potentially hazardous drug candidates. Results from genetic toxicity tests in combination with acute and subchronic data are used as basis to approve clinical trials of drug candidates. With few exceptions, mutagenic compounds are dropped from development. DNA damaging substances cannot be developed as pharmaceutical compounds except for some situations where unmet medical need, life-threatening diagnoses, or short-life expectancy exists. Therefore, genetic toxicology testing, for example in the Ames assay, in drug discovery and optimization serves to identify mutagens and remove them from development (Custer and Sweder, 2008. Current Drug metabolism 9, 978-985).

The Ames *Salmonella*/microsome mutagenicity assay (*Salmonella* test; Ames test) is a standard, short-term bacterial reverse mutation assay specifically designed to detect a wide range of chemical substances that can produce genetic damage leading to gene mutations. The test employs several histidine dependent *Salmonella* strains each carrying different mutations in various genes of the histidine operon (Mortelmans and Zeiger 2000, Mutation Research 455, 29-60).

It is known in the art that compounds containing phenyl urea moieties may form aniline metabolites which may be further metabolized to form genotoxic compounds.

The corresponding potential aniline metabolites both of compounds of the present invention with and without meta Fluoro group relative to the urea group have been synthesized and tested in the Ames assay without and with rat liver S9 fraction (see below, example 196). The unsubstituted potential aniline metabolite (compound metabolite example 137) is Ames positive when tested with rat liver S9 fraction. As shown in the example, the substitution with an ortho-Fluoro relative to the amino group results in a metabolite which is Ames positive with S9 metabolic extract. Surprisingly, an F-substitution of the phenyl ring in the meta position relative to the amino group is Ames negative with S9 metabolic extract. If the meta-Fluoro-substituted aniline metabolite is formed in the body, it is not expected to further convert into a genotoxic molecule, even if administered in a long-term treatment of chronic diseases such as inflammatory diseases.

Therefore, the present invention provides pharmaceutical compositions comprising a compound of formula (I) or a pharmaceutically acceptable salt thereof as active ingredient together with a pharmaceutically acceptable carrier, optionally in combination with one or more other pharmaceutical compositions.

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, including but not limited to peanut oil, soybean oil, mineral oil, sesame oil and the like. Water is a preferred carrier when the pharmaceutical composition is administered orally. Saline and aqueous dextrose are preferred carriers when the pharmaceutical composition is administered intravenously. Saline solutions and aqueous dextrose and glycerol solutions are preferably employed as liquid carriers for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsions, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the therapeutic, preferably in purified form, together with a suitable amount of carrier so as to provide the form for proper administration to the patient. The formulation should suit the mode of administration.

A pharmaceutical composition of the present invention may comprise one or more additional compounds as active ingredients like one or more compounds of formula (I) not being the first compound in the composition or mTOR inhibitors. Further bioactive compounds for may be steroids, leukotriene antagonists, cyclosporine or rapamycin.

The compounds of the present invention or pharmaceutically acceptable salt(s) thereof and the other pharmaceutically active agent(s) may be administered together or separately and, when administered separately, this may occur separately or sequentially in any order. When combined in the same formulation it will be appreciated that the two compounds must be stable and compatible with each other and the other components of the formulation. When formulated separately they may be provided in any convenient formulation, conveniently in such manner as are known for such compounds in the art.

It is further included within the present invention that the compound of formula (I), or a pharmaceutically acceptable salt thereof, or a pharmaceutical composition comprising a compound of formula (I) is administered in combination with another drug or pharmaceutically active agent and/or that the pharmaceutical composition of the invention further comprises such a drug or pharmaceutically active agent.

In this context, the term "drug or pharmaceutically active agent" includes a drug or pharmaceutical agent that will elicit the biological or medical response of a tissue, system, animal or human that is being sought, for instance, by a researcher or clinician.

"Combined" or "in combination" or "combination" should be understood as a functional coadministration, wherein some or all compounds may be administered separately, in different formulations, different modes of administration (for example subcutaneous, intravenous or oral) and different times of administration. The individual compounds of such combinations may be administered either sequentially in separate pharmaceutical compositions as well as simultaneously in combined pharmaceutical compositions.

For example, in rheumatoid arthritis therapy, combination with other chemotherapeutic or antibody agents is envisaged. Suitable examples of pharmaceutically active agents which may be employed in combination with the compounds of the present invention and their salts for rheumatoid arthritis therapy include: immunosuppresants such as amtolmetin guacil, mizoribine and rimexolone; anti-TNFα agents such as etanercept, infliximab, Adalimumab, Anakinra, Abatacept, Rituximab; tyrosine kinase inhibitors such as leflunomide; kallikrein antagonists such as subreum; interleukin 11 agonists such as oprelvekin; interferon beta 1 agonists; hyaluronic acid agonists such as NRD-101 (Aventis); interleukin 1 receptor antagonists such as anakinra; CD8 antagonists such as amiprilose hydrochloride; beta amyloid precursor protein antagonists such as reumacon; matrix metalloprotease inhibitors such as cipemastat and other disease modifying anti-rheumatic drugs (DMARDs) such as methotrexate, sulphasalazine, cyclosporin A, hydroxychoroquine, auranofin, aurothioglucose, gold sodium thiomalate and penicillamine.

In particular, the treatment defined herein may be applied as a sole therapy or may involve, in addition to the compounds of the invention, conventional surgery or radiotherapy or chemotherapy. Accordingly, the compounds of the invention can also be used in combination with existing therapeutic agents for the treatment proliferative diseases such as cancer. Suitable agents to be used in combination include:

(i) antiproliferative/antineoplastic drugs and combinations thereof, as used in medical oncology such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside, hydroxyurea and gemcitabine); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like paclitaxel and taxotere); and topoisomerase inhibitors (for example epipodophyllotoxins like etoposide and teniposide, amsacrine, topotecan and camptothecins);

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents (for example c-Src kinase family inhibitors like 4-(6-chloro-2,3-methylenedioxyanilino)-7-[2-(4-methylpiperazin-1-yl)ethoxy]-5-tetrahydropyran-4-yloxy-quinazoline (AZD0530) and N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825), and metalloproteinase inhibitors like marimastat and inhibitors of urokinase plasminogen activator receptor function);

(iv) inhibitors of growth factor function: for example such inhibitors include growth factor antibodies and growth factor receptor antibodies (for example the anti-erbB2 antibody trastuzumab [Herceptin™] and the anti-erbB1 antibody cetuximab [C225]); such inhibitors also include, for example, tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy) quinazolin-4-amine (gefitinib, ZD 1839), N/-(3-ethynylphenyl)-6,7-bis(2-methoxyethoxy)quinazolin-4-amine (erlotinib, OSI-774) and 6-acrylamido-N/-(3-chloro-4-fluorophenyl)-7-(3-morpholinopropoxy)-quinazolin-4-amine (CI 1033) and erbB2 tyrosine kinase inhibitors such as lapatinib), inhibitors of the hepatocyte growth factor family, inhibitors of the platelet-derived growth factor family such as imatinib, inhibitors of serine/threonine kinases (for example Ras/Raf signalling inhibitors such as farnesyl transferase inhibitors, for example sorafenib (BAY 43-9006)) and inhibitors of cell signalling through MEK and/or Akt kinases;

(v) antiangiogenic agents such as those which inhibit the effects of vascular endothelial growth factor, for example the anti-vascular endothelial cell growth factor antibody bevacizumab (Avastin™) and VEGF receptor tyrosine kinase inhibitors such as 4-(4-bromo-2-fluoroanilino)-6-methoxy-7-(1-methylpiperidin-4-ylmethoxy)quinazoline (ZD6474; Example 2 within WO 01/32651), 4-(4-fluoro-2-methylindol-5-yloxy)-6-methoxy-7-(3-pyrrolidin-1-yl-propoxy)quinazoline (AZD2171; Example 240 within WO 00/47212), vatalanib (PTK787; WO 98/35985) and SUI 1248 (sunitinib; WO 01/60814), and compounds that work by other mechanisms (for example linomide, inhibitors of integrin αvβ3 function and angiostatin);

(vi) vascular damaging agents such as combretastatin A4 and compounds disclosed in International Patent Application WO 99/02166;

(vii) antisense therapies, for example those which are directed to the targets listed above, such as ISIS 2503, an anti-ras antisense agent;

(viii) gene therapy approaches, including approaches to replace aberrant genes such as aberrant p53 or aberrant BRCA1 or BRCA2, GDEPT (gene-directed enzyme prodrug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapeutic approaches, including ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

Further combination treatments are described in WO-A 2009/008992, incorporated herein by reference.

Accordingly, the individual compounds of such combinations may be administered either sequentially in separate pharmaceutical compositions as well as simultaneously in combined pharmaceutical compositions.

The pharmaceutical compositions of the present invention include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of formula (I) can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or non-aqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally, for example, as liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula (I) may also be administered parenterally. Solutions or suspensions of these active compounds can be prepared in water suitably mixed with a surfactant such as hydroxypropyl-cellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of formula (I) are administered orally.

The effective dosage of active ingredient employed may vary depending on the particular compound employed, the mode of administration, the condition being treated and the severity of the condition being treated. Such dosage may be ascertained readily by a person skilled in the art.

A therapeutically effective amount of a compound of the present invention will normally depend upon a number of factors including, for example, the age and weight of the animal, the precise condition requiring treatment and its severity, the nature of the formulation, and the route of administration. However, an effective amount of a compound of formula (I) for the treatment of an inflammatory disease, for example rheumatoid arthritis (RA), will generally be in the range of 0.1 to 100 mg/kg body weight of recipient (mammal) per day and more usually in the range of 1 to 10 mg/kg body weight per day. Thus, for a 70 kg adult mammal, the actual amount per day would usually be from 70 to 700 mg and this amount may be given in a single dose per day or more usually in a number (such as two, three, four, five or six) of sub-doses per day such that the total daily dose is the same. An effective amount of a pharmaceutically acceptable salt, prodrug or metabolite thereof, may be determined as a proportion of the effective amount of the compound of formula (I) per se. It is envisaged that similar dosages would be appropriate for treatment of the other conditions referred to above.

As used herein, the term "effective amount" means that amount of a drug or pharmaceutical agent that will elicit the biological or medical response of a tissue, system, animal or human that is being sought, for instance, by a researcher or clinician.

Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

Another aspect of the present invention is a compound of the present invention or a pharmaceutically acceptable salt thereof for use as a medicament.

Another aspect of the present invention is a compound of the present invention or a pharmaceutically acceptable salt thereof for use in a method of treating or preventing a disease or disorder associated with mTOR.

In the context of the present invention, a disease or disorder associated with mTOR is defined as a disease or disorder where mTOR is involved.

In a preferred embodiment, the diseases or disorder associated with mTOR is an immunological, inflammatory, autoimmune, or allergic disorder or disease or a transplant rejection or a Graft-versus host disease.

Consequently, another aspect of the present invention is a compound or a pharmaceutically acceptable salt thereof of the present invention for use in a method of treating or preventing an immunological, inflammatory, autoimmune, or allergic disorder or disease or a transplant rejection or a Graft-versus host disease.

According to the present invention, an autoimmune disease is a disease which is at least partially provoked by an immune reaction of the body against own components, e.g. proteins, lipids or DNA.

In a preferred embodiment, the autoimmune disease is selected from the group consisting of rheumatoid arthritis (RA), inflammatory bowel disease (IBD; Crohns's disease and ulcerative colitis), psoriasis, systemic lupus erythematosus (SLE), and multiple sclerosis (MS).

Rheumatoid arthritis (RA) is a chronic progressive, debilitating inflammatory disease that affects approximately 1% of the world's population. RA is a symmetric polyarticular arthritis that primarily affects the small joints of the hands and feet. In addition to inflammation in the synovium, the joint lining, the aggressive front of tissue called pannus invades and destroys local articular structures (Firestein 2003, Nature 423:356-361).

Inflammatory bowel disease (IBD) is characterized by a chronic relapsing intestinal inflammation. IBD is subdivided into Crohn's disease and ulcerative colitis phenotypes. Crohn disease involves most frequently the terminal ileum and colon, is transmural and discontinuous. In contrast, in ulcerative colitis, the inflammation is continuous and limited to rectal and colonic mucosal layers. In approximately 10% of cases confined to the rectum and colon, definitive classification of Crohn disease or ulcerative colitis cannot be made and are designated 'indeterminate colitis.' Both diseases include extraintestinal inflammation of the skin, eyes, or joints. Neutrophil-induced injuries may be prevented by the use of neutrophils migration inhibitors (Asakura et al., 2007, World J Gastroenterol. 13(15):2145-9).

Psoriasis is a chronic inflammatory dermatosis that affects approximately 2% of the population. It is characterized by red, scaly skin patches that are usually found on the scalp, elbows, and knees, and may be associated with severe arthritis. The lesions are caused by abnormal keratinocyte proliferation and infiltration of inflammatory cells into the dermis and epidermis (Schön et al., 2005, New Engl. J. Med. 352: 1899-1912).

Systemic lupus erythematosus (SLE) is a chronic inflammatory disease generated by T cell-mediated B-cell activation, which results in glomerulonephritis and renal failure. Human SLE is characterized at early stages by the expansion of long-lasting autoreactive CD4+ memory cells (D'Cruz et al., 2007, Lancet 369(9561):587-596).

Multiple sclerosis (MS) is an inflammatory and demyelating neurological disease. It has bee considered as an autoimmune disorder mediated by CD4+ type 1 T helper cells, but recent studies indicated a role of other immune cells (Hemmer et al., 2002, Nat. Rev. Neuroscience 3, 291-301).

Graft-versus-host disease (GVDH) is a major complication in allogeneic bone marrow transplantation. GVDH is caused by donor T cells that recognize and react to recipient differences in the histocompatibility complex system, resulting in significant morbidity and mortality.

Transplant rejection (allograft transplant rejection) includes, without limitation, acute and chronic allograft rejection following for example transplantation of kidney, heart, liver, lung, bone marrow, skin and cornea. It is known that T cells play a central role in the specific immune response of allograft rejection.

In a further preferred embodiment, the disease or disorder associated with mTOR is a proliferative disease, especially cancer.

Diseases and disorders associated especially with mTOR are proliferative disorders or diseases, especially cancer.

Therefore, another aspect of the present invention is a compound or a pharmaceutically acceptable salt thereof of the present invention for use in a method of treating or preventing a proliferative disease, especially cancer.

Cancer comprises a group of diseases characterized by uncontrolled growth and spread of abnormal cells. All types of cancers generally involve some abnormality in the control of cell growth, division and survival, resulting in the malignant growth of cells. Key factors contributing to said malignant growth of cells are independence from growth signals, insensitivity to anti-growth signals, evasion of apoptosis, limitless replicative potential, sustained angiogenesis, tissue invasion and metastasis, and genome instability (Hanahan and Weinberg, 2000. The Hallmarks of Cancer. Cell 100, 57-70).

Typically, cancers are classified as hematological cancers (for example leukemias and lymphomas) and solid cancers such as sarcomas and carcinomas (for example cancers of the brain, breast, lung, colon, stomach, liver, pancreas, prostate, ovary).

Especially cancers in which the PI3K/Akt signal transduction pathway is activated, for example due to inactivation of the tumour suppressor PTEN or activating mutations in PIK3A, the gene encoding the catalytic phosphoinositide-3 kinase subunit p110α (p110alpha) are expected to respond to treatment with mTOR inhibitors (Garcia-Echeverria and Sellers, 2008, Oncogene 27, 5511-5526). Examples of cancers with a high incidence of PTEN mutations and/or activation of PI3K/Akt are endometrial carcinoma, glioblastoma, head and neck cancer, colon cancer, pancreatic cancer, gastric cancer, hepatocarcinoma, ovarian cancer, thyroid carcinoma, renal cell cancer, breast cancer, prostate cancer and gastrointestinal stromal tumours (GIST). The most promising results with mTOR inhibitors have been obtained in renal cell carcinoma (RCC), mantle cell lymphoma and endometrial cancers (Faivre et al., 2006. Nat. Rev. Drug. Discov. 5(8):671-688). In addition, mTOR inhibitors may be useful for the treatment of leukemias Including ALL and CML), multiple myeloma and lymphomas.

mTOR plays an important role in angiogenesis, the formation of new blood vessels to provide oxygen and nutrients to growing and dividing cells. In this context mTOR controls the production of the HIF1-α and HIF1-β proteins, which are subunits of hypoxia-inducible factor (HIF), a transcription factor that controls the expression of genes whose products play a role in angiogenesis, cell proliferation, motility and survival. Two important proteins induced by HIF are vascular endothelial growth factors (VEGFs) and angiopoietin-2. Recently it has been reported that a small molecule mTOR inhibitor can reduce tumour growth, tumour angiogenesis an vascular permeability (Xue et al., 2008. Cancer Research 68(22): 9551-9557).

In addition to tumourigenesis, there is evidence that mTOR plays a role in harmatoma syndromes. Recent studies have shown that the tumour suppressor proteins such as TSC1, TSC2, PTEN and LKB1 tightly control mTOR signalling. Loss of these tumour suppressor proteins leads to a range of hamartoma conditions as a result of elevated mTOR signalling (Rosner et al., 2008. Mutation Research 659(3):284-292). Syndromes with an established molecular link to dysregulation of mTOR include Peutz_Jeghers syndrome (PJS), Cowden disease, Bannayan-Riley-Ruvalcaba syndrome (BRRS), Proteus syndrome, Lhermitte-Duclos disease and Tuberous sclerosis (TSC). Patients with these syndromes characteristically develop benign hamartomatous tumours in multiple organs. Other tumour suppressor proteins having an influence on mTOR activity are VHL, NF1 and PKD whose loss can trigger von Hippel-Lindau disease, Neurofibromatosis type 1, and Polycystic kidney disease respectively.

Proliferative diseases or disorders comprise a group of diseases characterized by increased cell multiplication. One example is restenosis caused by the overgrowth of vascular smooth muscle (VSM) cells after coronary angioplasty with stents. To circumvent this issue, drug-eluting stents have been developed to inhibit the growth of VSM cells. Rapamycin-coated stents effectively reduce restenosis and have been approved by the FDA (Serruys et al., 2006. N. Engl. J. Med. 354(5):483-95).

In a further preferred embodiment, the disease or disorder associated with mTOR is a cardiovascular disease, a metabolic disease or a neurodegenerative disease.

Therefore, another aspect of the present invention is a compound or a pharmaceutically acceptable salt thereof of any of the present invention for use in a method of treating or preventing a cardiovascular disease, a metabolic disease or a neurodegenerative disease.

Recent studies have revealed a role of mTOR in cardiovascular diseases, for example elevated mTOR kinase activity has been associated with cardiac hypertrophy (heart enlargement), which is a major risk factor for heart failure. At the cellular level, cardiac hypertrophy is characterized by an increase in cell size and enhanced protein synthesis. Although there are various hypertrophic stimuli, such as neurohormones and peptide growth factors, and several protein kinase cascades are involved in cardiac hypertrophy, it is likely that all forms of hypertrophic stimuli activate the general protein translational machinery in an mTOR dependent manner. Remarkably, inhibition of mTOR by rapamycin prevents cardiac hypertrophy in numerous transgenic mouse models. In addition, stress-induced cardiac hypertrophy is dependent on mTOR in mice. These results indicate that mTOR is crucial for the abnormal cardiac overgrowth, and that mTOR inhibitors may be usefull for the treatment of human cardiac hypertrophy (Tsang et al., 2007, Drug Discovery Today 12, 112-124).

Metabolic diseases that may be treated with mTOR inhibitors comprise type 1 diabetes, type 2 diabetes, and obesity (Tsang et al., 2007, Drug Discovery Today 12, 112-124). Type 1 diabetes is caused by loss of insulin production due to destruction of pancreatic β-cells. Clinical studies using immunosuppressive regimen that contain rapamycin to prevent rejection of islet transplants have shown significant efficacy in type 1 diabetic patients. Type 2 diabetes arises when insulin secretion from pancreatic β-cells fails to compensate for the peripheral insulin resistance (or insensitivity to insulin) in skeletal muscle, liver and fat cells. Recent data indicate that sustained activation of mTOR signalling is a crucial event that renders insulin-receptors substrate (IRS) irresponsive to insulin. Moreover, it has been demonstrated that rapamycin restores the sensitivity of IRS to insulin (Shah et al., 2004. Curr. Biol. 14(18):1650-1656). Therefore, mTOR inhibitors are potentially useful in the management of type 2 diabetes. Obesity is a metabolic disease with a steadily increasing health risk worldwide. Recent evidence suggests that mTOR plays a role in lipid metabolism. During adipogenesis the expression of mTOR increases dramatically from barely detectable in preadipocytes to highly expressed in fully differentiated adipocytes, and rapamycin inhibits adipocyte differentiation (Yeh et al., 1995. Proc. Natl. Acad. Sci. USA. 92(24):11086-90).

Recent reports suggest that mTOR inhibitors may be useful to treat neurodegenerative diseases such as Huntingtons's, Alzheimer's and Parkinson's disease. Huntingtons's disease is a neurodegenerative disorder caused by a mutant form of the protein huntingtin with abnormally long glutamine repeats at the amino-terminus. The mutant protein aggregates in neuronal cells and can cause nerve cell damage and toxicity. Rapamycin attenuates the accumulation of huntingtin and cell death, and protects against neurodegeneration in animal models of Huntington's disease (Ravikumar et al., 2004. Nat. Genet. 36(6):585-95). In addition, rapamycin induces an autophagy response that has been suggested to play a role in the clearance of huntingtin aggregates.

Intracellular protein aggregates also occur in other neurodegenerative diseases, for example Alzheimer's disease. The Tau protein is frequently found in brains of Alzheimer's patients and is thought to contribute to the formation of neurofibrillary tangles (for example in tauopathies such as fronto-temporal dementia). In a fly model rapamycin reduces the concentration of tau protein and lowers the toxicity caused by tau accumulation (Berger et al., 2006. Hum Mol Genet. 2006 Feb. 1; 15(3):433-42). Therefore, mTOR inhibitors may be useful in preventing the accumulation of toxic tau protein in Alzheimer's patients.

Parkinson's disease (PD) is a neurodegenerative disease associated with the accumulation and aggregation of misfolded proteins. Preventing aggregation or disaggregating misfolded proteins may provide a therapeutic benefit by slowing or preventing the progression of PD. The ubiquitin-proteasome system (UPS) is an important degradation mechanism acting on aggregated proteins. It was reported that rapamycin provides neuroprotection against dopaminergic neuronal cell death induced by the proteasome inhibitor lactacystin. It was suggested that the rapamycin effect is partially mediated by autophagy enhancement through enhanced degradation of misfolded proteins (Pan et al., 2008. Neurobiol. Dis. 32(1):16-25). Therefore compounds that can enhance autophagy may represent a promising strategy to treat PD patients.

In a further preferred embodiment, the disease or disorder associated with mTOR is an autophagy associated disease.

Therefore, another aspect of the present invention is a compound or a pharmaceutically acceptable salt thereof of any of the present invention for use in a method of treating or preventing an autophagy associated disease.

Autophagy is a lysosome-dependent process whereby proteins or damaged organelles within a cell are degraded (Mizushima et al., 2008. Nature 451(7182):1069-75). During this process an autophagosome with a double membrane encloses the component of the cell to be degraded. Then the autophagosome fuses with a lysosome which for example degrades proteins leading to the recycling of amino acids. Autophagy is primarily involved in the degradation of long-lived proteins, protein aggregates, and cellular organelles and other cellular components. In addition to its physiological function autophagy could be expoited for the treatment of a variety of diseases caused by misfolded proteins aggregates, for example neurodegenerative diseases such as Huntington's, Alzheimer's or Parkinon's disease. Further autophagy associated diseases are described in WO-A2009/049242, incorporated herein with reference.

Autophagy inducing compound refers to a compound that induces autophagy in a cell. Autophagy associated disease refers to a disease that can be treated by the induction of autophagy. It has recently been shown that an ATP-competitive mTOR kinase inhibitor can induce autophagy (Thoreen et al., 2009. J. Biol. Chem. 284(12):8023-32). Interestingly, ATP competitive mTOR kinase inhibitors seem to induce autophagy more effectively than rapamycin in mammalian cells. Taken together, compounds of the present invention may be useful to induce autophagy in cells and to treat autophagy associated diseases.

Yet another aspect of the present invention is the use of a compound of the present invention or a pharmaceutically acceptable salt thereof for the manufacture of a medicament for the treatment or prophylaxis of diseases and disorders associated with mTOR.

Yet another aspect of the present invention is the use of a compound of the present invention or a pharmaceutically acceptable salt thereof for the manufacture of a medicament for treating or preventing an immunological, inflammatory, autoimmune, or allergic disorder or disease or a transplant rejection or a Graft-versus host disease.

Yet another aspect of the present invention is the use of a compound of the present invention or a pharmaceutically acceptable salt thereof for the manufacture of a medicament for treating or preventing a proliferative disease, especially cancer.

Yet another aspect of the present invention is the use of a compound of the present invention or a pharmaceutically acceptable salt thereof for the manufacture of a medicament for treating or preventing a cardiovascular disease, a metabolic disease or a neurodegenerative disease.

Yet another aspect of the present invention is the use of a compound of the present invention or a pharmaceutically acceptable salt thereof for the manufacture of a medicament for treating or preventing an autophagy associated disease.

In the context of these uses of the invention, diseases and disorders associated with mTOR are as defined above.

Yet another aspect of the present invention is a method for treating, controlling, delaying or preventing in a mammalian patient in need thereof one or more conditions selected from the group consisting of diseases and disorders associated with mTOR, wherein the method comprises the administration to said patient a therapeutically effective amount of a compound according to present invention or a pharmaceutically acceptable salt thereof.

Yet another aspect of the present invention is a method for treating, controlling, delaying or preventing in a mammalian patient in need thereof one or more conditions selected from the group consisting of an immunological, inflammatory, autoimmune, or allergic disorder or disease or a transplant rejection or a Graft-versus host disease, wherein the method comprises the administration to said patient a therapeutically effective amount of a compound according to present invention or a pharmaceutically acceptable salt thereof.

Yet another aspect of the present invention is a method for treating, controlling, delaying or preventing in a mammalian patient in need thereof a proliferative disease, especially cancer, wherein the method comprises the administration to said patient a therapeutically effective amount of a compound according to present invention or a pharmaceutically acceptable salt thereof.

Yet another aspect of the present invention is a method for treating, controlling, delaying or preventing in a mammalian patient in need thereof one or more conditions selected from the group consisting of a cardiovascular disease, a metabolic disease or a neurodegenerative disease, wherein the method comprises the administration to said patient a therapeutically effective amount of a compound according to present invention or a pharmaceutically acceptable salt thereof.

Yet another aspect of the present invention is a method for treating, controlling, delaying or preventing in a mammalian patient in need thereof an autophagy associated disease, wherein the method comprises the administration to said patient a therapeutically effective amount of a compound according to present invention or a pharmaceutically acceptable salt thereof.

In the context of these methods of the invention, diseases and disorders associated with mTOR are as defined above.

As used herein, the term "treating" or "treatment" is intended to refer to all processes, wherein there may be a slowing, interrupting, arresting, or stopping of the progression of a disease, but does not necessarily indicate a total elimination of all symptoms.

Preferred mammalian patients are human patients.

All embodiments discussed above with respect to the pharmaceutical composition of the invention also apply to the above mentioned first or second medical uses or methods of the invention.

In general compounds of the present invention may be prepared according to a method comprising the steps of
(a) reacting a compound of formula (III)

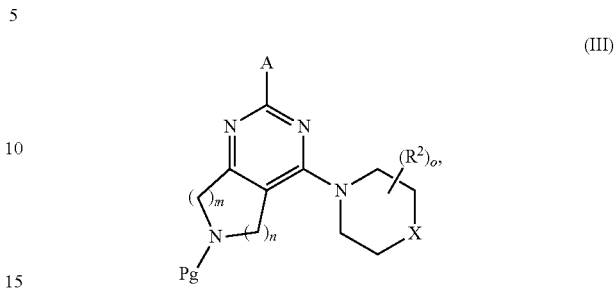

wherein Pg is a suitable protective group; A is a suitable leaving group; and m, n, o, X, $R^2$ have the meaning as indicated above either
(a1) with a compound of formula T-$X^0$, wherein $X^0$ is a suitable boronic acid or boronate ester functional group and T has the meaning as indicated above in a Suzuki reaction to yield a compound of formula (I), wherein $R^1$ is Pg; or
(a2) deprotect the compound of formula (II) to yield a compound of formula (IV)

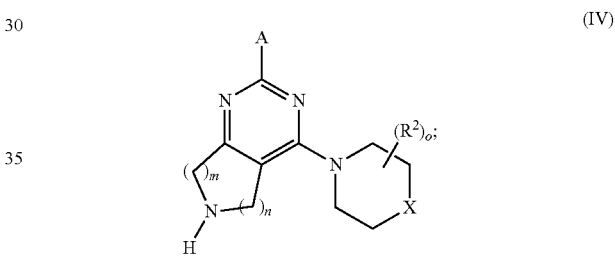

and
(b1) optionally, deprotect the product of step (a1) to yield a compound of formula (I), wherein $R^1$ is H followed by the optional step of reacting a compound of formula (I), wherein $R^1$ is H by a compound of formula $R^1$—$X^1$, wherein $X^1$ is a suitable leaving group and $R^1$ is defined as indicated above excluding H to yield a compound of formula (I), wherein $R^1$ is other than H; or
(b2) react a compound of formula (IV) with a compound of formula $R^1$—$X^1$, wherein $X^1$ is a suitable leaving group and $R^1$ is defined as indicated above excluding H to yield a compound of formula (V)

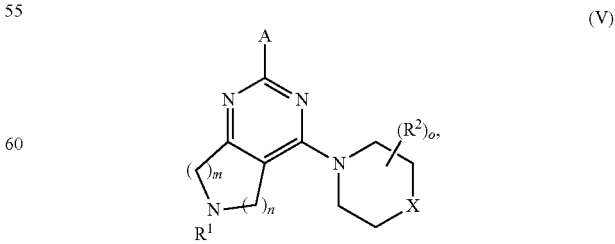

followed by reacting a compound of formula (V) with a compound of formula T-$X^0$, wherein $X^0$ is a suitable boronic acid or boronate ester functional group and T has the meaning as indicated above in a Suzuki reaction to yield a compound of formula (I).

Accordingly, a compound of formula (I) may be prepared starting from a compound of formula (III) by reacting with a compound T-X⁰ in a Suzuki reaction (a1). A suitable group A may be chloro. In case the chemical structure of Pg, like Boc, is encompassed by the definition of $R^1$, the respective compound already represents a compound of the present invention. If not, at least a further step (b1) is required representing the deprotection step resulting in a compound of the present invention, wherein $R^1$ is H. Optionally said compound may be reacted with a compound of formula $R^1$—$X^1$ to yield a compound of the present invention, wherein $R^1$ is given as defined above excluding H.

Alternatively, a compound of formula (III) may be deprotected in a step (a2) resulting in a compound of formula (IV) followed by reaction with a compound of formula $R^1$—$X^1$ to yield compound (V), which then is reacted with T-X⁰ to yield a compound of the present invention.

More specifically, by way of example only, the method for the preparation of a compound of the present invention may comprise the steps of Scheme 1

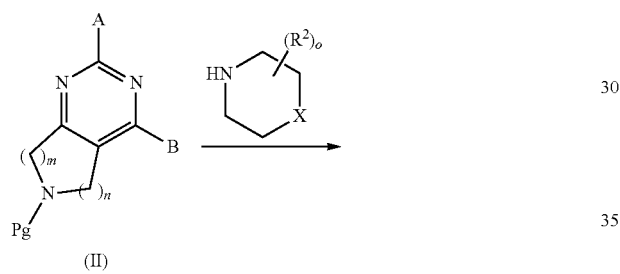

(II)

Scheme 2

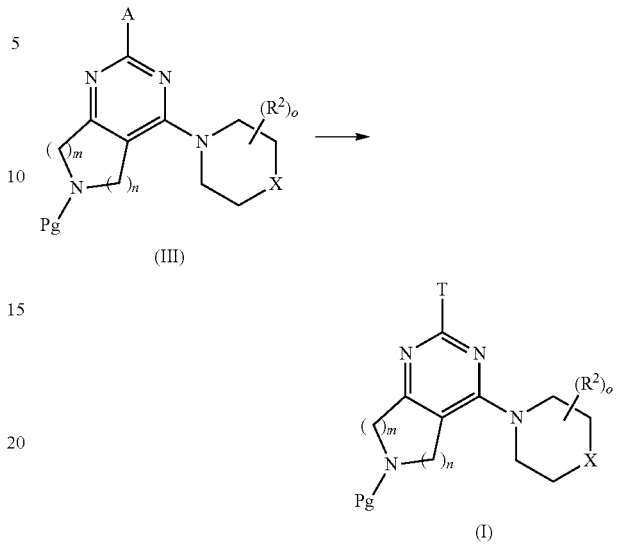

(III)

(I)

Compounds of formula (III) can be reacted under Suzuki coupling conditions with a suitable boronic acid or boronate ester derivative of T, where T is as defined above, to give compounds of formula (I), wherein Pg is $R^1$. Alternatively the group T may be introduced by initially introducing an aromatic amine or heteroaromatic amine derivative under Suzuki coupling conditions and subsequent conversion to a urea by methods well known to those skilled in the art.

Scheme 3

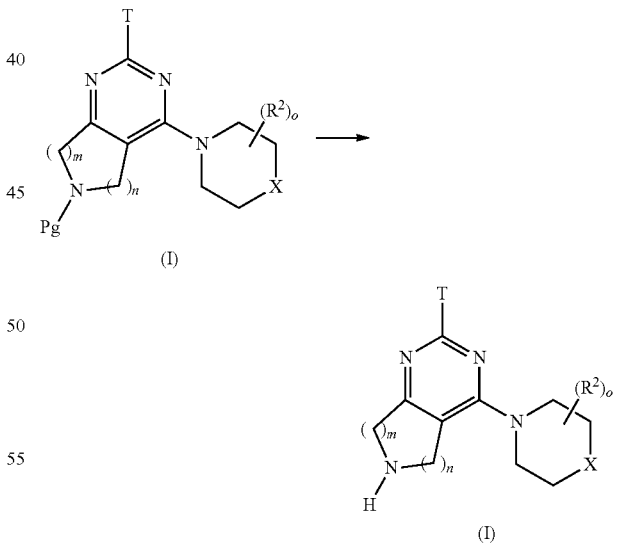

(I)

(I)

Compounds of formula (II) where Pg represents a suitable protecting group (for example Boc) and A and B are suitable leaving groups (for example Cl) are commercially available or may be synthesised by one skilled in the art. Compounds of formula (III) can be synthesised by the reaction of compounds of formula (II) with an appropriately substituted morpholine or thiomorpholine usually in the presence of an organic tertiary amine base (for example DIPEA) in a range of possible solvents. The morpholine or thiomorpholines are commercially available or can be synthesised by one skilled in the art.

Compounds of formula (I), wherein $R^1$ is H can be generated from compounds of formula (I), wherein $R^1$ is Pg by removal of the protecting group Pg. For example when Pg is Boc then deprotection can be achieved using methods well known to those skilled in the art (for example with HCl or TFA in organic solvent). Compounds of formula (I), wherein $R^1$ is H may be isolated in the form of salts or as free base.

Scheme 4

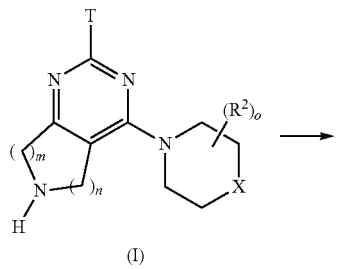
(I)

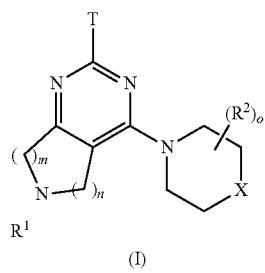
(I)

Compounds of formula (I), wherein R¹ is H can be derivatised using standard methods to generate a broad range of compounds of formula (I) where R¹ is as defined above (except H). The unsubstituted compounds of formula (I) (R¹=H) can be reacted under appropriate conditions with alkyl halides to give compounds of formula (I), where R¹ is optionally substituted $C_{1-6}$ alkyl. The unsubstituted compounds of formula (I) can be reacted under appropriate conditions with aldehydes or ketones under reductive amination conditions to give respective substituted compounds of formula (I). Unsubstituted compounds of formula (I) can be reacted under appropriate conditions with carboxylic acids or acid carboxylic chlorides to give compounds of formula (I), where R¹ is $C(O)R^3$ as defined above. Unsubstituted compounds of formula (I) can be reacted under appropriate conditions with sulfonyl chlorides to give compounds of formula (I) where R¹ is $S(O)_2R^3$ as defined above. Unsubstituted compounds of formula (I) can be reacted under appropriate conditions with isocyanates to give compounds of formula (I) where R¹ is $C(O)N(R^3R^{3a})$ as defined above. Unsubstituted compounds of formula (I) can be reacted under appropriate conditions with chloroformates to give compounds of formula (I) where R¹ is $C(O)OR^3$ as defined above.

Scheme 5

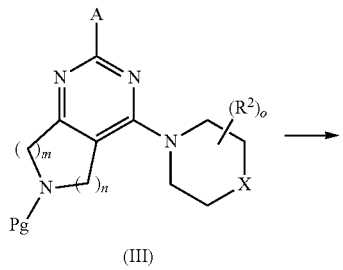
(III)

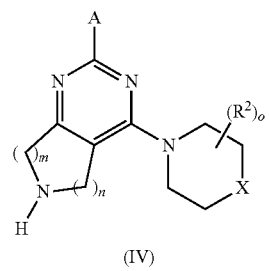
(IV)

Alternatively the orders steps of the synthesis can modified as described below. Compounds of formula (IV) can be generated from compounds of formula (III) by removal of the protecting group Pg. For example when Pg is Boc then deprotection can be achieved using methods well known to those skilled in the art (for example with HCl or TFA in organic solvent). Compounds of formula (IV) may be isolated in the form of salts or as free base.

Scheme 6

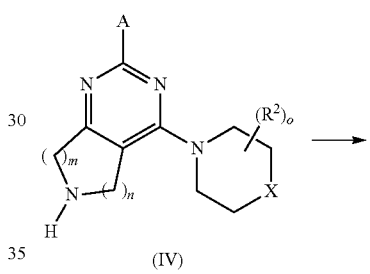
(IV)

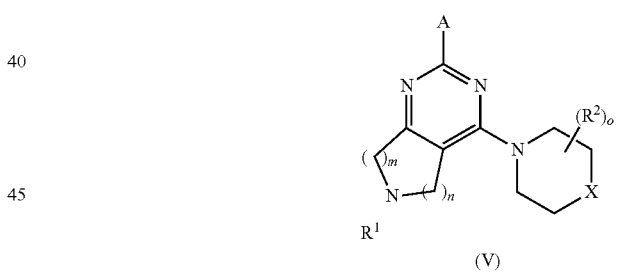
(V)

Compounds of formula (IV) can be derivatised in a similar way to that described for compounds of formula (I) with R¹=H above to give compounds of formula (V).

Scheme 7

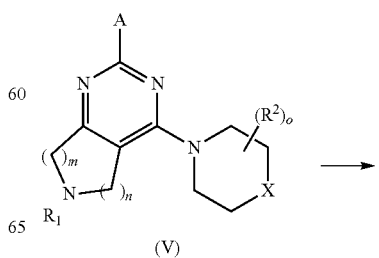
(V)

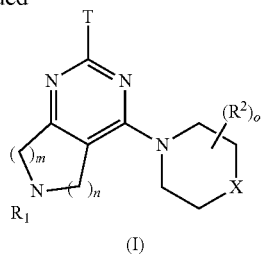

Compounds of formula (V) can be reacted under Suzuki coupling conditions with a suitable boronic acid or boronate ester derivative of T, where T is as defined above, to give compounds of formula (I). Alternatively the group T may be introduced by initially introducing an aromatic amine or heteroaromatic amine derivative under Suzuki coupling conditions and subsequent conversion to a urea by methods well known to those skilled in the art. Compounds of formula (V) if appropriate may be isolated in the form of salts or as free base.

Compounds of the present invention may be prepared by one of the methods described above or in an analogous way as well as by using methods well known in the art. For a practitioner in the art it is clear the above reactions may comprise further protection and/or activation steps depending upon the chemical nature of further substitutents.

It will be appreciated that novel intermediates described herein form another embodiment of the present invention.

EXAMPLES

Figure 1:
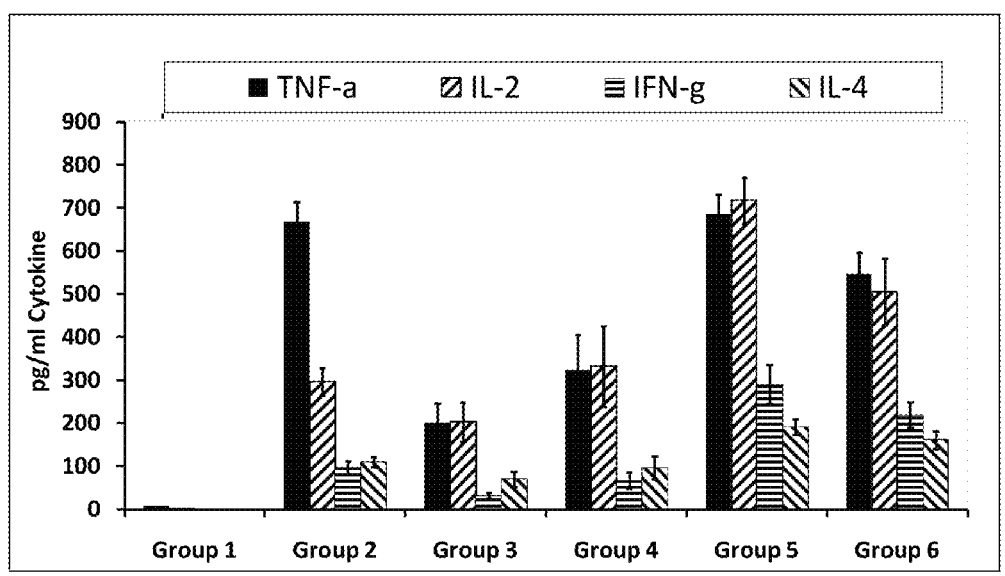
FIG. 1: Cytokine levels in the mouse anti-CD3 model
The experiment was performed as described in example 194. Animals were treated with test compounds or vehicle controls as described in Table 9.

Abbreviations:

| amu | Atomis mass units |
| --- | --- |
| Boc | Tert-butyl carboxylate |
| br | Broad |
| brine | Saturated aqueous solution of sodium chloride |
| CDCl$_3$ | Deuterated chloroform |
| CD$_3$OD | Deuterated methanol |
| CPME | Cyclopentyl methyl ether |
| d | Doublet |
| d6-DMSO | Deuterated dimethylsulfoxide |
| DCM | Dichloromethane |
| dd | Double doublet |
| DIPEA | Diisopropylethylamine |
| DME | 1,2-Dimethoxyethane |
| DMF | N,N-Dimethylformamide |
| DMSO | Dimethylsulfoxide |
| EDC | N-Ethyl-N'-(3-dimethylaminopropyl)carbodiimide hydrochloride |
| Et$_3$N | Triethyl amine |
| EtOAc | Ethyl acetate |
| EtOH | Ethanol |
| g | Grams |
| h | Hour(s) |
| H$_2$O | Water |
| HCl | Hydrogen chloride |
| HOBt | 1-hydroxybenzotriazole |
| HPLC | High Performance Liquid Chromatography |
| LCMS | Liquid Chromotography with Mass Spectrometry |
| m | Multiplet |
| MeCN | Acetonitrile |
| MeOH | Methanol |
| min | Minute(s) |
| mL | Milliliters |
| mmol | Millimolar |
| mp-TsOH | Polystyrene resin supported p-toluenesulfonic acid |
| Na$_2$CO$_3$ | Sodium carbonate |
| Na$_2$SO$_4$ | Sodium sulfate |
| NaHCO$_3$ | Sodium hydrogen carbonate |
| NH$_3$ | Ammonia |
| ° C. | Degrees celsius |
| Pd(PPh$_3$)$_2$(Cl)$_2$ | Bistriphenylphosphino-palladium(II)chloride |
| Prep. | Preparative |
| PTFE | Poly(tetrafluoroethene) |
| q | Quartet |
| qn | Quintet |
| Rt | Retention time |
| s | Singlet |
| sat | Saturated |
| sept | Septet |
| t | Triplet |
| TFA | Trifluoroacetic acid |
| THF | Tetrahydrofuran |
| uM | Micromolar |

Analytical Methods

Analysis was performed on an Agilent 1100 system with following conditions.
Solvents: A=Water with 0.1% formic acid
B=Acetonitrile with 0.1% formic acid
Temperature: 40° C.
Wavelength: 254 nm and 210 nm
Mass spec data were gathered in positive elector spray ionisation mode from 150 and 700 amu.
Method A
Column: Phenomenex Gemini-C18, 4.6×150 mm, 5 microns
Gradient Conditions:

| Time (min) | % A | % B |
| --- | --- | --- |
| 0.00 | 95.0 | 5.0 |
| 11.00 | 5.0 | 95.0 |
| 13.00 | 5.0 | 95.0 |
| 13.01 | 95.0 | 5.0 |
| 14.00 | 95.0 | 5.0 |

Flow Rate: 1 ml/min
Method B
Column: Phenomenex Gemini-C18, 3.0×30 mm, 3 microns
Gradient Conditions:

| Time (min) | % A | % B |
| --- | --- | --- |
| 0.00 | 95.0 | 5.0 |
| 3.00 | 5.0 | 95.0 |
| 4.50 | 5.0 | 95.0 |
| 4.60 | 95.0 | 5.0 |
| 5.00 | 95.0 | 5.0 |

Flow Rate: 1.2 mL/min
Method C
Column: Phenomenex Gemini-C18, 4.6×150 mm, 5 microns
Solvents: C=Water with 0.1% ammonia
D=(95%:5%, acetonitrile:water) with 0.1% ammonia Gradient Conditions:

| Time (min) | % C | % D |
|---|---|---|
| 0.00 | 95.0 | 5.0 |
| 11.00 | 0.0 | 95.0 |
| 13.00 | 0.0 | 95.0 |
| 13.01 | 95.0 | 5.0 |
| 14.00 | 95.0 | 5.0 |

Flow Rate: 1 ml/min
Method D
Column: Phenomenex Gemini-NX C18, 3.0×30 mm, 3 microns
Solvents: C=Water with 0.1% ammonia
D=(95%:5%, acetonitrile:water) with 0.1% ammonia
Gradient Conditions:

| Time (min) | % C | % D |
|---|---|---|
| 0.00 | 95.0 | 5.0 |
| 3.00 | 0.0 | 100.0 |
| 4.50 | 0.0 | 100.0 |
| 4.60 | 95.0 | 5.0 |
| 6.00 | 95.0 | 5.0 |

Flow Rate: 1.2 ml/min
Alternatively analysis was performed on a Waters uPLC-SQD system
Temperature: 40° C.
Wavelength: Photodiode array detection 210-400 nm
The mass spec data are gathered in positive or negative mode, scanning for masses between 150 and 700 amu.
Method E
Column: Waters Acquity UPLC BEH C18, 2.1×30 mm, 1.7 microns
Solvents: A1=Water with 0.1% formic acid
B1=Acetonitrile with 0.1% formic acid
Gradient Conditions:

| Time (min) | % A1 | % B1 |
|---|---|---|
| 0.00 | 95.0 | 5.0 |
| 0.20 | 95.0 | 5.0 |
| 1.00 | 5.0 | 95.0 |
| 1.50 | 5.0 | 95.0 |
| 1.70 | 95.0 | 5.0 |
| 2.70 | 95.0 | 5.0 |

Flow Rate: 0.5 ml/min
Method F
Column: Waters Acquity UPLC BEH C18, 2.1×30 mm, 1.7 microns
Solvents: A2=Water with 0.1% ammonia
B2=Acetonitrile with 0.1% ammonia
Gradient Conditions:

| Time (min) | % A2 | % B2 |
|---|---|---|
| 0.00 | 95.0 | 5.0 |
| 0.20 | 95.0 | 5.0 |
| 1.00 | 5.0 | 95.0 |
| 1.50 | 5.0 | 95.0 |
| 1.70 | 95.0 | 5.0 |
| 2.70 | 95.0 | 5.0 |

Flow Rate: 0.5 ml/min
NMR Spectra
NMR spectra were obtained on a Brucker DPX400 machine.
Preparative LCMS Conditions
Samples were purified on a Waters—ZQ prep system using the following conditions:
Column: Phenomenex Gemini C18 100×30 mm 5 µm
Solvents: Low pH
A=Water+0.1% Formic acid
B=(95% Acetonitrile: 5% Water)+0.1% Formic acid
High pH
C=Water with 0.1% ammonia
D=(95%:5%, acetonitrile:water) with 0.1% ammonia
Flow Rate: 35 ml/min
Temperature: Room temperature
Wavelength: Photo Diode Array 190-600 nm
Mass spec.: The mass spec. data were gathered in positive and negative mode, from 150 to 700 amu, using atmospheric pressure and electrospray ionisation modes.
Gradient conditions: Variable depending on the retention time of each compound.
Flash Chromatography Purification
Flash chromatography was generally carried out using Biotage Isolute Flash silica cartridges utilising either Flash Master II or Flash Master Personal equipment.

Intermediate 1

(S)-tert-butyl 2-chloro-4-(3-methylmorpholino)-5H-pyrrolo[3,4-d]pyrimidine-6(7H)-carboxylate

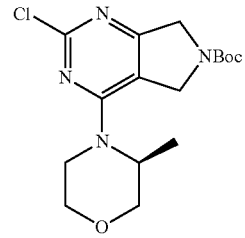 [SMILES: C[C@H]1COCCN1c1nc(Cl)nc2c1CN(C(=O)OC(C)(C)C)C2]

To a solution of tert-butyl 2,4-dichloro-5H-pyrrolo[3,4-d]pyrimidine-6(7H)-carboxylate (1.61 g, 5.54 mmol) and DIPEA (1.1 mL, 6.21 mmol) at room temperature (20° C.) in DCM (10 mL) was added 3-S-methyl morpholine (0.98 g, 9.65 mmol). The reaction mixture was heated to 35° C. and stirred for 24 h. The reaction was diluted with DCM and Sat. NaHCO$_3$. The organic layer was rinsed (brine), dried (anhydrous Na$_2$SO4) and concentrated in vacuo. The desired product was isolated by flash chromatography (silica, 50 g, 0-30% EtOAc in petroleum ether (40-60) over 40 min) as a white solid (1.80 g, 5.07 mmol, 82% yield).
LCMS (method B), (M+H$^+$) 355, Rt=2.81 min.

Intermediate 2 tert-butyl 2-chloro-4-morpholino-5H-pyrrolo[3,4-d]pyrimidine-6(7H)-carboxylate

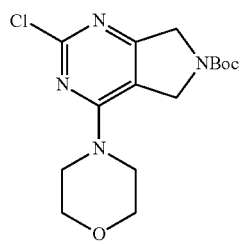 [SMILES: CC(C)(C)OC(=O)N1Cc2nc(Cl)nc(N3CCOCC3)c2C1]

To a solution of tert-butyl 2,4-dichloro-5H-pyrrolo[3,4-d]pyrimidine-6(7H)-carboxylate (1.00 g, 3.44 mmol) and DIPEA (0.672 mL, 3.86 mmol) at room temperature (20° C.) in DCM (7 mL) was added morpholine (0.33 mL, 3.86 mmol). After 2 h the reaction was diluted with DCM and Sat. NaHCO$_3$. The organic layer was rinsed (brine), dried (anhydrous Na$_2$SO$_4$) and concentrated in vacuo. The desired product was isolated by flash chromatography (silica, 50 g, 0-50% EtOAc in petroleum ether (40-60) over 25 min) as a white solid (0.63 g, 1.85 mmol, 54% yield).

LCMS (method B), (M+H$^+$) 341, Rt=2.66 min.

Intermediate 3

(S)-tert-butyl 2-chloro-4-(3-methylmorpholino)-7,8-dihydropyrido[4,3-d]pyrimidine-6(5H)-carboxylate

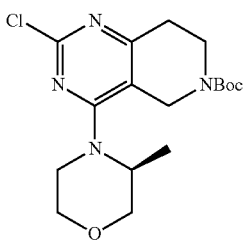 [SMILES: C[C@H]1COCCN1c1nc(Cl)nc2c1CN(C(=O)OC(C)(C)C)CC2]

To a solution of tert-butyl 2,4-dichloro-7,8-dihydropyrido[4,3-d]pyrimidine-6(5H)-carboxylate (1.00 g, 3.29 mmol) and DIPEA (1.21 mL, 6.97 mmol) at room temperature (20° C.) was added 3-S-methyl morpholine (0.54 g, 5.33 mmol). The reaction mixture was heated to 35° C. and stirred for 48 h. The reaction was diluted with DCM and Sat. NaHCO$_3$. The organic layer was rinsed (brine), dried (anhydrous Na$_2$SO$_4$) and concentrated in vacuo. The desired product was isolated by flash chromatography (silica, 50 g, 0-50% EtOAc in petroleum ether (40-60) over 25 min) as a white solid (0.71 g, 1.92 mmol, 59% yield).

LCMS (method B), (M+H$^+$) 369, Rt=2.78 min.

The R enantiomer was prepared using the same procedure with 3R-methyl morpholine.

Intermediate 4

(S)-tert-butyl 2-chloro-4-(3-methylmorpholino)-5,6-dihydropyrido[3,4-d]pyrimidine-7(8H)-carboxylate

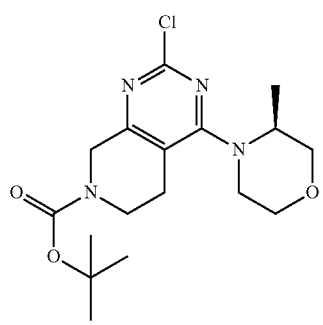 [SMILES: C[C@H]1COCCN1c1nc(Cl)nc2c1CCN(C(=O)OC(C)(C)C)C2]

To a solution of tert-butyl 2,4-dichloro-5,6-dihydropyrido[3,4d]pyrimidine-7(8H) carboxylate (1.0 g, 3.25 mmol) in DMF (20 mL) was added 3-(S)-methylmorpholine (0.329 g, 3.25 mmol) followed by DIPEA (2.9 mL, 16.25 mmol). The reaction mixture was then heated by microwave at 100° C. for 1 h. The crude reaction mixture was then partitioned between water and EtOAc, the phases separated and the organic layer washed with aqueous NaHCO$_3$ and brine, dried over magnesium sulfate, filtered and the solvent removed in vacuo. The residue was purified by flash chromatography (10-50% EtOAc/Petroleum Ether 40-60) to yield colourless oil (1.02 g, 84%).

LCMS (method B), (M+H$^+$) 369, Rt=2.88 min.

Intermediate 5

(S)-tert-butyl 2-(4-(3-ethylureido)phenyl)-4-(3-methylmorpholino)-5,6-dihydropyrido[3,4-d]pyrimidine-7(8H)-carboxylate

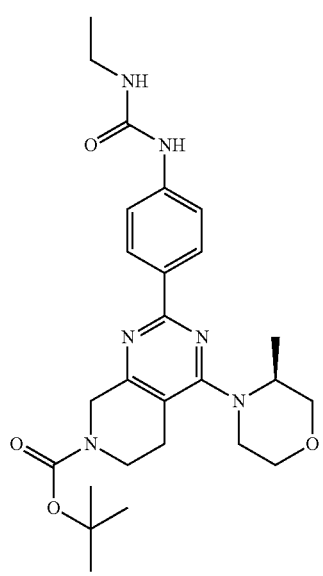 [SMILES: CCNC(=O)Nc1ccc(-c2nc3c(c(N4CCOC[C@@H]4C)n2)CCN(C(=O)OC(C)(C)C)C3)cc1]

To a solution of (S)-tert-butyl 2-chloro-4-(3-methylmorpholino)-5,6-dihydropyrido[3,4-d]pyrimidine-7(8H)-carboxylate (intermediate 4) (576 mg, 1.56 mmol) and 4-(3-ethylureido)phenylboronic acid pinacol ester (498 mg, 1.72 mmol) in DME/EtOH/H$_2$O (12/5/3) (15 mL) was added Pd(PPh$_3$)$_2$(Cl)$_2$ (55 mg, 0.078 mmol) and Na$_2$CO$_3$ (496 mg, 4.68 mmol). The reaction mixture was then heated by microwave at 120° C. for 1 h. The crude reaction mixture was then partitioned between water and EtOAc, the phases separated and the organic layer washed with aqueous NaHCO$_3$ and brine, dried over magnesium sulfate, filtered and the solvent removed in vacuo. The residue was purified by flash chromatography (20-50% EtOAc/Petroleum Ether 40-60) to yield a yellow solid (460 mg, 59%).

LCMS (method B), (M+H$^+$) 497, Rt=2.33 min.

Intermediate 6

(S)-4-(2-chloro-6,7-dihydro-5H-pyrrolo[3,4-d]pyrimidin-4-yl)-3-methylmorpholine hydrochloride

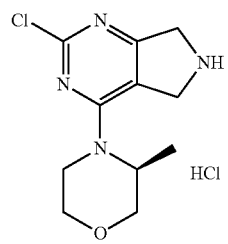 [SMILES: C[C@H]1COCCN1c1nc(Cl)nc2c1CNC2 ; Cl]

A solution of (S)-tert-butyl 2-chloro-4-(3-methylmorpholino)-5H-pyrrolo[3,4-d]pyrimidine-6(7H)-carboxylate (intermediate 1) (200 mg, 0.56 mmol) in 1M HCl in EtOH (5 mL) was stirred at room temperature (20° C.) overnight. The material was concentrated in vacuo to give a white solid.

LCMS (method B), (M+H$^+$) 255, Rt=0.66 min.

Intermediate 7

(S)-4-(2-chloro-6-neopentyl-6,7-dihydro-5H-pyrrolo[3,4-d]pyrimidin-4-yl)-3-methylmorpholine

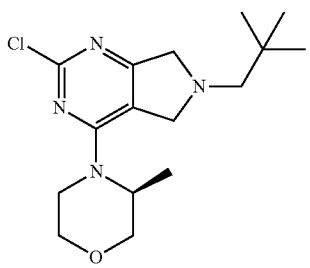 [SMILES: C[C@H]1COCCN1c1nc(Cl)nc2c1CN(CC(C)(C)C)C2]

(S)-4-(2-chloro-6,7-dihydro-5H-pyrrolo[3,4-d]pyrimidin-4-yl)-3-methylmorpholine hydrochloride (intermediate 6) (163 mg, 0.56 mmol) was stirred in THF (2 mL) with pivaldehyde (0.124 mL, 1.12 mmol) and triethylamine (0.234 mL, 1.68 mmol). After 1 h sodium triacetoxyborohydride (237 mg, 1.12 mmol) was added and the reaction was stirred overnight. Water and ethyl acetate were added. The organic layer was washed (brine) and concentrated in vacuo to give an orange oil, which was used crude.

LCMS (method B), (M+H$^+$) 325, Rt=1.56 min.

Example 1

(S)-tert-butyl 2-(4-(3-ethylureido)phenyl)-4-(3-methylmorpholino)-5H-pyrrolo[3,4-d]pyrimidine-6(7H)-carboxylate

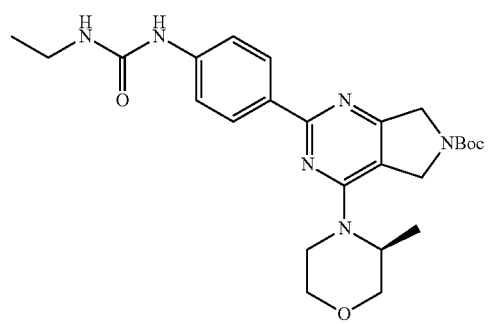 [SMILES: CCNC(=O)Nc1ccc(-c2nc3c(c(N4CCOC[C@@H]4C)n2)CN(C(=O)OC(C)(C)C)C3)cc1]

Method as described for intermediate 5 using intermediate 1 as starting material. Purified by prep LCMS (low pH).

$^1$H NMR (d$_6$-DMSO) 8.70 (s, 1H), 8.17 (dd, 2H), 7.47 (d, 2H), 6.19 (t, 1H), 4.79 (d, 1H), 4.72-4.67 (m, 1H), 4.42 (d, 2H), 3.95 (dd, 1H), 3.76-3.72 (m, 1H), 3.65 (br d, 1H), 3.53-3.49 (m, 2H), 3.14-3.07 (m, 2H), 2.60-2.54 (m, 1H), 1.46 (s, 9H), 1.25 (d, 3H), 1.05 (t, 3H).

LCMS (method A), (M+H$^+$) 483, Rt=8.88 min.

Example 2

(S)-tert-butyl 2-(4-(3-ethylureido)phenyl)-4-(3-methylmorpholino)-7,8-dihydropyrido[4,3-d]pyrimidine-6(5H)-carboxylate

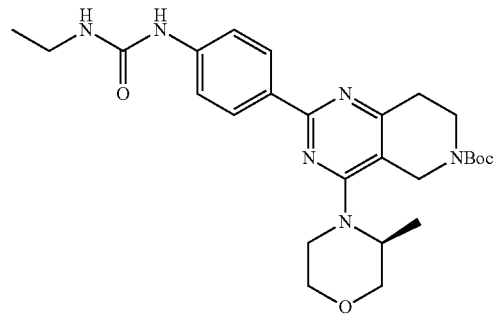 [SMILES: CCNC(=O)Nc1ccc(-c2nc3c(c(N4CCOC[C@@H]4C)n2)CN(C(=O)OC(C)(C)C)CC3)cc1]

Method as described for intermediate 5 using intermediate 3 as starting material. Purified by prep LCMS (low pH).

$^1$H NMR (d$_6$-DMSO) 8.71 (s, 1H), 8.18 (d, 2H), 7.48 (d, 2H), 6.20 (t, 1H), 4.47 (d, 1H), 4.35 (br d, 1H), 3.88 (br d, 2H), 3.66-3.60 (m, 4H), 3.15-3.08 (m, 2H), 2.48 (t, 2H), 1.41 (s, 9H), 1.25 (br s, 3H), 1.06 (t, 3H).

LCMS (method A), (M+H$^+$) 497, Rt=7.06 min.

Example 3

(S)-1-cyclopropyl-3-(4-(4-(3-methylmorpholino)-6,7-dihydro-5H-pyrrolo[3,4-d]pyrimidin-2-yl)phenyl)urea

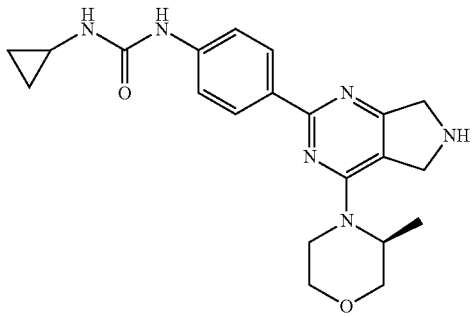 [SMILES: C[C@H]1COCCN1c1nc(-c2ccc(NC(=O)NC3CC3)cc2)nc2c1CNC2]

Step 1: (S)-tert-butyl 2-(4-(3-cyclopropylureido)phenyl)-4-(3-methylmorpholino)-5H-pyrrolo[3,4-d]pyrimidine-6(7H)-carboxylate was prepared by the method described for intermediate 5 using intermediate 1 and 1-cyclopropyl-3-(4-(4,4,5,5-tetramethyl-1,3,2-dioxaborolan-2-yl)phenyl)urea as starting materials Step 2: To a stirred solution of (S)-tert-butyl 2-(4-(3-cyclopropylureido)phenyl)-4-(3-methylmorpholino)-5H-pyrrolo[3,4-d]pyrimidine-6(7H)-carboxylate (0.99 g, 1.99 mmol) in DCM (5 mL) was added TFA (2.5 mL) and stirred at room temperature (20° C.) overnight. The reaction mixture was diluted with methanol and adsorbed onto a mp-TsOH cartridge (2.5 g, 3 mmol/g). The cartridge was rinsed with MeOH (3 column volumes) and the product was eluted with 7M $NH_3$ in MeOH. The basic fractions were concentrated in vacuo to leave a pale orange solid (0.46 g, 1.16 mmol, 58% yield).

$^1$H NMR ($d_6$-DMSO) 8.59 (br s, 1H), 8.18 (d, 2H), 7.47 (d, 2H), 6.51 (br d, 1 H), 4.27 (dd, 2H), 4.11 (br d, 1H), 3.94-3.92 (m, 3H), 3.72 (d, 1H), 3.64 (dd, 2H), 3.52-3.42 (m, 1H), 3.33-3.26 (m, 1H), 2.56-2.52 (m, 1H), 1.23 (d, 3H), 0.65-0.60 (m, 2H), 0.42-0.38 (m, 2H).

LCMS (method A), (M+H$^+$) 395, Rt=4.97 min.

Example 4

(S)-1-methyl-3-(4-(4-(3-methylmorpholino)-6,7-dihydro-5H-pyrrolo[3,4-d]pyrimidin-2-yl)phenyl)urea

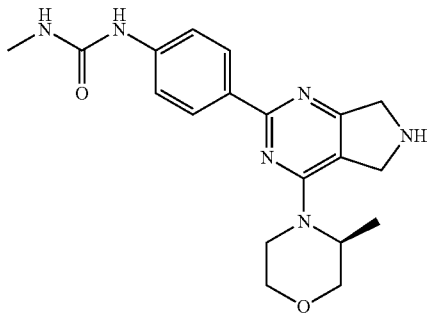 [SMILES: CNC(=O)Nc1ccc(-c2nc3c(c(N4CCOC[C@@H]4C)n2)CNC3)cc1]

Method as described for example 3 using intermediate 1 and 1-methyl-3-(4-(4,4,5,5-tetramethyl-1,3,2-dioxaborolan-2-yl)phenyl)urea as starting materials. The boc protected intermediate was purified by prep HPLC (high pH).

$^1$H NMR ($d_6$-DMSO) 8.77 (s, 1H), 8.18 (d, 2H), 7.47 (d, 2H), 6.10 (dd, 1H), 4.36 (br s, 1H), 4.26 (dd, 2H), 4.11 (br d, 1H), 3.96-3.93 (m, 3H), 3.72 (d, 1H), 3.65 (dd, 1H), 3.49 (td, 1H) 3.31-3.26 (m, 3H), 2.64 (d, 3H), 1.24 (d, 3H).

LCMS (method A), (M+H$^+$) 369, Rt=4.63 min.

Example 5

(S)-1-(4-(4-(3-methylmorpholino)-6,7-dihydro-5H-pyrrolo[3,4-d]pyrimidin-2-yl)phenyl)urea

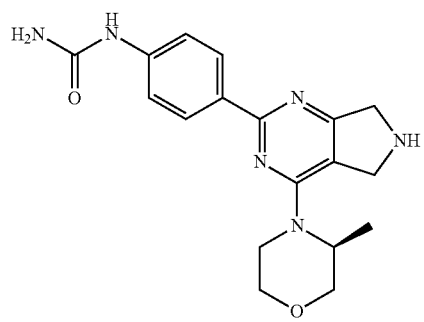 [SMILES: C[C@H]1COCCN1c1nc(-c2ccc(NC(N)=O)cc2)nc2c1CNC2]

Method as described for example 3 using intermediate 2 and 1-(4-(4,4,5,5-tetramethyl-1,3,2-dioxaborolan-2-yl)phenyl)urea as starting materials. The boc protected intermediate was purified by prep HPLC (high pH).

$^1$H NMR ($d_6$-DMSO) 8.75 (s, 1H), 8.18 (d, 2H), 7.46 (d, 2H), 5.93 (s, 1H), 4.36 (br s, 1H), 4.31-4.22 (m, 2H), 4.12-4.10 (m, 1H), 3.94 (t, 2H), 3.72 (d, 1H), 3.65 (dd, 1H), 3.49 (td, 1H), 3.30-3.26 (m, 1H), 1.24 (d, 3H).

LCMS (method A), (M+H$^+$) 355, Rt=4.31 min.

Example 6

(S)-1-(4-(6-formyl-4-(3-methylmorpholino)-6,7-dihydro-5H-pyrrolo[3,4-d]pyrimidin-2-yl)phenyl)urea

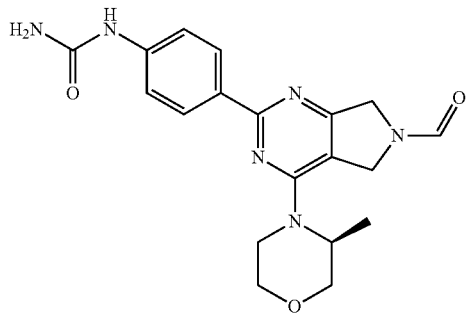 [SMILES: C[C@H]1COCCN1c1nc(-c2ccc(NC(N)=O)cc2)nc2c1CN(C=O)C2]

By-product formed from example 5 when concentrating HPLC fractions from acetonitrile, water, formic acid solution with heat in vacuo. Purified by HPLC (high pH).

$^1$H NMR ($d_6$-DMSO) 8.89 (s, 1H), 8.19 (dd, 2H), 7.49 (d, 2H), 6.00 (br s, 2H), 5.08 (dd, 1H), 4.85-4.72 (m, 2H), 4.49 (br s, 1H), 3.96 (dd, 1H), 3.74 (d, 1H), 3.66 (d, 1H), 1.27 (dd, 3H).

LCMS (method B), (M+H$^+$) 383, Rt=1.70 min.

Example 7

(S)-1-ethyl-3-(4-(4-(3-methylmorpholino)-6,7-dihydro-5H-pyrrolo[3,4-d]pyrimidin-2-yl)phenyl)urea

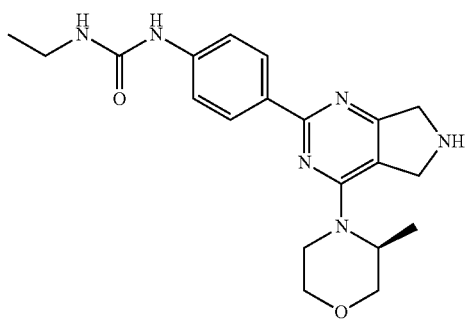 [SMILES: CCNC(=O)Nc1ccc(-c2nc3c(c(N4CCOC[C@@H]4C)n2)CNC3)cc1]

Method as described for example 3 step 2 using example 1 as starting material.

$^1$H NMR (d$_6$-DMSO) 8.65 (s, 1H), 8.17 (d, 2H), 7.46 (d, 2H), 6.17 (t, 1H), 4.35 (br s, 1H), 4.24 (dd, 2H), 4.09 (br d, 1H), 3.95-3.92 (m, 3H), 3.72 (d, 1H), 3.65 (dd, 1H), 3.49 (td, 1H), 3.28 (dd, 1H), 3.15-3.08 (m, 2H), 1.24 (d, 3H), 1.05 (t, 3H).

LCMS (method A), (M+H$^+$) 383, Rt=4.79 min.

Example 8

(S)-1-ethyl-3-(4-(6-formyl-4-(3-methylmorpholino)-6,7-dihydro-5H-pyrrolo[3,4-d]pyrimidin-2-yl)phenyl)urea

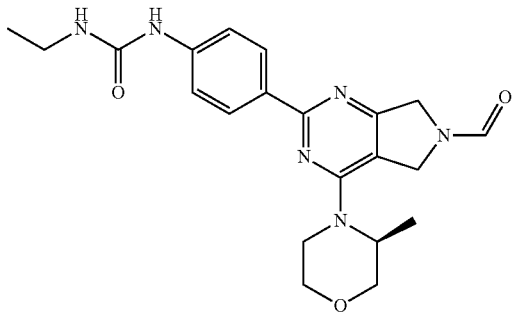 [SMILES: CCNC(=O)Nc1ccc(-c2nc3c(c(N4CCOC[C@@H]4C)n2)CN(C=O)C3)cc1]

By-product formed from example 7 when concentrating HPLC fractions from acetonitrile, water, formic acid solution with heat in vacuo. Purified by HPLC (high pH).

$^1$H NMR (d$_6$-DMSO) 8.72 (s, 1H), 8.35 (d, 1H), 8.18 (dd, 2H), 7.47 (d, 2H), 6.20 (t, 1H), 5.08 (dd, 1H), 4.78 (dd, 1H), 4.75 (s, 1H), 4.44 (s, 1H), 4.39 (br s, 1H), 4.12 (br s, 1H), 3.95 (dd, 1H), 3.74 (d, 1H), 3.66 (d, 1H), 3.54-3.47 (m, 1H), 3.14-3.07 (m, 2H), 1.26 (dd, 3H), 1.05 (t, 3H).

LCMS (method A), (M+H$^+$) 411, Rt=6.39 min.

Example 9

(R)-1-cyclopropyl-3-(4-(4-(3-methylmorpholino)-6,7-dihydro-5H-pyrrolo[3,4-d]pyrimidin-2-yl)phenyl)urea

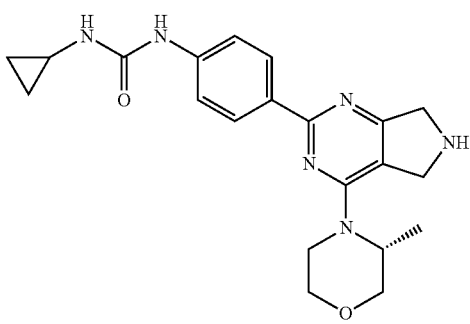 [SMILES: C[C@@H]1COCCN1c1nc(-c2ccc(NC(=O)NC3CC3)cc2)nc2c1CNC2]

Methods as described for example 3 using R-(3)-methylmorpholine in the first step.

$^1$H NMR (d$_6$-DMSO) 8.53 (s, 1H), 8.18 (d, 2H), 7.47 (d, 2H), 6.45 (d, 1H), 4.27 (dd, 2H), 4.36 (br s, 1H), 4.11 (br d, 1H), 3.94-3.92 (m, 2H), 3.72 (d, 1H), 3.64 (dd, 1H), 3.49 (td, 1H), 2.56-2.53 (m, 1H), 1.23 (d, 3H), 0.66-0.61 (m, 2H), 0.42-0.38 (m, 2H).

LCMS (method A), (M+H$^+$) 395, Rt=5.04 min.

Example 10

(S)-1-methyl-3-(4-(4-(3-methylmorpholino)-5,6,7,8-tetrahydropyrido[4,3-d]pyrimidin-2-yl)phenyl)urea

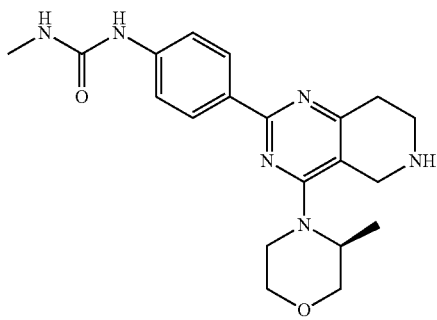 [SMILES: CNC(=O)Nc1ccc(-c2nc3c(c(N4CCOC[C@@H]4C)n2)CNCC3)cc1]

Method as described for example 3 using intermediate 3 and 1-methyl-3-(4-(4,4,5,5-tetramethyl-1,3,2-dioxaborolan-2-yl)phenyl)urea as starting materials. The boc protected intermediate was purified by prep HPLC (high pH).

$^1$H NMR (d$_6$-DMSO) 8.75 (s, 1H), 8.17 (d, 2H), 7.47 (d, 2H), 6.08-6.06 (m, 1H), 3.92-3.84 (m, 1H), 3.71-3.57 (m, 4H), 3.46-3.56 (m, 1H), 3.08-2.95 (m, 2H), 2.73 (t, 1H), 2.65 (d, 3H), 1.21 (d, 3H).

LCMS (method A), (M+H$^+$) 383, Rt=4.05 min.

Example 11

(S)-1-cyclopropyl-3-(4-(4-(3-methylmorpholino)-5,6,7,8-tetrahydropyrido[4,3-d]pyrimidin-2-yl)phenyl)urea

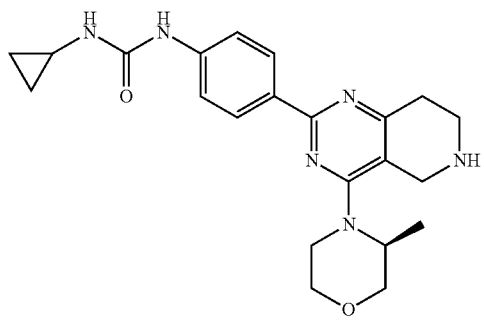 [SMILES: C[C@H]1COCCN1c1nc(-c2ccc(NC(=O)NC3CC3)cc2)nc2c1CNCC2]

Method as described for example 3 using intermediate 3 and 1-cyclopropyl-3-(4-(4,4,5,5-tetramethyl-1,3,2-dioxaborolan-2-yl)phenyl)urea as starting materials. The boc protected intermediate was purified by prep HPLC (low pH).

$^1$H NMR (d$_6$-DMSO) 8.57 (s, 1H), 8.18 (d, 2H), 7.49 (d, 2H), 6.48 (s, 1H), 3.92-3.85 (m, 2H), 3.74-3.69 (m, 2H), 3.65-3.58 (m, 2H), 3.12-2.98 (m, 2H), 2.75 (t, 2H), 2.56-2.53 (m, 1H), 1.21 (d, 3H), 0.66-0.62 (m, 2H), 0.43-0.39 (m, 2H).

LCMS (method A), (M+H$^+$) 409, Rt=4.52 min.

Example 12

(S)-1-ethyl-3-(4-(4-(3-methylmorpholino)-5,6,7,8-tetrahydropyrido[4,3-d]pyrimidin-2-yl)phenyl)urea

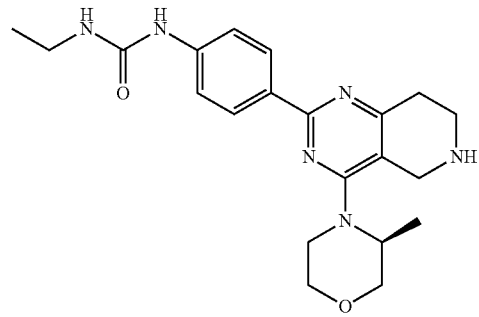 [SMILES: CCNC(=O)Nc1ccc(-c2nc3c(c(N4CCOC[C@@H]4C)n2)CNCC3)cc1]

Method as described for example 3 step 2 using example 2 as starting material.

$^1$H NMR (d$_6$-DMSO) 8.66 (s, 1H), 8.17 (d, 2H), 7.47 (d, 2H), 6.16 (t, 1H), 3.92-3.84 (m, 2H), 3.72-3.66 (m, 3H), 3.63-3.58 (m, 2H), 3.45-3.40 (m, 3H), 3.14-3.08 (m, 2H), 3.05-2.98 (m, 2H), 2.73 (t, 2H), 1.20 (d, 3H), 1.05 (t, 3H).

LCMS (method A), (M+H$^+$) 397, Rt=4.46 min.

Example 13

(S)-1-ethyl-3-(4-(4-(3-methylmorpholino)-5,6,7,8-tetrahydropyrido[3,4-d]pyrimidin-2yl)phenyl)urea

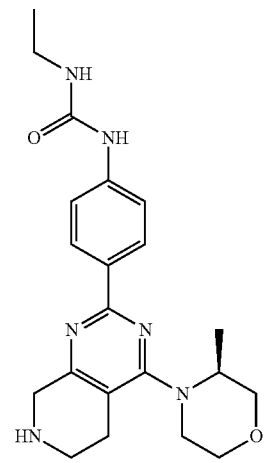

Method as described for example 3 step 2 using intermediate 5 as starting material.

$^1$H NMR (d$_6$-DMSO) 8.66 (s, 1H), 8.15 (d, 2H), 7.46 (d, 2H), 6.16 (t, 1H), 4.07 (d, 1H), 3.88 (d, 1H), 3.82 (d, 2H), 3.71 (dd, 1H) 3.62 (d, 2H), 3.55 (d, 1H), 3.42 (dd, 1H), 3.11 (qn, 2H), 2.88-2.98 (m, 1H), 2.74-2.83 (m, 1H), 2.55 (br s, 2H), 1.21 (d, 3H), 1.05 (t, 3H).

LCMS (method A), (M+H$^+$) 397, Rt=5.01 min.

Example 13a (S)-tert-butyl 2-(4-(3-ethylureido)phenyl)-4-(3-methylmorpholino)-5,6-dihydropyrido[3,4-d]pyrimidine-7(8H)-carboxylate

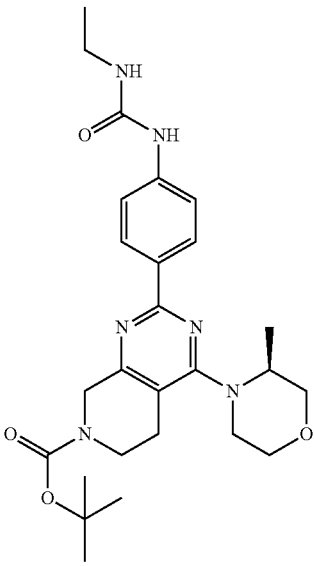 [SMILES: CCNC(=O)Nc1ccc(-c2nc3c(c(N4CCOC[C@@H]4C)n2)CCN(C(=O)OC(C)(C)C)C3)cc1]

To a solution of (S)-tert-butyl 2-chloro-4-(3-methylmorpholino)-5,6-dihydropyrido[3,4-d]pyrimidine-7(8H)-carboxylate (intermediate 4) (576 mg, 1.56 mmol) and 4-(3-ethylureido)phenylboronic acid pinacol ester (498 mg, 1.72 mmol) in DME/EtOH/H$_2$O (12/5/3) (15 mL) was added Pd(PPh$_3$)$_2$(Cl)$_2$ (55 mg, 0.078 mmol) and Na$_2$CO$_3$ (496 mg, 4.68 mmol). The reaction mixture was then heated by microwave at 120° C. for 1 h. The crude reaction mixture was then partitioned between water and EtOAc, the phases separated and the organic layer washed with aqueous NaHCO$_3$ and brine, dried over magnesium sulfate, filtered and the solvent removed in vacuo. The residue was purified by flash chromatography (20-50% EtOAc/Petroleum Ether 40-60) to yield a yellow solid (460 mg, 59%).

LCMS (method B), (M+H$^+$) 497, Rt=2.33 min.

Example 13b (S)-1-ethyl-3-(4-(4-(3-methylmorpholino)-5,6,7,8-tetrahydropyrido[3,4-d]pyrimidin-2-yl)phenyl)urea 2,2,2-trifluoroacetate

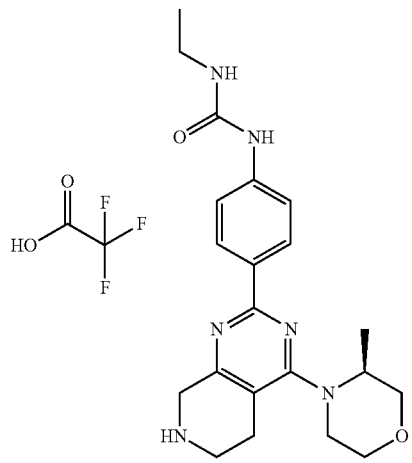 [SMILES: O=C(O)C(F)(F)F ; CCNC(=O)Nc1ccc(-c2nc3c(c(N4CCOC[C@@H]4C)n2)CCNC3)cc1]

To a stirred solution of (S)-tert-butyl 2-(4-(3-ethylureido)phenyl)-4-(3-methylmorpholino)-5,6-dihydropyrido[3,4-d]pyrimidine-7(8H)-carboxylate (intermediate 5) (2.72 g, 5.5 mmol) in DCM (40 mL) was added TFA (20 mL). The reaction mixture was stirred at room temperature for 2 h. The reaction mixture was concentrated and the resulting residue was dissolved in the minimum MeOH and precipitated from Et$_2$O to give a cream solid (2.35 g, 4.6 mmol, 84% yield).

LCMS (method B), (M+H$^+$) 497, Rt=1.61 min.

Example 14

1-ethyl-3-(4-(4-morpholino-6,7-dihydro-5H-pyrrolo[3,4-d]pyrimidin-2-yl)phenyl)urea

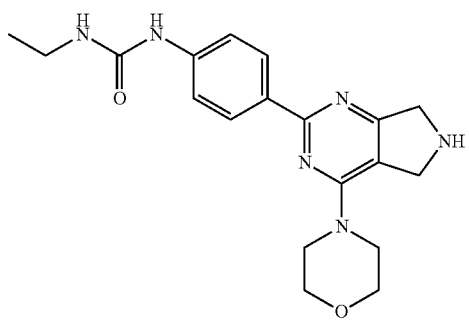 [SMILES: CCNC(=O)Nc1ccc(-c2nc3c(c(N4CCOCC4)n2)CNC3)cc1]

Method as described for example 3 from intermediate 2 and 1-ethyl-3-(4-(4,4,5,5-tetramethyl-1,3,2-dioxaborolan-2-yl)phenyl)urea. The boc protected intermediate was purified by prep HPLC (low pH).

$^1$H NMR (d$_6$-DMSO) 8.66 (s, 1H), 8.18 (d, 2H), 7.45 (d, 2H), 6.16 (br t, 1H), 4.24 (br s, 2H), 3.92 (br s, 2H), 3.70-3.68 (m, 8H), 3.14-3.07 (m, 2H), 1.05 (t, 3H).

LCMS (method A), (M+H$^+$) 369, Rt=4.79 min.

Example 15

(S)-1-cyclopropyl-3-(4-(4-(3-methylmorpholino)-5,6,7,8-tetrahydropyrido[3,4-d]pyrimidin-2-yl)phenyl)urea

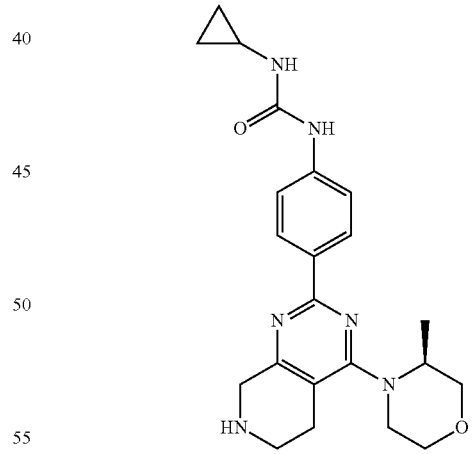

Method as described for intermediate 5 using 1-cyclopropyl-3-(4-(4,4,5,5-tetramethyl-1,3,2-dioxaborolan-2-yl)phenyl)urea and intermediate 4 as starting materials. Followed by method as described for example 3 step 2.

$^1$H NMR (d$_6$-DMSO) 8.54 (s, 1H), 8.16 (d, 2H), 7.48 (d, 2H), 6.45 (d, 1H), 4.07 (d, 1H), 3.88 (d, 1H), 3.82 (d, 2H), 3.70 (dd, 1H) 3.62 (d, 2H), 3.55 (d, 1H), 3.42 (dd, 1H), 2.85-2.98 (m, 1H), 2.70-2.83 (m, 1H), 2.54 (q, 2H), 2.55 (br s, 2H), 1.21 (d, 3H), 0.64 (ddd, 2H), 0.41 (ddd, 2H).

LCMS (method A), (M+H$^+$) 409, Rt=5.10 min.

Example 15a

S)-tert-butyl 2-(4-(3-cyclopropylureido)phenyl)-4-(3-methylmorpholino)-5,6-dihydropyrido[3,4-d]pyrimidine-7(8H)-carboxylate

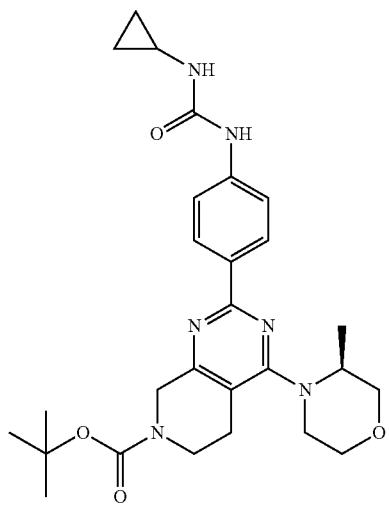 [SMILES: C[C@H]1COCCN1c1nc(-c2ccc(NC(=O)NC3CC3)cc2)nc2c1CCN(C(=O)OC(C)(C)C)C2]

Method as described for intermediate 5 using 1-cyclopropyl-3-(4-(4,4,5,5-tetramethyl-1,3,2-dioxaborolan-2-yl)phenyl)urea.

LCMS (method B), (M+H⁺) 509, Rt=2.43 min

Example 15b (S)-1-cyclopropyl-3-(4-(4-(3-methylmorpholino)-5,6,7,8-tetrahydropyrido[3,4-d]pyrimidin-2-yl)phenyl)urea 2,2,2-trifluoroacetate

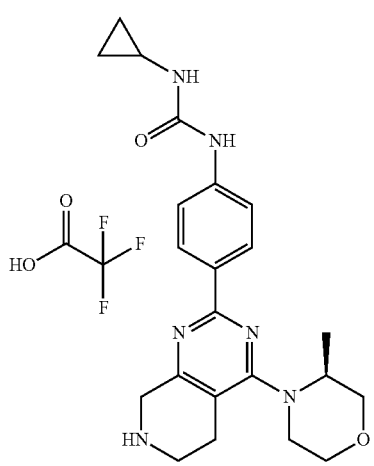

To a stirred solution of (S)-tert-butyl 2-(4-(3-cyclopropylureido)phenyl)-4-(3-methylmorpholino)-5,6-dihydropyrido[3,4-d]pyrimidine-7(8H)-carboxylate (3.27 g, 6.43 mmol) in DCM (40 mL) was added TFA (20 mL). The reaction mixture was stirred at room temperature for 2 h. The mixture was concentrated and the resulting residue was dissolved in the minimum MeOH and precipitated from Et₂O to give a pale yellow solid (498 mg, 0.95 mmol, 15% yield).

LCMS (method B), (M+H⁺) 409, Rt=1.65 min.

Example 16

(S)-1-methyl-3-(4-(4-(3-methylmorpholino)-5,6,7,8-tetrahydropyrido[3,4-d]pyrimidin-2-yl)phenyl)urea

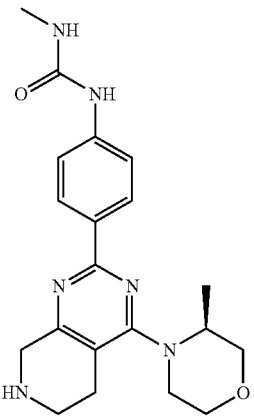

Method as described for intermediate 5 using 1-methyl-3-(4-(4,4,5,5-tetramethyl-1,3,2-dioxaborolan-2-yl)phenyl)urea and intermediate 4 as starting materials. Followed by method as described for example 3 step 2.

¹H NMR (d₆-DMSO) 8.75 (s, 1H), 8.15 (d, 2H), 7.47 (d, 2H), 6.07 (q, 1H), 4.07 (d, 1H), 3.88 (d, 1H), 3.84 (d, 2H), 3.70 (dd, 1H) 3.62 (d, 2H), 3.55 (d, 1H), 3.42 (dd, 1H), 2.89-2.99 (m, 1H), 2.75-2.85 (m, 1H), 2.65 (d, 3H), 2.55 (br s, 2H), 1.21 (d, 3H).

LCMS (method A), (M+H⁺) 383, Rt=4.70 min.

Example 17

(S)-1-(4-(6-(cyclopropanecarbonyl)-4-(3-methylmorpholino)-6,7-dihydro-5H-pyrrolo[3,4-d]pyrimidin-2-yl)phenyl)-3-cyclopropylurea

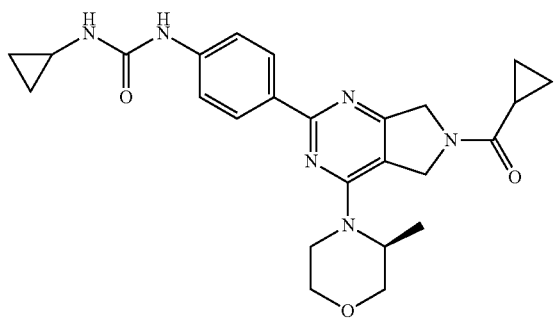 [SMILES: C[C@H]1COCCN1c1nc(-c2ccc(NC(=O)NC3CC3)cc2)nc2c1CN(C(=O)C1CC1)C2]

To a stirred solution of (S)-1-cyclopropyl-3-(4-(4-(3-methylmorpholino)-6,7-dihydro-5H-pyrrolo[3,4-d]pyrimidin-2-yl)phenyl)urea (example 3) (150 mg, 0.38 mmol) in 2-methyl THF (2 mL) and DMSO (1 mL) was added DIPEA (159 uL, 0.92 mmol), cyclopropane carboxylic acid (578 uL, 0.73 mmol) and EDC (139 mg, 0.73 mmol), followed by HOBt (98 mg, 0.73 mmol). The reaction mixture was stirred at room temperature for 4 h then diluted with water and ethyl acetate.

The organic layer was concentrated and purified by prep HPLC (low pH) to give a pale yellow solid (65 mg, 0.14 mmol, 37% yield).

$^1$H NMR (d$_6$-DMSO) 8.57 (s, 1H), 8.19 (d, 2H), 7.49 (dd, 2H), 6.47 (t, 1H), 5.17 (dd, 1H), 4.88 (s, 1H), 4.80 (dd, 1H), 4.47 (s, 1H), 4.15 (br d, 1H), 3.96 (br d, 1H), 3.75 (d, 1H), 3.70-3.65 (m, 1H), 3.56-3.48 (m, 1H), 3.40-3.35 (m, 1H), 2.57-2.53 (m, 1H), 1.27 (t, 3H), 0.83-0.80 (m, 4H), 0.66-0.62 (m, 2H), 0.43-0.39 (m, 2H).

LCMS (method A), (M+H$^+$) 463, Rt=7.30 min.

Example 18

(S)-1-(4-(6-acetyl-4-(3-methylmorpholino)-6,7-dihydro-5H-pyrrolo[3,4-d]pyrimidin-2-yl)phenyl)-3-ethylurea

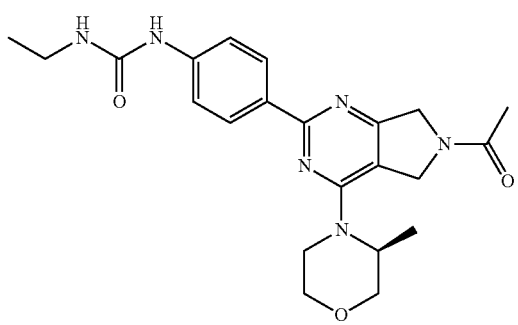 [SMILES: CCNC(=O)Nc1ccc(-c2nc3c(c(N4CCOC[C@@H]4C)n2)CN(C(C)=O)C3)cc1]

To a stirred solution of (S)-1-ethyl-3-(4-(4-(3-methylmorpholino)-6,7-dihydro-5H-pyrrolo[3,4-d]pyrimidin-2-yl)phenyl)urea (example 7) (60 mg, 0.16 mmol) in DCM (1.5 mL) was added triethylamine (42 uL, 0.31 mmol) and acetyl chloride (71 uL, 0.31 mmol). The reaction mixture was stirred overnight at room temperature, concentrated in vacuo, then diluted with water and ethyl acetate. The organic layer was concentrated and purified by prep HPLC (low pH) to give an off-white solid (5.7 mg, 0.013 mmol, 9% yield).

$^1$H NMR (d$_6$-DMSO) 8.70 (s, 1H), 8.18 (dd, 2H), 7.48 (d, 2H), 6.20-6.17 (m, 1H), 4.99 (dd, 2H), 4.82-4.71 (m, 3H), 4.43 (s, 1H), 3.96 (d, 1H), 3.74 (d, 1H), 3.66 (d, 1H), 3.54-3.46 (m, 2H), 3.14-3.07 (m, 2H), 2.08 (d, 3H), 1.27-1.25 (m, 3H), 1.05 (t, 3H).

LCMS (method A), (M+H$^+$) 425, Rt=6.37 min.

Example 19

(S)-1-ethyl-3-(4-(6-(4-fluorobenzoyl)-4-(3-methylmorpholino)-6,7-dihydro-5H-pyrrolo[3,4-d]pyrimidin-2-yl)phenyl)urea

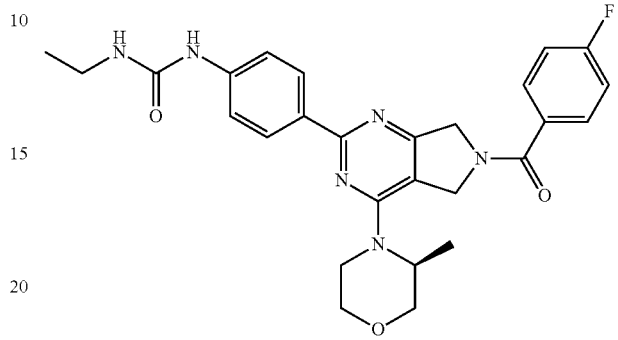

Method as described for example 17 using example 7 and 4-fluorobenzoic acid as starting materials. Purified by prep HPLC (low pH).

$^1$H NMR (d$_6$-DMSO) 8.69 (d, 1H), 8.17 (dd, 2H), 7.75-7.72 (m, 2H), 7.49-7.45 (m, 2H), 7.34-7.30 (m, 2H), 6.18 (t, 1H), 5.08-4.95 (m, 2H), 4.69 (s, 2H), 4.00-3.87 (m, 2H), 3.79-3.67 (m, 2H), 3.60-3.40 (m, 2H), 3.12-3.06 (m, 3H), 1.29-1.18 (m, 3H), 1.07-1.02 (m, 3H).

LCMS (method A), (M+H$^+$) 505, Rt=8.36 min.

Example 20

(S)-1-(4-(6-acetyl-4-(3-methylmorpholino)-6,7-dihydro-5H-pyrrolo[3,4-d]pyrimidin-2-yl)phenyl)-3-cyclopropylurea

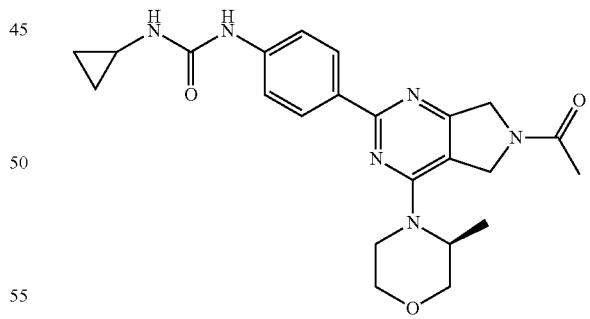

Method as described for example 18 using example 3 as starting material. Purified by prep HPLC (high pH).

$^1$H NMR (d$_6$-DMSO) 8.60 (s, 1H), 8.19 (dd, 2H), 7.49 (d, 2H), 6.49 (br s, 1H), 4.99 (dd, 1H), 4.83-4.71 (m, 2H), 4.44 (s, 1H), 4.13 (dd, 1H), 3.96 (d, 1H), 3.75 (d, 1H), 3.67 (d, 1H), 3.54-3.48 (m, 1H), 3.16 (d, 1H), 2.57-2.52 (m, 1H), 2.08 (d, 3H), 1.28-1.25 (m, 3H), 0.66-0.61 (m, 2H), 0.42-0.39 (m, 2H).

LCMS (method A), (M+H$^+$) 437, Rt=6.56 min.

Example 21

(S)-1-ethyl-3-(4-(6-isobutyryl-4-(3-methylmorpholino)-6,7-dihydro-5H-pyrrolo[3,4-d]pyrimidin-2-yl)phenyl)urea

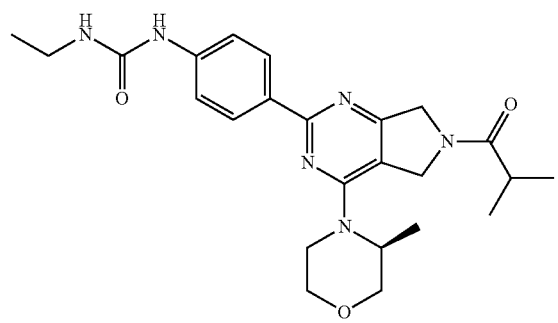 [SMILES: CCNC(=O)Nc1ccc(-c2nc3c(c(N4CCOC[C@@H]4C)n2)CN(C(=O)C(C)C)C3)cc1]

Method as described for example 17 using example 7 and isobutyric acid as starting materials. Purified by prep HPLC (low pH).

$^1$H NMR (d$_6$-DMSO) 8.73 (s, 1H), 8.17 (dd, 2H), 7.48 (dd, 2H), 6.25-6.21 (m, 1H), 5.05 (dd, 1H), 4.84-4.72 (m, 2H), 4.45 (br s, 1H), 4.17-4.10 (m, 1H), 3.96 (br d), 3.75 (d, 1H), 3.68-3.65 (m, 1H), 3.55-3.48 (m, 1H), 3.17 (s, 3H), 3.15-3.10 (m, 2H), 1.26 (d, 3H), 1.08-1.04 (m, 9H).

LCMS (method A), (M+H$^+$) 453, Rt=7.29 min.

Example 22

(S)-1-ethyl-3-(4-(4-(3-methylmorpholino)-6-pivaloyl-6,7-dihydro-5H-pyrrolo[3,4-d]pyrimidin-2-yl)phenyl)urea

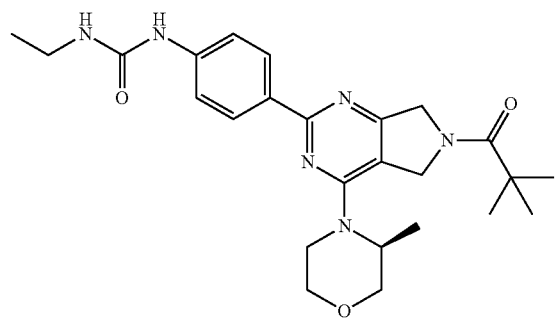 [SMILES: CCNC(=O)Nc1ccc(-c2nc3c(c(N4CCOC[C@@H]4C)n2)CN(C(=O)C(C)(C)C)C3)cc1]

Method as described for example 17 using example 7 and pivalic acid as starting materials. Purified by prep HPLC (low pH).

$^1$H NMR (d$_6$-DMSO) 8.69 (s, 1H), 8.18 (d, 2H), 7.48 (d, 2H), 6.19 (t, 1H), 4.86 (br s, 1H), 4.42 (br s, 1H), 4.14 (br d, 1H), 3.97 (dd, 1H), 3.76 (d, 1H), 3.69-3.65 (m, 1H), 3.15-3.08 (m, 2H), 1.28-1.26 (m, 12H), 1.06 (t, 3H).

LCMS (method A), (M+H$^+$) 467, Rt=8.00 min.

Example 23

(S)-1-(4-(6-(cyclopropanecarbonyl)-4-(3-methylmorpholino)-6,7-dihydro-5H-pyrrolo[3,4-d]pyrimidin-2-yl)phenyl)-3-ethylurea

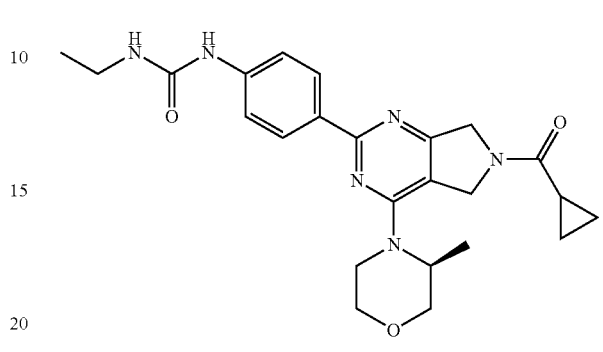

Method as described for example 17 using example 7 and cyclopropanecarboxylic acid as starting materials. Purified by prep HPLC (low pH).

$^1$H NMR (d$_6$-DMSO) 8.68 (s, 1H), 8.19 (d, 2H), 7.48 (d, 2H), 6.19-6.16 (m, 1H), 5.17 (dd, 1H), 4.88 (s, 1H), 4.85-4.73 (m, 1H), 4.46 (s, 1H), 4.15 (br d, 1H), 3.96 (d, 1H), 3.74 (d, 1H), 3.70-3.64 (m, 1H), 3.56-3.48 (m, 1H), 3.15-3.08 (m, 2H), 2.06-1.88 (m, 1H), 1.28-1.25 (m, 3H), 1.06 (t, 3H), 0.82-0.80 (m, 4H).

LCMS (method A), (M+H$^+$) 451, Rt=7.19 min.

Example 24

(S)-1-ethyl-3-(4-(7-(4-fluorobenzoyl)-4-(3-methylmorpholino)-5,6,7,8-tetrahydropyrido[3,4-d]pyrimidin-2-yl)phenyl)urea

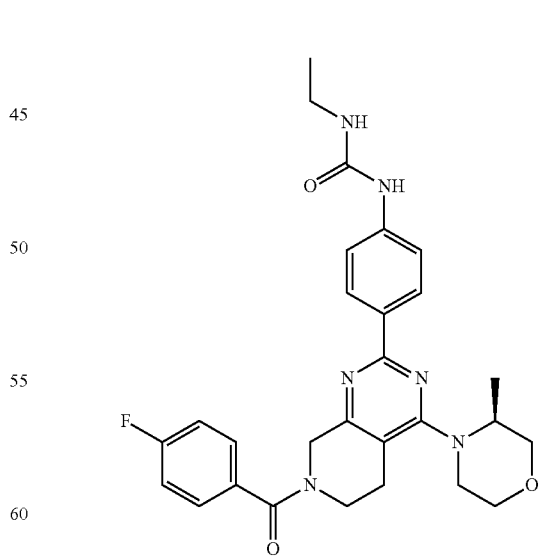

Method as described for example 17 using example 13 and 4-fluorobenzoic acid as starting materials, DCM as solvent and NEt$_3$ as base. Purified by flash chromatography (5-10% MeOH in DCM).

$^1$H NMR (CDCl$_3$/CD$_3$OD) 8.17 (dd, 2H), 7.58 (br s, 2H), 7.43 (dd, 2H), 7.22 (t, 2H), 4.65 (br s, 1H), 4.16 (br s, 1H), 4.06 (br s, 1H), 3.95 (dd, 1H), 3.83 (d, 2H), 3.64-3.78 (m, 4H), 3.57 (dd, 2H), 3.24 (br q, 2H), 2.80 (br s, 2H), 1.37 (d, 3H), 1.56 (t, 3H).

LCMS (method A), (M+H$^+$) 519, Rt=7.71 min.

Example 25

(S)-1-cyclopropyl-3-(4-(4-(3-methylmorpholino)-6-neopentyl-6,7-dihydro-5H-pyrrolo[3,4-d]pyrimidin-2-yl)phenyl)urea

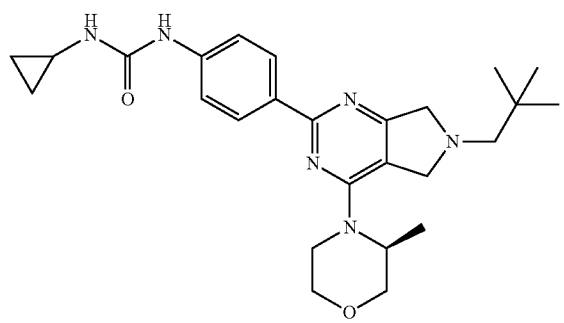 [SMILES: C[C@H]1COCCN1c1nc(-c2ccc(NC(=O)NC3CC3)cc2)nc2c1CN(CC(C)(C)C)C2]

(S)-4-(2-chloro-6-neopentyl-6,7-dihydro-5H-pyrrolo[3,4-d]pyrimidin-4-yl)-3-methylmorpholine (intermediate 7) (assumed 0.56 mmol) was stirred in CPME:EtOH:Water (7:3:2, freshly mixed, 2 mL) with 1-cyclopropyl-3-(4-(4,4,5,5-tetramethyl-1,3,2-dioxaborolan-2-yl)phenyl)urea (203 mg, 0.67 mmol), Pd(PPh$_3$)$_2$Cl$_2$ (20 mg, 0.028 mmol) and Na$_2$CO$_3$ (89 mg, 0.84 mmol) under a stream of nitrogen for 5 min, then irradiated in the microwave at 130° C. for 30 min. The reaction mixture was diluted with water and EtOAc and passed through a celite cartridge. The organic layer was concentrated in vacuo and purified by prep HPLC to give the desired compound as a yellow solid (48 mg, 0.103 mmol, 18% yield over three steps).

$^1$H NMR (d$_6$-DMSO) 8.53 (s, 1H), 8.17 (d, 2H), 7.47 (d, 2H), 6.45 (d, 1H), 4.36 (br s, 1H), 4.26 (d, 1H), 4.04 (d, 1H), 3.95-3.92 (m, 3H), 3.72 (d, 1H), 3.65 (dd, 1H), 3.49 (td, 1H), 3.31 (td, 1H), 2.58-2.53 (m, 3H), 1.24 (d, 3H), 0.93 (s, 9H), 0.66-0.61 (m, 2H), 0.43-0.39 (m, 2H).

LCMS (method A), (M+H$^+$) 465, Rt=5.97 min.

Example 26

(S)-1-ethyl-3-(4-(6-methyl-4-(3-methylmorpholino)-6,7-dihydro-5H-pyrrolo[3,4-d]pyrimidin-2-yl)phenyl)urea

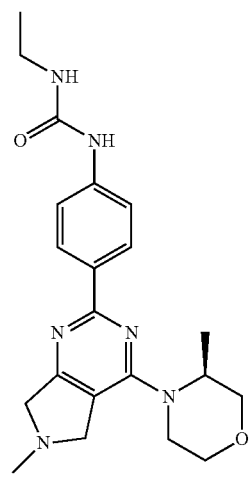 [SMILES: CCNC(=O)Nc1ccc(-c2nc3c(c(N4CCOC[C@@H]4C)n2)CN(C)C3)cc1]

To a solution of (S)-1-ethyl-3-(4-(4-(3-methylmorpholino)-6,7-dihydro-5H-pyrrolo[3,4-d]pyrimidin-2-yl)phenyl)urea (example 7) (150 mg, 0.36 mmol) in THF (3 mL) was added aqueous formaldehyde 37 Wt % (58 μL, 0.72 mmol) and Et$_3$N (149 μL, 1.07 mmol). The reaction mixture was then stirred at room temperature (20° C.) for 1 h. After this time sodium triacetoxyborohydride (152 mg, 0.72 mmol) was added and stirring at room temperature (20° C.) continued for 18 h. The crude reaction mixture was then partitioned between water and EtOAc, the phases separated and the organic layer washed with NaHCO$_3$ and brine, dried over magnesium sulfate, filtered and the solvent removed in vacuo. The residue was purified by prep HPLC (low pH) to give as a light brown solid (48 mg, 33%).

$^1$H NMR (d$_6$-DMSO) 8.67 (s, 1H), 8.17 (d, 2H), 7.46 (d, 2H), 6.18 (t, 1H), 4.30 (br s, 1H), 4.02 (dd, 3H), 3.95-3.91 (m, 1H), 3.72 (br s, 2H), 3.70 (br s, 1H), 3.66-3.63 (m, 1H), 3.52-3.46 (m, 2H), 3.14-3.07 (m, 2H), 1.24 (d, 3H), 1.05 (t, 3H).

LCMS (method A), (M+H$^+$) 397, Rt=5.09 min.

Example 27

(S)-1-ethyl-3-(4-(7-ethyl-4-(3-methylmorpholino)-5,6,7,8-tetrahydropyrido[3,4-d]pyrimidin-2-yl)phenyl)urea

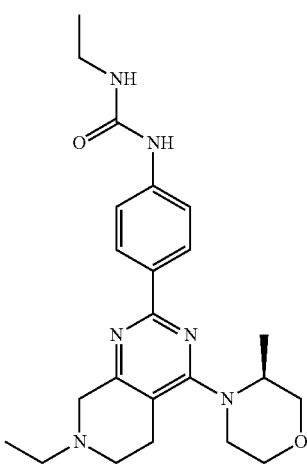 [SMILES: CCNC(=O)Nc1ccc(-c2nc3c(c(N4CCOC[C@@H]4C)n2)CCN(CC)C3)cc1]

To a solution of (S)-1-ethyl-3-(4-(4-(3-methylmorpholino)-5,6,7,8-tetrahydropyrido[3,4-d]pyrimidin-2-yl)phenyl)urea (130 mg, 0.33 mmol) in DMF (2.5 mL) was added bromoethane (29 µL, 0.39 mmol) and DIPEA (69 µL, 0.39 mmol). The reaction mixture was then heated by microwave at 100° C. for 1 h. The crude reaction mixture was then partitioned between water and EtOAc, the phases separated and the organic layer washed with NaHCO₃ and brine, dried over magnesium sulfate, filtered and the solvent removed in vacuo. The residue was purified by flash chromatography (2-10% MeOH/DCM) to give a light brown solid (79 mg, 57%).

¹H NMR (CDCl₃) 8.32 (d, 2H), 7.36 (d, 2H), 6.41 (s, 1H), 4.75 (t, 1H), 4.20-4.05 (m, 1H), 3.95 (d, 1H), 3.82 (d, 2H), 3.73 (td, 1H) 3.67 (dd, 1H), 3.47-3.64 (m, 3H), 3.31 (qn, 2H), 2.67-2.85 (m, 3H), 2.53-2.67 (m, 3H), 1.31 (d, 3H), 1.22 (t, 3H), 1.16 (t, 3H).

LCMS (method A), (M+H⁺) 425, Rt=5.14 min.

Example 28

(S)-1-(4-(6-(cyclopropylmethyl)-4-(3-methylmorpholino)-6,7-dihydro-5H-pyrrolo[3,4-d]pyrimidin-2-yl)phenyl)-3-ethylurea

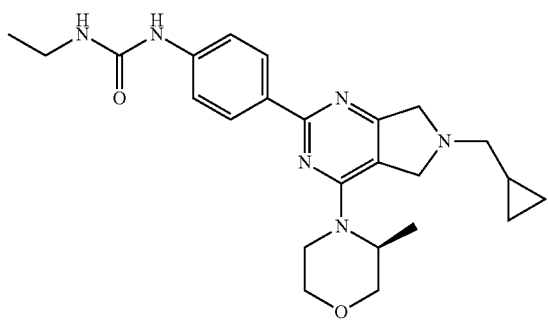 [SMILES: CCNC(=O)Nc1ccc(-c2nc3c(c(N4CCOC[C@@H]4C)n2)CN(CC2CC2)C3)cc1]

Method as described for example 26 using example 7 and 2-cyclopropylacetaldehyde as starting materials. Purified by prep HPLC (high pH).

¹H NMR (d₆-DMSO) 8.66 (s, 1H), 8.17 (d, 2H), 7.46 (d, 2H), 6.17 (t, 1H), 4.36 (br s, 1H), 4.14-4.04 (m, 3H), 3.93 (dd, 1H), 3.81 (br s, 2H), 3.65 (dd, 1H), 3.49 (td, 1H), 3.15-3.08 (m, 2H), 2.55 (d, 2H), 1.24 (d, 3H), 1.07-1.04 (m, 3H), 0.99-0.92 (m, 1H), 0.52-0.48 (m, 2H), 0.19-0.16 (m, 2H).

LCMS (method A), (M+H⁺) 437, Rt=5.45 min.

Example 29

(S)-1-ethyl-3-(4-(6-(4-fluorobenzyl)-4-(3-methylmorpholino)-6,7-dihydro-5H-pyrrolo[3,4-d]pyrimidin-2-yl)phenyl)urea

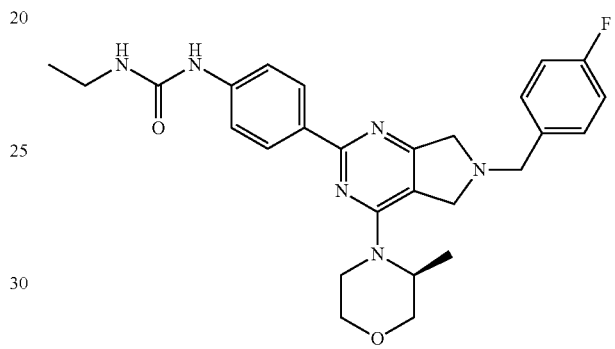

Method as described for example 27 using example 7 and 4-fluorobenzylbromide as starting materials. Purified by prep HPLC (low pH).

¹H NMR (d₆-DMSO) 8.67 (s, 1H), 8.16-8.14 (m, 2H), 7.46-7.40 (m, 2H), 7.20-7.15 (m, 2H), 6.18 (t, 1H), 4.33 (br s, 1H), 4.13-3.99 (m, 3H), 3.93-3.87 (m, 3H), 3.74 (s, 2H), 3.70 (d, 1H), 3.62 (dd, 1H), 3.50-3.43 (m, 2H), 3.30-3.25 (m, 1H), 3.13-3.07 (m, 2H), 1.22 (d, 3H), 1.04 (t, 3H).

LCMS (method A), (M+H⁺) 491, Rt=6.15 min.

Example 30

(S)-1-cyclopropyl-3-(4-(4-(3-methylmorpholino)-6-neopentyl-6,7-dihydro-5H-pyrrolo[3,4-d]pyrimidin-2-yl)phenyl)urea

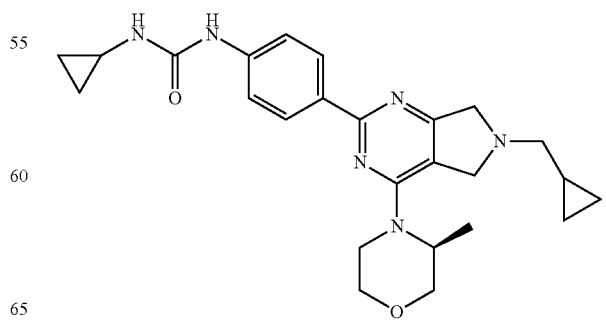

Method as described for example 26 using example 3 and 2-cyclopropylacetaldehyde as starting materials. Purified by prep HPLC (low pH).

¹H NMR (d₆-DMSO) 8.52 (s, 1H), 8.17 (d, 2H), 7.47 (d, 2H), 6.44 (br d, 1H), 4.37 (br d, 1H), 4.10 (dd, 3H), 3.94 (dd, 1H), 3.82 (s, 1H), 3.72 (d, 1H), 3.65 (dd, 1H), 3.50 (td, 1H), 3.32 (td, 1H), 2.57-2.54 (m, 2H), 1.25 (d, 3H), 1.00-0.90 (m, 1H), 0.66-0.62 (m, 2H), 0.52-0.48 (m, 2H), 0.43-0.39 (m, 2H), 0.20-0.16 (m, 2H).

LCMS (method A), (M+H⁺) 449, Rt=5.38 min.

Example 31

(S)-1-ethyl-3-(4-(7-(4-fluorobenzyl)-4-(3-methylmorpholino)-5,6,7,8-tetrahydropyrido[3,4-d]pyrimidin-2-yl)phenyl)urea

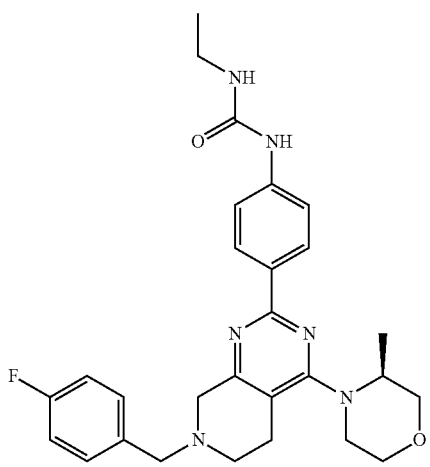 [SMILES: CCNC(=O)Nc1ccc(-c2nc3c(c(N4CCOC[C@@H]4C)n2)CCN(Cc2ccc(F)cc2)C3)cc1]

Method as described for example 26 using example 13 and 4-fluorobenzaldehyde as starting materials and DCM as solvent. Purified by flash chromatography (silica, 10 g, 50-100% EtOAc in petroleum ether (40-60)).

¹H NMR (CDCl₃) 8.29 (d, 2H), 7.33-7.38 (m, 4H), 7.03 (t, 2H), 6.34 (s, 1H), 4.70 (t, 1H), 4.08 (d, 1H), 3.94 (d, 1H), 3.81 (dd, 1H) 3.56-3.78 (m, 7H), 3.57 (ddd, 1H), 3.31 (q, 2H), 2.75-2.83 (m, 1H), 2.67-2.74 (br m, 2H), 2.53-2.62 (m, 1H), 1.31 (d, 3H), 1.16 (t, 3H).

LCMS (method A), (M+H⁺) 505, Rt=6.13 min.

Example 32

(S)-1-ethyl-3-(4-(4-(3-methylmorpholino)-6-(methylsulfonyl)-6,7-dihydro-5H-pyrrolo[3,4-d]pyrimidin-2-yl)phenyl)urea

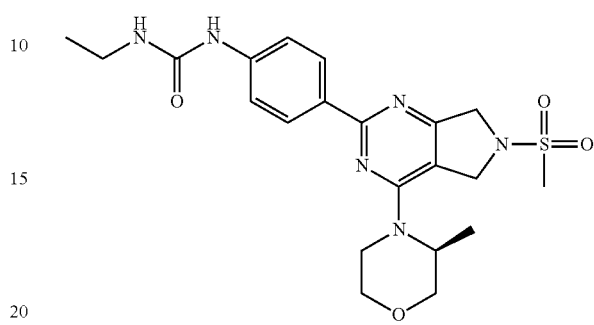

To a stirred solution of (S)-1-ethyl-3-(4-(4-(3-methylmorpholino)-6,7-dihydro-5H-pyrrolo[3,4-d]pyrimidin-2-yl)phenyl)urea (example 7) (60 mg, 0.16 mmol) in MeCN (1.5 mL) was added triethylamine (64 uL, 0.47 mmol) and methane sulfonyl chloride (36 uL, 0.47 mmol). The reaction mixture was stirred overnight at room temperature and concentrated in vacuo. The residue was partitioned between water and ethyl acetate. The organic layer was concentrated and the product isolated by Prep HPLC (low pH) as an off white/pink solid (36 mg, 0.078 mmol, 49% yield).

¹H NMR (d₆-DMSO) 8.72 (s, 1H), 8.17 (d, 2H), 7.47 (d, 2H), 6.20 (t, 1H), 4.88 (d, 1H), 4.76 (d, 1H), 4.50 (br s, 2H), 3.97-3.93 (m, 1H), 3.74 (d, 1H), 3.67-3.63 (m, 1H), 3.53-3.47 (m, 1H), 3.12-3.07 (m, 2H), 3.06 (s, 3H), 1.27 (d, 3H), 1.05 (t, 3H).

LCMS (method A), (M+H⁺) 461, Rt=7.51 min.

Example 33

(S)-2-(4-(3-cyclopropylureido)phenyl)-N-ethyl-4-(3-methylmorpholino)-5H-pyrrolo[3,4-d]pyrimidine-6(7H)-carboxamide

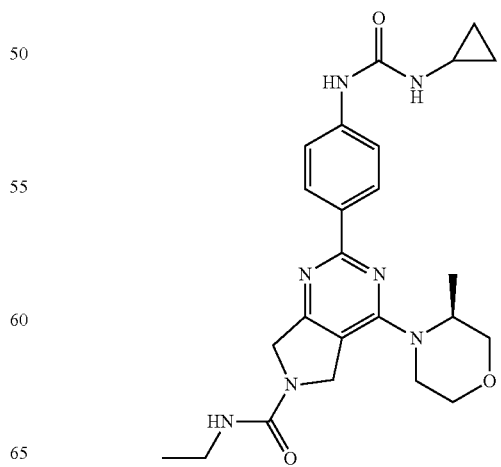

To a solution of (S)-1-cyclopropyl-3-(4-(4-(3-methylmorpholino)-6,7-dihydro-5H-pyrrolo[3,4-d]pyrimidin-2-yl)phenyl)urea (example 3) (50 mg 0.13 mmol) in dioxane (3 mL) at room temperature (20° C.) was added ethyl isocyanate (20 uL 0.26 mmol). The reaction mixture was stirred for 16 h. The solvent was removed in vacuo and the solid residue triturated with ether. The solid was collected by filtration and dried in vacuo to afford (32 mg 55%).

$^1$H NMR (d$_6$-DMSO) 8.53 (s, 1H), 8.18 (d, 2H), 7.48 (d, 2H), 6.45-6.41 (m, 2H), 4.71 (q, 2H), 4.45-4.35 (m, 1H), 4.42 (2, 2H), 4.28-4.10 (br m, 1H), 3.96 (br d, 1H), 3.75 (d, 1H), 3.67 (d, 1H), 3.52 (t, 1H), 3.34 (br t, 1H), 3.13 (qn, 2H), 2.60-2.52 (br m, 1H), 1.27 (d, 3H), 1.08 (t, 3H), 0.66-0.62 (m, 2H), 0.43-0.39 (m, 2H).

LCMS (method B), (M+H$^+$) 466, Rt=2.03 min

Example 34

(S)-ethyl 2-(4-(3-cyclopropylureido)phenyl)-4-(3-methylmorpholino)-5H-pyrrolo[3,4-d]pyrimidine-6(7H)-carboxylate

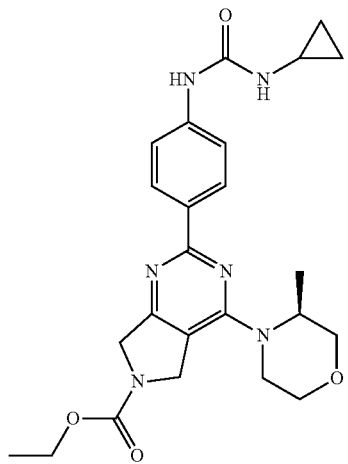 [SMILES: CCOC(=O)N1Cc2nc(-c3ccc(NC(=O)NC4CC4)cc3)nc(N3CCOC[C@@H]3C)c2C1]

To a solution of (S)-1-cyclopropyl-3-(4-(4-(3-methylmorpholino)-6,7-dihydro-5H-pyrrolo[3,4-d]pyrimidin-2-yl)phenyl)urea (example 3) (50 mg 0.13 mmol) in dioxane (3 mL) at room temperature (20° C.) was added sodium hydrogencarbonate (22 mg 0.26 mmol) followed by ethyl chloroformate (14 uL 0.15 mmol). The reaction mixture was stirred for 16 h. The solvent was removed in vacuo and the residue partitioned between DCM and water. The organic phase was passed through a 1 micron PTFE filter to dry and then evaporated in vacuo to afford (38 mg 64%).

$^1$H NMR (d$_6$-DMSO) 8.54 (s, 1H), 8.18 (d, 2H), 6.44 (d, 1H), 4.87-4.72 (m, 2H), 4.47 (d, 2H), 4.38 (br s, 1H), 4.17-4.12 (m, 3H), 3.96 (d, 1H), 3.75 (d, 1H) 3.66 (d, 1H), 3.51 (t, 1H), 3.34 (t, 1H), 2.58-2.52 (m, 1H), 1.27-1.22 (m, 6H), 0.66-0.61 (m, 2H), 0.43-0.39 (m, 2H).

LCMS (method B), (M+H$^+$) 467, Rt=2.26 min

Example 35

(S)-1-ethyl-3-(4-(7-methyl-4-(3-methylmorpholino)-5,6,7,8-tetrahydropyrido[3,4-d]pyrimidin-2-yl)phenyl)urea

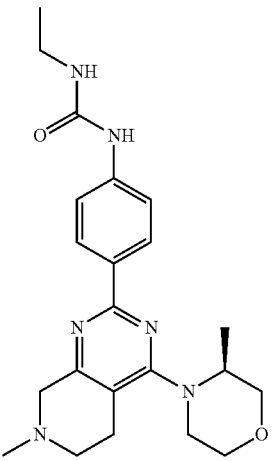 [SMILES: CCNC(=O)Nc1ccc(-c2nc3c(c(N4CCOC[C@@H]4C)n2)CCN(C)C3)cc1]

Method as described for example 26 using example 13 and formaldehyde as starting materials. Purified by flash chromatography (silica, 10 g, 5% MeOH in DCM).

$^1$H NMR (CDCl$_3$) 8.33 (d, 2H), 7.36 (d, 2H), 6.29 (s, 1H), 4.68 (t, 1H), 4.15-4.05 (m, 1H), 3.95 (dt, 1H), 3.83 (dd, 1H), 3.80-3.70 (m, 2H) 3.68 (dd, 1H), 3.59-3.47 (m, 3H), 3.37-3.28 (m, 2H), 2.81-2.65 (m, 3H), 2.54 (m, 1H), 2.49 (s, 3H), 1.30 (d, 3H), 1.17 (t, 3H).

LCMS (method A), (M+H$^+$) 411, Rt=5.13 min.

Example 36

(S)-1-cyclopropyl-3-(4-(6-ethyl-4-(3-methylmorpholino)-6,7-dihydro-5H-pyrrolo[3,4-d]pyrimidin-2-yl)phenyl)urea

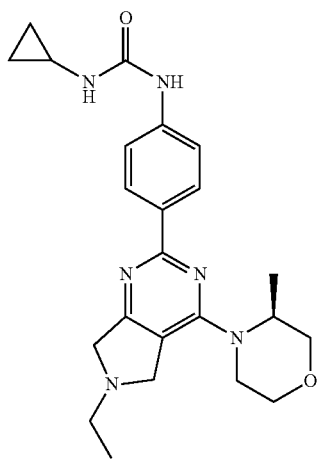 [SMILES: CCN1Cc2nc(-c3ccc(NC(=O)NC4CC4)cc3)nc(N3CCOC[C@@H]3C)c2C1]

Method as described for example 27 using example 3 and bromoethane as starting materials, Product isolated by Prep HPLC (low pH).

¹H NMR (d₆-DMSO) 8.55 (s, 1H), 8.17 (d, 2H), 7.47 (d, 2H), 6.47 (br s, 1H), 4.37 (br s, 1H), 4.08 (d, 2H), 4.00 (d, 1H), 3.93 (dd, 1H), 3.80-3.60 (m, 4H) 3.48 (td, 2H), 2.77-2.65 (m, 2H), 2.58-2.53 (m, 1H), 1.25 (d, 3H), 1.12 (t, 3H), 0.68-0.60 (m, 2H), 0.45-0.39 (m, 2H).
LCMS (method A), (M+H⁺) 423, Rt=5.60 min.

Example 37

(S)-1-(4-(7-(cyclopropylmethyl)-4-(3-methylmorpholino)-5,6,7,8-tetrahydropyrido[3,4-d]pyrimidin-2-yl)phenyl)-3-ethylurea

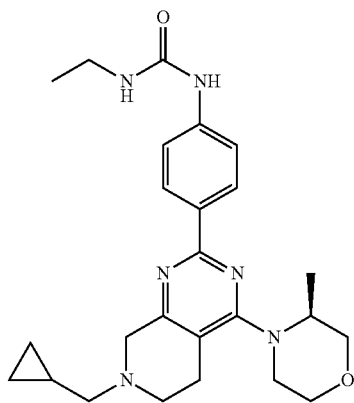 [SMILES: CCNC(=O)Nc1ccc(-c2nc3c(c(N4CCOC[C@@H]4C)n2)CCN(CC2CC2)C3)cc1]

Method as described for example 26 using example 13 and 2-cyclopropylacetaldehyde as starting materials and using DCM as solvent.
¹H NMR (CDCl₃) 8.33 (d, 2H), 7.36 (d, 2H), 6.41 (s, 1H), 4.75 (t, 1H), 4.15-4.05 (m, 1H), 3.98-3.88 (m, 2H), 3.81 (dd, 1H), 3.75 (dd, 1H), 3.73-3.57 (m, 3H) 3.56-3.50 (m, 1H), 3.36-3.27 (m, 2H), 2.92-2.84 (m, 1H), 2.83-2.68 (m, 2H), 2.68-2.59 (m, 1H), 2.53-2.40 (m, 2H), 1.31 (d, 3H), 1.16 (t, 3H), 1.05-0.94 (m, 1H), 0.60 (dd, 2H), 0.22 (dd, 2H).
LCMS (method A), (M+H⁺) 451, Rt=5.51 min.

Example 38

(S)-1-cyclopropyl-3-(4-(6-methyl-4-(3-methylmorpholino)-6,7-dihydro-5H-pyrrolo[3,4-d]pyrimidin-2-yl)phenyl)urea

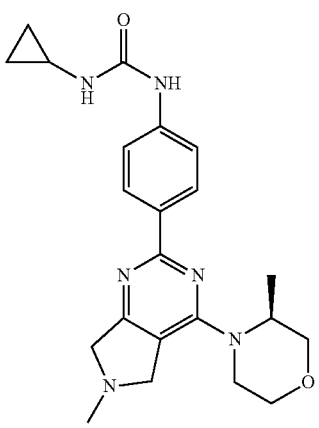 [SMILES: C[C@H]1COCCN1c1nc(-c2ccc(NC(=O)NC3CC3)cc2)nc2c1CN(C)C2]

Method as described for example 26 using example 3 and formaldehyde as starting materials. Purified by Prep HPLC (low pH).
¹H NMR (d₆-DMSO) 8.51 (s, 1H), 8.17 (d, 2H), 7.47 (d, 2H), 6.44 (br d, 1H), 4.35 (br s, 1H), 4.12-3.95 (m, 3H), 3.93 (dd, 1H), 3.80-3.60 (m, 4H) 3.49 (td, 2H), 2.58-2.53 (m, 1H), 1.25 (d, 3H), 0.67-0.61 (m, 2H), 0.44-038 (m, 2H).
LCMS (method A), (M+H⁺) 409, Rt=5.15 min.

Example 39

(S)-1-ethyl-3-(4-(6-ethyl-4-(3-methylmorpholino)-6,7-dihydro-5H-pyrrolo[3,4-d]pyrimidin-2-yl)phenyl)urea

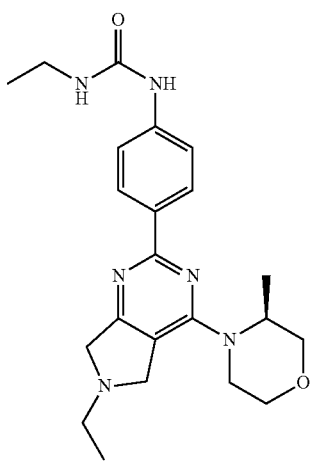 [SMILES: CCNC(=O)Nc1ccc(-c2nc3c(c(N4CCOC[C@@H]4C)n2)CN(CC)C3)cc1]

Method as described for example 27 using example 7 and bromoethane as starting materials. Purified by Prep HPLC (low pH).
¹H NMR (CDCl₃) 8.33 (s, 1H), 8.14 (d, 2H), 7.29 (d, 2H), 7.16 (br s, 1H), 4.38 (q, 2H), 4.26 (br s 1H), 4.12 (s 2H), 4.00 (dd, 2H), 3.78 (s, 2H) 3.65 (td, 1H), 3.40 (td, 1H), 3.31 (q, 2H), 3.05 (q, 2H) 1.37-1.29 (m, 6H), 1.17 (t, 3H).
LCMS (method A), (M+H⁺) 411, Rt=5.19 min.

Example 40

(S)-1-cyclopropyl-3-(4-(7-(cyclopropylmethyl)-4-(3-methylmorpholino)-5,6,7,8-tetrahydropyrido[3,4-d]pyrimidin-2-yl)phenyl)urea

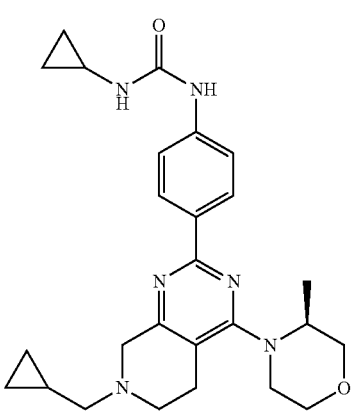 [SMILES: C[C@H]1COCCN1c1nc(-c2ccc(NC(=O)NC3CC3)cc2)nc2c1CCN(CC1CC1)C2]

Method as described for example 26 using example 15 and Cyclopropanecarboxaldehyde as starting materials and DCM as solvent.

¹H NMR (CDCl₃) 8.33 (d, 2H), 7.49 (d, 2H), 6.96 (s, 1H), 4.89 (s, 1H), 4.15-4.05 (m, 1H), 3.98-3.88 (m, 2H), 3.82 (dd, 1H), 3.75 (dd, 1H), 3.73-3.57 (m, 3H) 3.56-3.50 (m, 1H), 2.93-2.85 (m, 1H), 2.82-2.70 (m, 2H), 2.69-2.58 (m, 2H), 2.54-2.40 (m, 2H), 1.31 (d, 3H), 1.05-0.94 (m, 1H), 0.91-0.84 (m, 2H), 0.72-0.66 (m, 2H), 0.64-0.56 (m, 2H), 0.26-0.16 (m, 2H).

LCMS (method A), (M+H⁺) 463, Rt=5.57 min.

Example 41

(S)-1-cyclopropyl-3-(4-(4-(3-methylmorpholino)-7-neopentyl-5,6,7,8-tetrahydropyrido[3,4-d]pyrimidin-2-yl)phenyl)urea

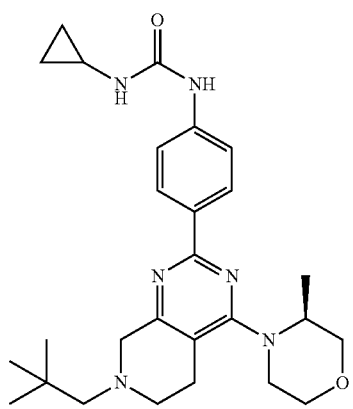 [SMILES: C[C@H]1COCCN1c1nc(-c2ccc(NC(=O)NC3CC3)cc2)nc2c1CCN(CC(C)(C)C)C2]

Method as described for example 26 using example 15 and pivaldehyde as starting materials and DCM as solvent.

¹H NMR (CDCl₃) 8.31 (d, 2H), 7.48 (d, 2H), 6.95 (s, 1H), 4.89 (s, 1H), 4.15-4.05 (m, 1H), 3.94 (dt, 1H), 3.90-3.80 (m, 2H), 3.80-3.70 (m, 2H), 3.70-3.57 (m, 2H) 3.58-3.47 (m, 1H), 2.84-2.75 (m, 1H), 2.74-2.69 (m, 3H), 2.68-2.60 (m, 1H), 2.29 (s, 2H), 1.34 (d, 3H), 0.94 (s, 9H), 0.90-0.83 (m, 2H), 0.72-0.66 (m, 2H).

LCMS (method A), (M+H⁺) 479, Rt=6.12 min.

Example 42

(S)-1-cyclopropyl-3-(4-(7-isobutyl-4-(3-methylmorpholino)-5,6,7,8-tetrahydropyrido[3,4-d]pyrimidin-2-yl)phenyl)urea

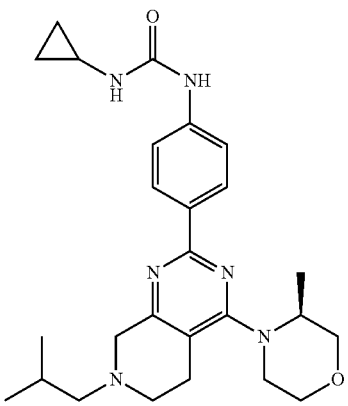 [SMILES: CC(C)CN1CCc2c(nc(-c3ccc(NC(=O)NC4CC4)cc3)nc2N2CCOC[C@@H]2C)C1]

Method as described for example 26 using example 15 and iso-butyraldehyde as starting materials and DCM as solvent.

¹H NMR (CDCl₃) 8.31 (d, 2H), 7.48 (d, 2H), 6.95 (s, 1H), 4.88 (s, 1H), 4.15-4.05 (m, 1H), 3.94 (dt, 1H), 3.82 (dd, 1H), 3.78-3.62 (m, 3H), 3.61-3.47 (m, 3H) 2.79-2.67 (m, 3H), 2.67-2.59 (m, 1H), 2.59-2.50 (m, 1H), 2.30 (d, 2H), 2.02-1.87 (m, 1H), 1.33 (d, 3H), 0.96 (d, 6H), 0.90-0.83 (m, 2H), 0.72-0.66 (m, 2H).

LCMS (method A), (M+H⁺) 465, Rt=5.65 min.

Example 43

(S)-1-cyclopropyl-3-(4-(7-isopropyl-4-(3-methylmorpholino)-5,6,7,8-tetrahydropyrido[3,4-d]pyrimidin-2-yl)phenyl)urea

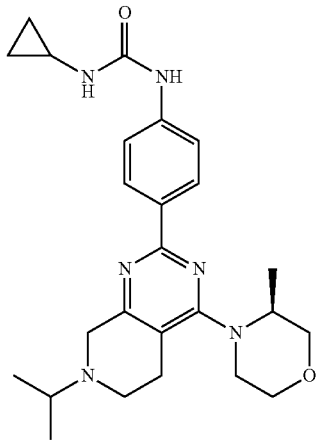 [SMILES: CC(C)N1CCc2c(nc(-c3ccc(NC(=O)NC4CC4)cc3)nc2N2CCOC[C@@H]2C)C1]

Method as described for example 26 using example 15 and acetone as starting materials and DCM as solvent.

¹H NMR (CDCl₃) 8.32 (d, 2H), 7.48 (d, 2H), 6.96 (s, 1H), 4.89 (s, 1H), 4.15-4.05 (m, 1H), 3.95 (dt, 1H), 3.86-3.78 (m, 2H), 3.78-3.67 (m, 2H), 3.66-3.58 (m, 2H), 3.55-3.47 (m, 1H), 2.99-2.86 (m, 1H), 2.86-2.80 (m, 1H), 2.75-2.70 (br m, 2H), 2.66-2.58 (m, 2H), 1.31 (d, 3H), 1.17 (d, 6H), 0.90-0.80 (m, 2H), 0.72-0.66 (m, 2H).

LCMS (method A), (M+H⁺) 451, Rt=5.50 min.

Example 44

(S)-1-cyclopropyl-3-(4-(6-isobutyryl-4-(3-methyl-morpholino)-6,7-dihydro-5H-pyrrolo[3,4-d]pyrimidin-2-yl)phenyl)urea

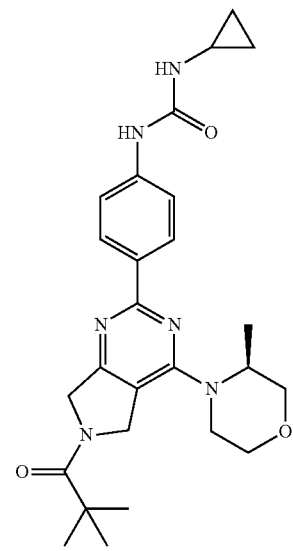 [SMILES: C[C@H]1COCCN1c1nc(-c2ccc(NC(=O)NC3CC3)cc2)nc2c1CN(C(=O)C(C)(C)C)C2]

Method as described for example 17 using example 3 and isobutyric acid. Purified by prep HPLC (low pH).

¹H NMR (d₆-DMSO) 8.59 (s, 1H), 8.19 (dd, 2H), 7.49 (dd, 2H), 6.50-6.48 (m, 1H), 5.05 (dd, 1H), 4.84-4.72 (m, 2H), 4.45 (br s, 1H), 4.40 (br s, 1H), 4.17-1.09 (m, 1H), 3.96 (br d, 1H), 3.75 (br d, 1H), 3.69-3.65 (m, 1H), 3.55-3.48 (m, 2H), 2.58-2.53 (m, 1H), 1.27 (d, 3H), 1.07 (d, 6H), 0.66-0.62 (m, 2H), 0.43-0.39 (m, 2H).

LCMS (method A), (M+H⁺) 465, Rt=7.51 min.

Example 45

(S)-1-cyclopropyl-3-(4-(4-(3-methylmorpholino)-6-pivaloyl-6,7-dihydro-5H-pyrrolo[3,4-d]pyrimidin-2-yl)phenyl)urea

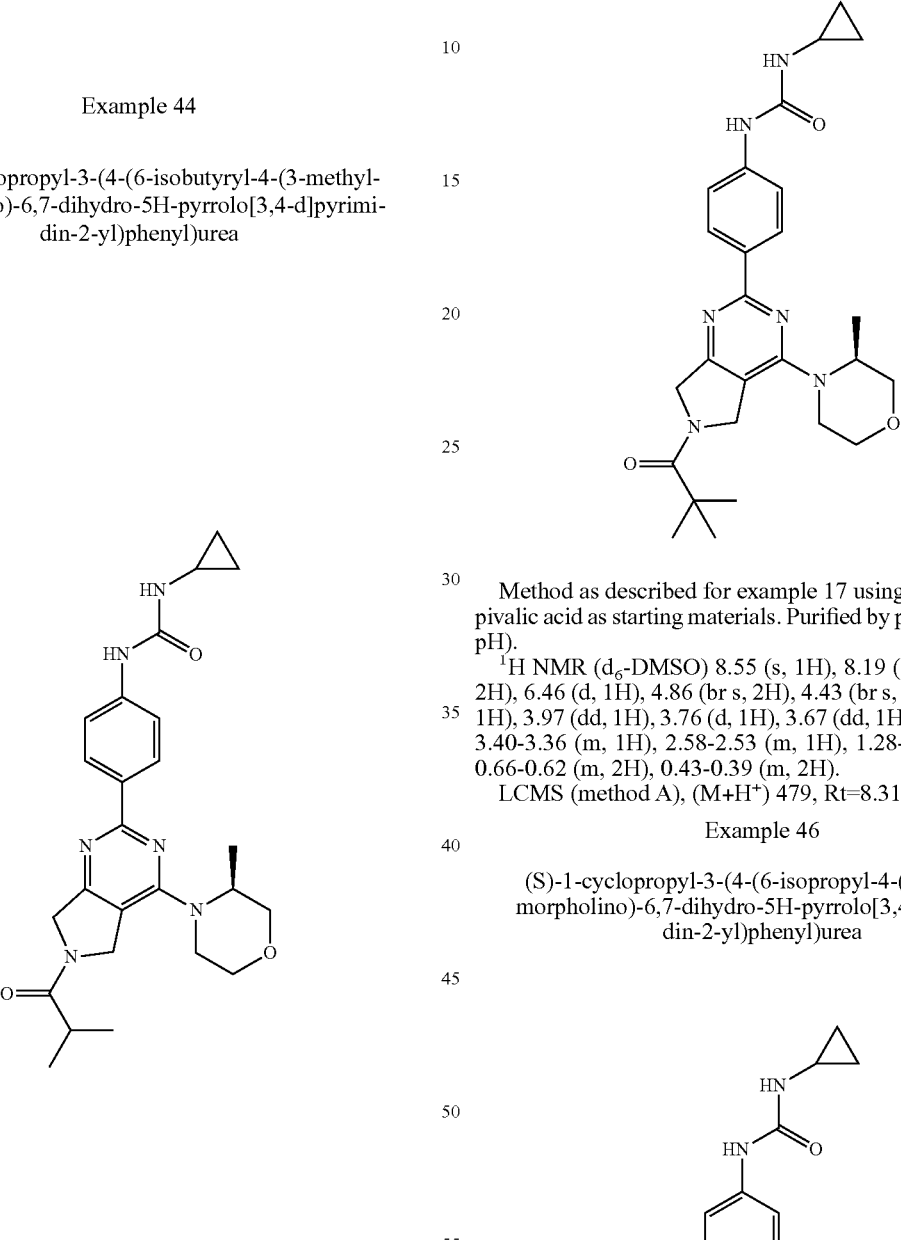

Method as described for example 17 using example 3 and pivalic acid as starting materials. Purified by prep HPLC (low pH).

¹H NMR (d₆-DMSO) 8.55 (s, 1H), 8.19 (d, 2H), 7.49 (d, 2H), 6.46 (d, 1H), 4.86 (br s, 2H), 4.43 (br s, 1H), 4.15 (br d, 1H), 3.97 (dd, 1H), 3.76 (d, 1H), 3.67 (dd, 1H), 3.52 (td, 1H), 3.40-3.36 (m, 1H), 2.58-2.53 (m, 1H), 1.28-1.26 (m, 12H), 0.66-0.62 (m, 2H), 0.43-0.39 (m, 2H).

LCMS (method A), (M+H⁺) 479, Rt=8.31 min.

Example 46

(S)-1-cyclopropyl-3-(4-(6-isopropyl-4-(3-methyl-morpholino)-6,7-dihydro-5H-pyrrolo[3,4-d]pyrimidin-2-yl)phenyl)urea

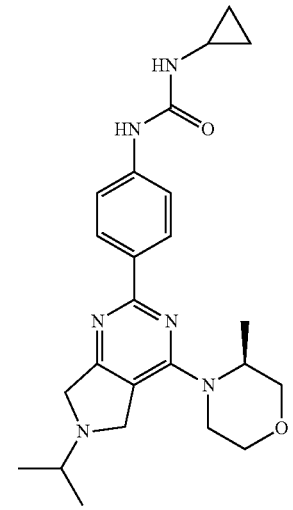 [SMILES: CC(C)N1Cc2nc(-c3ccc(NC(=O)NC4CC4)cc3)nc(N3CCOC[C@@H]3C)c2C1]

Method as described for example 26 using example 3 and acetone as starting materials. Purified by prep HPLC (low pH).

$^1$H NMR (d$_6$-DMSO) 8.59 (s, 1H), 8.17 (d, 2H), 7.48 (d, 2H), 6.51 (d, 1H), 4.40 (br s, 2H), 4.03 (d, 1H), 3.94 (dd, 1H), 3.81 (br s, 2H), 3.72 (d, 1H), 3.65 (dd, 1H), 3.50 (td, 1H), 3.32 (td, 1H), 2.58-2.76 (m, 1H), 2.58-2.53 (m, 1H), 1.25 (d, 3H), 1.13 (d, 6H), 0.66-0.62 (m, 2H), 0.43-0.40 (m, 2H).

LCMS (method A), (M+H$^+$) 437, Rt=5.41 min.

Intermediate 8

(S)-4-(2-chloro-6-(cyclopropylmethyl)-6,7-dihydro-5H-pyrrolo[3,4-d]pyrimidin-4-yl)-3-methylmorpholine

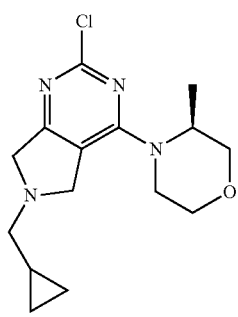 [SMILES: C[C@H]1COCCN1c1nc(Cl)nc2c1CN(CC1CC1)C2]

To a stirring solution of (S)-4-(2-chloro-6,7-dihydro-5H-pyrrolo[3,4-d]pyrimidin-4-yl)-3-methylmorpholine hydrochloride (intermediate 6) (870 mg, 3.01 mmol) in dichloroethane, was added cyclopropanecarboxaldehyde (450 uL, 6.02 mmol) and Et$_3$N (840 uL, 6.02 mmol). The reaction mixture was stirred at room temperature (20° C.) for 45 minutes, before adding sodium triacetoxy borohydride (1.28 g, 6.02 mmol). The reaction mixture was then stirred for a further 2 h at room temperature (20° C.) before partitioning between saturated NaHCO$_3$ solution and DCM. The organic layer was recovered, dried over MgSO$_4$, filtered and the solvent removed in vacuo, affording the title compound as a colourless oil (882 mg, 92% yield).

$^1$H NMR (CDCl$_3$) 4.08 (br s, 1H), 3.91-3.89 (m, 2H), 3.84-3.5 (dd, 2H), 3.69-3.67 (m, 2H), 3.52 (d, 1H), 3.39-3.32 (m, 1H), 3.25-3.16 (m, 1H), 2.43-2.38 (m, 2H), 1.16 (d, 3H), 0.81-0.69 (m, 1H), 0.43-0.35 (m, 2H), 0.26-0.01 (m, 2H).

LCMS (Method B), (M+H$^+$) 309, Rt=1.26 min

Example 47

(S)-1-(4-(6-(cyclopropylmethyl)-4-(3-methylmorpholino)-6,7-dihydro-5H-pyrrolo[3,4-d]pyrimidin-2-yl)phenyl)-3-methylurea

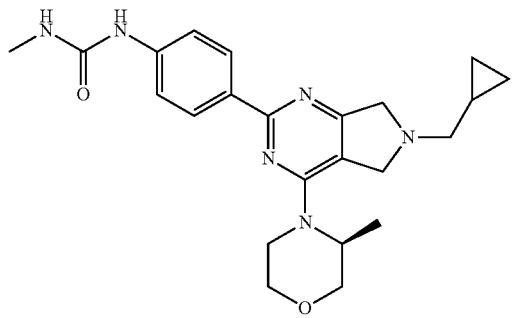 [SMILES: CNC(=O)Nc1ccc(-c2nc3c(c(N4CCOC[C@@H]4C)n2)CN(CC2CC2)C3)cc1]

To a solution of (S)-4-(2-chloro-6-(cyclopropylmethyl)-6,7-dihydro-5H-pyrrolo[3,4-d]pyrimidin-4-yl)-3-methylmorpholine (intermediate 8) (50 mg, 0.16 mmol) and 1-methyl-3-(4-(4,4,5,5-tetramethyl-1,3,2-dioxaborolan-2-yl)phenyl)urea (407 mg, 0.39 mmol) in DME/EtOH/H$_2$O (7:3:2) (5 mL) was added Pd(PPh$_3$)$_2$(Cl)$_2$ (7 mg, 0.008 mmol) and Na$_2$CO$_3$ (26 mg, 0.24 mmol). The reaction mixture was then heated by microwave at 130° C. for 30 minutes. The crude reaction mixture was then partitioned between water and EtOAc, the organic layer recovered, dried over MgSO$_4$, filtered and the solvent removed in vacuo. The residue was purified by prep. LCMS (low pH). The solvent was removed in vacuo. The residue was then re-purified by Flash SCX2 column chromatography, affording the title compound as a white solid (34.8 mg, 51% yield).

$^1$H NMR (CD$_3$OD) 8.33 (s, 1H), 8.22 (d, 2H), 7.48 (d, 2H), 4.57-4.45 (m, 3H), 4.23 (br s, 2H), 4.05-4.01 (dd, 1H), 3.82 (br s, 1H), 3.79 (d, 1H), 3.68-3.60 (m, 1H), 3.52-3.45 (m, 1H), 2.99 (d, 2H), 2.81 (s, 3H), 1.39 (d, 3H), 1.26 (br s, 1H), 1.21-1.09 (m, 1H), 0.75-0.68 (m, 2H), 0.41-0.37 (m, 2H).

LCMS (Method A), (M+H$^+$) 423, Rt=5.29 min.

Example 48

(S)-1-(4-(6-(cyclopropylmethyl)-4-(3-methylmorpholino)-6,7-dihydro-5H-pyrrolo[3,4-d]pyrimidin-2-yl)phenyl)urea

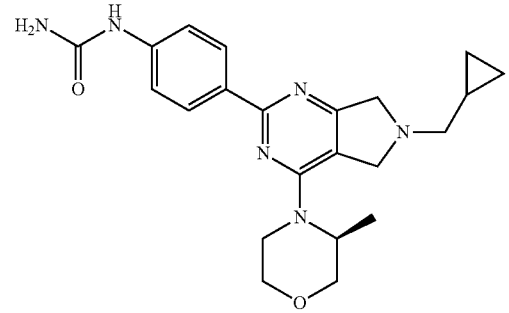 [SMILES: C[C@H]1COCCN1c1nc(-c2ccc(NC(N)=O)cc2)nc2c1CN(CC1CC1)C2]

Method as described for example 47 using intermediate 8 and 1-(4-(4,4,5,5-tetramethyl-1,3,2-dioxaborolan-2-yl)phenyl)urea as starting materials. Purified by prep. LCMS (high pH) and (low pH).

$^1$H NMR (CD$_3$OD) 8.26 (br s, 1H), 7.95 (d, 2H), 7.64 (d, 1H), 7.39 (d, 2H), 7.16 (d, 1H), 3.91 (d, 3H), 3.73-3.68 (d, 1H), 3.65-3.60 (dd, 1H), 3.54-3.46 (m, 2H), 1.33 (d, 3H), 1.22-1.11 (m, 1H), 0.52-0.45 (m, 2H), 0.32-0.27 (m, 2H).

LCMS (Method A), (M+H$^+$) 423, Rt=4.78 min.

Example 49

(S)-1-(4-(6-(cyclopropylmethyl)-4-(3-methylmorpholino)-6,7-dihydro-5H-pyrrolo[3,4-d]pyrimidin-2-yl)phenyl)-3-propylurea

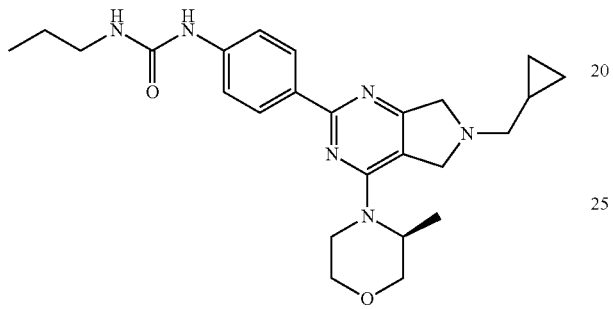

Method as described for example 47 using intermediate 8 and 1-propyl-3-(4-(4,4,5,5-tetramethyl-1,3,2-dioxaborolan-2-yl)phenyl)urea as starting materials. Purified by prep. LCMS (low pH).

$^1$H NMR (CD$_3$OD) 8.38 (br s, 1H), 8.12-8.07 (d, 2H), 7.38-7.32 (d, 2H), 4.43-4.28 (br s, 1H), 4.22-4.11 (m, 2H), 4.11-4.02 (m, 2H), 3.97-3.85 (m, 3H), 3.73-3.63 (m, 2H), 3.60-3.44 (m, 1H), 3.40-3.30 (m, 1H), 3.07 (t, 2H), 2.65 (d, 2H), 1.87 (s, 2H), 1.52-1.39 (m, 2H), 1.27 (d, 3H), 0.98-0.91 (m, 1H), 0.87 (t, 3H), 0.57-0.50 (m, 2H), 0.23-0.16 (m, 2H).

LCMS (Method A), (M+H$^+$) 451, Rt=5.98 min.

Example 50

(S)-1-(4-(6-(cyclopropylmethyl)-4-(3-methylmorpholino)-6,7-dihydro-5H-pyrrolo[3,4-d]pyrimidin-2-yl)phenyl)-3-isopropylurea

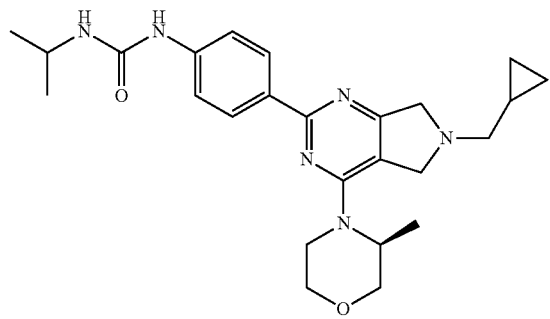 [SMILES: CC(C)NC(=O)Nc1ccc(-c2nc3c(c(N4CCOC[C@@H]4C)n2)CN(CC2CC2)C3)cc1]

Method as described for example 47 using intermediate 8 and 1-isopropyl-3-(4-(4,4,5,5-tetramethyl-1,3,2-dioxaborolan-2-yl)phenyl)urea as starting materials. Purified by prep. LCMS (low pH).

$^1$HNMR (CD$_3$OD) 8.09 (d, 2H), 7.34 (d, 2H), 4.41-4.29 (br s, 1H), 4.15-4.03 (m, 3H), 4.03-4.86 (m, 1H), 3.90 (dd, 1H), 3.85 (dd, 2H), 3.83-3.75 (m, 1H), 3.73-3.63 (m, 2H), 3.57-3.47 (m, 1H), 3.40-3.29 (m, 1H), 2.59 (d, 2H), 1.91 (s, 1H), 1.27 (d, 3H), 1.14-1.11 (m, 1H), 1.06 (d, 6H), 0.97-0.87 (m, 1H), 0.55-0.47 (m, 2H), 0.21-0.14 (m, 2H).

LCMS (Method A), (M+H$^+$) 451, Rt=5.75 min

Intermediate 9

(S)-4-(6-methyl-4-(3-methylmorpholino)-6,7-dihydro-5H-pyrrolo[3,4-d]pyrimidin-2-yl)aniline

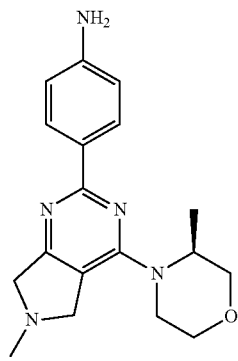 [SMILES: C[C@H]1COCCN1c1nc(-c2ccc(N)cc2)nc2c1CN(C)C2]

Step 1 Method as intermediate 7 using formaldehyde as starting material.

Step 2 Method as intermediate 5, using 4-(4,4,5,5-tetramethyl-1,3,2-dioxaborolan-2-yl)aniline and (S)-4-(2-chloro-6-methyl-6,7-dihydro-5H-pyrrolo[3,4-d]pyrimidin-4-yl)-3-methylmorpholine. The crude reaction mixture was partitioned between water and EtOAc, the phases separated and the organic layer dried over magnesium sulphate, filtered and the solvent removed in vacuo. The residue was purified by flash chromatography (0-15% MeOH/DCM), to yield a pale yellow oil (477 mg, 72%).

$^1$HNMR (CDCl$_3$) 8.12 (d, 2H), 6.63 (d, 2H), 4.32-4.21 (br s, 1H), 4.11-3.89 (m, 4H), 3.87-3.74 (m, 4H), 3.59-3.47 (m, 1H), 3.39-3.28 (m, 1H), 2.99 (s, 3H), 1.82-1.75 (m, 1H), 1.27 (d, 3H).

LCMS (Method B), (M+H$^+$) 325, Rt=0.81 min

Intermediate 10

(S)-phenyl 4-(6-methyl-4-(3-methylmorpholino)-6,7-dihydro-5H-pyrrolo[3,4-d]pyrimidin-2-yl)phenylcarbamate

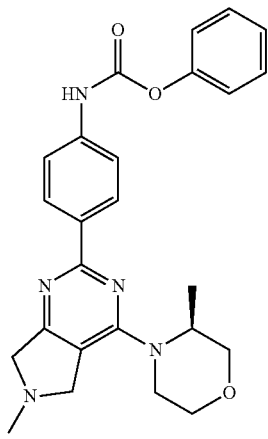 [SMILES: C[C@H]1COCCN1c1nc(-c2ccc(NC(=O)Oc3ccccc3)cc2)nc2c1CN(C)C2]

To a stirring solution of (S)-4-(6-methyl-4-(3-methylmorpholino)-6,7-dihydro-5H-pyrrolo[3,4-d]pyrimidin-2-yl)aniline (intermediate 9) (311 mg, 0.96 mmol) and NaHCO$_3$ (120 mg, 1.43 mmol) in dry THF, was added phenyl chloroformate (133 μL, 1.05 mmol) dropwise. The reaction mixture was stirred at room temperature (20° C.) for 2 hours, before partitioning the crude reaction mixture between water and EtOAc. The phases were separated and the organic layer dried over magnesium sulphate, filtered and then reduced in vacuo, affording the title compound as a pink solid (425 mg, 100%).

LCMS (Method B), (M+H$^+$) 446, Rt=1.95 min

Example 51

(S)-1-(3-hydroxypropyl)-3-(4-(6-methyl-4-(3-methylmorpholino)-6,7-dihydro-5H-pyrrolo[3,4-d]pyrimidin-2-yl)phenyl)urea

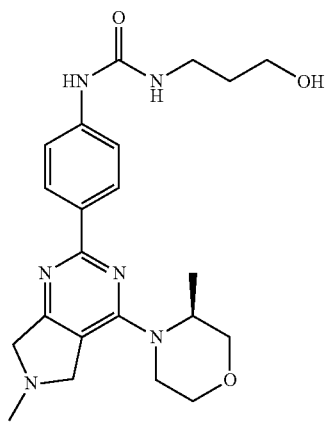 [SMILES: C[C@H]1COCCN1c1nc(-c2ccc(NC(=O)NCCCO)cc2)nc2c1CN(C)C2]

To a stirring solution of (S)-phenyl 4-(6-methyl-4-(3-methylmorpholino)-6,7-dihydro-5H-pyrrolo[3,4-d]pyrimidin-2-yl)phenylcarbamate (intermediate 10) (50 mg, 0.12 mmol) in dry DMF, was added Et$_3$N (51 μL, 0.36 mmol) and 3-aminopropan-1-ol (42 μL, 0.56 mmol). The reaction mixture was then heated at 50° C. for 2 hours. The solvent was then removed in vacuo and the crude residue was purified by prep. LCMS (high pH) affording the title compound as clear oil (12.5 mg, 0.029 mmol, 26%).

$^1$HNMR (CD$_3$OD) 8.17 (d, 2H), 7.48 (d, 2H), 4.45 (br s, 1H), 4.24-4.06 (m, 3H), 4.06-3.98 (m, 1H), 3.93-3.73 (m, 4H), 3.72-3.57 (m, 3H), 3.51-3.39 (m, 1H), 3.35 (d, 1H), 2.64 (s, 3H), 1.83-1.72 (m, 2H), 1.38 (d, 3H).

LCMS (Method A), (M+H$^+$) 426, Rt=4.70 min.

Example 52

(S)-1-(4-fluorophenyl)-3-(4-(6-methyl-4-(3-methylmorpholino)-6,7-dihydro-5H-pyrrolo[3,4-d]pyrimidin-2-yl)phenyl)urea

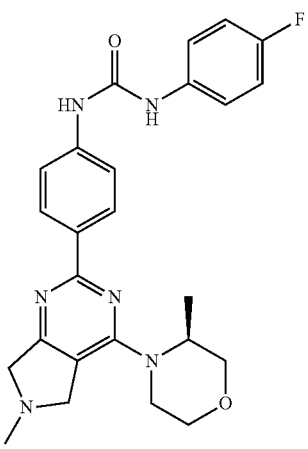 [SMILES: C[C@H]1COCCN1c1nc(-c2ccc(NC(=O)Nc3ccc(F)cc3)cc2)nc2c1CN(C)C2]

Method as described for example 51 using intermediate 10 and 4-fluoroaniline as starting materials. Purified by prep. LCMS (high pH).

$^1$H NMR 8.35 (br s, 1H), 8.27, (d, 2H), 7.53, (d, 2H), 7.48-7.43 (m, 2H), 7.10-7.02 (m, 2H), 4.45 (br s, 1H), 4.38-4.27 (m, 2H), 4.17 (br d, 1H), 4.10-3.99 (m, 3H), 3.86-3.75 (m, 2H), 3.68-3.59 (m, 1H), 3.53-3.43 (m, 1H), 2.77 (s, 3H), 1.39 (d, 3H),

LCMS (Method A), (M+H$^+$) 463, Rt=6.21 min.

Example 53

(S)-1-(3-methoxypropyl)-3-(4-(6-methyl-4-(3-methylmorpholino)-6,7-dihydro-5H-pyrrolo[3,4-d]pyrimidin-2-yl)phenyl)urea

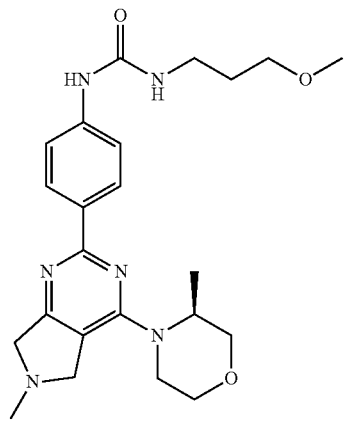

Method as described for example 51 using intermediate 10 and 3-methoxypropylamine as starting materials. Purified by prep. LCMS (high pH).
$^1$H NMR (CD$_3$OD) 8.38 (br s, 1H), 8.21 (d, 2H), 7.47 (d, 2H), 4.49-4.40 (br s, 1H), 4.32-4.22 (m, 2H), 4.21-4.13 (m, 1H), 4.06-3.97 (m, 3H), 3.85-3.74 (m, 2H), 3.68-3.58 (m, 1H), 3.54-3.43 (m, 3H), 2.74 (s, 3H), 1.86-1.75 (m, 2H), 1.39 (d, 3H),
LCMS (Method B), (M+H$^+$) 440, Rt=1.63 min.

Example 54

(S)-1-(2-(dimethylamino)ethyl)-3-(4-(6-methyl-4-(3-methylmorpholino)-6,7-dihydro-5H-pyrrolo[3,4-d]pyrimidin-2-yl)phenyl)urea

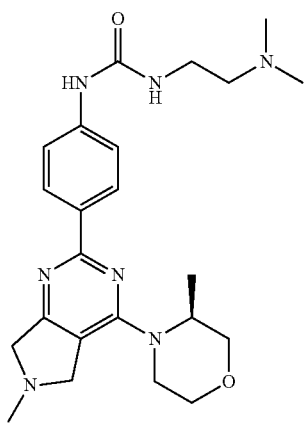

Method as described for example 51 using intermediate 10 and N1,N1-dimethylethane-1,2-diamine as starting materials. Purified by prep. LCMS (high pH).
$^1$H NMR (CD$_3$OD) 8.21 (d, 2H), 7.48 (d, 2H), 4.44 (br s, 1H), 4.24-4.06 (m, 3H), 4.06-3.98 (m, 1H), 3.92-3.73 (m, 4H), 3.69-3.57 (m, 1H), 3.50-3.40 (m, 1H), 3.39-3.33 (t, 2H), 2.63 (s, 3H), 2.51 (t, 2H), 2.31 (s, 6H), 1.39 (d, 3H)
LCMS (Method A), (M+H$^+$) 439, Rt=7.71 min.

Example 55

(S)-1-cyclobutyl-3-(4-(6-methyl-4-(3-methylmorpholino)-6,7-dihydro-5H-pyrrolo[3,4-d]pyrimidin-2-yl)phenyl)urea

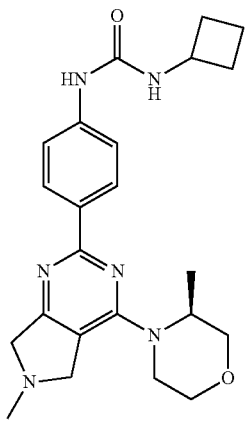 [SMILES: C[C@H]1COCCN1c1nc(-c2ccc(NC(=O)NC3CCC3)cc2)nc2c1CN(C)C2]

Method as described for example 51 using intermediate 10 and cyclobutanamine as starting materials. Purified by prep. LCMS (high pH).
$^1$H NMR (CD$_3$OD) 8.36 (br s, 1H), 8.20 (d, 2H), 7.45 (d, 2H), 4.48-4.32 (m, 3H), 4.31-4.19 (m, 1H), 4.19-3.97 (m, 4H), 3.86-3.72 (m, 2H), 3.68-3.58 (m, 1H), 3.52-3.40 (m, 1H), 2.83 (s, 3H), 2.40-2.28 (m, 2H), 2.01-1.88 (m, 2H), 1.80-1.67 (m, 2H), 1.38 (d, 3H).
LCMS (Method A), (M+H$^+$) 422, Rt=5.63 min.

Example 56

(S)-1-(4-(7-(cyclopropanecarbonyl)-4-(3-methylmorpholino)-5,6,7,8-tetrahydropyrido[3,4-d]pyrimidin-2-yl)phenyl)-3-ethylurea

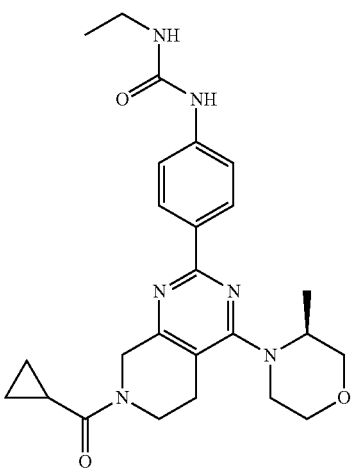 [SMILES: CCNC(=O)Nc1ccc(-c2nc3c(c(N4CCOC[C@@H]4C)n2)CCN(C(=O)C2CC2)C3)cc1]

To a stirred solution of (S)-1-ethyl-3-(4-(4-(3-methylmorpholino)-5,6,7,8-tetrahydropyrido[3,4-d]pyrimidin-2-yl)phenyl)urea 2,2,2-trifluoroacetate (100 mg, 0.20 mmol) in DCM was added $^{i}Pr_2NEt$ (70 uL, 0.40 mmol) and cyclopropanecarbonyl chloride (20 uL, 0.22 mmol). The reaction mixture was stirred at room temperature for 16 h. The reaction mixture was concentrated and purified by prep. HPLC to give a white solid (14 mg, 0.03 mmol, 15% yield).

$^1$H NMR (d$_6$-DMSO) 8.66 (s, 1H), 8.18 (d, 2H), 7.48 (d, 2H), 6.17 (t, 1H), 4.86 (br dd, 1H), 4.58 (br dd, 1H), 4.16-4.10 (m, 1H), 3.98-3.34 (m, 8H), 3.12 (q, 2H), 2.80-2.74 (m 1H), 2.69-2.57 (m, 1H), 2.14-2.07 (m, 1H), 1.26 (d, 3H), 1.06 (t, 3H), 0.78-0.76 (m, 4H).

LCMS (method A), (M+H$^+$) 465, Rt=6.46 min.

Example 57

(S)-1-ethyl-3-(4-(7-isobutyryl-4-(3-methylmorpholino)-5,6,7,8-tetrahydropyrido[3,4-d]pyrimidin-2-yl)phenyl)urea

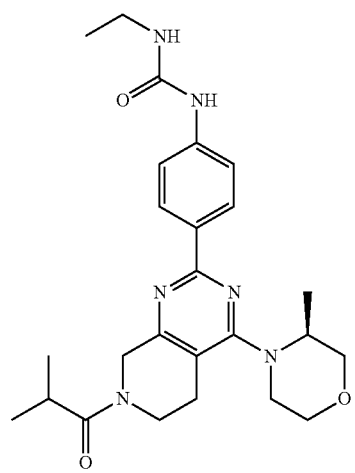 [SMILES: CCNC(=O)Nc1ccc(-c2nc3c(c(N4CCOC[C@@H]4C)n2)CCN(C(=O)C(C)C)C3)cc1]

Method as described for example 56 using example 13 TFA salt and isobutyryl chloride as starting materials. The reaction mixture was concentrated and purified by prep. HPLC to give a white solid (19 mg, 0.04 mmol, 21% yield).

$^1$H NMR (d$_6$-DMSO) 8.66 (s, 1H), 8.18 (d, 2H), 7.48 (d, 2H), 6.17 (t, 1H), 4.75-4.45 (m, 2H), 4.17-4.08 (m, 1H), 3.87 (d, 1H), 3.81-3.37 (m, 7H), 3.12 (q, 2H), 3.04-2.95 (m 1H), 2.77-2.70 (m, 1H), 2.64-2.57 (m, 1H), 1.26 (d, 3H), 1.08-1.03 (m, 9H).

LCMS (method A), (M+H$^+$) 467, Rt=6.65 min.

Example 58

(S)-1-ethyl-3-(4-(4-(3-methylmorpholino)-7-pivaloyl-5,6,7,8-tetrahydropyrido[3,4-d]pyrimidin-2-yl)phenyl)urea

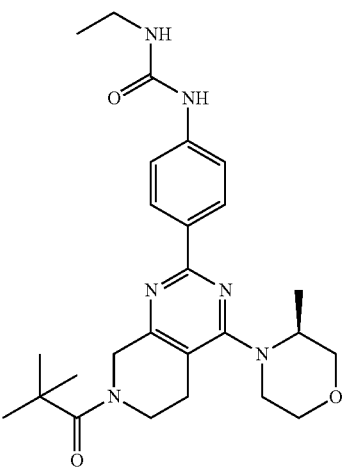 [SMILES: CCNC(=O)Nc1ccc(-c2nc3c(c(N4CCOC[C@@H]4C)n2)CCN(C(=O)C(C)(C)C)C3)cc1]

Method as described for example 56 using example 13 TFA salt and pivoyl chloride as starting materials The reaction mixture was concentrated and purified by prep. HPLC to give a white solid (7 mg, 0.01 mmol, 7% yield).

$^1$H NMR (d$_6$-DMSO) 8.68 (s, 1H), 8.17 (d, 2H), 7.49 (d, 2H), 6.17 (t, 1H), 4.70-4.53 (m, 2H), 4.22-4.13 (m, 1H), 3.89-3.38 (m, 10H), 3.12 (q, 2H), 2.73-2.65 (m, 2H), 1.28-1.26 (m 9H), 1.06 (t, 3H).

LCMS (method A), (M+H$^+$) 481, Rt=7.01 min.

Example 59

(S)-1-(4-(7-acetyl-4-(3-methylmorpholino)-5,6,7,8-tetrahydropyrido[3,4-d]pyrimidin-2-yl)phenyl)-3-ethylurea

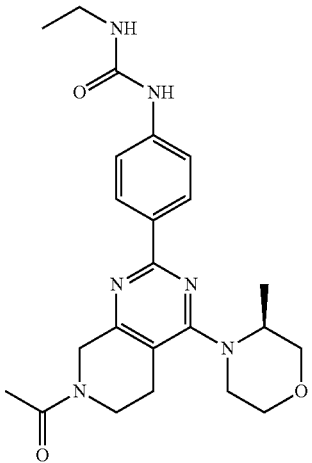 [SMILES: CCNC(=O)Nc1ccc(-c2nc3c(c(N4CCOC[C@@H]4C)n2)CCN(C(C)=O)C3)cc1]

Method as described for example 56 using example 13 TFA salt and acetyl chloride as starting materials The reaction

Example 60

(S)-1-(4-(7-(cyclopropanecarbonyl)-4-(3-methylmorpholino)-5,6,7,8-tetrahydropyrido[3,4-d]pyrimidin-2-yl)phenyl)-3-cyclopropylurea

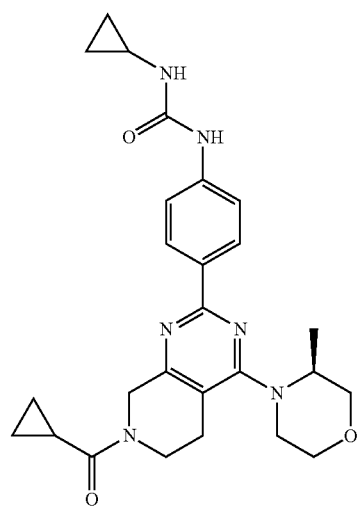 [SMILES: C[C@H]1COCCN1c1nc(-c2ccc(NC(=O)NC3CC3)cc2)nc2c1CCN(C(=O)C1CC1)C2]

To a stirred solution of (S)-1-cyclopropyl-3-(4-(4-(3-methylmorpholino)-5,6,7,8-tetrahydropyrido[3,4-d]pyrimidin-2-yl)phenyl)urea 2,2,2-trifluoroacetate (106 mg, 0.26 mmol) in DCM was added $^i$Pr$_2$NEt (91 uL, 0.52 mmol) and cyclopropane carbonyl chloride (26 uL, 0.29 mmol). The reaction mixture was stirred at room temperature for 16 h. The reaction mixture was concentrated and triturated from Et$_2$O:MeOH (10:1) to give a white solid (69 mg, 0.15 mmol, 58% yield).

$^1$H NMR (d$_6$-DMSO) 8.54 (s, 1H), 8.19 (d, 2H), 7.50 (d, 2H), 6.45 (s, 1H), 4.94-4.48 (m, 2H), 4.15-4.10 (m, 1H), 4.01-3.38 (m, 8H), 2.81-2.74 (m, 1H), 2.68-2.59 (m, 1H), 2.58-2.53 (m, 1H), 2.16-2.06 (m, 1H), 1.27-1.26 (d, 3H), 0.79-0.77 (m, 4H), 0.67-0.62 (m, 2H), 0.44-0.40 (m, 2H).

LCMS (method A), (M+H$^+$) 477, Rt=6.59 min.

Example 61

(S)-1-cyclopropyl-3-(4-(7-isobutyryl-4-(3-methylmorpholino)-5,6,7,8-tetrahydropyrido[3,4-d]pyrimidin-2-yl)phenyl)urea

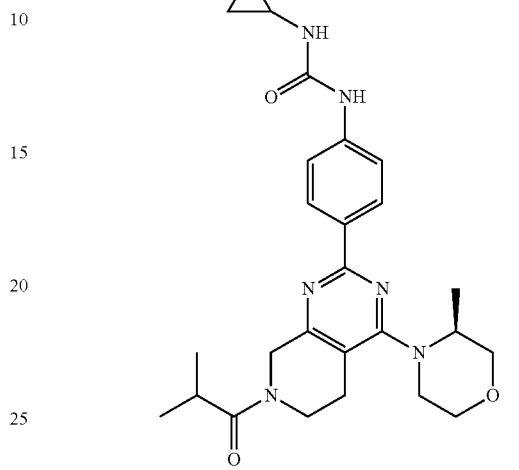

Method as described for example 60 using example 15 TFA salt and isobutyryl chloride as starting materials. The reaction mixture was concentrated and triturated from Et$_2$O:MeOH (10:1) to give a white solid (87 mg, 0.18 mmol, 70% yield).

$^1$H NMR (d$_6$-DMSO) 8.54 (s, 1H), 8.19 (d, 2H), 7.50 (d, 2H), 6.45 (s, 1H), 4.78-4.45 (m, 2H), 4.17-4.08 (m, 1H), 3.92-3.38 (m, 8H), 3.05-2.97 (m, 1H), 2.78-2.71 (m, 1H), 2.68-2.59 (m, 1H), 2.58-2.54 (m, 1H), 1.27-1.26 (d, 3H), 1.08 (m, 6H), 0.67-0.62 (m, 2H), 0.44-0.40 (m, 2H).

LCMS (method A), (M+H$^+$) 479, Rt=6.78 min.

Example 62

(S)-1-(4-(7-acetyl-4-(3-methylmorpholino)-5,6,7,8-tetrahydropyrido[3,4-d]pyrimidin-2-yl)phenyl)-3-cyclopropylurea

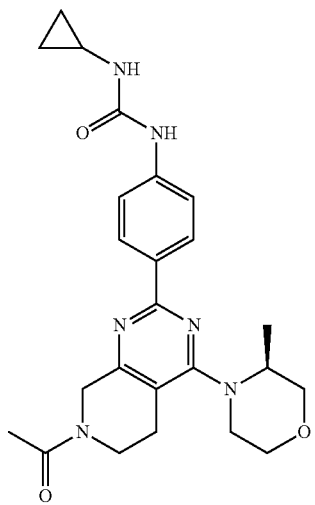 [SMILES: CC(=O)N1CCc2c(nc(-c3ccc(NC(=O)NC4CC4)cc3)nc2N2CCOC[C@@H]2C)C1]

mixture was concentrated and purified by prep. HPLC to give a white solid (20 mg, 0.05 mmol, 23% yield).

$^1$H NMR (d$_6$-DMSO) 8.79 (d, 1H), 8.18 (d, 2H), 7.49 (d, 2H), 6.34-6.29 (m, 1H), 4.69-4.44 (m, 2H), 4.12-4.10 (m, 1H), 3.90-3.87 (m, 1H), 3.82-3.51 (m, 7H), 3.15-3.09 (q, 2H), 2.76-2.74 (m 1H), 2.67-2.57 (m, 1H), 2.13 (s, 3H), 1.26 (t, 3H), 1.06 (t, 3H).

LCMS (method A), (M+H$^+$) 439, Rt=5.95 min.

85

Method as described for example 60 using example 15 TFA salt and acetylchloride as starting materials. The reaction mixture was concentrated and triturated from Et₂O:MeOH (10:1) to give a white solid (69 mg, 0.15 mmol, 58% yield).

¹H NMR (d₆-DMSO) 8.54 (s, 1H), 8.19 (dd, 2H), 7.50 (dd, 2H), 6.45 (br t, 1H), 4.70-4.44 (m, 2H), 4.15-4.07 (m, 1H), 3.90-3.87 (m, 1H), 3.83-3.71 (m, 2H), 3.64-3.53 (m, 4H), 3.49-3.39 (m, 1H), 2.75 (br t, 1H), 2.65-2.58 (m, 1H), 2.59-2.52 (m, 1H), 2.13 (s, 3H), 1.26 (t, 3H), 0.67-0.62 (m, 2H), 0.44-0.40 (m, 2H).

LCMS (method A), (M+H⁺) 451, Rt=6.05 min.

Example 63 tert-butyl 2-(4-(3-ethylureido)phenyl)-4-morpholino-5H-pyrrolo[3,4-d]pyrimidine-6(7H)-carboxylate

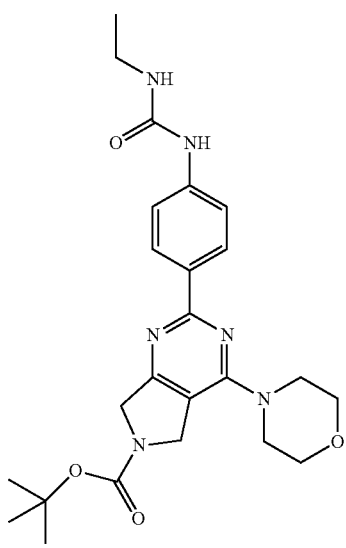 [SMILES: CCNC(=O)Nc1ccc(-c2nc3c(c(N4CCOCC4)n2)CN(C(=O)OC(C)(C)C)C3)cc1]

To a solution of tert-butyl 2-chloro-4-morpholino-5H-pyrrolo[3,4-d]pyrimidine-6(7H)-carboxylate (intermediate 2) (300 mg, 0.88 mmol) and 4-(3-ethylureido)phenylboronic acid pinacol ester (281 mg, 0.97 mmol) in CPME/EtOH/H₂O (7/2/3) (4.0 mL) was added Pd(PPh₃)₂(Cl)₂ (31 mg, 0.04 mmol) and Na₂CO₃ (140 mg, 1.32 mmol). The reaction mixture was then heated by microwave at 130° C. for 0.5 h. The crude reaction mixture was then partitioned between water and EtOAc, the phases separated and the solvent removed in vacuo. The residue was purified by flash chromatography (0-40% EtOAc/Petroleum Ether 40-60) to yield an off-white solid (275 mg, 67%).

¹H NMR (d₆-DMSO) 8.66 (br s, 1H), 8.16-8.20 (m, 2H), 7.48 (d, 2H), 6.17 (t, 1H), 4.76 (br s, 2H), 4.43 (br d, 2H), 3.72 (s, 8H), 3.08-3.16 (m, 2H), 1.47 (s, 9H), 1.06 (t, 3H).

LCMS (method A), (M+H⁺) 469, Rt=8.44 min.

86

Intermediate 11

(S)-ethyl 2-chloro-4-(3-methylmorpholino)-5H-pyrrolo[3,4-d]pyrimidine-6(7H)-carboxylate

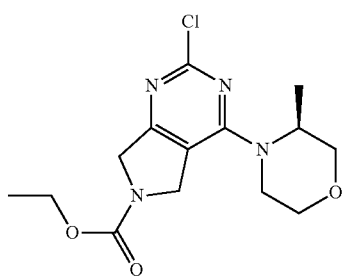 [SMILES: CCOC(=O)N1Cc2nc(Cl)nc(N3CCOC[C@@H]3C)c2C1]

(S)-4-(2-chloro-6,7-dihydro-5H-pyrrolo[3,4-d]pyrimidin-4-yl)-3-methylmorpholine hydrochloride (intermediate 6) (330 mg, 1.3 mmol), was dissolved in dry THF with srirring and treated with ethyl chloroformate (136 uL, 1.4 mmol) and NaHCO₃ (218 mg, 2.6 mmol) at room temperature (20° C.) overnight. The mixture was concentrated in vacuo and the residue purified by flash chromatography using a mixture of 0-100% petrol ether/ethyl acetate as eluent, yielding the title compound (475 mg, 1.46 mmol, 41%).

LCMS (Method B), (M+H⁺) 327,329, Rt=2.37 min.

Intermediate 12

(S)-4-(2-chloro-6-methyl-6,7-dihydro-5H-pyrrolo[3,4-d]pyrimidin-4-yl)-3-methylmorpholine

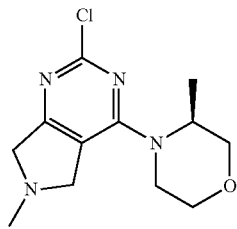 [SMILES: C[C@H]1COCCN1c1nc(Cl)nc2c1CN(C)C2]

Method as intermediate 8 using (S)-4-(2-chloro-6,7-dihydro-5H-pyrrolo[3,4-d]pyrimidin-4-yl)-3-methylmorpholine hydrochloride (intermediate 6) and formaldehyde as starting materials.

Intermediate 13

(S)-4-(2-chloro-7-methyl-5,6,7,8-tetrahydropyrido[3,4-d]pyrimidin-4-yl)-3-methylmorpholine

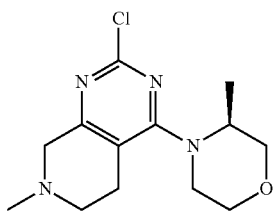 [SMILES: C[C@H]1COCCN1c1nc(Cl)nc2c1CCN(C)C2]

Method as described for intermediate 8 using formaldehyde (37% solution in water) and (S)-4-(2-chloro-5,6,7,8-tetrahydropyrido[3,4-d]pyrimidin-4-yl)-3-methylmorpholine hydrochloride as starting materials. The mixture was partitioned between saturated NaHCO$_3$ solution and DCM. The organic layer was recovered, dried over MgSO$_4$, filtered and reduced in vacuo, yielding the title compound (2.11 g, 7.47 mmol, 78%).

LCMS (Method B), (M+H$^+$) 283,285, Rt=0.73 min

Intermediate 14

2-(3-(4-(4,4,5,5-tetramethyl-1,3,2-dioxaborolan-2-yl)phenyl)ureido)acetamide

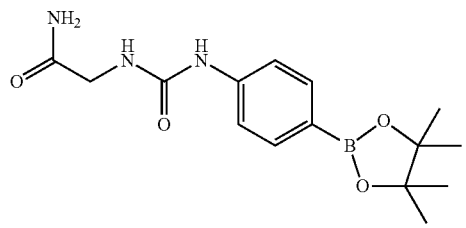 [SMILES: CC1(C)OB(c2ccc(NC(=O)NCC(N)=O)cc2)OC1(C)C]

2-(4-isocyanatophenyl)-4,4,5,5-tetramethyl-1,3,2-dioxaborolane (300 mg, 1.22 mmol) was dissolved in dry THF and stirred with 2-aminoacetamide hydrochloride (108 mg, 1.46 mmol) and triethylamine (drops) at 60° C. overnight. The mixture was reduced in vacuo, yielding the title compound (345 mg, 1.08 mmol, 88%).

LCMS (Method B), (M+H$^+$) 320 Rt=2.19 min

Intermediate 15

1-(5-methylisoxazol-3-yl)-3-(4-(4,4,5,5-tetramethyl-1,3,2-dioxaborolan-2-yl)phenyl)urea

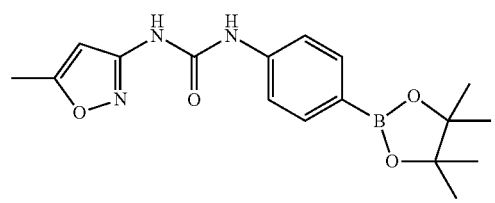

4-(4,4,5,5-tetramethyl-1,3,2-dioxaborolan-2-yl)aniline (100 mg, 0.46 mmol), and triphosgene (47 mg, 0.16 mmol) were dissolved in a mixture of dry pyridine:DCM (4:1) and stirred at room temperature (20° C.) under nitrogen atmosphere for 1 h. 5-methylisoxazol-3-amine (49 mg, 0.50 mmol) dissolved in dry DCM was added dropwise, and stirring allowed overnight. Saturated NaHCO$_3$ solution was added to the reaction mixture, and stirring allowed for 15 mins before partitioning between water and DCM. The organic layer was recovered, dried over MgSO$_4$, filtered and solvent removed in vacuo, affording the title compound (155 mg, 0.45 mmol, 99% yield).

LCMS (Method B), (M+H$^+$) 344, Rt=2.89 min

Intermediate 16

(S)-2-fluoro-4-(6-methyl-4-(3-methylmorpholino)-6,7-dihydro-5H-pyrrolo[3,4-d]pyrimidin-2-yl)aniline

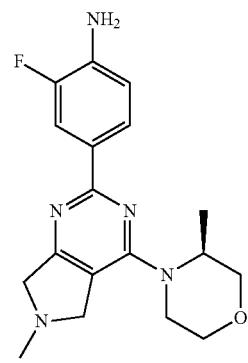

Method as described for intermediate 5 using 2-fluoro-4-(4,4,5,5-tetramethyl-1,3,2-dioxaborolan-2-yl)aniline as starting material. The crude reaction mixture was filtered through a celite 545 pre-packed cartridge (2.5 g), washed with MeOH and solvent removed in vacuo. The residue was purified by flash SCX2 chromatography affording the title compound (139 mg, 0.40 mmol, 98%).

LCMS (Method B), (M+H$^+$) 344, Rt=1.51 min.

Intermediate 17

(S)-tert-butyl 2-(4-amino-3-fluorophenyl)-4-(3-methylmorpholino)-5H-pyrrolo[3,4-d]pyrimidine-6(7H)-carboxylate

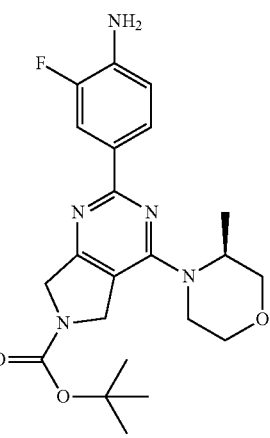

Method as intermediate 5 using (S)-tert-butyl 2-chloro-4-(3-methylmorpholino)-5H-pyrrolo[3,4-d]pyrimidine-6(7H)-carboxylate (intermediate 1) and 2-fluoro-4-(4,4,5,5-tetramethyl-1,3,2-dioxaborolan-2-yl)aniline as starting materials. The crude reaction mixture was then partitioned between water and EtOAc, the phases separated and the organic layer washed with brine, dried over magnesium sulfate, filtered and the solvent removed in vacuo. The residue was purified by flash chromatography (0-80% EtOAc/Petroleum Ether 40-60) to yield a white solid (660 mg, 1.54 mmol, 22%).

LCMS (Method B), (M+H$^+$) 430, Rt=2.62 min

Intermediate 18

(S)-1-ethyl-3-(2-fluoro-4-(4-(3-methylmorpholino)-6,7-dihydro-5H-pyrrolo[3,4-d]pyrimidin-2-yl)phenyl)urea hydrochloride

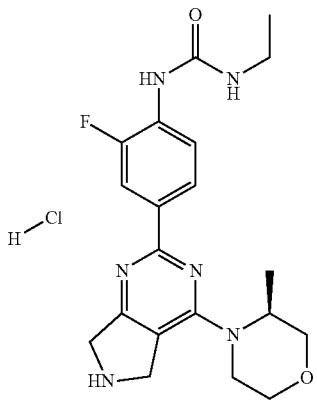 [SMILES: Cl ; CCNC(=O)Nc1ccc(-c2nc3c(c(N4CCOC[C@@H]4C)n2)CNC3)cc1F]

Step 1: To a stirring solution of (S)-tert-butyl 2-(4-amino-3-fluorophenyl)-4-(3-methylmorpholino)-5H-pyrrolo[3,4-d]pyrimidine-6(7H)-carboxylate (intermediate 17) (660 mg, 1.54 mmol) in THF was added ethyl isocyanate (183 µL, 2.31 mmol). The reaction mixture was stirred at 60° C. until analysis by LCMS indicated that reaction was complete. The solvent then was removed in vacuo. Purified by flash chromatography using 0-100% Ethyl acetate/Petroleum Ether 40-60 to yield a yellow solid (510 mg, 1.02 mmol, 66%).

LCMS (Method B), (M+H$^+$) 501, Rt=2.88 min.

Step 2: (S)-tert-butyl 2-(4-(3-ethylureido)-3-fluorophenyl)-4-(3-methylmorpholino)-5H-pyrrolo[3,4-d]pyrimidine-6(7H)-carboxylate (510 mg, 1.02 mmol) was stirred in a solution of 4M HCl in Dioxane (10 ml), and methanol (3 ml) until analysis by LCMS indicated reaction was complete. Solvent was removed in vacuo to afford a light brown solid (450 mg, 1.02 mmol, 100%).

LCMS (Method B), (M+H$^+$) 401, Rt=1.66 min.

Intermediate 19

(S)-ethyl 2-(4-amino-3-fluorophenyl)-4-(3-methylmorpholino)-5H-pyrrolo[3,4-d]pyrimidine-6(7H)-carboxylate

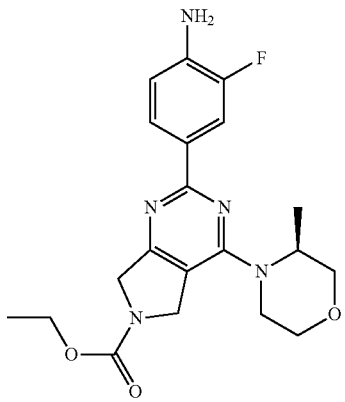 [SMILES: CCOC(=O)N1Cc2nc(-c3ccc(N)c(F)c3)nc(N3CCOC[C@@H]3C)c2C1]

Method as described for intermediate 5 using (S)-ethyl 2-chloro-4-(3-methylmorpholino)-5H-pyrrolo[3,4-d]pyrimidine-6(7H)-carboxylate (intermediate 11) and 2-fluoro-4-(4,4,5,5-tetramethyl-1,3,2-dioxaborolan-2-yl)aniline as starting materials. The reaction mixture was filtered through a celite 545 pre-packed cartridge (2.5 g), washed with MeOH and reduced in vacuo. The residue was purified by flash SCX2 chromatography affording the title compound (130 mg, 0.32 mmol, 88%).

LCMS (Method B), (M+H$^+$) 402, Rt=2.68 min.

Example 64

(S)-1-cyclopropyl-3-(4-(4-(3-methylmorpholino)-7-pivaloyl-5,6,7,8-tetrahydropyrido[3,4-d]pyrimidin-2-yl)phenyl)urea

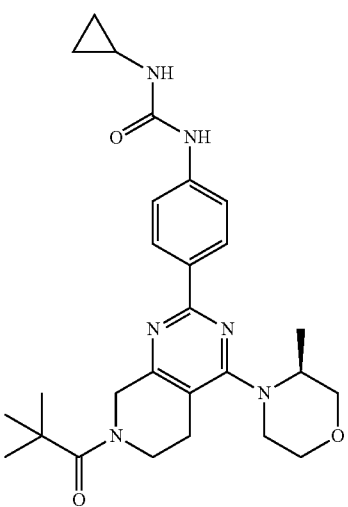 [SMILES: C[C@H]1COCCN1c1nc(-c2ccc(NC(=O)NC3CC3)cc2)nc2c1CCN(C(=O)C(C)(C)C)C2]

Method as example 18 using (S)-1-cyclopropyl-3-(4-(4-(3-methylmorpholino)-5,6,7,8-tetrahydropyrido[3,4-d]pyrimidin-2-yl)phenyl)urea (example 15) and pivoyl chloride as starting materials $^1$H NMR (d$_6$-DMSO) 8.54 (s, 1H), 8.19 (d, 2H), 8.14 (s, 0.6H formate), 7.49 (d, 2H), 6.44 (d, 1H), 4.60 (br dd, 2H), 4.15-4.12 (m, 1H), 3.91-3.80 (m, 2H), 3.71-3.55 (m, 5H), 3.47-3.38 (m, 1H), 2.70-2.67 (m, 2H), 2.58-2.52 (m, 1H), 1.26 (s, 12H), 0.66-0.62 (m, 2H), 0.43-0.38 (m, 2H).

LCMS (method A), (M+H$^+$) 493.20, Rt=7.65 min.

Example 65

(S)-1-cyclopropyl-3-(4-(6-isobutyl-4-(3-methylmorpholino)-6,7-dihydro-5H-pyrrolo[3,4-d]pyrimidin-2-yl)phenyl)urea

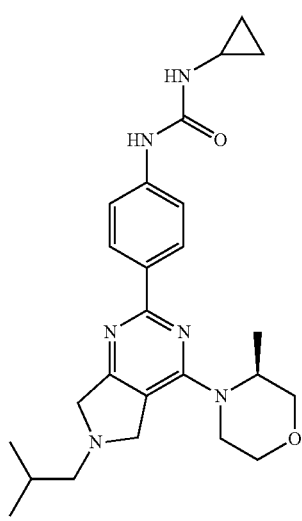 [SMILES: CC(C)CN1Cc2nc(-c3ccc(NC(=O)NC4CC4)cc3)nc(N3CCOC[C@@H]3C)c2C1]

Method as described for example 26 using (S)-1-cyclopropyl-3-(4-(4-(3-methylmorpholino)-6,7-dihydro-5H-pyrrolo[3,4-d]pyrimidin-2-yl)phenyl)urea (example 3) and iso-butyraldehyde as starting materials. Purified by prep HPLC (low pH).

$^1$H NMR (d$_6$-DMSO) 8.54 (s, 1H), 8.17 (d, 2H), 7.47 (d, 2H), 6.46 (d, 1H), 4.38 (br s, 1H), 4.10-3.91 (br s, 1H), 4.10-3.91 (m, 4H), 3.74-3.70 (m, 2H), 3.65 (dd, 1H), 3.49 (td, 1H), 3.41-3.36 (q, 1H), 2.57-2.45 (m, 1H), 2.46 (d, 2H), 1.86-1.76 (m, 1H), 1.24 (d, 3H), 0.92 (d, 6H), 0.66-0.61 (m, 2H), 0.43-0.39 (m, 2H).

LCMS (method A), (M+H$^+$) 451, Rt=5.72 min.

Example 66

(S)-1-ethyl-3-(4-(6-isobutyl-4-(3-methylmorpholino)-6,7-dihydro-5H-pyrrolo[3,4-d]pyrimidin-2-yl)phenyl)urea

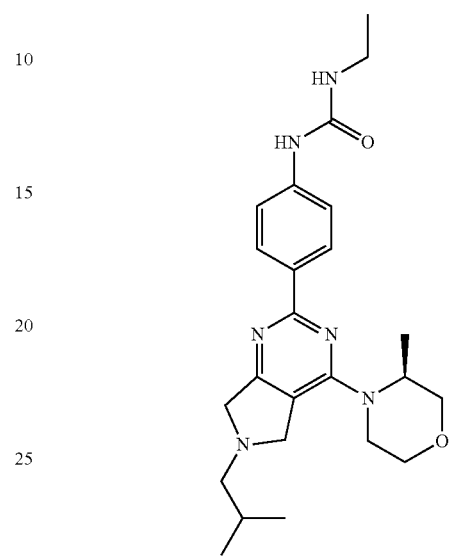

Method as described for example 26 using (S)-1-ethyl-3-(4-(4-(3-methylmorpholino)-6,7-dihydro-5H-pyrrolo[3,4-d]pyrimidin-2-yl)phenyl)urea (example 7) and iso-butyraldehyde as starting materials. Purified by prep HPLC (low pH).

$^1$H NMR (d$_6$-DMSO) 8.64 (s, 1H), 8.16 (d, 2H), 7.46 (d, 2H), 6.16 (t, 1H), 4.39 (br s, 1H), 4.11-4.07 (3H, m), 3.97-3.91 (m, 1H), 3.74-3.70 (m, 3H), 3.65 (dd, 1H), 3.57-3.42 (m, 2H), 3.13-3.10 (m, 2H), 2.46 (d, 2H), 1.84-1.77 (m, 1H), 1.24 (d, 3H) 1.06 (t, 3H), 0.92 (d, 6H).

LCMS (method A), (M+H$^+$) 439, Rt=6.21 min.

Example 67

(S)-1-ethyl-3-(4-(4-(3-methylmorpholino)-6-neopentyl-6,7-dihydro-5H-pyrrolo[3,4-d]pyrimidin-2-yl)phenyl)urea

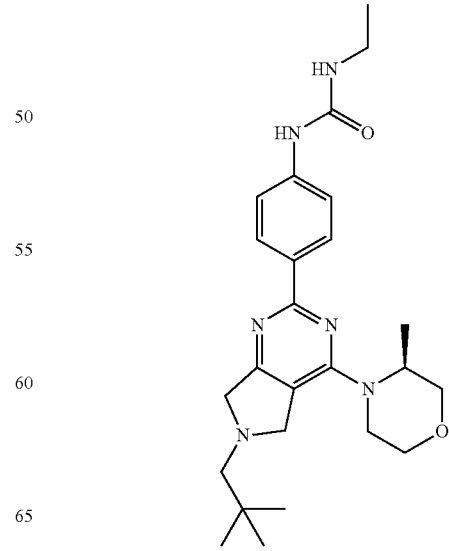

Method as described for example 26 using (S)-1-ethyl-3-(4-(4-(3-methylmorpholino)-6,7-dihydro-5H-pyrrolo[3,4-d]pyrimidin-2-yl)phenyl)urea (example 7) and pivaldehyde as starting materials. Purified by prep HPLC (low pH).

$^1$H NMR (d$_6$-DMSO) 8.65 (s, 1H), 8.16 (d, 2H), 7.46 (d, 2H), 6.17 (t, 1H), 4.36 (br s, 1H), 4.26 (d, 1H), 4.18 (d, 1H), 3.97-3.92 (m, 3H), 3.72 (d, 1H), 3.64 (dd, 1H), 3.52-3.46 (m, 2H), 3.15-3.08 (m, 3H), 2.54 (s, 2H), 1.24 (d, 3H), 1.06 (t, 3H), 0.94 (d, 9H).

LCMS (method A), (M+H$^+$) 453, Rt=6.53 min.

Example 68

(S)-1-ethyl-3-(4-(4-(3-methylmorpholino)-6-(2,2,2-trifluoroethyl)-6,7-dihydro-5H-pyrrolo[3,4-d]pyrimidin-2-yl)phenyl)urea

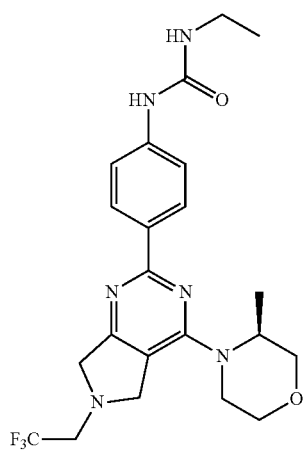 [SMILES: CCNC(=O)Nc1ccc(-c2nc3c(c(N4CCOC[C@@H]4C)n2)CN(CC(F)(F)F)C3)cc1]

To a stirred solution of (S)-1-ethyl-3-(4-(4-(3-methylmorpholino)-6,7-dihydro-5H-pyrrolo[3,4-d]pyrimidin-2-yl)phenyl)urea (example 7) (200 mg, 0.48 mmol) and Et$_3$N (133 µL, 0.95 mmol). in toluene (1.5 mL) was added 2,2,2-trifluoroethyltrichloromethane sulfonate (91 µL, 0.95 mmol) and DMSO (0.5 mL). The reaction mixture was heated to 100° C. overnight. The reaction was cooled, diluted with methanol and adsorbed onto a mp-TsOH cartridge (2.5 g, 3 mmol/g). The cartridge was rinsed with MeOH (3 column volumes) and the product was eluted with 7M NH$_3$ in MeOH. The basic fractions were concentrated in vacuo and purified by prep HPLC (low pH) to give the desired product (2.1 mg, 0.9% yield).

$^1$H NMR (CD$_3$OD) 8.39 (s, 2H), 8.19 (d, 2H), 7.45 (d, 2H), 4.43 (br d, 1H), 4.39-4.31 (m, 2H), 4.15 (br d, 1H), 4.07 (br d, 2H), 4.00 (dd, 1H), 3.79-3.74 (m, 2H), 3.62 (td, 1H), 3.54-3.41 (m, 3H), 3.24 (q, 2H), 1.36 (d, 3H), 1.17 (t, 3H).

LCMS (method A), (M+H$^+$) 465, Rt=7.44 min.

Example 69

1-Ethyl-3-(4-(6-methyl-4-morpholino-6,7-dihydro-5H-pyrrolo[3,4-d]pyrimidin-2-yl)phenyl)urea

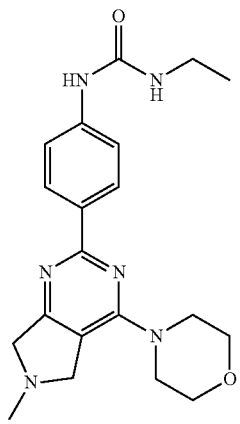 [SMILES: CCNC(=O)Nc1ccc(-c2nc3c(c(N4CCOCC4)n2)CN(C)C3)cc1]

Method as described for example 26 using 1-ethyl-3-(4-(4-morpholino-6,7-dihydro-5H-pyrrolo[3,4-d]pyrimidin-2-yl)phenyl)urea (example 14) and formaldehyde as starting materials.

$^1$H NMR (d$_6$-DMSO) 8.64 (s, 1H), 8.17 (d, 2H), 7.45 (d, 2H), 6.15 (t, 1H), 4.03 (br s, 2H), 3.74 (br s, 2H), 3.63-3.72 (m, 8H), 3.32 (s, 3H), 3.08-3.15 (m, 2H), 1.05 (t, 3H).

LCMS (method A), (M+H$^+$) 383, Rt=4.68 min.

Example 70

Ethyl 2-(4-(3-ethylureido)phenyl)-4-morpholino-5H-pyrrolo[3,4-d]pyrimidine-6(7H)-carboxylate

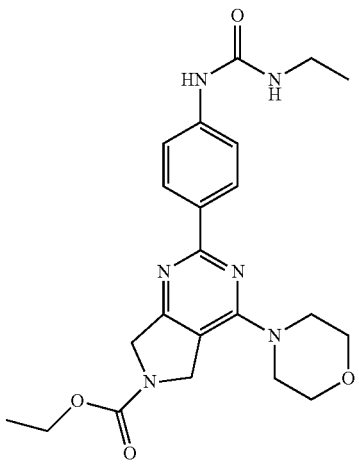 [SMILES: CCNC(=O)Nc1ccc(-c2nc3c(c(N4CCOCC4)n2)CN(C(=O)OCC)C3)cc1]

Method as described for example 34 using 1-ethyl-3-(4-(4-morpholino-6,7-dihydro-5H-pyrrolo[3,4-d]pyrimidin-2-yl)phenyl)urea (example 14) and ethyl chloroformate as starting materials.

$^1$H NMR (d$_6$-DMSO) 8.71 (s, 1H), 8.19 (d, 2H), 7.48 (d, 2H), 6.20 (t, 1H), 4.82 (d, 2H), 4.48 (d, 2H), 4.11-4.18 (m,

2H), 3.72 (s, 6H), 3.59-3.66 (m, 1H), 3.08-3.18 (m, 1H), 1.23-1.27 (m, 3H), 1.06 (t, 3H).
LCMS (method A), (M+H⁺) 441, Rt=7.18 min.

Example 71

(S)-1-(4-(6-methyl-4-(3-methylmorpholino)-6,7-dihydro-5H-pyrrolo[3,4-d]pyrimidin-2-yl)phenyl)urea

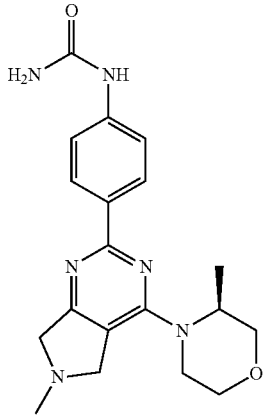 [SMILES: C[C@H]1COCCN1c1nc(-c2ccc(NC(N)=O)cc2)nc2c1CN(C)C2]

Method as intermediate 5 using (S)-4-(2-chloro-6-methyl-6,7-dihydro-5H-pyrrolo[3,4-d]pyrimidin-4-yl)-3-methylmorpholine (intermediate 12) and 1-(4-(4,4,5,5-tetramethyl-1,3,2-dioxaborolan-2-yl)phenyl)urea as starting materials.
¹HNMR (d₆-DMSO) 8.74 (br, s, 1H), 8.17 (d, 2H), 7.47 (d, 2H), 5.92 (br, s, 2H), 4.39-4.29 (br, s, 1H), 4.12-3.88 (m, 4H), 3.77-3.62 (m, 4H), 3.55-3.45 (m, 1H), 3.17 (d, 3H), 1.25 (d, 3H).
LCMS (Method A), (M+H⁺) 369.10, Rt=7.36 min.

Example 72

(S)-1-(4-(6-methyl-4-(3-methylmorpholino)-6,7-dihydro-5H-pyrrolo[3,4-d]pyrimidin-2-yl)phenyl)-3-(5-methylisoxazol-3-yl)urea

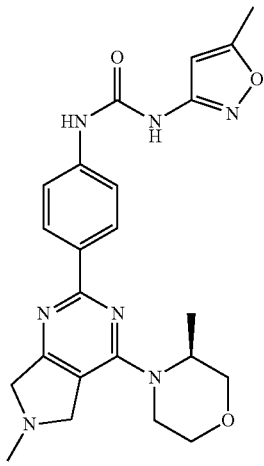 [SMILES: Cc1cc(NC(=O)Nc2ccc(-c3nc4c(c(N5CCOC[C@@H]5C)n3)CN(C)C4)cc2)no1]

Method as intermediate 5 using (S)-4-(2-chloro-6-methyl-6,7-dihydro-5H-pyrrolo[3,4-d]pyrimidin-4-yl)-3-methylmorpholine (intermediate 12) and 1-(5-methylisoxazol-3-yl)-3-(4-(4,4,5,5-tetramethyl-1,3,2-dioxaborolan-2-yl)phenyl)urea (intermediate 15) as starting materials.
¹HNMR (CD₃OD) 8.20-8.174 (M, 3H), 7.46 (d, 2H), 6.32 (br s, 1H), 4.38-4.24 (m, 3H), 4.10-4.95 (m, 3H), 3.95-3.88 (m, 1H), 3.74-3.62 (m, 2H), 3.57-3.47 (m, 1H), 3.40-3.31-(m, 1H), 2.72 (s, 3H), 2.29 (s, 3H), 1.28 (d, 3H).
LCMS (Method A), (M+H⁺) 450.20, Rt=5.78 min.

Example 73

(S)-1-(2-hydroxyethyl)-3-(4-(6-methyl-4-(3-methylmorpholino)-6,7-dihydro-5H-pyrrolo[3,4-d]pyrimidin-2-yl)phenyl)urea

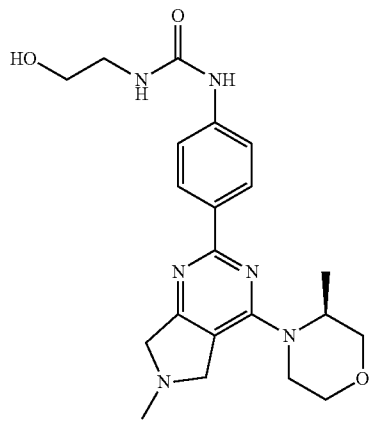 [SMILES: C[C@H]1COCCN1c1nc(-c2ccc(NC(=O)NCCO)cc2)nc2c1CN(C)C2]

Method as described for example 51 using (S)-phenyl 4-(6-methyl-4-(3-methylmorpholino)-6,7-dihydro-5H-pyrrolo[3,4-d]pyrimidin-2-yl)phenylcarbamate (intermediate 10) and 2-amino ethanol.
¹HNMR (CD₃OD) 8.08 (d, 2H), 7.35 (d, 2H), 4.37-4.26 (br, s, 1H), 4.11-3.95 (m, 3H), 3.93-3.86 (dd, 1H), 3.80-3.61 (m, 4H), 3.57-3.45 (m, 3H), 3.39-3.28 (m, 1H), 3.23 (d, 1H), 2.52 (s, 3H), 1.25 (d, 3H).
LCMS (Method A), (M+H⁺) 413.10, Rt=4.59 min.

Example 74

(S)-1-ethyl-3-(4-(6-isopropyl-4-(3-methylmorpholino)-6,7-dihydro-5H-pyrrolo[3,4-d]pyrimidin-2-yl)phenyl)urea

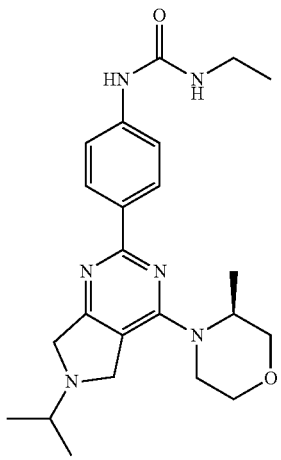 [SMILES: CCNC(=O)Nc1ccc(-c2nc3c(c(N4CCOC[C@@H]4C)n2)CN(C(C)C)C3)cc1]

Method as example 26 using (S)-1-ethyl-3-(4-(4-(3-methylmorpholino)-6,7-dihydro-5H-pyrrolo[3,4-d]pyrimidin-2-yl)phenyl)urea (example 7) and acetone as starting materials. Purification by prep HPLC (high pH).

$^1$H NMR (d$_6$-DMSO) 8.64 (s, 1H), 8.17 (d, 2H), 7.46 (d, 2H), 6.16 (t, 1H), 4.45-4.35 (m, 1H), 4.15-4.35 (m, 2H), 4.13-3.98 (m, 2H), 3.97-3.92 (m, 1H), 3.80-3.63 (m, 3H), 3.55-3.45 (m, 1H), 3.15-3.09 (m, 2H), 2.78-2.72 (m, 2H), 1.25 (d, 3H), 1.12 (m, 6H), 1.06 (t, 3H).

LCMS (method A), (M+H$^+$) 425, Rt=5.57 min.

Example 75

(S)-1-ethyl-3-(4-(7-isopropyl-4-(3-methylmorpholino)-5,6,7,8-tetrahydropyrido[3,4-d]pyrimidin-2-yl)phenyl)urea formate

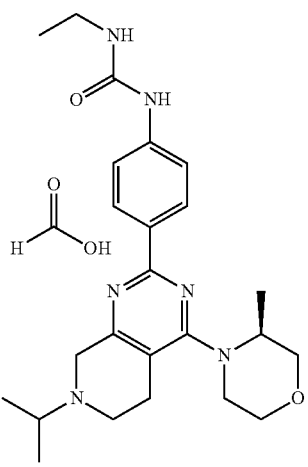

Method as example 26 using (S)-1-ethyl-3-(4-(4-(3-methylmorpholino)-5,6,7,8-tetrahydropyrido[3,4-d]pyrimidin-2-yl)phenyl)urea (example 13) and acetone as starting materials.

$^1$H NMR (d$_6$-DMSO) 8.65 (s, 1H), 8.17-8.15 (m, 3H), 7.47 (d, 2H), 6.17 (t, 1H), 4.13-4.11 (m, 1H), 3.88-3.85 (m, 1H), 3.71-3.57 (m, 6H), 3.43-3.36 (m, 1H under water peak), 3.15-3.08 (m, 2H), 3.12 (q, 2H), 2.87 (q, 1H), 2.75-2.70 (m, 1H), 2.67-2.64 (m, 2H), 2.58-2.54 (m, 1H), 1.22 (d, 3H), 1.08-1.04 (m, 9H).

LCMS (method A), (M+H$^+$) 439.20, Rt=5.39 min.

Example 76

(S)-1-ethyl-3-(4-(7-isobutyl-4-(3-methylmorpholino)-5,6,7,8-tetrahydropyrido[3,4-d]pyrimidin-2-yl)phenyl)urea formate

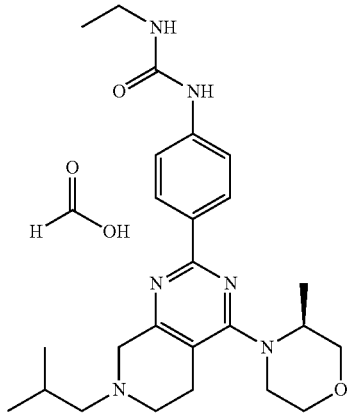

Method as example 26 using (S)-1-ethyl-3-(4-(4-(3-methylmorpholino)-5,6,7,8-tetrahydropyrido[3,4-d]pyrimidin-2-yl)phenyl)urea (example 13) and isobutyraldehyde as starting materials.

$^1$H NMR (d$_6$-DMSO) 8.65 (s, 1H), 8.17-8.15 (m, 3H), 7.47 (d, 2H), 6.17 (br t, 1H), 4.15-4.11 (m, 1H), 3.89-3.86 (m, 1H), 3.72-3.69 (m, 1H), 3.66-3.60 (m, 3H), 3.58-3.57 (m, 1H), 3.48-3.38 (m, 2H under water peak), 3.17-3.09 (m, 3H), 2.67-2.65 (m, 3H), 2.26-2.24 (m, 2H), 1.94-1.87 (m, 1H), 1.24 (d, 3H), 1.06 (m, 3H), 0.92 (d, 6H).

LCMS (method A), (M+H$^+$) 453.20, Rt=5.69 min

Example 77

(S)-ethyl 2-(4-(3-ethylureido)phenyl)-4-(3-methyl-morpholino)-5,6-dihydropyrido[3,4-d]pyrimidine-7(8H)-carboxylate

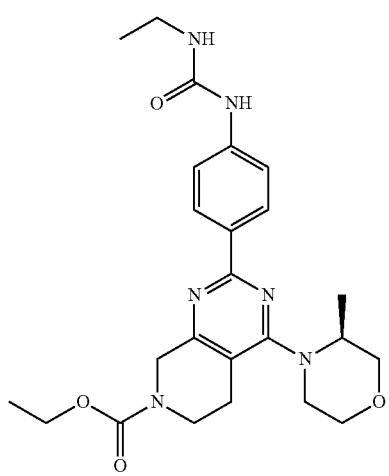 [SMILES: CCNC(=O)Nc1ccc(-c2nc3c(c(N4CCOC[C@@H]4C)n2)CCN(C(=O)OCC)C3)cc1]

Method as example 34 using (S)-1-ethyl-3-(4-(4-(3-methylmorpholino)-5,6,7,8-tetrahydropyrido[3,4-d]pyrimidin-2-yl)phenyl)urea (example 13) and ethyl chloroformate as starting materials.

$^1$H NMR (d$_6$-DMSO) 8.66 (s, 1H), 8.18 (d, 2H), 7.49 (d, 2H), 6.17 (br t, 1H), 4.60-4.42 (m, 1H), 4.14-4.09 (m, 3H), 3.89-3.86 (m, 1H), 3.71-3.39 (m, 7H), 3.16-3.09 (m, 2H), 2.69-2.66 (m, 2H), 1.26-1.22 (m, 6H), 1.08-1.05 (m, 3H).

LCMS (method A), (M+H$^+$) 469.20, Rt=7.17 min.

Example 78

(S)-ethyl 2-(4-(3-cyclopropylureido)phenyl)-4-(3-methylmorpholino)-5,6-dihydropyrido[3,4-d]pyrimidine-7(8H)-carboxylate

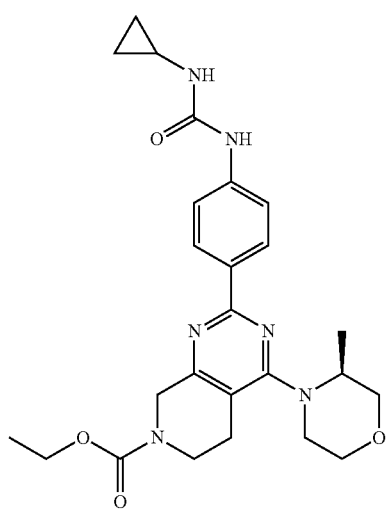 [SMILES: CCOC(=O)N1CCc2c(nc(-c3ccc(NC(=O)NC4CC4)cc3)nc2N2CCOC[C@@H]2C)C1]

Method as example 34 using (S)-1-cyclopropyl-3-(4-(4-(3-methylmorpholino)-5,6,7,8-tetrahydropyrido[3,4-d]pyrimidin-2-yl)phenyl)urea (example 15) and ethyl chloro formate as starting materials.

$^1$H NMR (d$_6$-DMSO) 8.53 (s, 1H), 8.18 (d, 2H), 7.49 (d, 2H), 6.44 (br d, 1H), 4.58-4.43 (m, 2H), 4.14-4.08 (m, 3H), 3.88-3.85 (m, 1H), 3.70-3.57 (m, 5H), 3.51-3.38 (m, 2H), 2.68-2.66 (m, 2H), 2.58-2.53 (m, 1H), 1.25-1.22 (m, 6H), 0.67-0.62 (2H), 0.43-0.39 (m, 2H).

LCMS (method A), (M+H$^+$) 481.2, Rt=7.39 min.

Example 79

N-ethyl-2-(4-(3-ethylureido)phenyl)-4-morpholino-5H-pyrrolo[3,4-d]pyrimidine-6(7H)-carboxamide

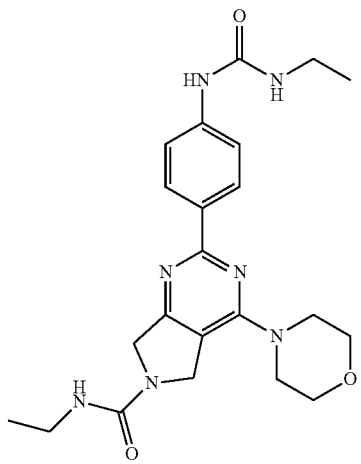

Method as described for example 33 using 1-ethyl-3-(4-(4-morpholino-6,7-dihydro-5H-pyrrolo[3,4-d]pyrimidin-2-yl)phenyl)urea (example 14) and ethyl isocyanate as starting materials.

$^1$H NMR (d$_6$-DMSO) 8.75 (br s, 1H), 8.18 (d, 2H), 7.48 (d, 2H), 6.43 (t, 1H), 6.25 (t, 1H), 4.72-4.74 (m, 2H), 4.42-4.44 (m, 2H), 3.32 (br s, 8H), 3.09-3.18 (m, 4H), 1.04-1.10 (q, 6H).

LCMS (method A), (M+H$^+$) 440, Rt=6.24 min.

Example 80

(S)-1-(6-hydroxypyridin-2-yl)-3-(4-(6-methyl-4-(3-methylmorpholino)-6,7-dihydro-5H-pyrrolo[3,4-d]pyrimidin-2-yl)phenyl)urea

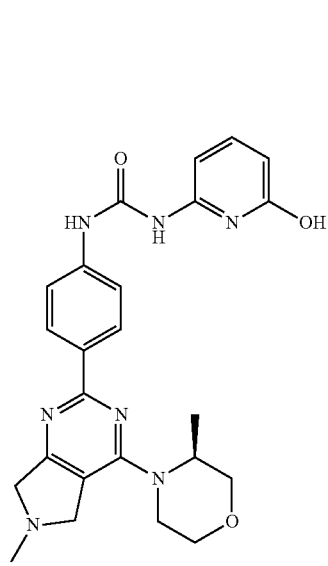 [SMILES: C[C@H]1COCCN1c1nc(-c2ccc(NC(=O)Nc3cccc(O)n3)cc2)nc2c1CN(C)C2]

Step 1: Method as described for intermediate 15 using 6-aminopyridin-2-ol as starting material. Saturated NaHCO$_3$ solution was added to the reaction mixture, and stirring allowed for 15 mins before partitioning with DCM. The organic layer was recovered, dried over MgSO$_4$, filtered and reduced in vacuo, affording the title compound (90 mg, 0.25 mmol, 56% yield).

Step 2: Method as described for example 47 using 1-(6-hydroxypyridin-2-yl)-3-(4-(4,4,5,5-tetramethyl-1,3,2-dioxaborolan-2-yl)phenyl)urea and (S)-4-(2-chloro-6-methyl-6,7-dihydro-5H-pyrrolo[3,4-d]pyrimidin-4-yl)-3-methylmorpholine (intermediate 12) as starting materials. The reaction mixture was filtered through a celite 545 prepacked cartridge (2.5 g), washed with MeOH and reduced in vacuo. The residue was purified by prep LCMS (high pH), to yield the title compound (7.9 mg, 0.017 mmol, 9.2%).

$^1$HNMR (CD$_3$OD) 8.25 (d, 2H), 7.77 (d, 2H), 7.40 (t, 1H), 6.09 (t, 2H), 4.46 (br, s, 1H), 4.26-4.07 (m, 3H), 4.02 (dd, 1H), 3.94-3.74 (m, 4H), 3.69-3.59 (m, 1H), 3.52-3.41 (m, 1H), 2.64 (s, 3H), 1.38 (d, 3H).

LCMS (Method A), (M+H$^+$) 462.10, Rt=5.23 min.

Example 81

(S)-methyl 2-(4-(3-ethylureido)phenyl)-4-(3-methylmorpholino)-5,6-dihydropyrido[3,4-d]pyrimidine-7(8H)-carboxylate

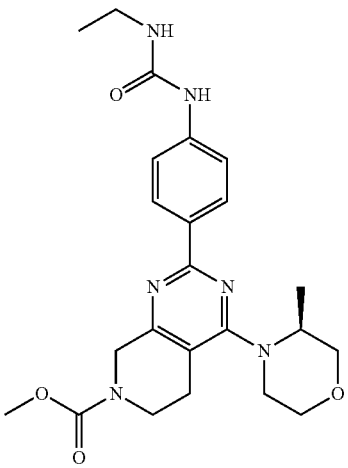 [SMILES: CCNC(=O)Nc1ccc(-c2nc3c(c(N4CCOC[C@@H]4C)n2)CCN(C(=O)OC)C3)cc1]

Method as example 34 using (S)-1-ethyl-3-(4-(4-(3-methylmorpholino)-5,6,7,8-tetrahydropyrido[3,4-d]pyrimidin-2-yl)phenyl)urea (example 13) and methylchloroformate as starting materials.

$^1$H NMR (d$_6$-DMSO) 8.65 (s, 1H), 8.17 (d, 2H), 7.48 (d, 2H), 6.16 (br t, 1H), 4.57-4.43 (m, 2H), 4.12-4.11 (m, 1H), 3.88-3.85 (m, 1H), 3.71-3.55 (m, 8H), 3.50-3.32 (m, 2H), 3.15-3.09 (m, 2H), 2.69-2.67 (m, 2H), 1.25 (d, 3H), 1.06 (t, 3H).

LCMS (method A), (M+H$^+$) 455.2, Rt=6.63 min.

Example 82

1-ethyl-3-(4-(4-morpholino-5,6,7,8-tetrahydropyrido[3,4-d]pyrimidin-2-yl)phenyl)urea

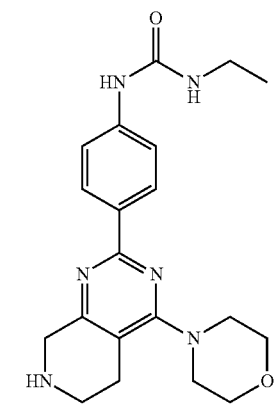 [SMILES: CCNC(=O)Nc1ccc(-c2nc3c(c(N4CCOCC4)n2)CCNC3)cc1]

Step 1: Method as described for intermediate 2 using tert-butyl 2,4-dichloro-5,6-dihydropyrido[3,4d]pyrimidine-7(8H) carboxylate and morpholine as starting materials.

Step 2: Method as intermediate 5 using tert-butyl 2-chloro-4-morpholino-5,6-dihydropyrido[3,4-d]pyrimidine-7(8H)-carboxylate and 4-(3-ethylureido)phenylboronic acid pinacol ester Step 3: Method as example 3 step 2. Purified using MP-TsOH cartridge eluting with 2M ammonia in methanol.

$^1$H NMR ($d_6$-DMSO) 8.69 (s, 1H), 8.19 (d, 2H), 7.47 (d, 2H), 6.18 (t, 1H), 4.11-4.16 (m, 1H), 3.86 (s, 2H), 3.71-3.76 (m, 4H), 3.41-3.45 (m, 4H), 3.08-3.15 (m, 2H), 2.90 (t, 2H), 2.58 (t, 2H), 1.06 (t, 3H).

LCMS (method A), (M+H$^+$) 383, Rt=4.88 min.

Example 83

(S)-methyl 2-(4-(3-cyclopropylureido)phenyl)-4-(3-methylmorpholino)-5,6-dihydropyrido[3,4-d]pyrimidine-7(8H)-carboxylate

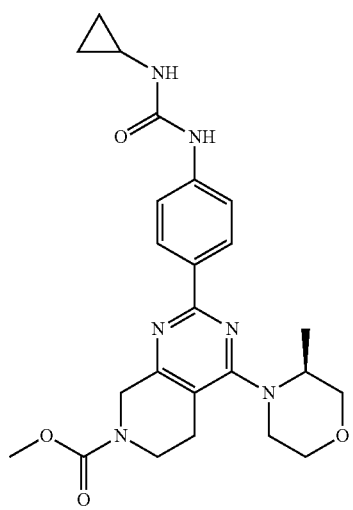 [SMILES: COC(=O)N1CCc2c(nc(-c3ccc(NC(=O)NC4CC4)cc3)nc2N2CCOC[C@@H]2C)C1]

Method as example 34 using (S)-1-cyclopropyl-3-(4-(4-(3-methylmorpholino)-5,6,7,8-tetrahydropyrido[3,4-d]pyrimidin-2-yl)phenyl)urea (example 15) and methylchloroformate as starting materials.

$^1$H NMR ($d_6$-DMSO) 8.56 (s, 1H), 8.18 (d, 2H), 7.49 (d, 2H), 6.47-6.46 (m, 1H), 4.57-4.42 (m, 2H), 4.10-4.09 (m, 1H), 3.88-3.85 (m, 1H), 3.70-3.56 (m, 8H), 3.50-3.39 (m, 2H), 2.68-2.65 (m, 2H), 2.56-2.52 (m, 1H), 1.24 (d, 3H), 0.66-0.61 (m, 2H), 0.43-0.39 (m, 2H).

LCMS (method A), (M+H$^+$) 467.2, Rt=6.78 min.

Example 84

(S)-1-(1-methyl-1H-pyrazol-3-yl)-3-(4-(6-methyl-4-(3-methylmorpholino)-6,7-dihydro-5H-pyrrolo[3,4-d]pyrimidin-2-yl)phenyl)urea

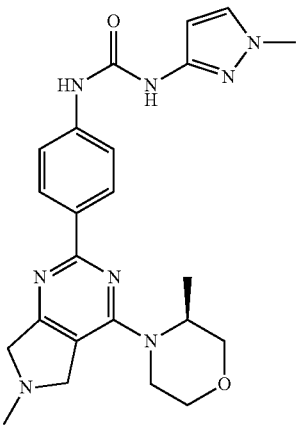

Step 1: Method as described for intermediate 15 using 1-methyl-1H-pyrazol-4-amine as starting material. Saturated NaHCO$_3$ solution was added to the reaction mixture, and stirring allowed for 15 mins before partitioning between water and DCM. The organic layer was recovered, dried over MgSO$_4$, filtered and reduced in vacuo, affording the title compound (145 mg, 0.42 mmol, 93% yield).

LCMS (Method B), (M+H$^+$) 343, Rt=2.50 min.

Step 2: Method as described for example 47 using 1-(1-methyl-1H-pyrazol-4-O-3-(4-(4,4,5,5-tetramethyl-1,3,2-dioxaborolan-2-yl)phenyl)urea and S)-4-(2-chloro-6-methyl-6,7-dihydro-5H-pyrrolo[3,4-d]pyrimidin-4-yl)-3-methylmorpholine (intermediate 12) as starting materials. The reaction mixture was filtered through a celite 545 prepacked cartridge (2.5 g), washed with MeOH and solvent removed in vacuo. The residue was purified by prep LCMS (high pH), to yield the title compound (19.4 mg, 0.043 mmol, 12%).

$^1$HNMR (CD$_3$OD) 8.29 (br, s, 1H), 8.24 (d, 2H), 7.74 (br, s, 1H), 7.53 (d, 2H), 7.47 (br, s 1H), 4.63-4.51 (m, 2H), 4.42 (br, s, 1H), 4.22-4.21 (m, 2H), 4.13 (br, d, 1H), 4.02 (dd, 1H), 3.87 (s, 3H), 3.84-3.72 (m, 2H), 3.67-3.58 (m, 1H), 3.54-3.41 (m, 1H), 2.94 (s, 3H), 1.39 (d, 3H).

LCMS (Method A), (M+H$^+$) 449.20, Rt=4.98 min.

Example 85

(S)-1-ethyl-3-(2-fluoro-4-(6-methyl-4-(3-methylmorpholino)-6,7-dihydro-5H-pyrrolo[3,4-d]pyrimidin-2-yl)phenyl)urea

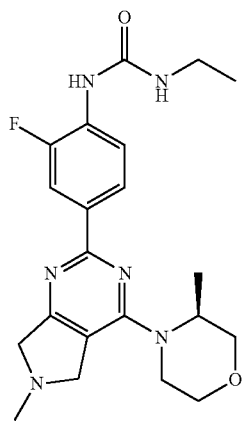

To a stirred solution of (S)-2-fluoro-4-(6-methyl-4-(3-methylmorpholino)-6,7-dihydro-5H-pyrrolo[3,4-d]pyrimidin-2-yl)aniline (intermediate 16) (139 mg, 0.40 mmol) in dry THF, was added ethyl isocyanate (70 µL, 0.89 mmol) dropwise. The reaction mixture was stirred at 40° C. for 48 hours, before removal of the solvent in vacuo. The crude material was then purified prep. HPLC (high pH), affording the title compound as a white solid (23.3 mg, 13.7%).

$^1$HNMR (CD$_3$OD) 8.17 (t, 1H), 8.04 (dd), 1H), 7.98 (dd, 1H), 4.42 (br, s, 1H), 4.22-4.06 (m, 3H), 4.03-3.98 (m, 1H), 3.90-3.72 (m, 4H), 3.68-3.58 (m, 1H), 3.50-3.38 (m, 1H), 2.63 (s, 3H), 1.37 (d, 3H), 1.18 (t, 3H).

LCMS (Method A), (M+H$^+$) 415.20, Rt=5.30 min.

Example 86

(S)-methyl 2-(4-(3-cyclopropylureido)phenyl)-4-(3-methylmorpholino)-5H-pyrrolo[3,4-d]pyrimidine-6(7H)-carboxylate

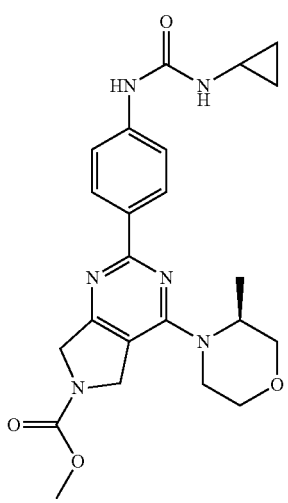 [SMILES: COC(=O)N1Cc2nc(-c3ccc(NC(=O)NC4CC4)cc3)nc(N3CCOC[C@@H]3C)c2C1]

To a solution of (S)-1-cyclopropyl-3-(4-(4-(3-methylmorpholino)-6,7-dihydro-5H-pyrrolo[3,4-d]pyrimidin-2-yl)phenyl)urea (example 3) (103 mg, 0.26 mmol) in dioxane (5 mL) at room temperature (20° C.) was added methyl chloroformate (32 uL, 0.23 mmol). The reaction mixture was stirred for 5 h. The solvent was removed in vacuo and the residue purified by prep HPLC (low pH) to afford an orange solid (18 mg, 15%).

$^1$H NMR (d$_6$-DMSO) 8.65 (s, 1H), 8.24 (d, 2H), 7.55 (d, 2H), 6.54 (d, 1H) 4.95-4.78 (m, 2H), 4.54 (d, 2H), 4.44 (br s, 1H), 4.18 (br s, 1H), 4.02 (d, 1H), 3.81 (d, 1H) 3.71 (d, 1H), 3.56 (t, 1H), 2.63-2.59 (m, 1H), 1.32 (d, 3H), 0.73-0.68 (m, 2H), 0.49-0.45 (m, 2H).

LCMS (method A), (M+H$^+$) 453, Rt=7.36 min.

Example 87

(S)—N-ethyl-2-(4-(3-ethylureido)phenyl)-4-(3-methylmorpholino)-5,6-dihydropyrido[3,4-d]pyrimidine-7(8H)-carboxamide

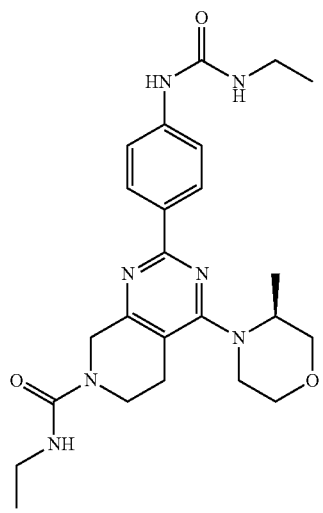 [SMILES: CCNC(=O)Nc1ccc(-c2nc3c(c(N4CCOC[C@@H]4C)n2)CCN(C(=O)NCC)C3)cc1]

To a solution of (S)-1-ethyl-3-(4-(4-(3-methylmorpholino)-5,6,7,8-tetrahydropyrido[3,4-d]pyrimidin-2-yl)phenyl)urea hydrochloride (example 13 as a hydrochloride salt) (99 mg, 0.25 mmol) in DCM (3 mL) at room temperature (20° C.) was added DIPEA (44 uL, 0.26 mmol) followed by ethyl isocyanate (22 uL, 0.27 mmol). The reaction mixture was stirred overnight. The solvent was removed in vacuo and the residue purified by prep HPLC (low pH) to afford a brown solid (55 mg, 47%).

$^1$H NMR (d$_6$-DMSO) 8.71 (s, 1H), 8.16 (d, 2H), 7.47 (d, 2H), 6.69 (t, 1H), 6.22 (t, 1H), 4.49 (q, 2H), 4.11 (d, 1H), 3.74-3.55 (m, 5H), 3.15-3.06 (m, 4H), 2.63-2.62 (m, 2H), 1.25 (d, 3H), 1.06 (t, 3H), 1.04 (t, 3H).

LCMS (method A), (M+H$^+$) 468, Rt=6.06 min.

Example 88

(S)-2-(4-(3-cyclopropylureido)phenyl)-N-ethyl-4-(3-methylmorpholino)-5,6-dihydropyrido[3,4-d]pyrimidine-7(8H)-carboxamide

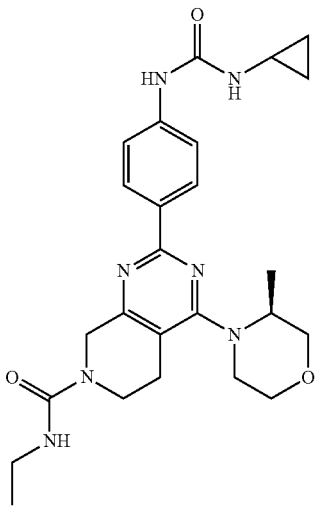 [SMILES: CCNC(=O)N1CCc2c(nc(-c3ccc(NC(=O)NC4CC4)cc3)nc2N2CCOC[C@@H]2C)C1]

To a solution of (S)-1-cyclopropyl-3-(4-(4-(3-methylmorpholino)-5,6,7,8-tetrahydropyrido[3,4-d]pyrimidin-2-yl)phenyl)urea (example 15) (102 mg, 0.25 mmol) in DCM (3 mL) at room temperature (20° C.) was added ethyl isocyanate (32 uL, 0.27 mmol). The reaction mixture was stirred for 5 h. The solvent was removed in vacuo and the residue purified by prep HPLC (low pH) to afford an orange solid (40 mg, 33%).

$^1$H NMR (d$_6$-DMSO) 8.60 (s, 1H), 8.16 (d, 2H), 7.49 (d, 2H), 6.69 (t, 1H), 6.52 (d, 1H), 4.49 (q, 2H), 4.11 (d, 1H), 3.89 (d, 1H), 3.68 (d, 1H), 3.69-3.60 (m, 4H), 3.15-3.02 (m, 2H), 2.66-2.58 (m, 2H), 2.57-2.53 (m, 1H), 1.25 (d, 3H), 1.04 (t, 3H), 0.66-0.62 (m, 2H), 0.43-0.39 (m, 2H).

LCMS (method A), (M+H$^+$) 480, Rt=6.23 min.

Example 89

(S)-methyl 2-(4-(3-ethylureido)phenyl)-4-(3-methylmorpholino)-5H-pyrrolo[3,4-d]pyrimidine-6(7H)-carboxylate

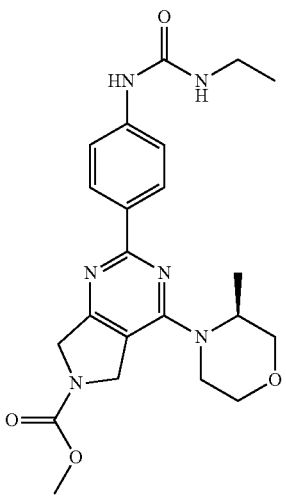 [SMILES: CCNC(=O)Nc1ccc(-c2nc3c(c(N4CCOC[C@@H]4C)n2)CN(C(=O)OC)C3)cc1]

To a solution of (S)-methyl 2-(4-(3-ethylureido)phenyl)-4-(3-methylmorpholino)-5H-pyrrolo[3,4-d]pyrimidine-6(7H)-carboxylate hydrochloride (example 7 as a hydrochloride salt) (88 mg, 0.21 mmol) in dioxane (5 mL) at room temperature (20° C.) was added DIPEA (19 uL, 0.1 mmol) followed by methyl chloroformate (18 uL, 0.23 mmol). The reaction mixture was stirred overnight. The solvent was removed in vacuo and the residue purified by prep HPLC (low pH) to afford a brown solid (6 mg, 6%).

$^1$H NMR (d$_6$-DMSO) 8.77 (s, 1H), 8.16 (d, 2H), 7.47 (d, 2H), 6.25 (t, 1H), 4.89-4.69 (m, 2H), 4.47 (d, 2H), 4.37 (br s, 1H), 4.11 (br s, 1H), 3.95 (d, 1H), 3.76 (d, 1H), 3.69 (s, 3H), 3.50 (t, 1H), 3.15-3.08 (m, 2H), 1.26 (d, 3H), 1.05 (t, 3H).

LCMS (method A), (M+H$^+$) 441, Rt=7.26 min.

Example 90

(S)-ethyl 2-(4-(3-ethylureido)phenyl)-4-(3-methylmorpholino)-5H-pyrrolo[3,4-d]pyrimidine-6(7H)-carboxylate

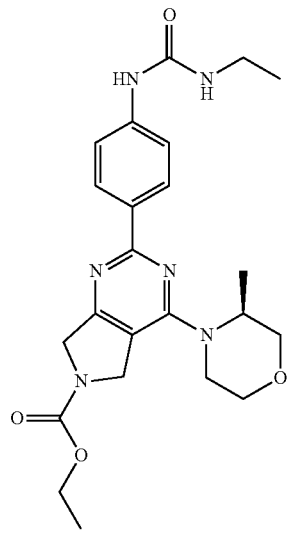 [SMILES: CCNC(=O)Nc1ccc(-c2nc3c(c(N4CCOC[C@@H]4C)n2)CN(C(=O)OCC)C3)cc1]

To a solution of (S)-ethyl 2-(4-(3-ethylureido)phenyl)-4-(3-methylmorpholino)-5H-pyrrolo[3,4-d]pyrimidine-6(7H)-carboxylate trifluoroacetate (example 7 as a trifluoroacetic acid salt) (155 mg, 0.25 mmol) in dioxane (4 mL) at room temperature (20° C.) was added DIPEA (22 uL, 0.26 mmol) followed by ethyl chloroformate (24 uL, 0.25 mmol). The reaction mixture was stirred for 3 h. The solvent was removed in vacuo and the residue purified by prep HPLC (low pH) to afford a brown solid (36 mg, 32%).

$^1$H NMR (d$_6$-DMSO) 8.73 (s, 1H), 8.17 (d, 2H), 7.48 (d, 2H), 6.21 (t, 1H), 4.88-4.73 (m, 2H), 4.51 (d, 2H), 4.20-4.08 (m, 3H), 3.96 (d, 1H), 3.74 (d, 1H), 3.67 (d, 1H), 3.51 (t, 1H), 3.39-3.30 (m, 1H), 3.13-3.06 (m, 2H), 1.26 (t, 3H), 1.24 (t, 3H), 1.06 (t, 3H).

LCMS (method A), (M+H$^+$) 455, Rt=7.79 min.

Example 91

(S)-1-ethyl-3-(4-(4-(3-methylmorpholino)-7-(2-(pyridin-3-yl)acetyl)-5,6,7,8-tetrahydropyrido[3,4-d]pyrimidin-2-yl)phenyl)urea

Example 92

(S)-1-(4-(6-(3-(dimethylamino)propanoyl)-4-(3-methylmorpholino)-5,6,7,8-tetrahydropyrido[4,3-d]pyrimidin-2-yl)phenyl)-3-ethylurea

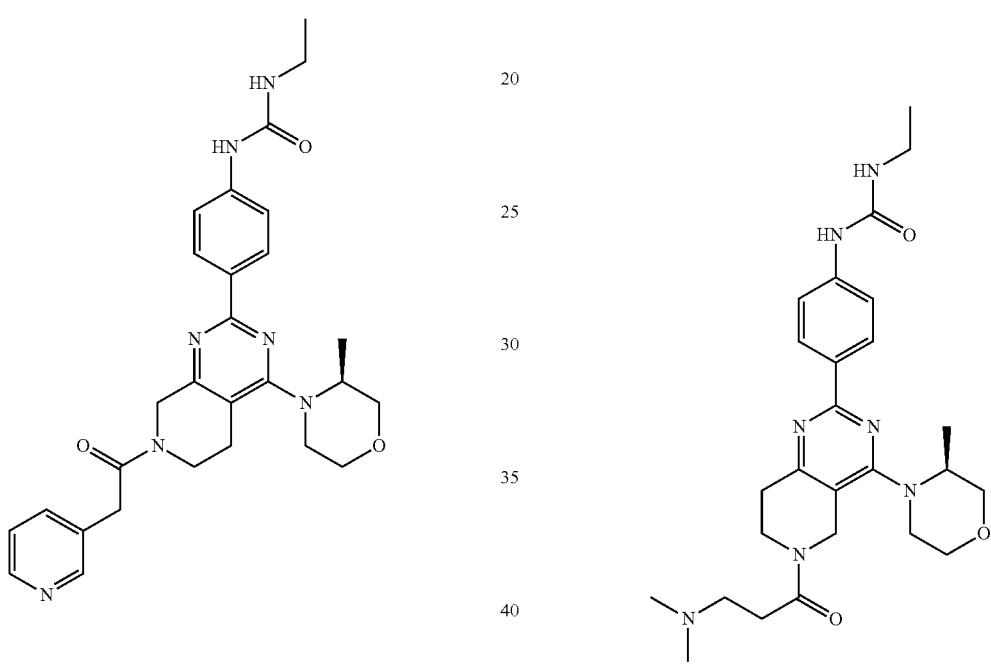

Method as described for example 17 using example 13b and 3-pyridyleacetic acid hydrochloride as starting materials, DCM as solvent and NEt₃ as base. The reaction mixture was stirred at room temperature overnight and then diluted with water. The product was collected by filtration and then purified by trituration with water, collected by filtration and washed with ether to give a cream solid (66 mg, 0.10 mmol, 42% yield).

$^1$H NMR (d$_6$-DMSO) 8.69 (s, 1H), 8.47-8.43 (m, 2H), 8.19 (dd, 2H), 7.66 (t 1H), 7.49 (dd, 2H), 7.37-7.33 (m, 1H). 6.18 (q, 1H), 4.76 (q, 1H), 4.58 (q, 1H), 4.17-4.05 (br, s, 1H), 3.97-3.78 (m, 4H), 3.74-3.56 (m, 4H), 3.54-3.39 (m, 2H), 3.11 (qn, 2H), 2.79-2.72 (br, m, 1H), 2.69-2.62 (br, m, 1H), 1.26 (t, 3H), 1.06 (t, 3H)

LCMS (method A), (M+H$^+$) 516, Rt=5.16 min.

Method as described for example 17 using (S)-1-ethyl-3-(4-(4-(3-methylmorpholino)-5,6,7,8-tetrahydropyrido[4,3-d]pyrimidin-2-yl)phenyl)urea (example 12) and 3-dimethylamino propionic acid hydrochloride as starting materials. Purified by prep HPLC (low pH).

$^1$H NMR (d$_6$-DMSO) 8.81 (s, 1H), 8.17 (d, 2H), 7.49 (d, 2H), 6.32 (t, 1H), 4.56-4.41 (m, 1H), 3.95-3.84 (m, 4H), 3.81-3.70 (m, 2H), 3.66-3.60 (m, 2H), 3.51-3.39 (m, 4H), 3.15-3.08 (m, 2H), 2.94 (t, 1H), 2.59-2.54 (m, 3H), 2.17 (d, 6H), 1.25 (d, 3H), 1.06 (t, 3H).

LCMS (method A), (M+H$^+$) 496, Rt=4.50 min.

Example 93

1-ethyl-3-(4-(7-methyl-4-morpholino-5,6,7,8-tetrahydropyrido[3,4-d]pyrimidin-2-yl)phenyl)urea

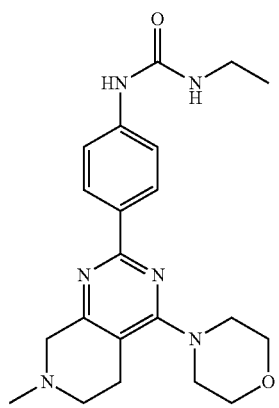 [SMILES: CCNC(=O)Nc1ccc(-c2nc3c(c(N4CCOCC4)n2)CCN(C)C3)cc1]

Method as example 26 using 1-Ethyl-3-(4-(4-morpholino-5,6,7,8-tetrahydropyrido[3,4-d]pyrimidin-2-yl)phenyl)urea (example 82) and formaldehyde as starting materials.

$^1$H NMR (d$_6$-DMSO) 8.68 (s, 1H), 8.17 (d, 2H), 7.47 (d, 2H), 6.18 (t, 1H), 3.73 (br t, 4H), 3.50 (s, 2H), 3.45 (br t, 4H), 3.08-3.15 (m, 2H), 2.68 (br t, 2H), 2.55 (br t, 2H), 2.36 (s, 3H), 1.05 (t, 3H).

LCMS (method A), (M+H$^+$) 397, Rt=4.86 min.

Example 94

N-ethyl-2-(4-(3-ethylureido)phenyl)-4-morpholino-5,6-dihydropyrido[3,4-d]pyrimidine-7(8H)-carboxamide

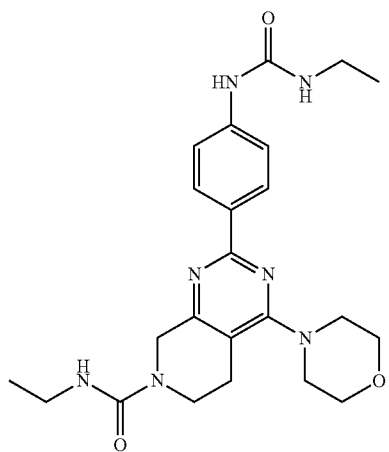 [SMILES: CCNC(=O)Nc1ccc(-c2nc3c(c(N4CCOCC4)n2)CCN(C(=O)NCC)C3)cc1]

Method as example 33 using 1-Ethyl-3-(4-(4-morpholino-5,6,7,8-tetrahydropyrido[3,4-d]pyrimidin-2-yl)phenyl)urea (example 82) and ethyl isocyanate as starting materials.

$^1$H NMR (d$_6$-DMSO) 8.70 (s, 1H), 8.20 (d, 2H), 7.50 (d, 2H), 6.70 (t, 1H), 6.20 (t, 1H), 4.48 (s, 2H), 3.75 (t, 4H), 3.50 (t, 2H), 3.45 (t, 4H), 3.05-3.18 (m, 4H), 2.60 (t, 1H), 1.00-1.10 (m, 6H).

LCMS (method A), (M+H$^+$) 454, Rt=5.87 min.

Example 95 methyl 2-(4-(3-ethylureido)phenyl)-4-morpholino-5,6-dihydropyrido[3,4-d]pyrimidine-7(8H)-carboxylate

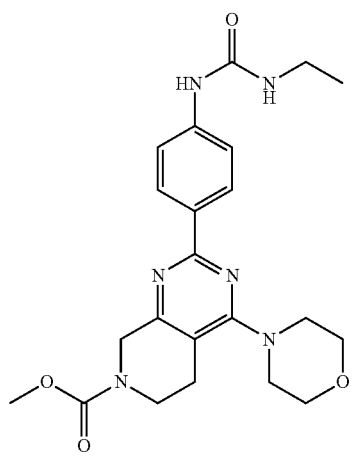 [SMILES: CCNC(=O)Nc1ccc(-c2nc3c(c(N4CCOCC4)n2)CCN(C(=O)OC)C3)cc1]

Method as example 34 using 1-ethyl-3-(4-(4-morpholino-5,6,7,8-tetrahydropyrido[3,4-d]pyrimidin-2-yl)phenyl)urea (example 82) and methyl chloroformate as starting materials.

$^1$H NMR (d$_6$-DMSO) 8.70 (s, 1H), 8.18 (d, 2H), 7.48 (d, 2H), 6.18 (t, 1H), 4.51 (s, 2H), 3.70-3.75 (m, 4H), 3.67 (s, 3H), 3.56 (br s, 2H), 3.47 (br s, 4H), 3.07-3.17 (m, 2H), 2.64-2.72, (t, 2H), 1.05 (t, 3H).

LCMS (method A), (M+H$^+$) 441, Rt=6.40 min.

Example 96 ethyl 2-(4-(3-ethylureido)phenyl)-4-morpholino-5,6-dihydropyrido[3,4-d]pyrimidine-7(8H)-carboxylate

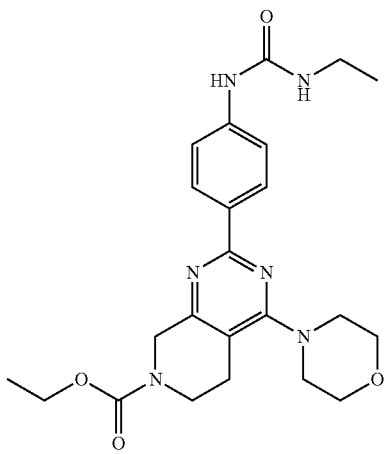 [SMILES: CCNC(=O)Nc1ccc(-c2nc3c(c(N4CCOCC4)n2)CCN(C(=O)OCC)C3)cc1]

Method as example 34 using 1-Ethyl-3-(4-(4-morpholino-5,6,7,8-tetrahydropyrido[3,4-d]pyrimidin-2-yl)phenyl)urea (example 82) and ethyl chloroformate as starting materials.

$^1$H NMR (d$_6$-DMSO) 8.69 (s, 1H), 8.19 (d, 2H), 7.49 (d, 2H), 6.18 (t, 1H), 4.47-4.54 (br m, 2H), 4.08-4.41 (m, 2H), 3.71-3.75 (t, 4H), 3.57 (br s, 2H), 3.44-3.48 (t, 4H), 3.08-3.16 (m, 2H), 2.67-2.71 (m, 2H), 1.24 (t, 3H), 1.06 (t, 3H).
LCMS (method A), (M+H¹) 455, Rt=6.95 min.

Example 97

1-(4-(7-acetyl-4-morpholino-5,6,7,8-tetrahydropyrido[3,4-d]pyrimidin-2-yl)phenyl)-3-ethylurea

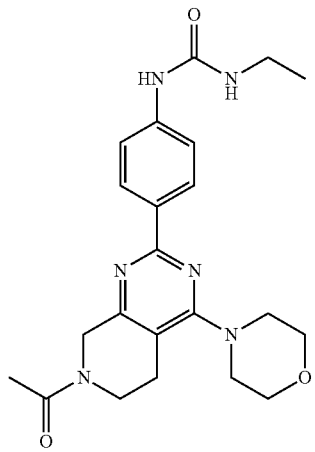 [SMILES: CCNC(=O)Nc1ccc(-c2nc3c(c(N4CCOCC4)n2)CCN(C(C)=O)C3)cc1]

Method as example 18 using 1-ethyl-3-(4-(4-morpholino-5,6,7,8-tetrahydropyrido[3,4-d]pyrimidin-2-yl)phenyl)urea (example 82) and acetyl chloride as starting materials.
¹H NMR (d₆-DMSO) 8.75 (d, 1H), 8.19 (dd, 2H), 7.49 (dd, 2H), 6.25 (q, 1H), 4.64 (s, 1H), 4.55 (s, 1H), 3.71-3.75 (m, 4H), 3.62 (t, 3H), 3.08-3.15 (m, 3H), 2.76 (t, 1H), 2.63 (t, 1H), 2.55 (s, 2H), 2.13 (s, 3H), 1.06 (t, 3H).
LCMS (method A), (M+H⁺) 425, Rt=5.03 min.

Example 98

1-ethyl-3-(4-(4-morpholino-7-pivaloyl-5,6,7,8-tetrahydropyrido[3,4-d]pyrimidin-2-yl)phenyl)urea

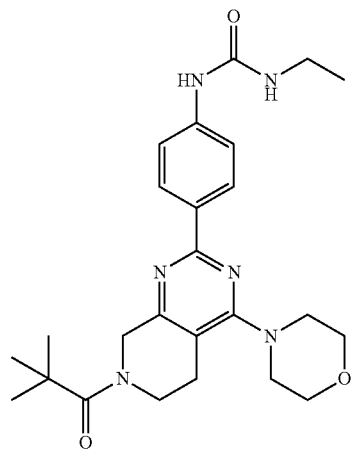 [SMILES: CCNC(=O)Nc1ccc(-c2nc3c(c(N4CCOCC4)n2)CCN(C(=O)C(C)(C)C)C3)cc1]

Method as example 18 using 1-ethyl-3-(4-(4-morpholino-5,6,7,8-tetrahydropyrido[3,4-d]pyrimidin-2-yl)phenyl)urea (example 82) and pivaloyl chloride as starting materials.
¹H NMR (d₆-DMSO) 8.70 (s, 1H), 8.20 (d, 2H), 7.48 (d, 2H), 6.18 (t, 1H), 4.61 (s, 2H), 3.75-3.79 (m, 2H), 3.73-3.75 (m, 4H), 3.46-3.51 (m, 4H), 3.08-3.15 (m, 2H), 2.71 (t, 2H), 1.27 (s, 9H), 1.06 (t, 3H).
LCMS (method A), (M+H⁺) 467, Rt=6.92 min.

Example 99

1-(4-(6-acetyl-4-morpholino-6,7-dihydro-5H-pyrrolo[3,4-d]pyrimidin-2-yl)phenyl)-3-ethylurea

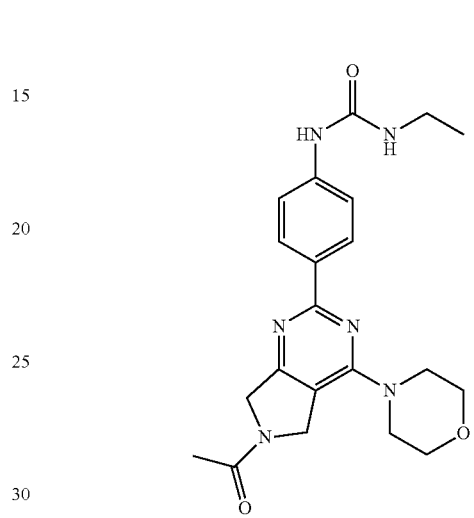

Method as example 18 using 1-ethyl-3-(4-(4-morpholino-6,7-dihydro-5H-pyrrolo[3,4-d]pyrimidin-2-yl)phenyl)urea (example 14) and acetyl chloride as starting materials.
¹H NMR (d₆-DMSO) 8.78 (s, 1H), 8.25 (dd, 2H), 7.55 (d, 2H), 6.25 (t, 1H), 5.07 (s, 1H), 4.81 (d, 2H), 4.50 (s, 1H), 3.77-3.81 (br m, 7H), 3.15-3.21 (m, 3H), 2.15 (d, 3H), 1.32 (t, 1H), 1.12 (t, 3H).
LCMS (method A), (M+H⁺) 411, Rt=6.09 min.

Example 100

1-ethyl-3-(4-(4-morpholino-6-pivaloyl-6,7-dihydro-5H-pyrrolo[3,4-d]pyrimidin-2-yl)phenyl)urea

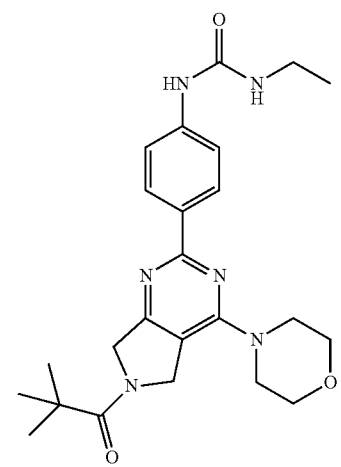 [SMILES: CCNC(=O)Nc1ccc(-c2nc3c(c(N4CCOCC4)n2)CN(C(=O)C(C)(C)C)C3)cc1]

Method as example 18 using 1-ethyl-3-(4-(4-morpholino-6,7-dihydro-5H-pyrrolo[3,4-d]pyrimidin-2-yl)phenyl)urea (example 14) and pivaloyl chloride as starting materials.

$^1$H NMR (d$_6$-DMSO) 8.70 (s, 1H), 8.20 (d, 2H), 7.48 (d, 2H), 6.19 (t, 1H), 4.80-4.94 (br s, 2H), 3.72-3.74 (br s, 7H), 3.08-3.15 (m, 2H), 1.27 (s, 9H), 1.11 (s, 1H), 1.05 (t, 3H).

LCMS (method A), (M+H$^+$) 453, Rt=7.62 min.

Example 101

(S)-1-cyclopropyl-3-(4-(4-(3-methylmorpholino)-6-(2,2,2-trifluoroethyl)-6,7-dihydro-5H-pyrrolo[3,4-d]pyrimidin-2-yl)phenyl)urea

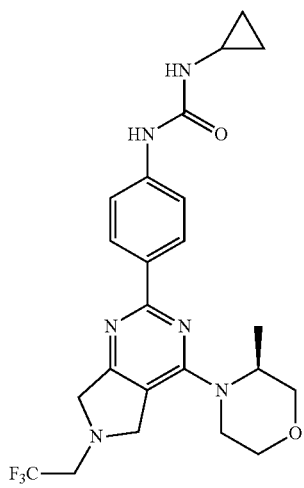 [SMILES: C[C@H]1COCCN1c1nc(-c2ccc(NC(=O)NC3CC3)cc2)nc2c1CN(CC(F)(F)F)C2]

Method as described for example 68 using (S)-1-cyclopropyl-3-(4-(4-(3-methylmorpholino)-6,7-dihydro-5H-pyrrolo[3,4-d]pyrimidin-2-yl)phenyl)urea (example 3). Additional trituration with ether gave a pale brown solid.

$^1$H NMR (CD$_3$OD) 8.54 (s, 1H), 8.18 (d, 2H), 7.47 (d, 2H), 6.44 (br d, 1H), 4.36 (dd, 2H), 4.05 (br, 1H), 4.01 (s, 2H), 3.93 (dd, 1H), 3.73 (d, 1H), 3.67-3.59 (m, 1H), 3.58 (q, 2H), 3.54-3.48 (m, 2H), 3.19-3.15 (m, 1H), 2.58-2.50 (m, 1H), 1.25 (d, 3H), 0.66-0.62 (m, 2H), 0.43-0.39 (m, 2H).

LCMS (method A), (M+H$^+$) 477, Rt=7.60 min.

Example 102

(S)-1-ethyl-3-(4-(7-(2-hydroxyacetyl)-4-(3-methylmorpholino)-5,6,7,8-tetrahydropyrido[3,4-d]pyrimidin-2-yl)phenyl)urea

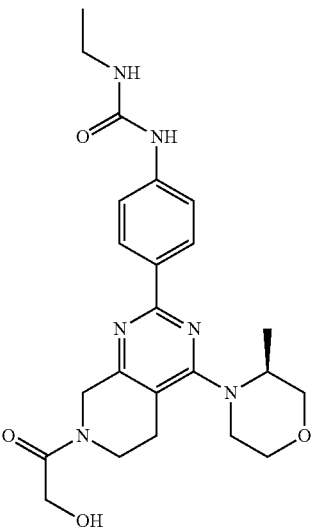 [SMILES: CCNC(=O)Nc1ccc(-c2nc3c(c(N4CCOC[C@@H]4C)n2)CCN(C(=O)CO)C3)cc1]

Method as described for example 17 using example 13 hydrochloride salt and glycolic acid as starting materials, DCM as solvent and NEt$_3$ as base. The reaction mixture was stirred at room temperature overnight and then diluted with water. The product was collected by filtration and then purified by flash chromatography (5% MeOH/DCM) to yield a beige solid (16 mg, 0.035 mmol, 15% yield).

$^1$H NMR (CDCl$_3$) 8.32 (dd, 2H), 7.39 (dd, 2H), 6.28 (s, 1H), 4.94 (d, 1H), 4.75-4.59 (m, 2H), 4.46 (s, 1H), 4.30 (d, 2H), 4.04 (dd, 1H), 3.97 (d, 1H), 3.81 (dd, 1H), 3.78-3.47 (m, 6H), 3.38-3.29 (m, 2H), 2.78-2.65 (m, 2H), 1.35 (t, 3H), 1.19 (t, 3H).

LCMS (method A), (M+H$^+$) 455, Rt=5.70 min.

Example 103

(S)-ethyl-2-(4-(3-ethylureido)-3-fluorophenyl)-4-(3-methylmorpholino)-5H-pyrrolo[3,4-d]pyrimidine-6(7H)-carboxylate

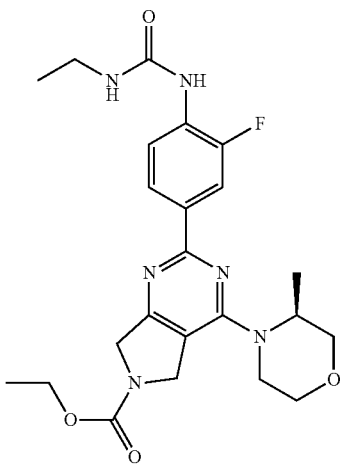 [SMILES: CCNC(=O)Nc1ccc(-c2nc3c(c(N4CCOC[C@@H]4C)n2)CN(C(=O)OCC)C3)cc1F]

Method as described for example 85 using (S)-ethyl 2-(4-amino-3-fluorophenyl)-4-(3-methylmorpholino)-5H-pyrrolo[3,4-d]pyrimidine-6(7H)-carboxylate (intermediate 19) and ethyl isocyanate as starting materials. The solvent was removed in vacuo and the residue purified by prep HPLC (high pH) yielding the title compound (10 mg, 0.021 mmol, 22%).

$^1$HNMR (CD$_3$OD) 8.16 (t, 1H), 8.07-8.01 (m, 1H), 8.01-7.94 (m, 1H), 4.86-4.73 (m, 2H), 4.56-4.50 (m, 2H), 4.50-4.38 (br, s, 1H), 4.22 (q, 2H), 4.19-4.07 (br, d, 1H), 4.06-3.98 (m, 1H), 4.86-4.74 (m, 2H), 3.68-3.58 (m, 1H), 3.52-3.40 (m, 1H), 3.25 (q, 2H), 1.36 (d, 3H), 1.36-1.29 (m, 3H), 1.17 (t, 3H).

LCMS (Method A), (M+H$^+$) 473, Rt=9.40 min

Example 104

(S)-ethyl-2-(3-fluoro-4-(3-(2-hydroxyethyl)ureido)phenyl)-4-(3-methylmorpholino)-5H-pyrrolo[3,4-d]pyrimidine-6(7H)-carboxylate

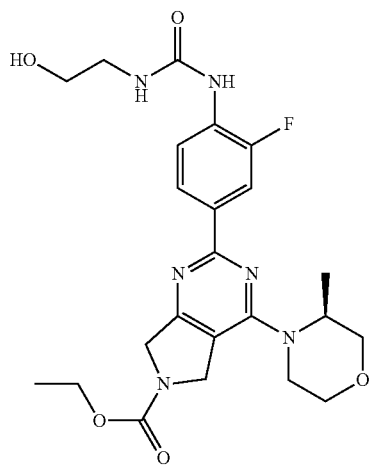 [SMILES: CCOC(=O)N1Cc2nc(-c3ccc(NC(=O)NCCO)c(F)c3)nc(N3CCOC[C@@H]3C)c2C1]

Step 1: Method as described for intermediate 10 using (S)-ethyl 2-(4-amino-3-fluorophenyl)-4-(3-methylmorpholino)-5H-pyrrolo[3,4-d]pyrimidine-6(7H)-carboxylate (intermediate 19) as starting material.

Step 2: Method as described for example 51, using 2-aminoethanol and (S)-ethyl 2-(3-fluoro-4-((phenoxycarbonyl)amino)phenyl)-4-(3-methylmorpholino)-5H-pyrrolo[3,4-d]pyrimidine-6(7H)-carboxylate as starting materials. The mixture was reduced in vacuo and purified by flash SCX2 chromatography affording the title compound (10 mg, 0.020 mmol, 36%).

$^1$HNMR (CD$_3$OD) 8.16 (t, 1H), 8.07-8.02 (m, 1H), 8.02-7.95 (m, 1H), 4.87-4.76 (m, 2H), 4.58-4.51 (m, 2H), 4.51-4.40 (br, s, 1H), 4.22 (q, 2H), 4.17-4.07 (m, 1H), 4.05-3.99 (m, 1H), 3.85-3.73 (m, 2H), 3.67-3.59 (m, 3H), 3.52-3.41 (m, 1H), 3.34 (t, 2H), 1.37 (d, 3H), 1.35-1.26 (m, 3H).

LCMS (Method A), (M+H$^+$) 489, Rt=7.88 min

Example 105

(S)-ethyl 2-(4-(3-cyclopropylureido)-3-fluorophenyl)-4-(3-methylmorpholino)-5H-pyrrolo[3,4-d]pyrimidine-6(7H)-carboxylate

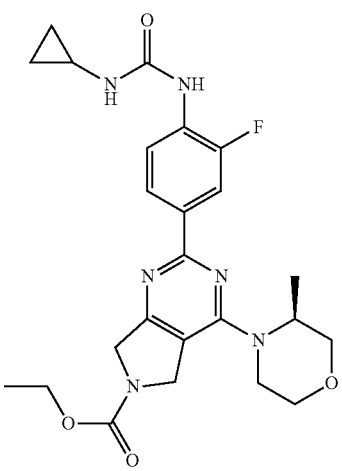 [SMILES: CCOC(=O)N1Cc2nc(-c3ccc(NC(=O)NC4CC4)c(F)c3)nc(N3CCOC[C@@H]3C)c2C1]

Step 1: Method as described for intermediate 10 using (S)-ethyl 2-(4-amino-3-fluorophenyl)-4-(3-methylmorpholino)-5H-pyrrolo[3,4-d]pyrimidine-6(7H)-carboxylate (intermediate 19) as starting material.

Example 106

(S)-1-ethyl-3-(5-(7-methyl-4-(3-methylmorpholino)-5,6,7,8-tetrahydropyrido[3,4-d]pyrimidin-2-yl)thiazol-2-yl)urea

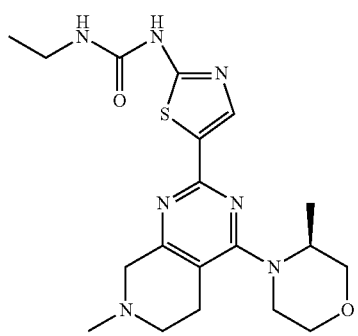 [SMILES: CCNC(=O)Nc1ncc(-c2nc3c(c(N4CCOC[C@@H]4C)n2)CCN(C)C3)s1]

Step 1: Method as described for intermediate 5 using tert-butyl (5-(4,4,5,5-tetramethyl-1,3,2-dioxaborolan-2-yl)thiazol-2-yl)carbamate and (S)-4-(2-chloro-7-methyl-5,6,7,8-tetrahydropyrido[3,4-d]pyrimidin-4-yl)-3-methylmorpholine (intermediate 13) as starting materials. The tert-butyl carboxylate group was removed under the reaction conditions. The mixture was concentrated in vacuo and purified by flash SCX2 chromatography affording (S)-5-(7-methyl-4-(3-methylmorpholino)-5,6,7,8-tetrahydropyrido[3,4-d]pyrimidin-2-yl)thiazol-2-amine.

Step 2: The product from step 1 was treated as described for example 85 with ethyl isocyanate. The mixture was concentrated in vacuo and the material purified by prep HPLC at high and low pH, yielding the title compound (15.5 mg, 0.037 mmol, 11% over 2 steps).

¹HNMR (CD₃OD) 7.98 (s, 1H), 4.20-4.09 (m, 1H), 3.95-3.86 (m, 1H), 3.82-3.74 (m, 1H), 3.74-3.65 (m, 2H), 3.65 (br s, 1H), 3.60 (br s, 1H), 3.56 (br s, 1H), 3.54-3.43 (m, 1H), 3.27 (t, 2H), 2.80-2.71 (m, 3H), 2.69-2.61 (m, 2H), 2.48 (s, 3H), 1.33 (d, 3H), 1.18 (t, 3H),

LCMS (Method A), (M+H⁺) 418 Rt=5.15 min

Example 107

(S)-ethyl 2-(4-(3-ethylureido)phenyl)-4-(3-methylmorpholino)-7,8-dihydropyrido[4,3-d]pyrimidine-6(5H)-carboxylate

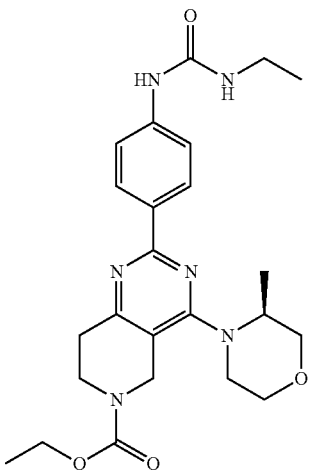 [SMILES: CCNC(=O)Nc1ccc(-c2nc3c(c(N4CCOC[C@@H]4C)n2)CN(C(=O)OCC)CC3)cc1]

Method as example 34 using (S)-1-ethyl-3-(4-(4-(3-methylmorpholino)-5,6,7,8-tetrahydropyrido[4,3-d]pyrimidin-2-yl)phenyl)urea (example 12) and ethyl chloroformate as starting materials.

¹H NMR (d₆-DMSO) 8.72 (s, 1H), 8.18 (d, 2H), 7.49 (d, 2H), 6.21 (t, 1H), 4.54-4.50 (m, 1H), 4.45-4.35 (m, 2H), 4.13-4.04 (m, 2H), 3.95-3.61 (m, 4H), 3.18 (d, 2H), 3.13-3.10 (m, 2H), 2.88-2.85 (m, 2H), 1.25 (d, 3H), 1.21 (t, 3H), 1.06 (t, 3H).

LCMS (method A), (M+H⁺) 469, Rt=6.35 min.

Example 108

(S)-1-(2,5-difluoro-4-(7-methyl-4-(3-methylmorpholino)-5,6,7,8-tetrahydropyrido[3,4-d]pyrimidin-2-yl)phenyl)-3-ethylurea

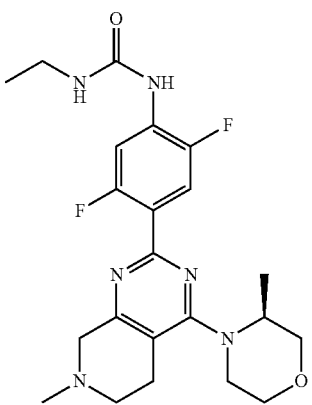 [SMILES: CCNC(=O)Nc1cc(F)c(-c2nc3c(c(N4CCOC[C@@H]4C)n2)CCN(C)C3)cc1F]

Step 1: Method as described for intermediate 5 using (S)-4-(2-chloro-7-methyl-5,6,7,8-tetrahydropyrido[3,4-d]pyrimidin-4-yl)-3-methylmorpholine (intermediate 13) and 2,5- difluoro-4-(4,4,5,5-tetramethyl-1,3,2-dioxaborolan-2-yl) aniline as starting materials. The mixture was filtered through a celite 545 pre-packed cartridge (2.5 g), washed with MeOH and solvent removed in vacuo. The residue was purified first by flash SCX2 chromatography, then by triturating with a (9:1) mixture of petrol ether (40-60)/ethyl acetate, yielding the title compound after filtration and drying of the solid obtained (55 mg, 0.14 mmol, 42%).

LCMS (Method A), (M+H$^+$) 376 Rt=5.12 min

Step 2: Method as example 85 using (S)-2,5-difluoro-4-(7-methyl-4-(3-methylmorpholino)-5,6,7,8-tetrahydropyrido[3,4-d]pyrimidin-2-yl)aniline and ethyl isocyanate as starting material. The solvent was removed in vacuo and purified twice by flash chromatography using 0-20% DCM/MeOH as eluent yielding the title compound (6.2 mg, 0.013 mmol, 11%).

$^1$HNMR (CD$_3$OD) 8.10-7.98 (m, 1H), 7.73-7.63 (m, 1H), 4.25-4.14 (m, 1H), 3.95-3.87 (m, 1H), 3.83-3.74 (m, 1H), 3.74-3.66 (m, 3H), 3.65 (br s, 1H), 3.60 (br s, 1H), 3.57-3.45 (m, 1H), 3.24 (q, 2H), 2.83-2.77 (m, 2H), 2.77-2.73 (m, 1H), 2.71-2.62 (m, 1H), 2.50 (s, 3H), 1.33 (d, 3H), 1.17 (t, 3H).

LCMS (Method A), (M+H$^+$) 447 Rt=5.63 min

Example 109

(S)-1-ethyl-3-(3-methyl-4-(7-methyl-4-(3-methylmorpholino)-5,6,7,8-tetrahydropyrido[3,4-d]pyrimidin-2-yl)phenyl)urea

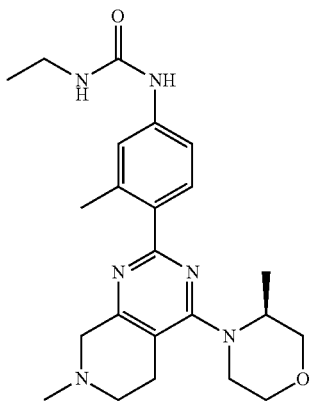 [SMILES: CCNC(=O)Nc1ccc(-c2nc3c(c(N4CCOC[C@@H]4C)n2)CCN(C)C3)c(C)c1]

Step 1: Method as described for intermediate 5 using (S)-4-(2-chloro-7-methyl-5,6,7,8-tetrahydropyrido[3,4-d]pyrimidin-4-yl)-3-methylmorpholine (intermediate 13) and 3-methyl-4-(4,4,5,5-tetramethyl-1,3,2-dioxaborolan-2-yl) aniline as starting materials. The mixture was filtered through a celite 545 pre-packed cartridge (2.5 g), washed with MeOH and solvent removed in vacuo. The residue was purified by triturating with a (9:1) mixture of petrol ether (40-60)/ethyl acetate, yielding the title compound after filtration and drying of the solid obtained (85 mg, 0.24 mmol, 68%).

LCMS (Method A), (M+H$^+$) 354 Rt=4.05 min

Step 2: Method as example 85 using (S)-3-methyl-4-(7-methyl-4-(3-methylmorpholino)-5,6,7,8-tetrahydropyrido[3,4-d]pyrimidin-2-yl)aniline and ethyl isocyanate as starting materials. The solvent was removed in vacuo and purified by prep HPLC (high pH) yielding the title compound (11.8 mg, 0.027 mmol, 20%).

$^1$HNMR (CD$_3$OD) 7.58 (d, 1H), 7.31 (d, 1H), 7.29 (s, 1H), 4.21-4.10 (m, 1H), 3.95-3.86 (m, 1H), 3.85-3.75 (m, 1H), 3.75-3.63 (m, 3H), 3.63-3.45 (m, 3H), 3.23 (q, 2H), 2.88-2.76 (m, 3H), 2.69-2.63 (m, 1H), 2.50 (s, 3H), 2.46 (s, 3H), 1.92 (s, 1H), 1.30 (d, 3H), 1.16 (t, 3H).

LCMS (Method A), (M+H$^+$) 425 Rt=5.03 min

Example 110

(S)-1-ethyl-3-(3-fluoro-4-(7-methyl-4-(3-methylmorpholino)-5,6,7,8-tetrahydropyrido[3,4-d]pyrimidin-2-yl)phenyl)urea

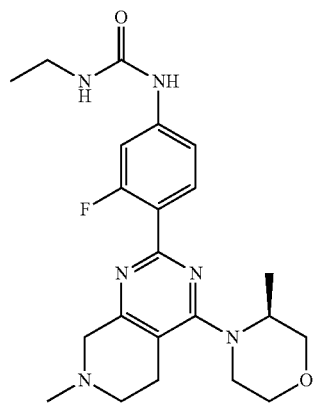 [SMILES: CCNC(=O)Nc1ccc(-c2nc3c(c(N4CCOC[C@@H]4C)n2)CCN(C)C3)c(F)c1]

Step 1: Method as described for intermediate 5 using (S)-4-(2-chloro-7-methyl-5,6,7,8-tetrahydropyrido[3,4-d]pyrimidin-4-yl)-3-methylmorpholine (intermediate 13) and as 3-fluoro-4-(4,4,5,5-tetramethyl-1,3,2-dioxaborolan-2-yl) aniline as starting materials. The reaction mixture was filtered through a celite 545 pre-packed cartridge (2.5 g), washed with methanol and solvent removed in vacuo. The residue was purified by trituration with a (9:1) mixture of petrol ether (40-60)/ethyl acetate, yielding the title compound after filtration and drying of the solid obtained (85 mg, 0.24 mmol, 67%).

LCMS (Method A), (M+H$^+$) 358 Rt=4.55 min

Step 2: Method as example 85 using (S)-3-fluoro-4-(7-methyl-4-(3-methylmorpholino)-5,6,7,8-tetrahydropyrido[3,4-d]pyrimidin-2-yl)aniline and ethyl isocynate as starting materials. The solvent was removed in vacuo and purified by prep HPLC (low pH) yielding the title compound (4.3 mg, 0.01 mmol, 6%).

$^1$HNMR (CD$_3$OD) 8.42 (br s, 2H), 7.83 (t, 1H), 7.46 (dd, 1H), 7.09 (dd, 1H), 4.25-4.13 (m, 1H), 3.98-3.74 (m, 4H), 3.74-3.63 (m, 3H), 3.57-3.46 (m, 1H), 3.23 (q, 2H), 2.88-2.70 (m, 2H), 2.65 (s, 3H), 1.34 (d, 3H), 1.16 (t, 3H).

LCMS (Method A), (M+H$^+$) 429 Rt=5.25 min

Example 111

(S)-ethyl 2-(4-(3-(3-hydroxyphenyl)ureido)phenyl)-4-(3-methylmorpholino)-5H-pyrrolo[3,4-d]pyrimidine-6(7H)-carboxylate

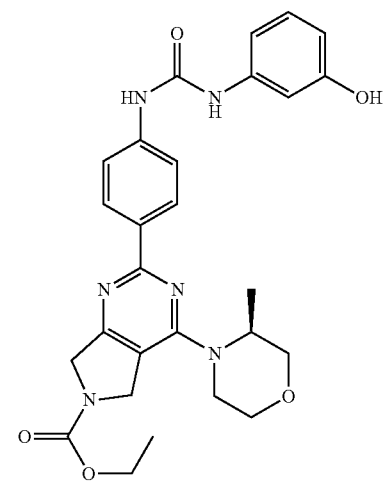 [SMILES: CCOC(=O)N1Cc2nc(-c3ccc(NC(=O)Nc4cccc(O)c4)cc3)nc(N3CCOC[C@@H]3C)c2C1]

Step 1: To a stirred solution of 3-aminophenol (66 mg, 0.55 mmol) and triethylamine (0.6 mmol, 84 μL) in DCM (5 ml) was added 4-isocyanatobenzene boronic acid pinacol ester. Reaction mixture was stirred at room temperature over the weekend. Solvent was removed in vacuo and used crude in the next reaction.

LCMS (method B), (M+H$^+$) 355, Rt=2.72 min.

Step 2: Method as intermediate 5 using 1-(3-hydroxyphenyl)-3-(4-(4,4,5,5-tetramethyl-1,3,2-dioxaborolan-2-yl)phenyl)urea and (S)-ethyl 2-chloro-4-(3-methylmorpholino)-5H-pyrrolo[3,4-d]pyrimidine-6(7H)-carboxylate (intermediate 11) as starting materials. Reaction mixture was concentrated in vacuo and purified by prep. HPLC (low pH) to afford a brown solid, 22 mg (8% over 2 steps).

$^1$H NMR (d$_6$-DMSO) 9.11 (s, 1H), 8.87 (s, 1H), 8.22 (d, 2H), 7.55 (d, 2H), 7.07 (s, 1H), 6.82 (d, 1H), 6.39 (dd, 1H), 4.78 (q, 2H), 4.52-4.38 (m, 3H), 4.17-4.10 (m, 2H), 3.89 (d, 1H), 3.70 (d, 1H), 3.67 (d, 1H), 3.51 (t, 1H), 3.43 (t, 1H), 1.27-1.22 (m, 6H).

LCMS (method A), (MH$^+$) 519, Rt=8.08 min.

Example 112

(S)-ethyl 2-(4-(3-(2-aminoethyl)ureido)phenyl)-4-(3-methylmorpholino)-5H-pyrrolo[3,4-d]pyrimidine-6(7H)-carboxylate

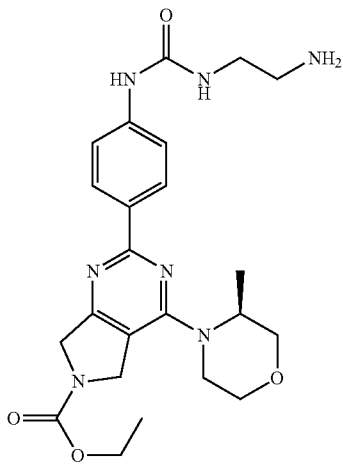 [SMILES: CCOC(=O)N1Cc2nc(-c3ccc(NC(=O)NCCN)cc3)nc(N3CCOC[C@@H]3C)c2C1]

Step 1: Method as example 111 step 1 using 4-isocyanatobenzene boronic acid pinacol ester and tert-butyl-2-aminoethyl carbamate as starting material.

LCMS (method B), (M+H$^+$) 355, Rt=2.72 min.

Step 2: Method as intermediate 5 was performed using tert-butyl (2-(3-(4-(4,4,5,5-tetramethyl-1,3,2-dioxaborolan-2-yl)phenyl)ureido)ethyl)carbamate and (S)-ethyl 2-chloro-4-(3-methylmorpholino)-5H-pyrrolo[3,4-d]pyrimidine-6(7H)-carboxylate (intermediate 11) as starting materials. Reaction mixture was concentrated in vacuo and purified by prep. HPLC (low pH) to afford a brown solid.

Step 3: Product from step 2 deprotected using method in intermediate 6. The compound was isolated as a free base using a tosic acid cartridge to give a brown solid, 18 mg (7% over 2 steps).

$^1$H NMR (d$_6$-DMSO) 8.94 (s, 1H), 8.19 (d, 2H), 7.49 (d, 2H), 6.40 (t, 1H), 4.86-4.72 (m, 2H), 4.49 (d, 2H), 4.38 (br s, 1H), 4.17-4.08 (m, 2H), 3.94 (d, 1H), 3.74 (d, 1H), 3.68 (d, 1H), 3.51 (t, 1H), 3.17-3.11 (m, 2H), 2.69-2.66 (m, 2H), 1.27-1.22 (m, 6H).

LCMS (method A), (MH$^+$) 470, Rt=5.75 min.

Example 113

(S)-ethyl-2-(4-(3-ethylureido)-2-fluorophenyl)-4-(3-methylmorpholino)-5H-pyrrolo[3,4-d]pyrimidine-6(7H)-carboxylate

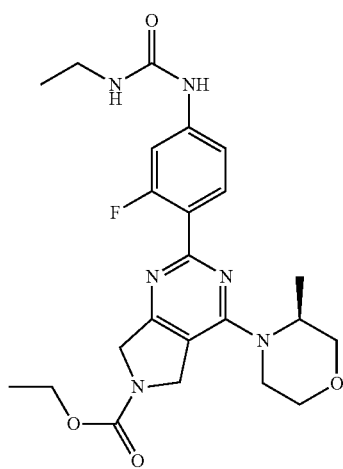 [SMILES: CCNC(=O)Nc1ccc(-c2nc3c(c(N4CCOC[C@@H]4C)n2)CN(C(=O)OCC)C3)c(F)c1]

Step 1 Method as described for intermediate 5 using (S)-ethyl 2-chloro-4-(3-methylmorpholino)-5H-pyrrolo[3,4-d]pyrimidine-6(7H)-carboxylate (intermediate 11) and 3-fluoro-4-(4,4,5,5-tetramethyl-1,3,2-dioxaborolan-2-yl)aniline as starting materials. The mixture was filtered through a celite 545 pre-packed cartridge (2.5 g), washed with MeOH and solvent removed in vacuo. The residue was purified by prep HPLC (high pH) yielding the title compound (54.7 mg, 0.13 mmol, 44%).

LCMS (Method A), (M+H$^+$) 02 Rt=6.70 min

Step 2: Method as example 85 using (S)-ethyl 2-(4-amino-2-fluorophenyl)-4-(3-methylmorpholino)-5H-pyrrolo[3,4-d]pyrimidine-6(7H)-carboxylate and ethyl isocyanate as starting materials. The solvent was removed in vacuo and purified by prep HPLC (low pH) yielding the title compound (14.6 mg, 0.03 mmol, 34%).

$^1$HNMR (CD$_3$OD) 7.92-7.82 (m, 1H), 7.47 (dd, 1H), 7.09, (d, 1H), 4.88-4.75 (m, 2H), 4.56 (br s, 2H), 4.47 (br s, 1H), 4.28-4.20 (q, 2H), 4.20-4.06 (m, 1H), 4.00 (dd, 1H), 3.84-3.72 (m, 2H), 3.67-3.56 (m, 1H), 3.52-3.39 (m, 1H), 3.25 (q, 2H), 1.24-1.28 (m, 6H), 1.18 (t, 3H).

LCMS (Method A), (M+H$^+$) 473 Rt=7.63 min

Example 114

(S)-ethyl 2-(4-(3-(2-amino-2-oxoethyl)ureido)phenyl)-4-(3-methylmorpholino)-5H-pyrrolo[3,4-d]pyrimidine-6(7H)-carboxylate

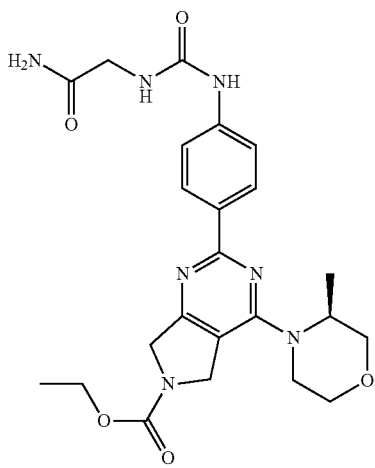 [SMILES: CCOC(=O)N1Cc2nc(-c3ccc(NC(=O)NCC(N)=O)cc3)nc(N3CCOC[C@@H]3C)c2C1]

Step 1: 2-(4-isocyanatophenyl)-4,4,5,5-tetramethyl-1,3,2-dioxaborolane (300 mg, 1.22 mmol) was dissolved in dry THF and stirred with 2-amino acetamide hydrochloride (108 mg, 1.46 mmol) and triethylamine (drops) and stirred at 60° C. overnight. The solvent was removed in vacuo, yielding the title compound (345 mg, 1.08 mmol, 88%).

LCMS (Method B), (M+H$^+$) 320 Rt=2.19 min

Step 2: Method as described for intermediate 5 using (S)-ethyl 2-chloro-4-(3-methylmorpholino)-5H-pyrrolo[3,4-d]pyrimidine-6(7H)-carboxylate (intermediate 11) and 2-(3-(4-(4,4,5,5-tetramethyl-1,3,2-dioxaborolan-2-yl)phenyl)ureido)acetamide as starting materials, and [1,1'-bis(diphenylphosphino)ferrocene]dichloropalladium(II) as catalyst. The mixture was filtered through a celite 545 pre-packed cartridge (2.5 g), washed with MeOH and solvent removed in vacuo. The residue was purified by prep HPLC (high pH) yielding the title compound (10.6 mg, 0.02 mmol, 12%).

$^1$HNMR (CD$_3$OD) 8.23-8.16 (m, 2H), 7.47 (d, 2H), 4.87-4.77 (m, 2H), 4.55 (br s, 2H), 4.51-4.40 (br s, 1H), 4.29-4.17 (m, 2H), 4.14-4.06 (m, 1H), 4.06-3.97 (m, 1H), 3.88 (s, 2H), 3.85-3.73 (m, 2H), 3.68-3.58 (m, 1H), 3.53-3.43 (m, 1H), 2.01 (s, 2H), 1.38 (d, 3H), 1.36-1.27 (m, 3H), 1.24 (t, 2H).

LCMS (Method A), (M+H$^+$) 484 Rt=6.17 min

Example 115

(S)-2-(3-(4-(6-(ethoxycarbonyl)-4-(3-methylmorpholino)-6,7-dihydro-5H-pyrrolo[3,4-d]pyrimidin-2-yl)phenyl)ureido)acetic acid

Example 116

(S)-ethyl-2-(5-(3-ethylureido)pyrazin-2-yl)-4-(3-methylmorpholino)-5H-pyrrolo[3,4-d]pyrimidine-6(7H)-carboxylate

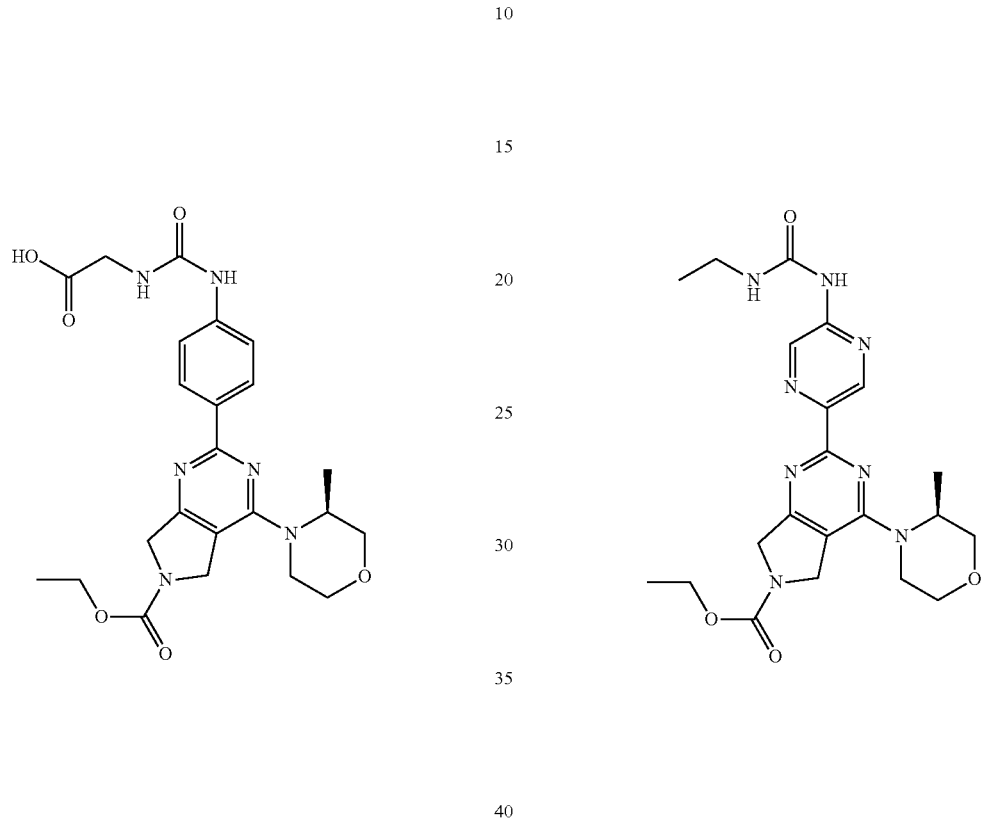

Step 1: Method as described for example 114, step 1 using 2-amino acetic acid as starting material. The mixture was reduced in vacuo, yielding the title compound (492 mg, 1.53 mmol, 100%).

LCMS (Method B), (M+H$^+$) 321 Rt=2.34 min

Step 2: Method as described for intermediate 5, using (S)-ethyl 2-chloro-4-(3-methylmorpholino)-5H-pyrrolo[3,4-d]pyrimidine-6(7H)-carboxylate (intermediate 11) and 2-(3-(4-(4,4,5,5-tetramethyl-1,3,2-dioxaborolan-2-yl)phenyl)ureido)acetic acid as starting materials, and [1,1'-bis(diphenylphosphino)ferrocene]dichloropalladium(II) as catalyst. The mixture was filtered through a celite 545 pre-packed cartridge (2.5 g), washed with MeOH and solvent removed in vacuo. The residue was purified by prep HPLC (low pH) yielding (6.5 mg, 0.01 mmol, 9%).

$^1$HNMR (CD$_3$OD) 8.18 (d, 2H), 7.46 (d, 2H), 4.86-4.71 (m, 2H), 4.53 (d, 2H), 4.50-4.39 (br s, 1H), 4.26-4.16 (m, 2H), 4.16-4.07 (m, 1H), 4.06-3.96 (m, 1H), 3.90 (s, 2H), 3.85-3.71 (m, 2H), 3.66-3.57 (m, 1H), 3.52-3.39 (m, 1H), 1.37 (d, 3H), 1.35-1.29 (m, 3H).

LCMS (Method A), (M+H$^+$) 485 Rt=7.18 min

Step 1: Method as described for intermediate 5 using (S)-ethyl 2-chloro-4-(3-methylmorpholino)-5H-pyrrolo[3,4-d]pyrimidine-6(7H)-carboxylate (intermediate 11), 5-(4,4,5,5-tetramethyl-1,3,2-dioxaborolan-2-yl)pyrazin-2-amine as starting materials, and [1,1'-bis(diphenylphosphino)ferrocene]dichloropalladium(II) as catalyst. The reaction mixture was filtered through a celite 545 pre-packed cartridge (2.5 g), washed with MeOH and solvent removed in vacuo. The residue was purified by flash chromatography using a gradient of 0-40% DCM/MeOH yielding the title compound (69 mg, 0.18 mmol, 58%).

LCMS (Method B), (M+H$^+$) 386 Rt=1.70 min

Step 2: Method as example 85 using (S)-ethyl 2-(5-aminopyrazin-2-yl)-4-(3-methylmorpholino)-5H-pyrrolo[3,4-d]pyrimidine-6(7H)-carboxylate as starting material. The solvent was removed in vacuo and purified by prep HPLC (low pH) yielding the title compound (1.4 mg, 1.7%).

$^1$HNMR (CD$_3$OD) 9.20 (s, 1H), 8.69 (dd, 1H), 8.44 (br s, 1H), 4.64-4.59 (m, 2H), 4.53 (br s, 1H), 4.32-4.21 (m, 3H), 4.44 (dd, 1H), 3.87-3.76 (m, 2H), 3.70-3.60 (m, 2H), 3.57-3.45 (m, 1H), 3.41-3.33 (q, 2H), 1.41 (dd, 3H), 1.35 (t, 3H), 1.24 (t, 3H).

LCMS (Method A), (M+H$^+$) 457 Rt=7.01 min

Example 117

(S)-1-(4-(6-(1-acetylpiperidin-4-yl)-4-(3-methylmorpholino)-6,7-dihydro-5H-pyrrolo[3,4-d]pyrimidin-2-yl)-2-fluorophenyl)-3-ethylurea

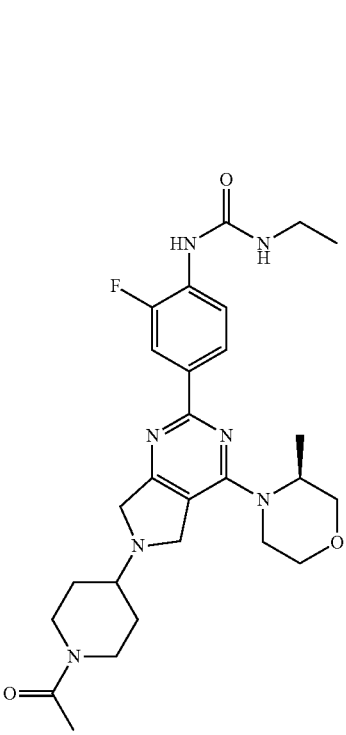 [SMILES: CCNC(=O)Nc1ccc(-c2nc3c(c(N4CCOC[C@@H]4C)n2)CN(C2CCN(C(C)=O)CC2)C3)cc1F]

To (S)-1-ethyl-3-(2-fluoro-4-(4-(3-methylmorpholino)-6,7-dihydro-5H-pyrrolo[3,4-d]pyrimidin-2-yl)phenyl)urea (intermediate 18) (100 mg, 0.23 mmol) and triethylamine (64 μL, 0.46 mmol) in dry THF (3 ml) was added 1-acetylpiperidin-4-one (56 μL, 0.46 mmol) and stirred at room temperature for 30 min. To this sodium triacetoxyborohydride (97 mg, 0.46 mmol) was added. The reaction mixture was stirred at room temperature until analysis by LCMS indicated reaction was complete. The solvent was then removed in vacuo. Crude reaction mixture then was partitioned between ethyl acetate and water. The organic layer was recovered, dried with sodium sulphate and solvent removed in vacuo. Residue was then purified by prep HPLC (low pH) to afford a white solid (6.7 mg, 0.013 mmol, 6%).

$^1$H NMR (400 MHz, CD$_3$OD) 8.25 (s, 1H), 8.18 (t, 1H), 8.10-7.97 (m, 2H), 4.49 (br, d, 2H), 4.32-4.11 (m, 3H), 4.07-3.91 (m, 4H), 3.86-3.75 (m, 2H), 3.70-3.58 (m, 1H), 3.54-3.41 (m, 2H), 3.30-3.21 (m, 3H), 2.95-2.78 (m, 2H), 2.15-2.04 (m, 3H), 1.62-1.42 (br, m, 2H), 1.38 (d, 3H), 1.19 (t, 3H)

LCMS (Method A), (M+H$^+$) 526, Rt=5.98 min

Example 118

(S)-ethyl 4-(3-methylmorpholino)-2-(4-(3-(pyridin-3-yl)ureido)phenyl)-5H-pyrrolo[3,4-d]pyrimidine-6(7H)-carboxylate Step 1: Method as described for (intermediate 15) using pyridin-3-amine as starting material. Saturated solution of NaHCO$_3$ was added, and the mixture stirred for 15 mins before partitioning between water and DCM. The organic layer was recovered, dried over MgSO$_4$, filtered and solvent removed in vacuo. The crude residue was purified by flash chromatography using a gradient of 0-100% petrol ether (40-60)/ethyl acetate, yielding the title compound (47 mg, 0.14 mmol, 10%).

LCMS (Method B), (M+H$^+$) 340 Rt=2.10 min

Step 2: Method as described for intermediate 5 using (S)-ethyl 2-chloro-4-(3-methylmorpholino)-5H-pyrrolo[3,4-d]pyrimidine-6(7H)-carboxylate (intermediate 11) and 1-(pyridin-3-yl)-3-(4-(4,4,5,5-tetramethyl-1,3,2-dioxaborolan-2-yl)phenyl)urea as starting materials, and [1,1'-bis(diphenylphosphino)ferrocene]dichloropalladium(II) as catalyst. The reaction mixture was filtered through a celite 545 pre-packed cartridge (2.5 g), washed with MeOH and reduced in vacuo. The residue was purified first by flash chromatography using a gradient of 0-40% DCM/MeOH, then triturating with a mixture of petrol ether/ethyl acetate (9:1) affording the title compound after filtration and drying of the solid obtained (23 mg, 0.05 mmol, 30%).

$^1$HNMR (CD$_3$OD) 8.62 (d, 1H), 8.24-8.16 (m, 3H), 8.06-8.00 (m, 1H), 7.55-7.47 (dd, 2H), 7.41-7.39 (m, 1H), 4.83-4.67 (m, 2H), 4.52 (d, 2H), 4.50-4.36 (br s, 1H), 4.25-4.13 (m, 2H), 4.16-4.06 (m, 1H), 4.05-3.96 (m, 1H), 3.86-3.74 (m, 2H), 3.69-3.58 (m, 1H), 3.50-3.38 (m, 1H), 1.38 (d, 3H), 1.35-1.25 (m, 3H),

LCMS (Method A), (M+H$^+$) 504 Rt=6.19 min

Example 119

(S)-ethyl 2-(4-(3-(4-(hydroxymethyl)phenyl)ureido)phenyl)-4-(3-methylmorpholino)-5H-pyrrolo[3,4-d]pyrimidine-6(7H)-carboxylate

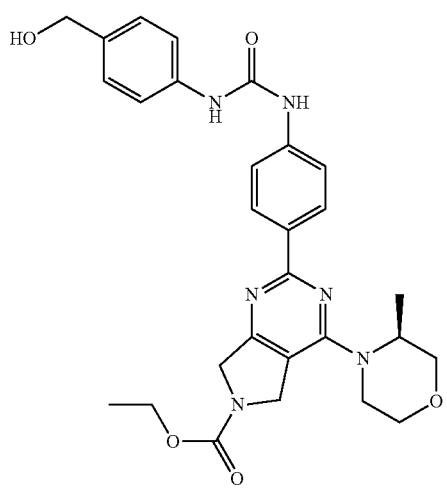 [SMILES: CCOC(=O)N1Cc2nc(-c3ccc(NC(=O)Nc4ccc(CO)cc4)cc3)nc(N3CCOC[C@@H]3C)c2C1]

Step 1: Method as described for (intermediate 15) using (4-aminophenyl)methanol as starting material. Saturated solution of NaHCO₃ was added to the reaction mixture, and stirring allowed for 15 mins before partitioning between water and DCM. The organic layer was recovered, dried over MgSO₄, filtered and solvent removed in vacuo. The crude residue was purified by flash chromatography using a gradient of 0-100% ethyl acetate/petrol ether (40-60), yielding the title compound (320 mg, 0.87 mmol, 64%).

LCMS (Method B), (M+H$^+$) 369 Rt=2.72 min

Step 2: Method as described for intermediate 5 using (S)-ethyl 2-chloro-4-(3-methylmorpholino)-5H-pyrrolo[3,4-d]pyrimidine-6(7H)-carboxylate (intermediate 11) and 1-(4-(hydroxymethyl)phenyl)-3-(4-(4,4,5,5-tetramethyl-1,3,2-dioxaborolan-2-yl)phenyl)urea as starting materials, and [1,1'-bis(diphenylphosphino)ferrocene]dichloropalladium(II) as catalyst. The reaction mixture was filtered through a celite 545 pre-packed cartridge (2.5 g), washed with MeOH and solvent removed in vacuo. The residue was purified first by prep HPLC (low pH) yielding the title compound (34 mg, 0.06 mmol, 41%).

¹HNMR (CD₃OD) 8.20 (d, 2H), 7.50 (dd, 2H), 7.42 (d, 2H), 7.29 (d, 2H), 4.84-4.69 (m, 2H), 4.55 (s, 2H), 4.53-4.48 (m, 1H), 4.47-4.39 (br s, 1H), 4.25-4.17 (m, 2H), 4.17-4.07 (m, 1H), 4.05-3.97 (m, 1H), 3.85-3.74 (m, 2H), 3.69-3.58 (m, 1H), 3.51-3.39 (m, 1H), 1.38 (d, 3H), 1.35-1.27 (m, 3H).

LCMS (Method A), (M+H$^+$) 533 Rt=7.76 min

Example 120

(S)-ethyl 2-(4-(3-(2-fluoroethyl)ureido)phenyl)-4-(3-methylmorpholino)-5H-pyrrolo[3,4-d]pyrimidine-6(7H)-carboxylate

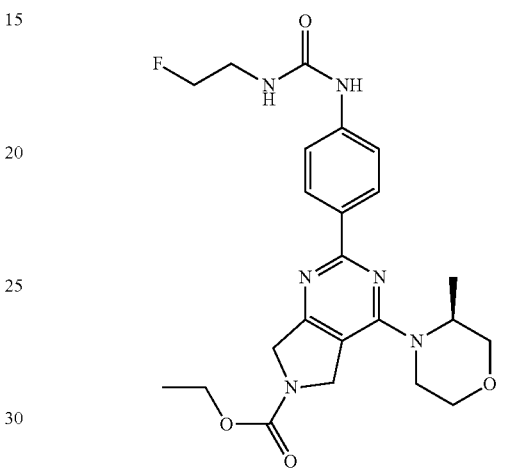

Step 1: Method as intermediate 10 using 4-(4,4,5,5-tetramethyl-1,3,2-dioxaborolan-2-yl)aniline and phenyl chloroformate as starting materials.

Step 2: Method as example 51 using 2-fluoroethylamine hydrochloride and phenyl (4-(4,4,5,5-tetramethyl-1,3,2-dioxaborolan-2-yl)phenyl)carbamate as starting materials. The solvent was removed in vacuo and the residue purified by flash chromatography using a gradient of 0-100% ethyl acetate/petrol ether (40-60) as eluent, yielding the title compound (65 mg, 0.21 mmol, 78%).

Step 3: Method as described for intermediate 5 using (S)-ethyl 2-chloro-4-(3-methylmorpholino)-5H-pyrrolo[3,4-d]pyrimidine-6(7H)-carboxylate (intermediate 11) and 1-(2-fluoroethyl)-3-(4-(4,4,5,5-tetramethyl-1,3,2-dioxaborolan-2-yl)phenyl)urea as starting materials and [1,1'-bis(diphenylphosphino)ferrocene]dichloropalladium(II) as catalyst. The mixture was filtered through a celite 545 pre-packed cartridge (2.5 g), washed with MeOH and solvent removed in vacuo. The residue was purified first by flash chromatography using a gradient of 0-20% MeOH/DCM as eluent, then prep HPLC (low pH) yielding the title compound (9.2 mg, 0.02 mmol, 13%).

¹HNMR (CD₃OD) 8.24-8.17 (dd, 2H), 7.47 (d, 2H), 4.86-4.75 (m, 2H), 4.58-4.53 (m, 3H), 4.46-4.41 (t, 2H), 4.27-4.19 (q, 2H), 4.06-3.99 (m, 1H), 3.85-3.75 (m, 2H), 3.68-3.59 (m, 1H), 3.57-3.52 (m, 1H), 3.52-3.45 (m, 2H), 2.66 (s, 1H), 1.42-1.27 (m, 6H).

LCMS (Method A), (M+H$^+$) 473 Rt=7.45 min

Example 121

(S)-ethyl 4-(3-methylmorpholino)-2-(4-(3-(pyridin-4-yl)ureido)phenyl)-5H-pyrrolo[3,4-d]pyrimidine-6(7H)-carboxylate

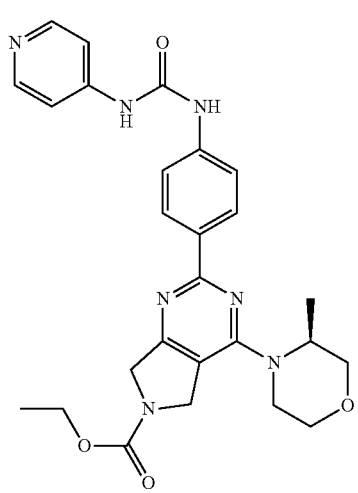 [SMILES: CCOC(=O)N1Cc2nc(-c3ccc(NC(=O)Nc4ccncc4)cc3)nc(N3CCOC[C@@H]3C)c2C1]

Step 1: Method as (intermediate 14) using pyridin-4-amine as starting material. The solvent was removed in vacuo, and the residue purified by flash chromatography using a gradient of 0-100% ethyl acetate/petrol ether (40-60) as eluent, yielding the title compound (115 mg, 0.33 mmol, 27%).

LCMS (Method B), (M+H$^+$) 340 Rt=1.92 min

Step 2: Method as described for intermediate 5 using (S)-ethyl 2-chloro-4-(3-methylmorpholino)-5H-pyrrolo[3,4-d]pyrimidine-6(7H)-carboxylate (intermediate 11) and 1-(pyridin-4-yl)-3-(4-(4,4,5,5-tetramethyl-1,3,2-dioxaborolan-2-yl)phenyl)urea as starting materials and [1,1'-bis(diphenylphosphino)ferrocene]dichloropalladium(II) as catalyst. The mixture was filtered through a celite 545 prepacked cartridge (2.5 g), washed with MeOH and solvent removed in vacuo. The residue was purified by prep HPLC (low pH) yielding the title compound (38.2 mg, 0.08 mmol, 49%).

$^1$HNMR (d$_6$-DMSO) 9.28 (s, 1H), 9.24 (s, 1H), 8.37 (dd, 2H), 8.26 (dd, 2H), 8.15 (s, 1H), 7.57 (dd, 2H), 7.46 (dd, 2H), 4.91-4.69 (m, 2H), 4.50 (d, 2H), 4.45-4.33 (br s, 1H), 4.19-4.09 (m, 3H), 3.98 (dd, 1H), 3.79-3.73 (d, 1H), 3.67 (dd, 1H), 3.58-3.47 (m, 1H), 1.31-1.21 (m, 6H).

LCMS (Method A), (M+H$^+$) 504 Rt=5.70 min

Example 122

(S)-methyl 4-(2-(4-(3-ethylureido)-3-fluorophenyl)-4-(3-methylmorpholino)-5H-pyrrolo[3,4-d]pyrimidin-6(7H)-yl)piperidine-1-carboxylate

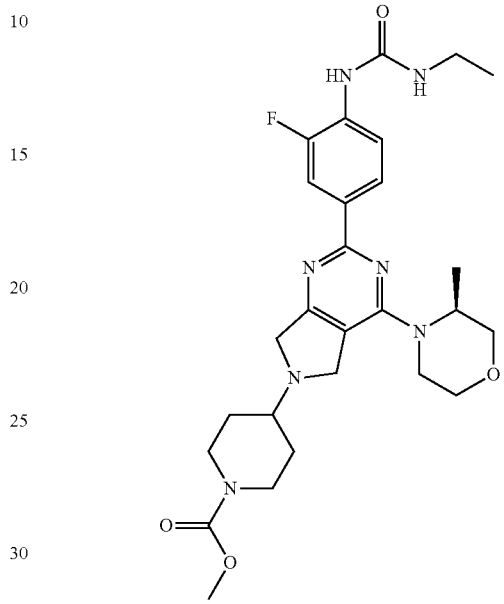

Step 1: To a solution of (S)-1-ethyl-3-(2-fluoro-4-(4-(3-methylmorpholino)-6,7-dihydro-5H-pyrrolo[3,4-d]pyrimidin-2-yl)phenyl)urea hydrochloride (intermediate 18) (120 mg, 0.27 mmol) and triethylamine (77 µL, 0.55 mmol) in DCE (4 mL, anhydrous) was added tert-butyl 4-oxopiperidine-1-carboxylate (130 mg, 0.621 mmol). Reaction mixture was stirred at room temperature for 30 min. To this sodium triacetoxyborohydride (116 mg, 0.55 mmol) was added. The reaction mixture was stirred at room temperature until analysis by LCMS indicated reaction was complete. Solvent was then removed in vacuo. Purified by normal phase chromatography using 0-100% Ethyl acetate/cyclohexane to yield a white solid (95.6 mg, 0.16 mmol, 61%)

Step 2: (S)-tert-butyl 4-(2-(4-(3-ethylureido)-3-fluorophenyl)-4-(3-methylmorpholino)-5H-pyrrolo[3,4-d]pyrimidin-6(7H)-yl)piperidine-1-carboxylate) (96 mg, 0.16 mmol) was stirred in a solution of HCl (4 mL, 4M dioxane), and methanol (0.5 mL) until analysis by LCMS indicated reaction was complete. Solvent was removed in vacuo to afford a white solid (130 mg).

Step 3: To a stirred solution of (S)-1-ethyl-3-(2-fluoro-4-(4-(3-methylmorpholino)-6-(piperidin-4-yl)-6,7-dihydro-5H-pyrrolo[3,4-d]pyrimidin-2-yl)phenyl)urea (90 mg, 0.17 mmol) and DIPEA (30 µL, 0.17 mmol) in Dioxane (5 mL) was added methyl chloroformate (14 µL, 0.19 mmol). Reaction mixture was stirred at room temperature until analysis by LCMS indicated reaction was complete. Solvent was then removed in vacuo. Purified by prep. HPLC (low pH) to afford an orange gum. This was then further purified using a TsOH cartridge to remove residual formic acid from HPLC (loaded in MeOH eluted with 2M methanolic ammonia). This gave a creamy pink solid (4.9 mg, 0.009 mmol, 5.3%).

¹H NMR (400 MHz, d₆-DMSO) 8.46 (d, 1H), 8.26 (t, 1H), 8.01 (ddd, 2H), 6.68 (t, 1H), 4.42 (s, 1H), 4.18-3.98 (m, 3H), 3.97-3.90 (m, 1H), 3.90-3.76 (m, 4H), 3.75-3.61 (m, 3H), 3.60 (s, 3H), 3.56-3.42 (m, 1H), 3.18-3.08 (m, 3H), 3.00 (s, 2H), 2.70-2.58 (m, 1H), 1.90 (d, 2H), 1.46-1.35 (m, 2H), 1.24 (d, 3H), 1.07 (t, 3H).

LCMS (Method A), (M+H⁺) 542, Rt=5.76 min

Example 123

(S)-1-(4-(6-(1-acetylpiperidine-4-carbonyl)-4-(3-methylmorpholino)-6,7-dihydro-5H-pyrrolo[3,4-d]pyrimidin-2-yl)-2-fluorophenyl)-3-ethylurea

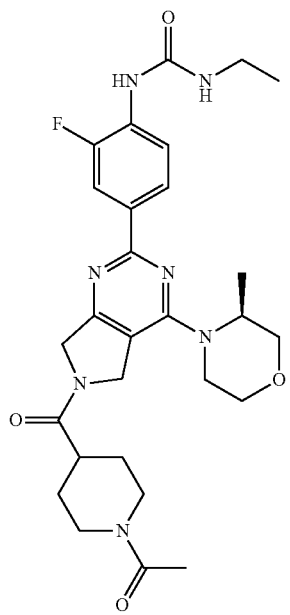 [SMILES: CCNC(=O)Nc1ccc(-c2nc3c(c(N4CCOC[C@@H]4C)n2)CN(C(=O)C2CCN(C(C)=O)CC2)C3)cc1F]

A stirred solution of (S)-1-ethyl-3-(2-fluoro-4-(4-(3-methylmorpholino)-6,7-dihydro-5H-pyrrolo[3,4-d]pyrimidin-2-yl)phenyl)urea (intermediate 18) (133 mg, 0.25 mmol) and N-methylmorpholine (55 µL, 0.5 mmol) in DMF (5 mL, anhydrous) was added EDC (53 mg, 0.275 mmol), HOBT (37 mg, 0.275 mmol), and 1-acetylpiperidine-4-carboxylic acid (43 mg, 0.25 mmol). The reaction mixture was stirred at room temperature until analysis by LCMS deemed reaction complete. Solvent was then removed in vacuo. Purified by prep. HPLC (low pH) Then further purified using a TsOH cartridge to remove residual formic acid from HPLC (loaded in MeOH eluted with 2M methanolic ammonia). Yielding a light pink solid (9.6 mg, 0.017 mmol, 7%).

¹H NMR (d₆-DMSO) 8.56 (s, 1H), 8.39-8.33 (m, 1H), 8.16-8.05 (m, 2H), 6.80-6.74 (m, 1H), 5.17 (dd, 1H), 4.96-4.80 (m, 3H), 4.55 (s, 1H), 4.48 (d, 1H), 4.09-4.02 (m, 1H), 3.93 (d, 1H), 3.88-3.79 (m, 1H), 3.77-3.71 (m, 1H), 3.63-3.54 (m, 1H), 3.25-3.16 (m, 3H), 3.05-2.86 (m, 1H), 2.74-2.61 (m, 2H), 2.09 (d, 3H), 1.91-1.79 (m, 2H), 1.68-1.38 (m, 3H), 1.35 (t, 3H), 1.15 (t, 3H).

LCMS (Method A), (M+H⁺) 554, Rt=7.10 min

Example 124

(S)-ethyl 2-(4-(3-(2-acetamidoethyl)ureido)phenyl)-4-(3-methylmorpholino)-5H-pyrrolo[3,4-d]pyrimidine-6(7H)-carboxylate

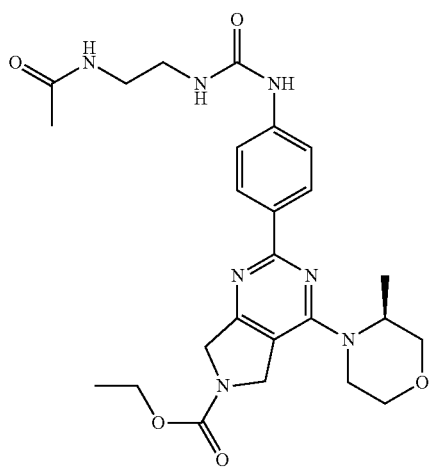 [SMILES: CCOC(=O)N1Cc2nc(-c3ccc(NC(=O)NCCNC(C)=O)cc3)nc(N3CCOC[C@@H]3C)c2C1]

Step 1: Method as described for (intermediate 14) using N-(2-aminoethyl)acetamide as starting material. The solvent was removed in vacuo and the residue purified by flash chromatography using a gradient of 0-100% ethyl acetate/petrol ether (40-60) followed by 0-10% methanol/ethyl acetate as eluent, yielding the title compound (245 mg, 0.71 mmol, 58%).

LCMS (Method B), (M+H⁺) 348, Rt=2.26 min

Step 2: Method as described for intermediate 5 using (S)-ethyl 2-chloro-4-(3-methylmorpholino)-5H-pyrrolo[3,4-d]pyrimidine-6(7H)-carboxylate (intermediate 11) and N-(2-(3-(4-(4,4,5,5-tetramethyl-1,3,2-dioxaborolan-2-yl)phenyl)ureido)ethyl)acetamide as starting materials and 1,1'-Bis(diphenylphosphino)ferrocene]dichloropalladium(II) as catalyst. The mixture was filtered through a celite 545 pre-packed cartridge (2.5 g), washed with MeOH and solvent removed in vacuo. The residue was purified by prep HPLC (high pH) yielding the title compound (30 mg, 0.05 mmol, 38%).

¹HNMR (d₆-DMSO) 8.83 (s, 1H), 8.18 (dd, 2H), 7.97-7.91 (m, 1H), 7.48 (d, 2H), 6.29-6.22 (m, 1H), 4.88-4.68 (m, 2H), 4.51-4.43 (m, 2H), 4.43-4.32 (br s, 1H), 4.17-4.08 (m, 3H), 3.99-3.90 (m, 1H), 3.78-3.70 (m, 1H), 3.70-3.62 (m, 1H), 3.55-3.43 (m, 1H), 3.16-3.10 (m, 4H), 1.81 (s, 3H), 1.28-1.21 (m, 6H).

LCMS (Method C), (M+H⁺) 512 Rt=7.33 min

Example 125

(S)-ethyl 2-(4-(3-(2-(methylamino)-2-oxoethyl)ureido)phenyl)-4-(3-methylmorpholino)-5H-pyrrolo[3,4-d]pyrimidine-6(7H)-carboxylate

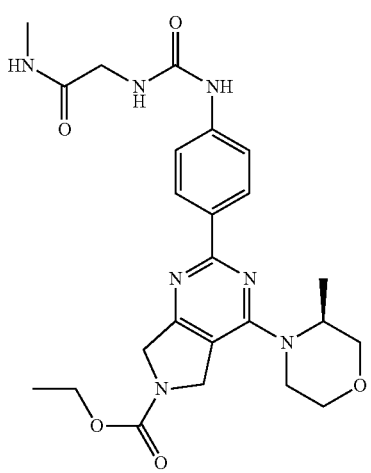 [SMILES: CCOC(=O)N1Cc2nc(-c3ccc(NC(=O)NCC(=O)NC)cc3)nc(N3CCOC[C@@H]3C)c2C1]

Step 1: Method as described for (intermediate 14) 2-amino-N-methylacetamide as starting material. The solvent was removed in vacuo and the residue purified by flash chromatography using a gradient of 0-100% ethyl acetate/petrol ether (40-60) followed by 0-10% MeOH/ethyl acetate as eluent, yielding (160 mg, 0.48 mmol, 39%).

LCMS (Method B), (M+H⁺) 334 Rt=2.24 min

Step 2: Method as described for intermediate 5 using (S)-ethyl 2-chloro-4-(3-methylmorpholino)-5H-pyrrolo[3,4-d]pyrimidine-6(7H)-carboxylate (intermediate 11) and N-methyl-2-(3-(4-(4,4,5,5-tetramethyl-1,3,2-dioxaborolan-2-yl)phenyl)ureido)acetamide as starting materials and [1,1'-bis(diphenylphosphino)ferrocene]dichloropalladium(II) as catalyst. The mixture was filtered through a celite 545 prepacked cartridge (2.5 g), washed with MeOH and solvent removed in vacuo. The residue was purified by prep HPLC (high pH) yielding the title compound (35 mg, 0.07 mmol, 46%).

¹HNMR (d₆-DMSO) 9.04 (s, 1H), 8.19 (dd, 2H), 7.93-7.83 (m, 1H), 7.48 (d, 2H), 6.46-6.39 (m, 1H), 491-4.67 (m, 2H), 4.52-4.41 (m, 2H), 4.43-4.29 (br s, 1H), 4.20-4.06 (m, 3H), 3.99-3.91 (m, 1H), 3.79-3.61 (m, 4H), 3.53-3.43 (m, 1H), 2.61 (d, 3H), 1.29-1.20 (m, 6H).

LCMS (Method C), (M+H⁺), 498 Rt=7.34 min

Example 126

(S)-1-ethyl-3-(2-fluoro-4-(4-(3-methylmorpholino)-6-(piperidine-4-carbonyl)-6,7-dihydro-5H-pyrrolo[3,4-d]pyrimidin-2-yl)phenyl)urea

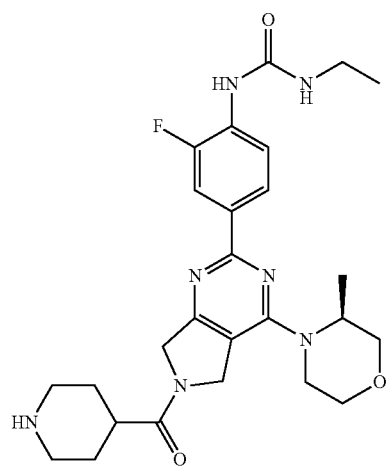 [SMILES: CCNC(=O)Nc1ccc(-c2nc3c(c(N4CCOC[C@@H]4C)n2)CN(C(=O)C2CCNCC2)C3)cc1F]

Step 1: Method as described for example 123 using (S)-1-ethyl-3-(2-fluoro-4-(4-(3-methylmorpholino)-6,7-dihydro-5H-pyrrolo[3,4-d]pyrimidin-2-yl)phenyl)urea (intermediate 18) and N-Boc-isonipecotic acid as starting materials. Reaction mixture was concentrated in vacuo, purified by prep. HPLC (high pH).

Step 2: Method as intermediate 6. The compound was isolated as a free base using a tosic acid cartridge to give a brown solid, 6.8 mg.

1H NMR (d6-DMSO) 8.30 (s, 1H), 8.06 (t, 1H), 7.77-7.95 (m, 2H), 6.47 (t, 1H), 4.91-4.75 (t, 1H), 4.64-4.47 (m, 3H), 4.32-4.10 (m, 2H), 3.88-3.80 (m, 1H), 3.78-3.68 (m, 2H), 3.56-3.50 (m, 1H), 3.48-3.42 (m, 1H), 3.29-3.22 (m, 1H), 2.98-2.88 (m, 1H), 2.58-2.48 (m, 2H), 2.31 (s, 4H), 1.60-1.51 (m, 2H), 1.45-1.33 (m, 2H), 1.18-1.01 (m, 3H), 0.83 (t, 3H).

LCMS (Method A), (M+H⁺) 512, Rt=5.43 min

Example 127

(S)-4-(2-(4-(3-cyclopropylureido)phenyl)-4-(3-methylmorpholino)-5H-pyrrolo[3,4-d]pyrimidin-6(7H)-yl)-4-oxobutanamide

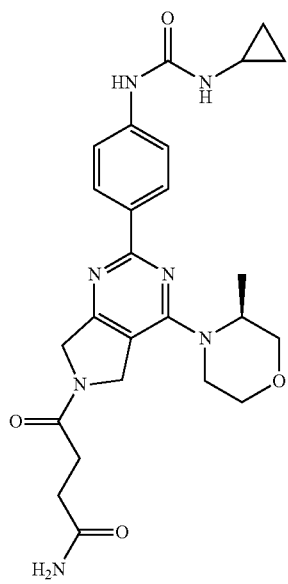 [SMILES: C[C@H]1COCCN1c1nc(-c2ccc(NC(=O)NC3CC3)cc2)nc2c1CN(C(=O)CCC(N)=O)C2]

To a stirred solution of (S)-1-cyclopropyl-3-(4-(4-(3-methylmorpholino)-6,7-dihydro-5H-pyrrolo[3,4-d]pyrimidin-2-yl)phenyl)urea (Example 3) (100 mg, 0.25 mmol) and N-methylmorpholine (56 μL, 0.5 mmol) in DMF (5 ml, anhydrous) was added EDC (53 mg, 0.28 mmol), HOBT (38 mg, 0.28 mmol), and 4-amino-4-oxobutanoic acid (29.7 mg, 0.25 mmol). The reaction mixture was stirred at room temperature until analysis by LCMS deemed reaction complete. Solvent was then removed in vacuo. Purified by prep. HPLC (high pH) to afford a white solid (25.7 mg, 0.052 mmol, 21%).

$^1$H NMR (400 MHz, d$_6$-DMSO) 8.60 (s, 1H), 8.19 (d, 2H), 7.50 (dd, 2H), 7.35 (d, 1H), 6.80 (s, 1H), 6.49 (s, 1H), 5.08-4.92 (m, 1H), 4.84-4.70 (m, 2H), 4.49-4.32 (m, 2H), 4.14 (s, 1H), 3.97 (d, 1H), 3.80-3.63 (m, 2H), 3.52 (ddd, 1H), 2.65-2.52 (m, 3H), 2.39 (t, 2H), 1.27 (t, 3H), 0.68-0.60 (m, 2H), 0.46-0.37 (m, 2H).

LCMS (Method A), (M+H$^+$) 494, Rt=5.74 min

Example 128

(S)-tert-butyl 4-((2-(4-(3-cyclopropylureido)phenyl)-4-(3-methylmorpholino)-5H-pyrrolo[3,4-d]pyrimidin-6(7H)-yl)methyl)piperidine-1-carboxylate

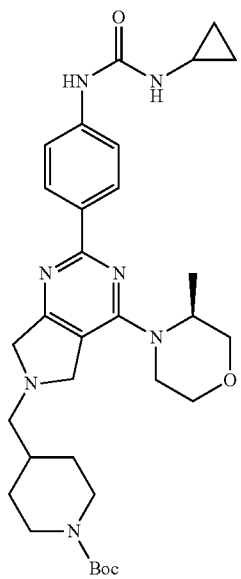 [SMILES: C[C@H]1COCCN1c1nc(-c2ccc(NC(=O)NC3CC3)cc2)nc2c1CN(CC1CCN(C(=O)OC(C)(C)C)CC1)C2]

To a solution of (S)-1-cyclopropyl-3-(4-(4-(3-methylmorpholino)-6,7-dihydro-5H-pyrrolo[3,4-d]pyrimidin-2-yl)phenyl)urea (Example 3) (147 mg, 0.37 mmol) and triethyamine (52 μL, 0.37 mmol) in DMF (3 mL, anhydrous) was added tert-butyl 4-(bromomethyl)piperidine-1-carboxylate (103 mg, 0.37 mmol). The reaction mixture was stirred at 75° C. until LCMS indicated reaction was complete. Solvent was then removed in vacuo. Purified by prep. HPLC (high pH) to afford a brown solid (28.9 mg, 0.049 mmol, 13%).

$^1$H NMR (400 MHz, d$_6$-DMSO) 8.55 (s, 1H), 8.17 (d, 2H), 7.48 (d, 2H), 6.47 (d, 1H), 4.39 (s, 1H), 4.14-3.89 (m, 6H), 3.78-3.62 (m, 4H), 3.54-3.46 (m, 1H), 3.17 (d, 1H), 2.74 (br, s, 2H), 2.58-2.53 (m, 3H), 1.80-1.67 (m, 3H), 1.40 (s, 9H), 1.24 (d, 3H), 1.06-0.92 (m, 2H), 0.68-0.61 (m, 2H), 0.44-0.38 (m, 2H).

LCMS (Method A), (M+H$^+$) 592, Rt=6.51 min

Example 129

(S)-1-cyclopropyl-3-(4-(4-(3-methylmorpholino)-6-(tetrahydro-2H-pyran-4-carbonyl)-6,7-dihydro-5H-pyrrolo[3,4-d]pyrimidin-2-yl)phenyl)urea

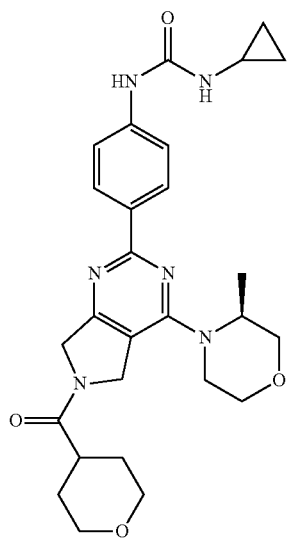 [SMILES: C[C@H]1COCCN1c1nc(-c2ccc(NC(=O)NC3CC3)cc2)nc2c1CN(C(=O)C1CCOCC1)C2]

To a solution of (S)-1-cyclopropyl-3-(4-(4-(3-methylmorpholino)-6,7-dihydro-5H-pyrrolo[3,4-d]pyrimidin-2-yl)phenyl)urea (Example 3) (100 mg, 0.37 mmol) and triethyamine (42.4 µL, 0.30 mmol) in DCM (3 mL, anhydrous), and DMF (1 mL, anhydrous) was added tetrahydro-2H-pyran-4-carbonyl chloride (45.2 mg, 0.30 mmol). The reaction mixture was stirred at room temperature until LCMS indicated reaction was complete. Solvent was then removed in vacuo.

Purified by prep. HPLC (low pH). This was then further purified using a TsOH cartridge (loaded in MeOH eluted with 2M methanolic ammonia), to afford a light brown solid (15.1 mg, 0.030 mmol, 12%).

$^1$H NMR (d$_6$-DMSO) 8.38 (d, 1H), 7.97 (dd, 2H), 7.29 (dd, 2H), 6.27 (s, 1H), 4.95-4.79 (m, 1H), 4.67-4.50 (m, 3H), 4.35-4.16 (m, 2H), 3.94 (br, s, 1H), 3.83-3.63 (m, 4H), 3.59-3.43 (m, 3H), 3.20-3.14 (m, 2H), 2.77-2.54 (m, 2H), 1.49-1.36 (m, 4H), 1.07 (t, 3H), 0.47-0.40 (m, 2H), 0.23-0.17 (m, 2H).

LCMS (Method A), (M+H$^+$) 507, Rt=6.64 min

Example 130

(S)-1-cyclopropyl-3-(4-(4-(3-methylmorpholino)-6-(piperidin-4-ylmethyl)-6,7-dihydro-5H-pyrrolo[3,4-d]pyrimidin-2-yl)phenyl)urea

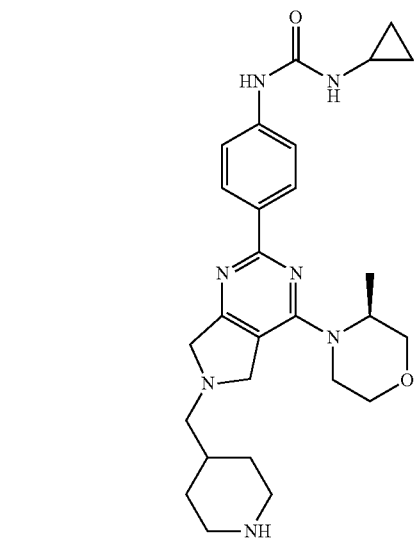 [SMILES: C[C@H]1COCCN1c1nc(-c2ccc(NC(=O)NC3CC3)cc2)nc2c1CN(CC1CCNCC1)C2]

(S)-tert-butyl 4-((2-(4-(3-cyclopropylureido)phenyl)-4-(3-methylmorpholino)-5H-pyrrolo[3,4-d]pyrimidin-6(7H)-yl)methyl)piperidine-1-carboxylate (example 128) (24 mg, 0.04 mmol) was stirred in a solution of 4M HCl in dioxane (1 mL), and methanol (0.5 mL) until analysis by LCMS indicated reaction was complete. Reaction mixture was then purified by TsOH cartridge (loaded in MeOH eluted with 2M methanolic ammonia) to afford an orange brown solid (4.9 mg, 0.009 mmol, 25%).

$^1$H NMR (400 MHz, d$_6$-DMSO) 8.56 (s, 1H), 8.17 (d, 2H), 7.48 (d, 2H), 6.48 (s, 1H), 4.39 (s, 1H), 4.14-3.90 (m, 5H), 3.80-3.62 (m, 5H), 3.55-3.45 (m, 3H), 3.18 (d, 2H), 2.76 (t, 2H), 2.59-2.53 (m, 2H), 1.85 (d, 2H), 1.80-1.71 (m, 1H), 1.27-1.13 (m, 5H), 0.67-0.61 (m, 2H), 0.44-0.38 (m, 2H).

LCMS (Method A), (M+H$^+$) 492, Rt=4.17 min

Example 131

(S)-ethyl 2-(4-(3-cyclopropylureido)-2-fluorophenyl)-4-(3-methylmorpholino)-5H-pyrrolo[3,4-d]pyrimidine-6(7H)-carboxylate

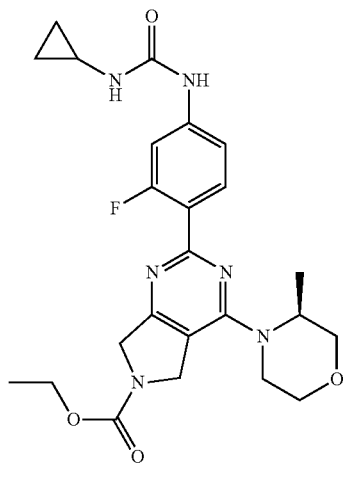 [SMILES: CCOC(=O)N1Cc2nc(-c3ccc(NC(=O)NC4CC4)cc3F)nc(N3CCOC[C@@H]3C)c2C1]

Step 1: Method as example 113

Step 2: Method as example 113 step 2 using (S)-ethyl 2-(4-amino-2-fluorophenyl)-4-(3-methylmorpholino)-5H-pyrrolo[3,4-d]pyrimidine-6(7H)-carboxylate and isocyanatocyclopropane as starting materials. The solvent was removed in vacuo and the residue purified by prep HPLC (low pH) yielding the final compound (17 mg, 0.04 mmol, 47%).

$^1$HNMR (d$_6$-DMSO) 8.82 (s, 1H), 7.98-7.89 (m, 1H), 7.58-7.48 (m, 1H), 7.17-7.09 (m, 1H), 6.65-6.59 (m, 1H), 4.92-4.71 (m, 2H), 4.47 (d, 2H), 4.43-4.29 (br s, 1H), 4.19-4.08 (m, 3H), 3.99-3.90 (m, 1H), 3.77-3.69 (m, 1H), 3.68-3.59 (m, 1H), 3.54-3.43 (m, 1H), 2.59-2.52 (m, 1H), 1.29-1.20 (m, 6H), 0.68-0.61 (m, 2H), 0.45-0.38 (m, 2H).

LCMS (Method C) (M+H$^+$) 485, Rt=8.54 min

Example 132

(S)-1-cyclopropyl-3-(4-(4-(3-methylmorpholino)-6-(3-(2-oxopyrrolidin-1-yl)propanoyl)-6,7-dihydro-5H-pyrrolo[3,4-d]pyrimidin-2-yl)phenyl)urea

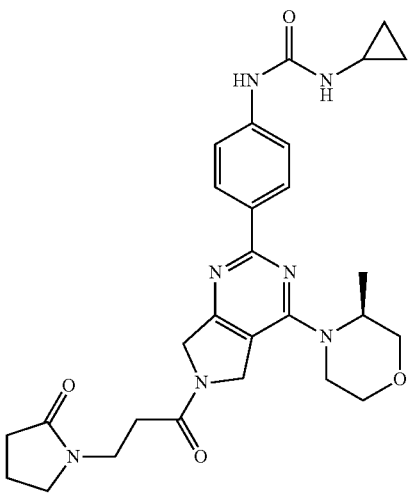 [SMILES: C[C@H]1COCCN1c1nc(-c2ccc(NC(=O)NC3CC3)cc2)nc2c1CN(C(=O)CCN1CCCC1=O)C2]

Method as example 127 using 3-(2-oxopyrrolidin-1-yl) propanoic acid and (S)-1-cyclopropyl-3-(4-(4-(3-methyl-morpholino)-6,7-dihydro-5H-pyrrolo[3,4-d]pyrimidin-2-yl) phenyl)urea (example 3) as starting materials. Purified by prep HPLC at low pH to afford a white solid. (35.3 mg, 0.066 mmol, 29%).

$^1$H NMR (400 MHz, d$_6$-DMSO) 8.38 (s, 1H), 7.98 (dd, 2H), 7.29 (d, 2H), 6.28 (s, 1H), 4.78 (q, 1H), 4.66-4.48 (m, 3H), 4.29-4.15 (m, 2H), 3.90 (br, s, 1H), 3.79-3.73 (m, 1H), 3.58-3.43 (m, 3H), 3.36-3.15 (m, 7H), 2.00 (t, 2H), 1.75-1.65 (m, 2H), 1.06 (d, 3H), 0.47-0.40 (m, 2H), 0.23-0.17 (m, 2H).

LCMS (Method A), (M+H$^+$) 534, Rt=6.29 min

Example 133

(S)—N-(4-(2-(4-(3-cyclopropylureido)phenyl)-4-(3-methylmorpholino)-5H-pyrrolo[3,4-d]pyrimidin-6(7H)-yl)-4-oxobutyl)acetamide

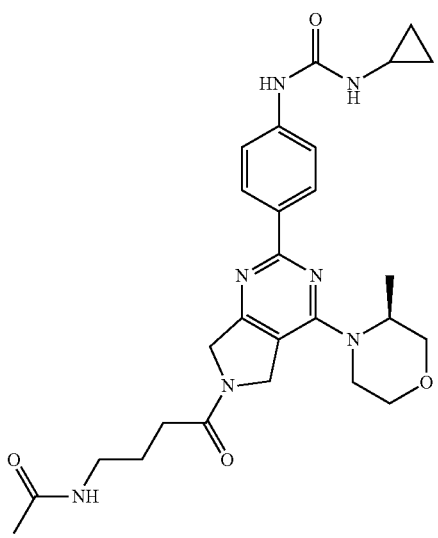 [SMILES: CC(=O)NCCCC(=O)N1Cc2nc(-c3ccc(NC(=O)NC4CC4)cc3)nc(N3CCOC[C@@H]3C)c2C1]

Method as example 127 using 4-acetamidobutanoic acid and (S)-1-cyclopropyl-3-(4-(4-(3-methylmorpholino)-6,7-dihydro-5H-pyrrolo[3,4-d]pyrimidin-2-yl)phenyl)urea (example 3) as starting materials. Purified by Prep HPLC at low pH to afford a white solid (46.5 mg, 0.089 mmol, 39%).

$^1$H NMR (400 MHz, d$_6$-DMSO) 8.37 (s, 1H), 7.98-7.94 (m, 2H), 7.66-7.60 (m, 1H), 7.27 (d, 2H), 6.27 (s, 1H), 4.75 (q, 1H), 4.63-4.44 (m, 3H), 4.26-4.10 (m, 2H), 3.92 (br, s, 1H), 3.74 (d, 1H), 3.56-3.40 (m, 2H), 3.34-3.24 (m, 1H), 2.89-2.80 (m, 2H), 2.35-2.30 (m, 1H), 2.21-2.12 (m, 2H), 1.57 (d, 3H), 1.51-1.41 (m, 2H), 1.07-1.00 (m, 3H), 0.44-0.37 (m, 2H), 0.21-0.15 (m, 2H).

LCMS (Method A), (M+H$^+$) 522, Rt=6.03 min

Example 134

(S)-4-(2-(4-(3-cyclopropylureido)phenyl)-4-(3-methylmorpholino)-5H-pyrrolo[3,4-d]pyrimidin-6(7H)-yl)butanoic acid

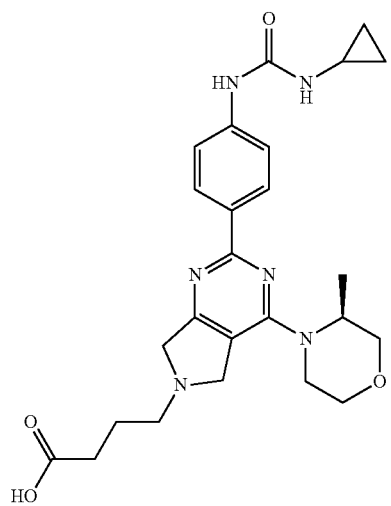 [SMILES: C[C@H]1COCCN1c1nc(-c2ccc(NC(=O)NC3CC3)cc2)nc2c1CN(CCCC(=O)O)C2]

To a solution of (S)-1-cyclopropyl-3-(4-(4-(3-methylmorpholino)-6,7-dihydro-5H-pyrrolo[3,4-d]pyrimidin-2-yl)phenyl)urea (Example 3) as a HCl salt (100 mg, 0.23 mmol) and triethyamine (64 µL, 0.46 mmol) in DCE (3 mL, anhydrous), and DMF 0.5 mL, anhydrous) was added 4-oxobutanoic acid (45 µL, 0.46 mmol). Reaction mixture was stirred at room temperature for 30 mins. To this sodium triacetoxyborohydride (97 mg, 0.46 mmol) was added. The reaction mixture was stirred at room temperature until analysis by LCMS indicated reaction was complete. Solvent was then removed in vacuo. Purified by prep. HPLC (high pH) to afford a white solid (4.2 mg, 0.008 mmol, 4%).

$^1$H NMR (400 MHz, d$_6$-DMSO) 8.61 (s, 1H), 8.17 (d, 2H), 7.48 (d, 2H), 6.53 (s, 1H), 4.38 (s, 1H), 4.13-3.97 (m, 3H), 3.93 (dd, 1H), 3.79-3.61 (m, 6H), 2.69 (t, 2H), 2.58-2.52 (m, 1H), 2.29 (t, 2H), 1.75 (m, 2H), 1.24 (d, 3H), 0.68-0.60 (m, 2H), 0.44-0.39 (m, 2H).

LCMS (Method A), (M+H$^+$) 481, Rt=5.01 min

Example 135

(S)—N-(3-(2-(4-(3-cyclopropylureido)phenyl)-4-(3-methylmorpholino)-5H-pyrrolo[3,4-d]pyrimidin-6(7H)-yl)-3-oxopropyl)-N-methylacetamide

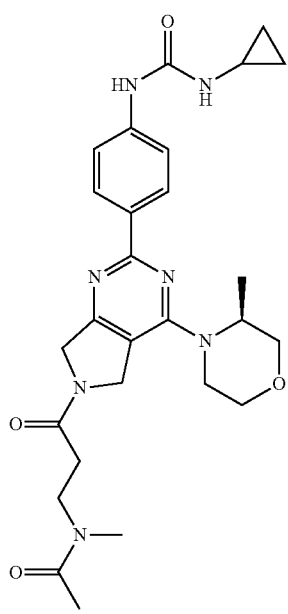 [SMILES: CC(=O)N(C)CCC(=O)N1Cc2nc(-c3ccc(NC(=O)NC4CC4)cc3)nc(N3CCOC[C@@H]3C)c2C1]

Method as example 127 using 3-(N-methylacetamido)propanoic acid and (S)-1-cyclopropyl-3-(4-(4-(3-methylmorpholino)-6,7-dihydro-5H-pyrrolo[3,4-d]pyrimidin-2-yl)phenyl)urea (example 3) as starting materials to yield a white solid (36.8 mg, 0.071 mmol, 26%).

$^1$H NMR (400 MHz, d$_6$-DMSO) 8.58 (s, 1H), 8.22-8.17 (m, 2H), 7.50 (d, 2H), 6.48 (s, 1H), 5.10-4.90 (m, 1H), 4.88-4.68 (m, 2H), 4.50-3.34 (m, 2H), 4.22-4.06 (m, 1H), 3.98 (d, 1H), 3.80-3.64 (m, 2H), 3.62-3.47 (m, 3H), 3.01 (d, 2H), 2.82 (d, 1H), 2.77-2.67 (m, 1H), 2.65-2.53 (m, 2H), 2.01 (d, 3H), 1.31-1.24 (m, 3H), 0.68-0.61 (m, 2H), 0.44-0.39 (m, 2H).

LCMS (Method A), (M+H$^+$) 522, Rt=6.22 min

Example 136

(S)-1-cyclopropyl-3-(4-(4-(3-methylmorpholino)-6-(3-ureidopropanoyl)-6,7-dihydro-5H-pyrrolo[3,4-d]pyrimidin-2-yl)phenyl)urea

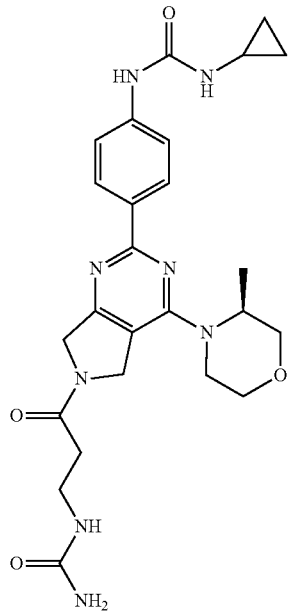 [SMILES: C[C@H]1COCCN1c1nc(-c2ccc(NC(=O)NC3CC3)cc2)nc2c1CN(C(=O)CCNC(N)=O)C2]

Method as example 127 using 3-ureidopropanoic acid and (S)-1-cyclopropyl-3-(4-(4-(3-methylmorpholino)-6,7-dihydro-5H-pyrrolo[3,4-d]pyrimidin-2-yl)phenyl)urea (example 3) as starting materials to afford a white solid (22.3 mg, 0.044 mmol, 16%).

$^1$H NMR (400 MHz, d$_6$-DMSO) 8.58 (s, 1H), 8.20 (d, 2H), 7.50 (d, 2H), 6.48 (s, 1H), 5.99 (dt, 1H), 5.51 (d, 2H), 4.98 (q, 1H), 4.80 (q, 1H), 4.70 (s, 1H), 4.50-4.33 (m, 2H), 4.12 (br, s, 1H), 3.97 (d, 1H), 3.72 (q, 2H), 3.52 (td, 1H), 3.30-3.22 (m, 2H), 2.59-2.52 (m, 2H), 1.28 (d, 3H), 0.68-0.61 (m, 2H), 0.44-0.39 (m, 2H).

LCMS (Method A), (M+H$^+$) 509, Rt=5.71 min

Intermediate 20

4-(2-chloro-6,7-dihydro-5H-pyrrolo[3,4-d]pyrimidin-4-yl)morpholine trifluoroacetate

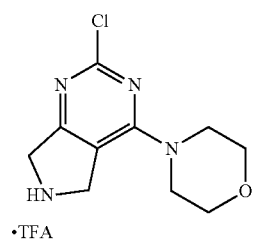

A solution of tert-butyl 2-chloro-4-morpholino-5H-pyrrolo[3,4-d]pyrimidine-6(7H)-carboxylate (intermediate 2)

(2.05 g, 6.0 mmol) in TFA (15 ml) and DCM (30 ml) was stirred at room temperature (20° C.) overnight. The material was concentrated in vacuo to give an orange oil, which was used without further purification.

LCMS (method B), (M+H$^+$) 241, Rt=0.44 min.

Intermediate 21

4-(2-chloro-6-methyl-6,7-dihydro-5H-pyrrolo[3,4-d]pyrimidin-4-yl)morpholine

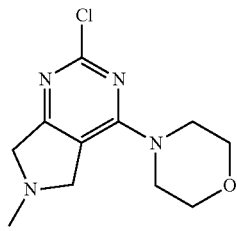 [SMILES: CN1Cc2nc(Cl)nc(N3CCOCC3)c2C1]

To a stirring solution of 4-(2-chloro-6,7-dihydro-5H-pyrrolo[3,4-d]pyrimidin-4-yl)morpholine trifluoroacetate (intermediate 20) (2.16 g, 2.0 mmol) in DMF, was added aqueous formaldehyde (0.3 ml, 4.0 mmol) and Et$_3$N (560 uL, 4.0 mmol). The reaction mixture was stirred at room temperature (20° C.) for 45 minutes, before adding sodium triacetoxy borohydride (848 mg, 4.0 mmol). The reaction mixture was then stirred over-night at room temperature (20° C.). The reaction mixture was basified (with 2M NaOH) before partitioning between water (25 ml) and DCM (50 ml). The organic layer was recovered, passed through a hydrophobic frit and the solvent removed in vacuo, affording the title compound as a pink solid, which was used without further purification.

LCMS (method B), (M+H$^+$) 255, Rt=1.83 min.

Intermediate 22

(S)-4-(2-chloro-6-isopropyl-6,7-dihydro-5H-pyrrolo[3,4-d]pyrimidin-4-yl)-3-methylmorpholine

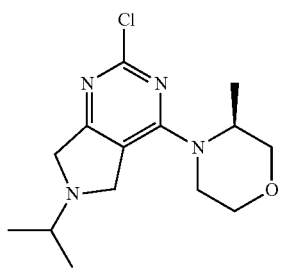 [SMILES: CC(C)N1Cc2nc(Cl)nc(N3CCOC[C@@H]3C)c2C1]

To a stirred solution of (S)-4-(2-chloro-6,7-dihydro-5H-pyrrolo[3,4-d]pyrimidin-4-yl)-3-methylmorpholine (intermediate 6) as a TFA salt (820 mg, 2.0 mmol) in anhydrous THF (5 ml) was added anhydrous acetone (500 μl) and glacial acetic acid (four drops). The reaction was stirred at RT for 30 minutes after which time sodium triacetoxyborohydride (848 mg, 4.0 mmols) was added. After stirring for a further 30 minutes at RT, the reaction was partitioned between water and DCM. The aqueous phase was extracted into DCM and the organic extracts were combined, dried over magnesium sulphate and concentrated in vacuo to afford the title compound as a brown oil, which was used without further purification.

LCMS (Method D), (M+H$^+$) 297, RT=2.25 mins

Intermediate 23

1-(2-chloro-4-morpholino-5H-pyrrolo[3,4-d]pyrimidin-6(7H)-yl)ethanone

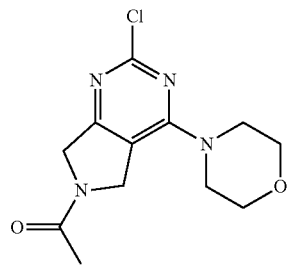 [SMILES: CC(=O)N1Cc2nc(Cl)nc(N3CCOCC3)c2C1]

To a stirring solution of 4-(2-chloro-6,7-dihydro-5H-pyrrolo[3,4-d]pyrimidin-4-yl)morpholine trifluoroacetate (intermediate 20) (2.16 g, 2.0 mmol) in DMF (10 ml), was added Et$_3$N (560 uL, 4.0 mmol). Reaction mixture was stirred at room temperature (20° C.) for 2 minutes followed by the addition of acetyl chloride (157 uL, 2.2 mmol) followed by stirring at room temperature overnight. The reaction mixture was basified (with 2M NaOH) before partitioning between water (25 ml) and DCM (50 ml). The organic layer was recovered, passed through a hydrophobic frit and the solvent removed in vacuo, affording the title compound as a pink solid, which was used without further purification.

LCMS (method B), (M+H$^+$) 283 Rt=1.75 min.

Intermediate 24

(S)-1-(2-chloro-4-(3-methylmorpholino)-5H-pyrrolo[3,4-d]pyrimidin-6(7H)-yl)ethanone

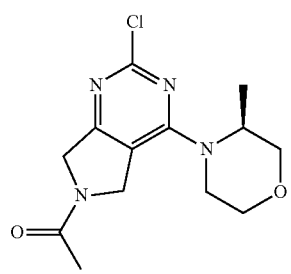 [SMILES: CC(=O)N1Cc2nc(Cl)nc(N3CCOC[C@@H]3C)c2C1]

Method as described for 1-(2-chloro-4-morpholino-5H-pyrrolo[3,4-d]pyrimidin-6(7H)-yl)ethanone (intermediate 23) using (S)-4-(2-chloro-6,7-dihydro-5H-pyrrolo[3,4-d]pyrimidin-4-yl)-3-methylmorpholine (intermediate 6) as a TFA salt to yield a dark brown oil, which was used without further purification.

LCMS (method B), (M+H$^+$) 297 Rt=1.90 min.

Intermediate 25 methyl 2-chloro-4-morpholino-5H-pyrrolo[3,4-d]pyrimidine-6(7H)-carboxylate

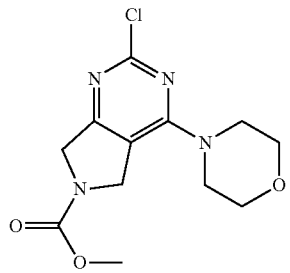 [SMILES: COC(=O)N1Cc2nc(Cl)nc(N3CCOCC3)c2C1]

To a stirring solution of 4-(2-chloro-6,7-dihydro-5H-pyrrolo[3,4-d]pyrimidin-4-yl)morpholine trifluoroacetate (intermediate 20) (2.16 g, 2.0 mmol) in DMF (10 ml), was added Et₃N (560 uL, 4.0 mmol). Reaction mixture was stirred at room temperature (20° C.) for 2 minutes followed by the addition of methylchloroformate (186 uL, 2.4 mmol) followed by stirring at room temperature overnight. The reaction mixture was basified (with 2M NaOH) before partitioning between water (25 ml) and DCM (50 ml). The organic layer was recovered, passed through a hydrophobic frit and the solvent removed in vacuo, affording the title compound as a brown solid used without further purification.

LCMS (method B), (M+H⁺) 299 Rt=1.99 min.

Intermediate 26

(S)-methyl 2-chloro-4-(3-methylmorpholino)-5H-pyrrolo[3,4-d]pyrimidine-6(7H)-carboxylate

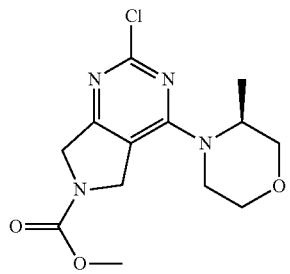 [SMILES: COC(=O)N1Cc2nc(Cl)nc(N3CCOC[C@@H]3C)c2C1]

Method as described for methyl 2-chloro-4-morpholino-5H-pyrrolo[3,4-d]pyrimidine-6(7H)-carboxylate (intermediate 25) using (S)-4-(2-chloro-6,7-dihydro-5H-pyrrolo[3,4-d]pyrimidin-4-yl)-3-methylmorpholine (intermediate 6) as a TFA salt to yield a dark brown oil, which was used without further purification.

LCMS (method B), (M+H⁺) 313 Rt=2.17 min.

Intermediate 27 ethyl 2-chloro-4-morpholino-5H-pyrrolo[3,4-d]pyrimidine-6(7H)-carboxylate

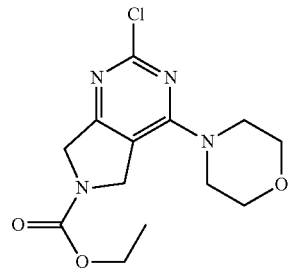 [SMILES: CCOC(=O)N1Cc2nc(Cl)nc(N3CCOCC3)c2C1]

To a stirred solution of 4-(2-chloro-6,7-dihydro-5H-pyrrolo[3,4-d]pyrimidin-4-yl)morpholine trifluoroacetate (intermediate 20) as a TFA salt (708 mg, 2.0 mmol) in anhydrous DMF (5 ml) was added triethylamine (5550, 4.0 mmol) and the reaction was stirred at RT for two hours. After this time, ethyl chloroformate (228 μl, 2.4 mmol) was added dropwise and the reaction was stirred at RT overnight. The reaction was partitioned between water and ethyl acetate and the aqueous phase was extracted into ethyl acetate. The organic extracts were combined, washed with brine, dried over magnesium sulphate and concentrated in vacuo to afford the title compound which was used without further purification.

LCMS (Method E), (M+H⁺) 313, RT=0.99 mins

Intermediate 28

1-ethyl-3-(3-fluoro-4-(4,4,5,5-tetramethyl-1,3,2-dioxaborolan-2-yl)phenyl)urea

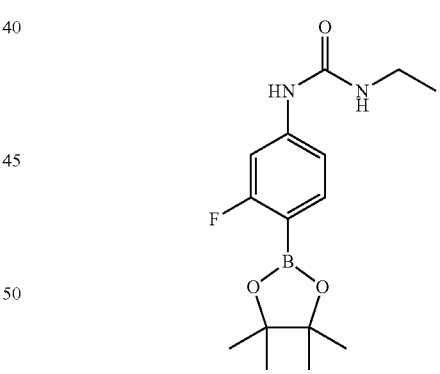

To a stirred solution of 3-fluoro-4-(4,4,5,5-tetramethyl-1,3,2-dioxaborolan-2-yl)aniline (1.5 g, 6.33 mmol) in DCM (30 ml) was added ethyl isocyanate (1503 μL, 19 mmol). Reaction mixture was stirred at 35° C. for 20 hours. Additional isocyanate was added and reaction mixture left for sufficient time to ensure reaction completion. The crude reaction mixture was then partitioned between water and DCM. The organic layer was recovered, passed through a hydrophobic frit and the solvent removed in vacuo. The residue was purified by flash chromatography using 0-60% ethyl acetate/petroleum ether 40-60 to yield a yellow solid (1.054 g, 3.42 mmol, 54%).

LCMS (Method B), (M+H⁺) 309, Rt=2.51 min.

Intermediate 29

1-cyclopropyl-3-(3-fluoro-4-(4,4,5,5-tetramethyl-1,3,2-dioxaborolan-2-yl)phenyl)urea

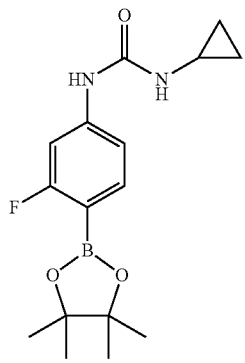

Prepared as 1-ethyl-3-(3-fluoro-4-(4,4,5,5-tetramethyl-1,3,2-dioxaborolan-2-yl)phenyl)urea (intermediate 28) using 3-fluoro-4-(4,4,5,5-tetramethyl-1,3,2-dioxaborolan-2-yl)aniline and cyclopropyl isocyanate as starting materials. The crude reaction mixture was then partitioned between DCM and water. The organic layer was recovered, passed through a hydrophobic frit and the solvent removed in vacuo to yield a light orange solid (3.2 g, 10 mmol, 100%).

LCMS (Method B), (M+H$^+$) 321, Rt=2.52 min.

Intermediate 30 phenyl (3-fluoro-4-(4,4,5,5-tetramethyl-1,3,2-dioxaborolan-2-yl)phenyl)carbamate

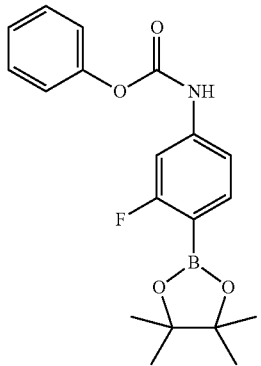 [SMILES: CC1(C)OB(c2ccc(NC(=O)Oc3ccccc3)cc2F)OC1(C)C]

3-fluoro-4-(4,4,5,5-tetramethyl-1,3,2-dioxaborolan-2-yl)aniline (3 g, 12.65 mmol) dissolved in dry THF was stirred with NaHCO$_3$ (1.6 g, 19 mmol) and phenyl chloroformate (1.92 mL, 15.20 mmol) at room temperature overnight. The reaction mixture was partitioned between water and DCM, the organic layer recovered, dried over MgSO$_4$, filtered and the solvent removed in vacuo, affording the title compound which was used without further purification.

LCMS (Method B), (M+H$^+$) 358 Rt=3.08 min

Intermediate 31

1-(3-fluoro-4-(4,4,5,5-tetramethyl-1,3,2-dioxaborolan-2-yl)phenyl)-3-(2-fluoroethyl)urea

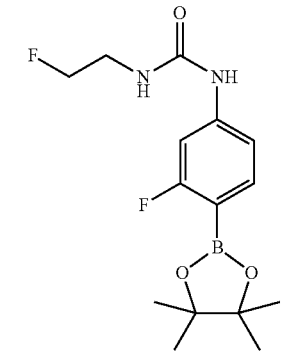 [SMILES: CC1(C)OB(c2ccc(NC(=O)NCCF)cc2F)OC1(C)C]

To a stirring solution of phenyl (3-fluoro-4-(4,4,5,5-tetramethyl-1,3,2-dioxaborolan-2-yl)phenyl)carbamate (intermediate 30) (1.6 g, 4.48 mmol) in dry DMF was added triethylamine (2.03 mL, 14.55 mmol) and 2-fluoroethanamine hydrochloride (2.23 g, 22.40 mmol). The mixture was stirred at 50° C. for 2 h. The solvent was then removed in vacuo affording the title compound which was used without further purification.

LCMS (Method B), (M+H$^+$) 327 Rt=2.48 min

Intermediate 32

1-(3-fluoro-4-(4,4,5,5-tetramethyl-1,3,2-dioxaborolan-2-yl)phenyl)-3-(2-hydroxyethyl)urea

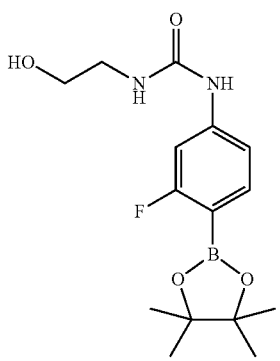 [SMILES: CC1(C)OB(c2ccc(NC(=O)NCCO)cc2F)OC1(C)C]

Method as described for 1-(3-fluoro-4-(4,4,5,5-tetramethyl-1,3,2-dioxaborolan-2-yl)phenyl)-3-(2-fluoroethyl)urea (intermediate 31) using ethanolamine as starting material.

LCMS (Method B), (M+H$^+$) 325 Rt=2.22 min

Intermediate 33

(R)-1-cyclopropyl-3-(3-fluoro-4-(4-(3-methylmorpholino)-6,7-dihydro-5H-pyrrolo[3,4-d]pyrimidin-2-yl)phenyl)urea hydrochloride

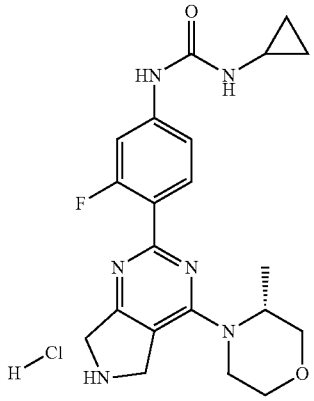

Step 1: Method as (S)-tert-butyl 2-chloro-4-(3-methylmorpholino)-5H-pyrrolo[3,4-d]pyrimidine-6(7H)-carboxylate (intermediate 1) using tert-butyl 2,4-dichloro-5H-pyrrolo[3,4-d]pyrimidine-6(7H)-carboxylate and (R)-3-methylmorpholine as starting materials to yield (R)-tert-butyl 2-chloro-4-(3-methylmorpholino)-5H-pyrrolo[3,4-d]pyrimidine-6(7H)-carboxylate a white solid (4.55 g, 12.8 mmol, 70%)

LCMS (Method B), (M+H$^+$) 355, Rt=2.72 min

Step 2: A solution of (R)-tert-butyl 2-chloro-4-(3-methylmorpholino)-5H-pyrrolo[3,4-d]pyrimidine-6(7H)-carboxylate (from step 1) (985 mg, 2.77 mmol), 1-cyclopropyl-3-(3-fluoro-4-(4,4,5,5-tetramethyl-1,3,2-dioxaborolan-2-yl)phenyl)urea (intermediate 29) (978 mg, 3.0 mmol), [1,1'-Bis(diphenylphosphino)ferrocene]dichloropalladium (II), complex with dichloromethane (113 mg, 0.139 mmol) and sodium carbonate (881 mg, 8.31 mmol) in 8 ml of a 7:3:2 mixture of DME:H$_2$O:EtOH respectively was heated in the microwave at 110° C. for 1 hour. Reaction solvent was removed in vacuo. The residue was then partitioned between DCM (100 ml) and water (80 ml). The organic layer was recovered, passed through a hydrophobic frit and the solvent removed in vacuo. The residue was purified by flash chromatography using 20-100% ethyl acetate/petroleum ether 40-60 to yield an off white solid (1.107 g, 2.16 mmol, 78%).

$^1$H NMR (d$_6$-DMSO) 8.52 (s, 1H), 7.72 (t, 1H), 7.32 (d, 1H), 6.92 (dd, 1H), 6.33 (s, 1H), 4.63-4.47 (m, 2H), 4.26-4.09 (m, 3H), 3.88 (q, 1H), 3.76-3.69 (m, 1H), 3.55-3.40 (m, 2H), 3.27 (td, 1H), 2.96 (d, 1H), 2.38-2.31 (m, 1H), 1.26 (s, 9H), 1.04 (d, 3H), 0.47-0.40 (m, 2H), 0.24-0.18 (m, 2H).

LCMS (Method A), (M+H$^+$) 513, Rt=8.74 min

Step 3: To a stirred solution of (R)-tert-butyl 2-(4-(3-cyclopropylureido)-2-fluorophenyl)-4-(3-methylmorpholino)-5H-pyrrolo[3,4-d]pyrimidine-6(7H)-carboxylate (1.1 g, 2.1 mmol) in methanol (15 ml) was added 4M HCl in dioxane (4 ml) and the reaction was stirred at RT overnight. The reaction was concentrated in vacuo to yield the titled compound as a yellow solid which was used without further purification.

LCMS (Method E), (M+H$^+$) 413, RT=0.76 mins

Intermediate 34

4-(2-chloro-6-isopropyl-6,7-dihydro-5H-pyrrolo[3,4-d]pyrimidin-4-yl)morpholine

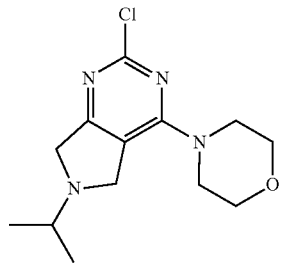 [SMILES: CC(C)N1Cc2nc(Cl)nc(N3CCOCC3)c2C1]

To a stirred solution of 4-(2-chloro-6,7-dihydro-5H-pyrrolo[3,4-d]pyrimidin-4-yl)morpholine (intermediate 20) as a HCl salt (455 mg, 1.6 mmol) in anhydrous THF (5 ml) was added anhydrous acetone (500 μl) and glacial acetic acid (two drops). The reaction was stirred at RT for 30 minutes after which time sodium triacetoxyborohydride (696 mg, 3.3 mmol) was added. After stirring for a further 2 hours at RT the reaction was partitioned between water and DCM. The aqueous phase was extracted into DCM and the organic extracts were combined and concentrated in vacuo to afford the title compound as a brown oil which was used without further purification.

LCMS (Method F), (M+H$^+$) 283, RT=0.92 mins

Metabolite Example 137

(S)-ethyl 2-(4-aminophenyl)-4-(3-methylmorpholino)-5H-pyrrolo[3,4-d]pyrimidine-6(7H)-carboxylate

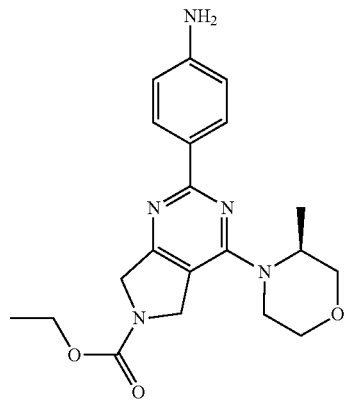 [SMILES: CCOC(=O)N1Cc2nc(-c3ccc(N)cc3)nc(N3CCOC[C@@H]3C)c2C1]

(S)-ethyl 2-chloro-4-(3-methylmorpholino)-5H-pyrrolo[3,4-d]pyrimidine-6(7H)-carboxylate (intermediate 11) (1.0 g, 3.06 mmol), 4-(4,4,5,5-tetramethyl-1,3,2-dioxaborolan-2-yl)aniline (805 mg, 3.67 mmol), Pd(PPh$_3$)$_2$(Cl)$_2$ (107 mg, 0.15 mmol) and Na$_2$CO$_3$ (487 mg, 4.59 mmol) were stirred in CPME/Water/EtOH (14/1/6 mL) under nitrogen for 5 mins, followed by heating at 100° C. overnight. The reaction mixture was then diluted with water and CPME, and precipitate collected by filtration to give 1.05 g of a brown solid. A portion of the brown solid was further purified by prep. HPLC to give 32.6 mg of an off-white solid.

¹H NMR (d₆-DMSO) 8.0 (d, 2H), 6.58 (d, 2H), 5.58 (s, 2H), 4.86-4.63 (m, 2H), 4.44 (d, 2H), 4.34 (br s, 1H), 4.13 (q, 2H), 4.07-4.00 (br m, 1H), 3.95 (dd, 1H), 3.74 (d, 1H), 3.65 (dd, 1H) 3.49 (t, 1H), 3.34-3.27 (m, 1H), 1.30-1.20 (m, 6H).

LCMS (Method B), (M+H⁺) 384 Rt=6.50 mins

Metabolite Example 138

(S)-ethyl 2-(4-amino-2-fluorophenyl)-4-(3-methylmorpholino)-5H-pyrrolo[3,4-d]pyrimidine-6(7H)-carboxylate

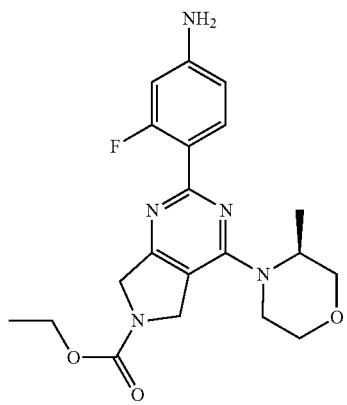 [SMILES: CCOC(=O)N1Cc2nc(-c3ccc(N)cc3F)nc(N3CCOC[C@@H]3C)c2C1]

Method as described for example 47 using (S)-ethyl 2-chloro-4-(3-methylmorpholino)-5H-pyrrolo[3,4-d]pyrimidine-6(7H)-carboxylate (intermediate 11) and 3-fluoro-4-(4,4,5,5-tetramethyl-1,3,2-dioxaborolan-2-yl)aniline as starting materials. The mixture was filtered through a celite 545 pre-packed cartridge (2.5 g), washed with MeOH and the solvent removed in vacuo. The residue was purified by prep. HPLC at high pH, yielding the title compound (55 mg, 0.14 mmol, 45%).

¹H NMR (CD₃OD) 7.80-7.70 (m, 1H), 6.51 (dd, 1H), 6.42 (dd, 1H), 4.66 (br s, 3H), 4.58-4.51 (m, 2H), 4.46 (br s, 1H), 4.22 (q, 2H), 4.20-4.07 (m, 1H), 3.99 (dd, 1H), 3.84-3.73 (m, 2H), 3.68-3.57 (m, 1H), 3.52-3.39 (m, 1H), 1.40-1.30 (m, 6H).

LCMS (Method A), (M+H⁺) 402 Rt=6.70 min

Example 139

(S)-1-(2,6-difluoro-4-(6-methyl-4-(3-methylmorpholino)-6,7-dihydro-5H-pyrrolo[3,4-d]pyrimidin-2-yl)phenyl)-3-ethylurea

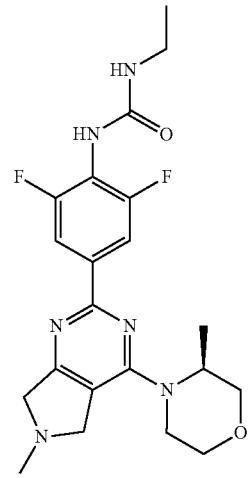 [SMILES: CCNC(=O)Nc1c(F)cc(-c2nc3c(c(N4CCOC[C@@H]4C)n2)CN(C)C3)cc1F]

Step 1: 5-bromo-1,3-difluoro-2-isocyanatobenzene (200 mg, 0.85 mmol) was dissolved in dry THF and stirred at room temperature for 5 minutes under nitrogen, before adding ethylamine (2M solution in THF) (859 uL, 1.7 mmol) drop wise to the mixture. A white emulsion was immediately formed. The mixture was stirred at 40° C. overnight, before removing the solvent in vacuo to give (239 mg, 0.85 mmol) of solid.

LCMS (Method B), (M+H⁺) 278,280 Rt=2.17 min

Step 2: 1-(4-bromo-2,6-difluorophenyl)-3-ethylurea (170 mg, 0.61 mmol) was dissolved in dry DMF and stirred with 4,4,4',4',5,5,5',5'-octamethyl-2,2'-bi(1,3,2-dioxaborolane) (171 g, 0.67 mmol), potassium acetate (180 mg, 1.83 mmol) and [1,1'-Bis(diphenylphosphino)ferrocene]dichloropalladium (II), complex with dichloromethane (15 mg, 0.02 mmol) at 80° C. under nitrogen for 48 h. The reaction mixture was filtered through a celite 545 pre-packed cartridge (2.5 g), washed with MeOH and the solvent removed in vacuo, yielding 1-(2,6-difluoro-4-(4,4,5,5-tetramethyl-1,3,2-dioxaborolan-2-yl)phenyl)-3-ethylurea used without further purification.

LCMS (Method D), (M+H⁺) 327 Rt=1.40 min

Step 3: Method as example 47 using (S)-4-(2-chloro-6-methyl-6,7-dihydro-5H-pyrrolo[3,4-d]pyrimidin-4-yl)-3-methylmorpholine (intermediate 12) and 1-(2,6-difluoro-4-(4,4,5,5-tetramethyl-1,3,2-dioxaborolan-2-yl)phenyl)-3-ethylurea as starting materials. The reaction mixture was filtered through a celite 545 pre-packed cartridge (2.5 g), washed with MeOH and the solvent removed in vacuo. The crude material was then purified by prep. HPLC at high pH yielding the title compound (18.5 mg, 0.04 mmol, 9.2%).

¹HNMR (CD₃OD) 7.90 (d, 2H), 4.48-4.35 (br s, 1H), 4.20-4.06 (m, 3H), 4.04-3.96 (m, 1H), 3.92-3.71 (m, 4H), 3.66-3.56 (m, 1H), 3.49-3.38 (m, 1H), 3.28-3.19 (q, 2H), 2.62 (s, 3H), 1.36 (d, 3H), 1.16 (t, 3H).

LCMS (Method A), (M+H⁺) 433, Rt=5.14 min.

Example 140

(S)-1-(2,3-difluoro-4-(6-methyl-4-(3-methylmorpholino)-6,7-dihydro-5H-pyrrolo[3,4-d]pyrimidin-2-yl)phenyl)-3-ethylurea

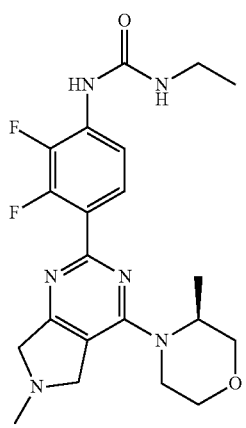

Step 1: To a stirring solution of 4-bromo-2,3-difluoroaniline (500 mg, 2.42 mmol) in dry THF was added ethyl isocyanate (229 uL, 2.90 mmol) dropwise. The reaction mixture was stirred at 60° C. overnight. The solvent was then removed in vacuo, yielding the title compound as a white solid (650 mg, 2.34 mmol, 97%).

LCMS (Method D), (M+H$^+$) 278,280 Rt=2.55 min

Step 2: Method as described for example 139 step 2 using 1-(4-bromo-2,3-difluorophenyl)-3-ethylurea as starting material.

Step 3: Method as example 47 using (S)-4-(2-chloro-6-methyl-6,7-dihydro-5H-pyrrolo[3,4-d]pyrimidin-4-yl)-3-methylmorpholine (intermediate 12) and 1-(2,3-difluoro-4-(4,4,5,5-tetramethyl-1,3,2-dioxaborolan-2-yl)phenyl)-3-ethylurea as starting materials. The mixture was filtered through a celite 545 pre-packed cartridge (2.5 g), washed with MeOH and the solvent removed in vacuo. The crude material was purified first by Flash Chromatography using a gradient of 0-40% DCM/MeOH, then prep. HPLC at low pH yielding the title compound (8.7 mg, 0.01 mmol, 4.2%).

$^1$H NMR (CD$_3$OD) 8.02-7.93 (m, 1H), 7.77-7.68 (m, 1H), 4.51-4.30 (m, 2H), 4.19-4.05 (m, 2H), 4.05-3.97 (m, 1H), 3.84-3.71 (m, 2H), 3.67-3.56 (m 1H), 3.50-3.39 (m, 1H), 3.26 (q, 2H), 2.80 (br s, 3H), 2.68 (s, 2H), 1.38 (d, 3H), 1.18 (t, 3H).

LCMS (Method A), (M+H$^+$) 433 Rt=5.44 min

Example 141

(S)-ethyl 2-(4-(3-ethylureido)-2,5-difluorophenyl)-4-(3-methylmorpholino)-5H-pyrrolo[3,4-d]pyrimidine-6(7H)-carboxylate

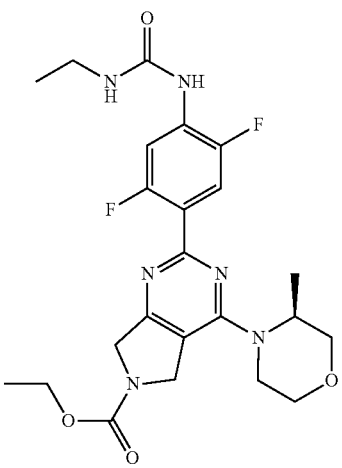 [SMILES: CCNC(=O)Nc1cc(F)c(-c2nc3c(c(N4CCOC[C@@H]4C)n2)CN(C(=O)OCC)C3)cc1F]

Step 1: Method as described for example 47 using (S)-ethyl 2-chloro-4-(3-methylmorpholino)-5H-pyrrolo[3,4-d]pyrimidine-6(7H)-carboxylate (intermediate 11) and 2,5-difluoro-4-(4,4,5,5-tetramethyl-1,3,2-dioxaborolan-2-yl)aniline as starting materials. The mixture was filtered through a celite 545 pre-packed cartridge (2.5 g), washed with MeOH and the solvent removed in vacuo. The residue was purified by prep. HPLC at low pH, yielding the title compound (25 mg, 0.06 mmol, 13%).

$^1$H NMR (CD$_3$OD) 7.68-7.58 (m, 1H), 6.60-6.53 (m, 1H), 4.88-4.78 (m, 2H), 4.65 (br s, 1H), 4.59-4.52 (m, 2H), 4.46 (br s, 1H), 4.24 (q, 2H), 4.19-4.09 (m, 1H), 4.01 (dd, 1H), 3.84-3.74 (m, 2H), 3.68-3.57 (m, 1H), 3.52-3.39 (m, 1H), 1.40-1.31 (m, 6H).

LCMS (Method A), (M+H$^+$) 420 Rt=8.12 min

Step 2: Method as described for example 85 using (S)-ethyl 2-(4-amino-2,5-difluorophenyl)-4-(3-methylmorpholino)-5H-pyrrolo[3,4-d]pyrimidine-6(7H)-carboxylate as staring material. Stirring was allowed at 60° C. overnight. The solvent was removed in vacuo and the residue purified by prep. HPLC at low pH, yielding the title compound (3.3 mg, 0.006 mmol, 17%).

$^1$H NMR (CD$_3$OD) 8.08-8.00 (m, 1H), 7.77-7.69 (m, 1H), 4.64 (br s, 3H), 4.56 (br s, 2H), 4.52-4.39 (br s, 1H), 4.26-4.17 (m, 2H), 4.17-4.06 (m, 1H), 4.04-3.96 (m, 1H), 3.84-3.72 (m, 2H), 3.65-3.57 (m, 1H), 3.51-3.38 (m, 1H), 3.29-3.21 (q, 2H), 1.39-1.29 (m. 6H), 1.17 (t, 3H).

LCMS (Method A), (M+H$^+$) 491 Rt=8.93 min

Example 142

(S)-ethyl 2-(4-(3-ethylureido)-2,6-difluorophenyl)-4-(3-methylmorpholino)-5H-pyrrolo[3,4-d]pyrimidine-6(7H)-carboxylate

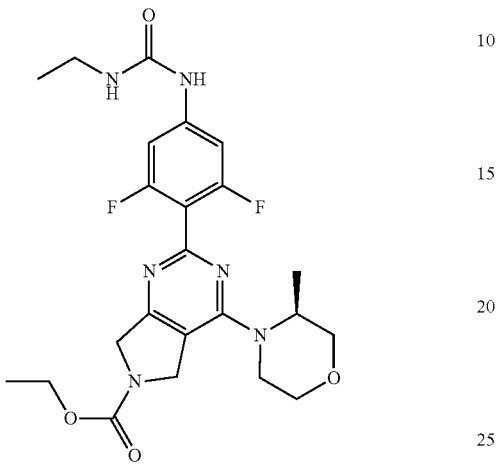

Step 1: 4-bromo-3,5-difluoroaniline (1 g, 4.863 mmol) was dissolved in dry DMF and stirred with 4,4,4',4',5,5,5',5'-octamethyl-2,2'-bi(1,3,2-dioxaborolane) (2.70 g, 0.67120.6 mmol), potassium acetate (1.42 g, 14.5 mmol) and [1,1'-Bis(diphenylphosphino)ferrocene]dichloropalladium (II), complex with dichloromethane (197 mg, 0.24 mmol) with microwave heating at 110° C. for 4 h. The reaction mixture was filtered through a celite 545 pre-packed cartridge (2.5 g), washed with MeOH and the solvent removed in vacuo, yielding 3,5-difluoro-4-(4,4,5,5-tetramethyl-1,3,2-dioxaborolan-2-yl)aniline which was used without further purification.

LCMS (Method B), (M+H$^+$) 256 Rt=2.61 min

Step 2: Method as described for example 47 using (S)-ethyl 2-chloro-4-(3-methylmorpholino)-5H-pyrrolo[3,4-d]pyrimidine-6(7H)-carboxylate (intermediate 11) and 3,5-difluoro-4-(4,4,5,5-tetramethyl-1,3,2-dioxaborolan-2-yl) aniline as starting materials. Reaction mixture heated in by microwave at 130° C. for 1 h. The mixture was filtered through a celite 545 pre-packed cartridge (2.5 g), washed with MeOH and the solvent removed in vacuo. The residue was purified by prep. HPLC at high pH, yielding the title compound (55 mg, 0.13 mmol, 14%).

$^1$H NMR (CD$_3$OD) 6.27 (d, 2H), 4.57 (br s, 3H), 4.51-4.38 (br s, 1H), 4.29-4.19 (m, 2H), 4.17-4.03 (m, 1H), 4.01-3.95 (m, 1H), 3.83-3.72 (m, 2H), 3.66-3.56 (m, 1H), 3.52-3.40 (m, 1H), 1.39-1.30 (m, 6H).

LCMS (Method A), (M+H$^+$) 420 Rt=7.79 min

Step 3: Method as described for example 85 using (S)-ethyl 2-(4-amino-2,6-difluorophenyl)-4-(3-methylmorpholino)-5H-pyrrolo[3,4-d]pyrimidine-6(7H)-carboxylate as starting material. Stirring was allowed at 60° C. overnight. The solvent was removed in vacuo and the residue purified by prep. HPLC at low pH, yielding the title compound (6.4 mg, 0.01 mmol, 15%).

$^1$H NMR (CD$_3$OD) 7.20-7.11 (d, 2H), 4.59 (br, s, 2H), 4.46 (br, s, 1H), 4.29-4.19 (m, 2H), 4.17-4.03 (m, 1H), 3.99 (dd, 1H), 3.83-3.72 (m, 2H), 3.66-3.56 (m, 1H), 3.53-3.40 (m, 1H), 3.36 (s, 2H), 3.25 (q, 2H), 1.41-1.29 (m, 6H), 1.17 (t, 3H).

LCMS (Method A), (M+H$^+$) 491 Rt=8.46 min

Example 143 tert-Butyl 2-(4-(3-cyclopropylureido)-2-fluorophenyl)-4-morpholino-5H-pyrrolo[3,4-d]pyrimidine-6(7H)-carboxylate

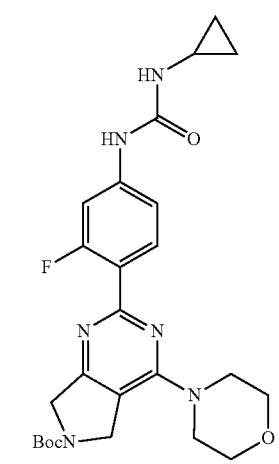 [SMILES: CC(C)(C)OC(=O)N1Cc2nc(-c3ccc(NC(=O)NC4CC4)cc3F)nc(N3CCOCC3)c2C1]

A solution of tert-butyl 2-chloro-4-morpholino-5H-pyrrolo[3,4-d]pyrimidine-6(7H)-carboxylate (intermediate 2) (85 mg, 0.25 mmol), 1-cyclopropyl-3-(3-fluoro-4-(4,4,5,5-tetramethyl-1,3,2-dioxaborolan-2-yl)phenyl)urea (intermediate 29) (100 mg, 0.31 mmol), [1,1'-Bis(diphenylphosphino)ferrocene]dichloropalladium (II), complex with dichloromethane (10 mg, 0.012 mmol) and sodium carbonate (40 mg, 0.38 mmol) in 2 ml of a 7:3:2 mixture of DME:EtOH:H$_2$O respectively was heated in the microwave at 130° C. for 30 minutes. The mixture was filtered through a celite 545 pre-packed cartridge (2.5 g), washed with MeOH and the solvent removed in vacuo. The residue was purified by prep. HPLC at low pH, yielding the title compound (72 mg, 0.14 mmol, 58%).

$^1$H NMR (CD$_3$OD) 7.86 (td, 1H), 7.50 (dd, 1H), 7.13 (d, 1H), 4.85-4.82 (br s, 3H), 4.80 (br s, 1H), 4.52 (br s, 2H), 3.79 (s, 6H), 2.62-2.57 (m, 1H), 1.53 (s, 9H), 0.78-0.73 (m, 2H), 0.54-0.50 (m, 2H).

LCMS (Method E), (M+H$^+$) 499, Rt=0.98 min.

Example 144

(S)-tert-Butyl 2-(4-(3-cyclopropylureido)-2-fluorophenyl)-4-(3-methylmorpholino)-5H-pyrrolo[3,4-d]pyrimidine-6(7H)-carboxylate

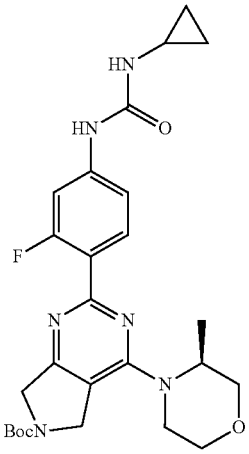 [SMILES: C[C@H]1COCCN1c1nc(-c2ccc(NC(=O)NC3CC3)cc2F)nc2c1CN(C(=O)OC(C)(C)C)C2]

Method as described for tert-Butyl 2-(4-(3-cyclopropylureido)-2-fluorophenyl)-4-morpholino-5H-pyrrolo[3,4-d]pyrimidine-6(7H)-carboxylate (example 143) using (S)-tert-butyl 2-chloro-4-(3-methylmorpholino)-5H-pyrrolo[3,4-d]pyrimidine-6(7H)-carboxylate (intermediate 1).

$^1$H NMR (CD$_3$OD) 7.86 (td, 1H), 7.48 (dd, 1H), 7.13 (d, 1H), 4.85-4.82 (m, 3H), 4.52-4.47 (m, 2H), 4.19-4.10 (m, 1H), 4.00 (dd, 1H), 3.79-3.77 (m, 2H), 3.59 (td, 1H), 3.49-3.46 (m, 1H), 2.62-2.57 (m, 1H), 1.53 (s, 9H), 1.37 (d, 3H), 0.78-0.73 (m, 2H), 0.54-0.50 (m, 2H).

LCMS (Method B), (M+H$^+$) 513, Rt=2.42 min.

Example 145 tert-butyl 2-(4-(3-ethylureido)-2-fluorophenyl)-4-morpholino-5H-pyrrolo[3,4-d]pyrimidine-6(7H)-carboxylate

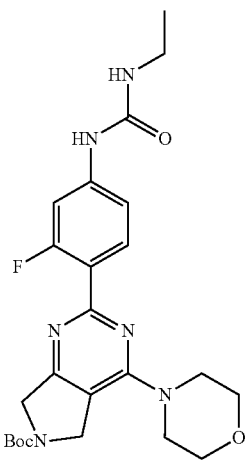 [SMILES: CCNC(=O)Nc1ccc(-c2nc3c(c(N4CCOCC4)n2)CN(C(=O)OC(C)(C)C)C3)c(F)c1]

Method as described for tert-Butyl 2-(4-(3-cyclopropylureido)-2-fluorophenyl)-4-morpholino-5H-pyrrolo[3,4-d]pyrimidine-6(7H)-carboxylate (example 143) using 1-ethyl-3-(3-fluoro-4-(4,4,5,5-tetramethyl-1,3,2-dioxaborolan-2-yl)phenyl)urea (intermediate 28).

$^1$H NMR (CD$_3$OD) 7.86 (td, 1H), 7.46 (dd, 1H), 7.10 (d, 1H), 4.90-4.85 (m, 3H), 4.80 (br s, 1H), 4.52 (br s, 2H), 3.79 (s, 6H), 3.24 (q, 2H), 1.53 (s, 9H), 1.17 (t, 3H).

LCMS (Method E), (M+H$^+$) 487, Rt=0.96 min.

Example 146

(S)-methyl 2-(4-(3-cyclopropylureido)-2-fluorophenyl)-4-(3-methylmorpholino)-5H-pyrrolo[3,4-d]pyrimidine-6(7H)-carboxylate

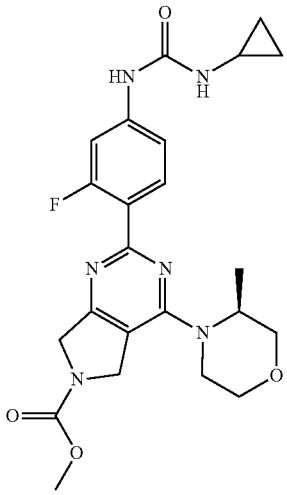 [SMILES: COC(=O)N1Cc2nc(-c3ccc(NC(=O)NC4CC4)cc3F)nc(N3CCOC[C@@H]3C)c2C1]

Method as described for tert-Butyl 2-(4-(3-(cyclopropylureido)-2-fluorophenyl)-4-morpholino-5H-pyrrolo[3,4-d]pyrimidine-6(7H)-carboxylate (example 143) using (S)-methyl 2-chloro-4-(3-methylmorpholino)-5H-pyrrolo[3,4-d]pyrimidine-6(7H)-carboxylate (intermediate 26) (193 mg, 0.5 mmol) and 1-cyclopropyl-3-(3-fluoro-4-(4,4,5,5-tetramethyl-1,3,2-dioxaborolan-2-yl)phenyl)urea (intermediate 29) (182 mg, 0.57 mmol) as starting materials. Reaction mixture was partitioned between EtOAc (50 ml) and water (35 ml), the organic layer passed through a hydrophobic frit and concentrated in vacuo to leave a brown solid. The solid was purified by prep. HPLC at low pH to afford a colourless solid (22 mg, 10%).

$^1$H NMR (d$_6$-DMSO) 8.76 (s, 1H), 8.00-7.86 (m, 1H), 7.53 (dd, 1H), 7.12 (dd, 1H), 6.56 (d, 1H), 4.90-4.70 (m, 2H), 4.46 (d, 2H), 4.35 (br s, 1H), 4.12-3.98 (m, 1H), 3.94 (d, 1H), 3.76-3.60 (m, 5H), 3.49 (dd, 1H), 3.30 (dd, 1H), 2.60-2.53 (m, 1H), 1.25 (d, 3H), 0.70-0.60 (m, 2H), 0.46-0.37 (m, 2H).

LCMS (method A), (M+H$^+$) 471, Rt=7.13 min.

Example 147

(S)-1-cyclopropyl-3-(3-fluoro-4-(6-methyl-4-(3-methylmorpholino)-6,7-dihydro-5H-pyrrolo[3,4-d]pyrimidin-2-yl)phenyl)urea

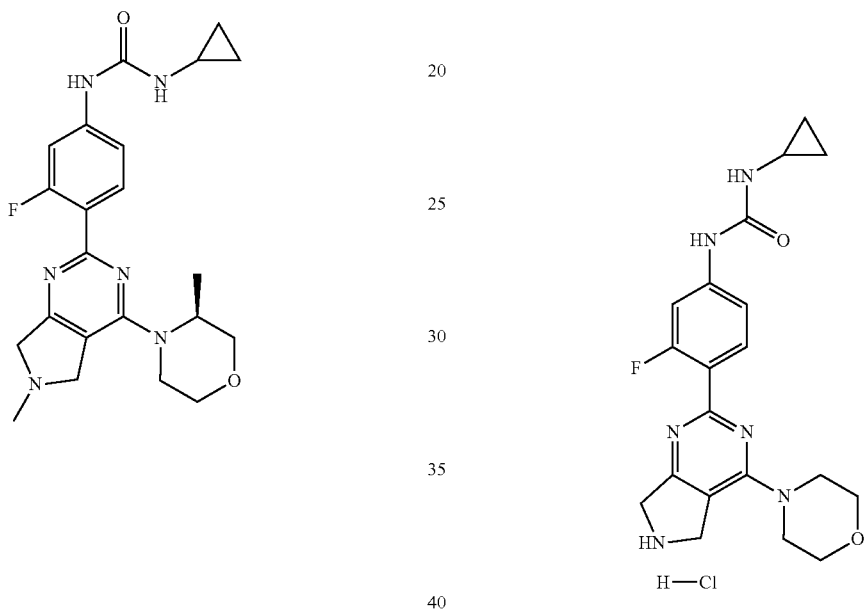

To a solution of (S)-4-(2-chloro-6-methyl-6,7-dihydro-5H-pyrrolo[3,4-d]pyrimidin-4-yl)-3-methylmorpholine (intermediate 12) (150 mg, 0.55 mmol) and 1-cyclopropyl-3-(3-fluoro-4-(4,4,5,5-tetramethyl-1,3,2-dioxaborolan-2-yl)phenyl)urea (intermediate 29) (212 mg, 0.69 mmol) in DME/EtOH/H$_2$O (7/3/2) (2 mL) was added [1,1'-Bis(diphenylphosphino)ferrocene]dichloropalladium (II), complex with dichloromethane (22 mg, 0.027 mmol) and Cs$_2$CO$_3$ (538 mg, 1.65 mmol). The reaction mixture was then heated by microwave at 115° C. for 45 min. The crude reaction mixture was partitioned between EtOAc (25 ml) and water (25 ml). The organic layer was recovered, passed through a hydrophobic frit and the solvent removed in vacuo. Residue was then purified by preparative HPLC at low pH to afford a yellow solid (25 mg, 0.06 mmol, 11%).

$^1$H NMR (d$_6$-DMSO) δ 8.77 (s, 1H), 7.92 (t, 1H), 7.52 (dd, 1H), 7.12 (dd, 1H), 6.59 (d, 1H), 4.32 (br, s, 1H), 4.12-3.99 (m, 3H), 3.92 (dd, 1H), 3.74 (d, 2H), 3.73-3.60 (m, 2H), 3.52-3.44 (m, 1H), 3.30 (ddd, 1H), 2.59-2.52 (m, 1H), 2.50-2.48 (m, 3H), 1.24 (d, 3H), 0.69-0.62 (m, 2H), 0.46-0.39 (m, 2H).

LCMS (Method A), (M+H$^+$) 427, Rt=5.00 min

Example 148

1-(Cyclopropyl)-3-(3-fluoro-4-(4-morpholino-6,7-dihydro-5H-pyrrolo[3,4-d]pyrimidin-2-yl)phenyl)urea hydrochloride Method as described for (R)-1-cyclopropyl-3-(3-fluoro-4-(4-(3-methylmorpholino)-6,7-dihydro-5H-pyrrolo[3,4-d]pyrimidin-2-yl)phenyl)urea hydrochloride (intermediate 33) step 3 using tert-Butyl 2-(4-(3-(cyclopropylureido)-2-fluorophenyl)-4-morpholino-5H-pyrrolo[3,4-d]pyrimidine-6(7H)-carboxylate (example 143). The resulting solid was triturated from methanol/ether to give a cream solid (82% yield).

$^1$H NMR (d$_6$-DMSO) 9.71 (br s, 2H), 8.87 (s, 1H), 7.96 (t, 1H), 7.54 (dd, 1H), 7.14 (dd, 1H), 6.62 (br s, 1H), 4.71 (t, 2H), 4.37 (t, 2H), 3.69-3.64 (m, 8H), 2.56-2.52 (m, 1H), 0.67-0.62 (m, 2H), 0.43-0.40 (m, 2H).

LCMS (method A), (M+H$^+$) 399, Rt=4.67 min.

Example 149

(S)-1-(Cyclopropyl)-3-(3-fluoro-4-(4-(3-methylmorpholino)-6,7-dihydro-5H-pyrrolo[3,4-d]pyrimidin-2-yl)phenyl)urea hydrochloride

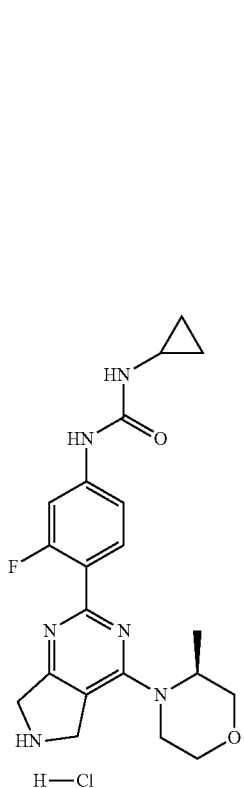

Method as described for (R)-1-cyclopropyl-3-(3-fluoro-4-(4-(3-methylmorpholino)-6,7-dihydro-5H-pyrrolo[3,4-d]pyrimidin-2-yl)phenyl)urea hydrochloride (intermediate 33) step 3 using (S)-tert-Butyl 2-(4-(3-cyclopropylureido)-2-fluorophenyl)-4-(3-methylmorpholino)-5H-pyrrolo[3,4-d]pyrimidine-6(7H)-carboxylate(example 144). The resulting solid was triturated from methanol/ether to give a cream solid (37% yield).

$^1$H NMR (d$_6$-DMSO) 9.81 (br s, 2H), 8.93 (s, 1H), 7.95 (t, 1H), 7.54 (dd, 1H), 7.14 (dd, 1H), 6.66 (br s, 1H), 4.77-4.67 (br m, 2H), 4.38-3.94 (br m, 4H), 3.95 (br dd, 1H), 3.73 (d, 1H), 3.64 (dd, 1H), 3.49 (td, 1H), 3.39-3.31 (m, 1H), 2.55-2.53 (m, 1H), 1.25 (d, 3H), 0.67-0.62 (m, 2H), 0.43-0.39 (m, 2H).

LCMS (method A), (M+H$^+$) 413, Rt=4.94 min.

Example 150

1-Ethyl-3-(3-fluoro-4-(4-morpholino-6,7-dihydro-5H-pyrrolo[3,4-d]pyrimidin-2-yl)phenyl)urea hydrochloride

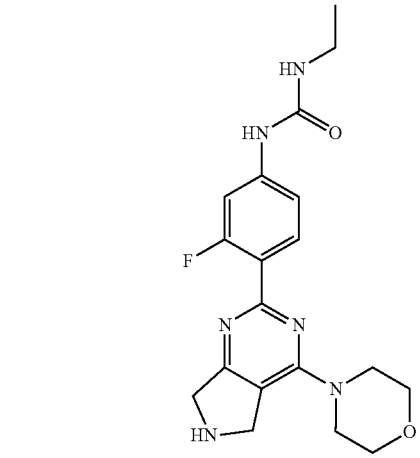 [SMILES: CCNC(=O)Nc1ccc(-c2nc3c(c(N4CCOCC4)n2)CNC3)c(F)c1]

Method as described for (R)-1-cyclopropyl-3-(3-fluoro-4-(4-(3-methylmorpholino)-6,7-dihydro-5H-pyrrolo[3,4-d]pyrimidin-2-yl)phenyl)urea hydrochloride (intermediate 33) step 3 tert-butyl 2-(4-(3-ethylureido)-2-fluorophenyl)-4-morpholino-5H-pyrrolo[3,4-d]pyrimidine-6(7H)-carboxylate (example 145). The resulting solid was triturated from methanol/ether to give a cream solid (60% yield).

$^1$H NMR (d$_6$-DMSO) 9.71 (br s, 2H), 8.87 (s, 1H), 7.96 (t, 1H), 7.54 (dd, 1H), 7.14 (dd, 1H), 6.62 (br s, 1H), 4.71 (t, 2H), 4.37 (t, 2H), 3.69-3.64 (m, 8H), 2.55-2.52 (m, 1H), 0.67-0.62 (m, 2H), 0.43-0.40 (m, 2H).

LCMS (method A), (M+H$^+$) 387, Rt=4.61 min.

Example 151

Ethyl 2-(4-(3-ethylureido)-2-fluorophenyl)-4-morpholino-5H-pyrrolo[3,4-d]pyrimidine-6(7H)-carboxylate A solution of ethyl 2-chloro-4-morpholino-5H-pyrrolo[3,4-d]pyrimidine-6(7H)-carboxylate (intermediate 27) (156 mg, 0.498 mmol), 1-ethyl-3-(3-fluoro-4-(4,4,5,5-tetramethyl-1,3,2-dioxaborolan-2-yl)phenyl)urea (intermediate 28) (174 mg, 0.567 mmol), [1,1'-Bis (diphenylphosphino)ferrocene]dichloropalladium (II), complex with dichloromethane (20 mg, 0.0249 mmol) and sodium carbonate (148 mg, 1.39 mmol) in 2 ml of a 7:3:1 mixture of DME:H$_2$O:EtOH respectively was heated in the microwave at 115° C. for 45 minutes. The reaction was concentrated in vacuo and the residue re-dissolved in a mix of MeOH/DCM. It was loaded onto an SCX cartridge and washed with two column volumes of MeOH/DCM before being eluted with 2M NH$_3$ in MeOH and concentrated in vacuo to give a solid. The solid was triturated in acetone and filtered to yield the title compound (45 mg, 20%).

$^1$H NMR (CD$_3$OD) 7.87 (td, 1H), 7.47 (dd, 1H), 7.10 (dd, 1H), 4.89 (s, 2H), 4.57 (s, 2H), 4.23 (q, 2H), 3.79 (s, 8H), 3.24 (q, 2H), 1.33 (t, 3H), 1.16 (t, 3H).

LCMS (method A), (M+H$^+$) 459, Rt=7.15 min.

Example 152

(S)-methyl 2-(4-(3-ethylureido)-2-fluorophenyl)-4-(3-methylmorpholino)-5H-pyrrolo[3,4-d]pyrimidine-6-(7H)-carboxylate

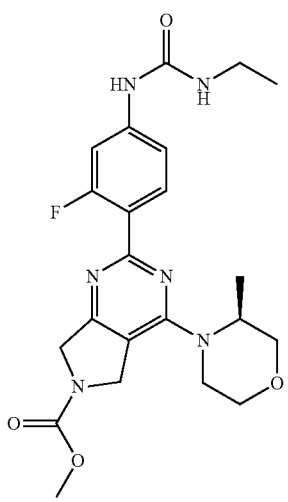 [SMILES: CCNC(=O)Nc1ccc(-c2nc3c(c(N4CCOC[C@@H]4C)n2)CN(C(=O)OC)C3)c(F)c1]

A solution of (S)-methyl 2-chloro-4-(3-methylmorpholino)-5H-pyrrolo[3,4-d]pyrimidine-6(7H)-carboxylate (intermediate 26) (98 mg, 0.313 mmol), 1-ethyl-3-(3-fluoro-4-(4,4,5,5-tetramethyl-1,3,2-dioxaborolan-2-yl)phenyl)urea (intermediate 28) (110 mg, 0.357 mmol), [1,1'-Bis(diphenylphosphino)ferrocene]dichloropalladium (II), complex with dichloromethane (13 mg, 0.0157 mmol) and sodium carbonate (93 mg, 0.876 mmol) in 2 ml of a 7:3:1 mixture of DME:H$_2$O:EtOH respectively was heated in the microwave at 115° C. for 45 minutes. The reaction was concentrated in vacuo and the residue was re-dissolved in a mix of H$_2$O and EtOAc. The aqueous phase was extracted into EtOAc and the organic extracts were combined and concentrated in vacuo. The sample was then purified via preparative HPLC at low pH and then triturated in MeOH and filtered to yield the title compound (6 mg, 4%).

$^1$H NMR (d$_6$-DMSO) 8.86 (s, 1H), 7.93 (td, 1H), 7.52 (dd, 1H), 7.09 (dd, 1H), 6.25 (t, 1H), 4.82 (dt, 2H), 4.47 (d, 2H), 4.35 (br s, 1H), 4.13-3.91 (m, 3H), 3.73 (d, 1H), 3.69 (s, 3H), 3.64 (d, 1H), 3.52-3.44 (m, 1H), 3.16-3.08 (m, 2H), 1.25 (d, 3H), 1.06 (t, 3H).

LCMS (method A), (M+H$^+$) 459, Rt=6.93 min.

Example 153

(S)-tert-butyl 2-(4-(3-ethylureido)-2-fluorophenyl)-4-(3-methylmorpholino)-5H-pyrrolo[3,4-d]pyrimidine-6-(7H)-carboxylate

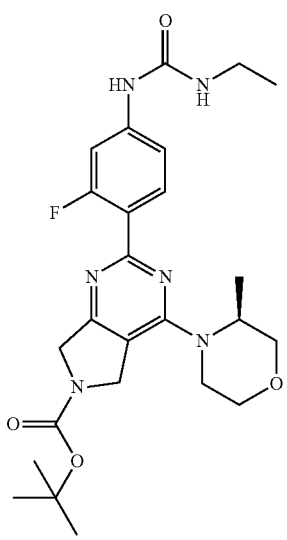 [SMILES: CCNC(=O)Nc1ccc(-c2nc3c(c(N4CCOC[C@@H]4C)n2)CN(C(=O)OC(C)(C)C)C3)c(F)c1]

A solution of (S)-tert-butyl 2-chloro-4-(3-methylmorpholino)-5H-pyrrolo[3,4-d]pyrimidine-6(7H)-carboxylate (intermediate 1) (214 mg, 0.603 mmol), 1-ethyl-3-(3-fluoro-4-(4,4,5,5-tetramethyl-1,3,2-dioxaborolan-2-yl)phenyl)urea (intermediate 28) (211 mg, 0.685 mmol), [1,1'-Bis(diphenylphosphino)ferrocene]dichloropalladium (II), complex with dichloromethane (25 mg, 0.0306 mmol) and sodium carbonate (179 mg, 1.69 mmol) in 2 ml of a 7:3:1 mixture of DME:H$_2$O:EtOH respectively was heated in the microwave at 115° C. for 45 minutes then at 130° C. for 15 minutes. The reaction mixture was concentrated in vacuo and the residue was re-dissolved in a mix of H$_2$O and EtOAc. The aqueous phase was basified by the addition of aqueous NaOH and extracted into EtOAc. The organic extracts were combined, dried over magnesium sulphate and concentrated in vacuo. The sample was purified via preparative HPLC at low pH to yield the title compound (36 mg, 13%).

$^1$H NMR (CD$_3$OD) 7.88-7.82 (m, 1H), 7.45 (dd, 1H), 7.07 (d, 1H), 4.79-4.69 (m, 2H), 4.49 (s, 2H), 4.44 (br s, 1H), 4.19-4.03 (m, 1H), 3.98 (d, 1H), 3.82-3.72 (m, 2H), 3.60 (t, 1H), 3.48-3.37 (m, 1H), 3.23 (q, 2H), 1.53 (s, 9H), 1.35 (d, 3H), 1.17 (t, 3H)

LCMS (method A), (M+H$^+$) 501, Rt=8.57 min.

Example 154

1-ethyl-3-(3-fluoro-4-(6-methyl-4-morpholino-6,7-dihydro-5H-pyrrolo[3,4-d]pyrimidin-2-yl)phenyl)urea

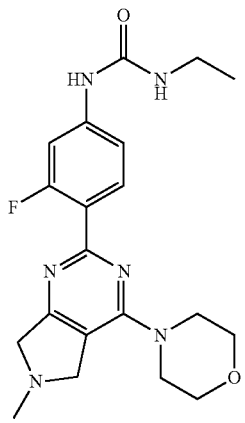

Method as example 147 using 4-(2-chloro-6-methyl-6,7-dihydro-5H-pyrrolo[3,4-d]pyrimidin-4-yl)morpholine (intermediate 21) and 1-ethyl-3-(3-fluoro-4-(4,4,5,5-tetramethyl-1,3,2-dioxaborolan-2-yl)phenyl)urea (intermediate 28) as starting materials. The crude reaction mixture was partitioned between EtOAc (25 ml) and water (25 ml). The organic layer was recovered, passed through a hydrophobic frit and the solvent removed in vacuo. Residue was then purified by prep. HPLC at high pH to afford a light yellow solid (61 mg, 0.15 mmol, 26%).

$^1$HNMR (d$_6$-DMSO) 8.85 (s, 1H), 7.92 (t, 1H), 7.51 (dd, 1H), 7.09 (dd, 1H), 6.26 (t, 1H), 4.04 (s, 2H), 3.73 (s, 2H), 3.70-3.60 (m, 8H), 3.16-3.08 (m, 2H), 2.50 (s, 3H), 1.06 (t, 3H).

LCMS (Method A), (M+H$^+$) 401, Rt=4.64 min

Example 155

(S)-1-(4-(6-acetyl-4-(3-methylmorpholino)-6,7-dihydro-5H-pyrrolo[3,4-d]pyrimidin-2-yl)-3-fluorophenyl)-3-cyclopropylurea

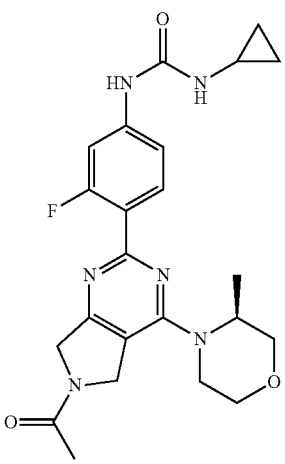 [SMILES: CC(=O)N1Cc2nc(-c3ccc(NC(=O)NC4CC4)cc3F)nc(N3CCOC[C@@H]3C)c2C1]

Method as example 143 using (S)-1-(2-chloro-4-(3-methylmorpholino)-5H-pyrrolo[3,4-d]pyrimidin-6(7H)-yl)ethanone (intermediate 24) (212 mg, 0.5 mmol) and 1-cyclopropyl-3-(3-fluoro-4-(4,4,5,5-tetramethyl-1,3,2-dioxaborolan-2-yl)phenyl)urea (intermediate 29) (182 mg, 0.57 mmol) as starting materials. Reaction mixture was partitioned between EtOAc (50 ml) and water (35 ml), the organic layer passed through a hydrophobic frit and concentrated in vacuo to leave a purple solid. The solid was purified by prep. HPLC at high pH to afford a brown/red solid which was re-purified by prep. HPLC at low pH to afford a yellow solid (9 mg, 4%).

$^1$H NMR (d$_6$-DMSO) 8.82 (s, 1H), 7.98-7.91 (m, 1H), 7.53 (d, 1H), 7.13 (d, 1H), 6.63 (d, 1H), 5.10-4.91 (m, 1H), 4.84-4.68 (m, 2H), 4.47-4.32 (m, 2H), 4.15-4.00 (m, 1H), 3.94 (d, 1H), 3.73 (d, 1H), 3.65 (dd, 1H), 3.56-3.44 (m, 1H), 3.39-3.25 (m, 1H), 2.60-2.53 (m, 1H), 2.08 (d, 3H), 1.26 (d, 3H), 0.68-0.62 (m, 2H), 0.46-0.40 (m, 2H).

LCMS (method A), (M+H$^+$) 455, Rt=6.47 min.

Example 156

Ethyl 2-(4-(3-cyclopropylureido)-2-fluorophenyl)-4-morpholino-5H-pyrrolo[3,4-d]pyrimidine-6(7H)-carboxylate

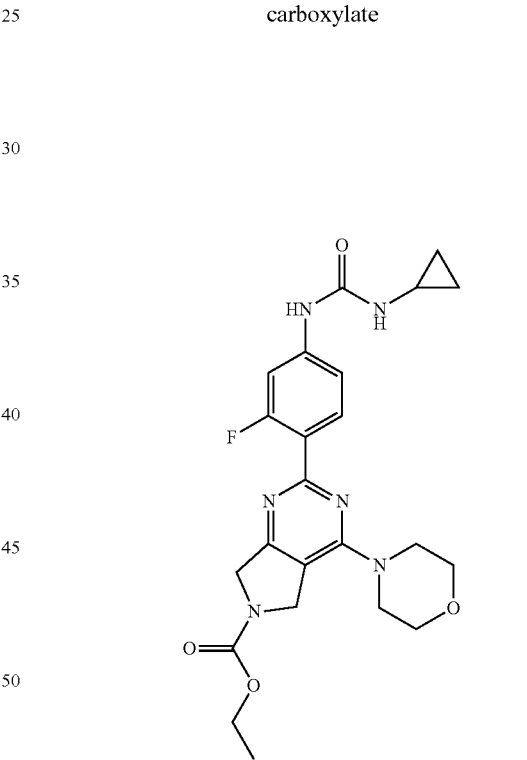

A solution of ethyl 2-chloro-4-morpholino-5H-pyrrolo[3,4-d]pyrimidine-6(7H)-carboxylate (intermediate 27) (156 mg, 0.498 mmol), 1-cyclopropyl-3-(3-fluoro-4-(4,4,5,5-tetramethyl-1,3,2-dioxaborolan-2-yl)phenyl)urea (intermediate 29) (182 mg, 0.567 mmol), [1,1'-Bis(diphenylphosphino)ferrocene]dichloropalladium (II), complex with dichloromethane (20 mg, 0.0249 mmol) and sodium carbonate (148 mg, 1.39 mmol) in 2 ml of a 7:3:1 mixture of DME:H$_2$O:EtOH respectively was heated in the microwave at 115°

Example 157

(S)-1-(4-(6-acetyl-4-(3-methylmorpholino)-6,7-dihydro-5H-pyrrolo[3,4-d]pyrimidin-2-yl)-3-fluorophenyl)-3-ethylurea

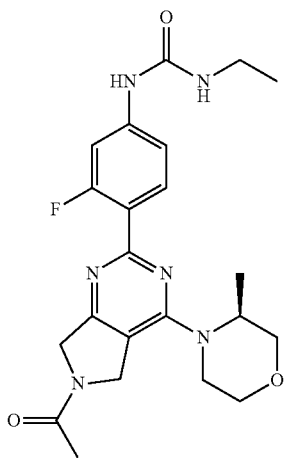 [SMILES: CCNC(=O)Nc1ccc(-c2nc3c(c(N4CCOC[C@@H]4C)n2)CN(C(C)=O)C3)c(F)c1]

A solution of (S)-1-(2-chloro-4-(3-methylmorpholino)-5H-pyrrolo[3,4-d]pyrimidin-6(7H)-yl)ethanone (intermediate 24) (99 mg, 0.334 mmol), 1-ethyl-3-(3-fluoro-4-(4,4,5,5-tetramethyl-1,3,2-dioxaborolan-2-yl)phenyl)urea (intermediate 28) (103 mg, 0.334 mmol), [1,1'-Bis(diphenylphosphino)ferrocene]dichloropalladium (II), complex with dichloromethane (14 mg, 0.0167 mmol) and sodium carbonate (99 mg, 0.934 mmol) in 2 ml of a 7:3:1 mixture of DME:H$_2$O:EtOH respectively was heated in the microwave at 115° C. for 45 minutes. The reaction was concentrated in vacuo and the residue was re-dissolved in a mix of H$_2$O and EtOAc. The aqueous phase was basified by the addition of aqueous NaOH and extracted into EtOAc. The organic extracts were combined and concentrated in vacuo. The sample was purified via preparative HPLC at low pH, and then at high pH, to yield the title compound (6 mg, 4%).

$^1$H NMR (d$_6$-DMSO) 8.97 (s, 1H), 7.94 (td, 1H), 7.52 (dd, 1H), 7.15-7.07 (m, 1H), 6.37 (q, 1H), 5.00 (dd, 1H), 4.84-4.69 (m, 2H), 4.43 (s, 1H), 4.37 (br s, 1H), 4.13-4.05 (m, 1H), 3.94 (dd, 1H), 3.73 (d, 1H), 3.68-3.62 (m, 1H), 3.54-3.45 (m, 1H), 3.17 (d, 1H), 3.15-3.08 (m, 2H), 2.08 (d, 3H), 1.26 (dd, 3H), 1.06 (t, 3H)

LCMS (method A), (M+H$^+$) 443, Rt=6.22 min

Example 158

(S)-1-ethyl-3-(3-fluoro-4-(4-(3-methylmorpholino)-6,7-dihydro-5H-pyrrolo[3,4-d]pyrimidin-2-yl)phenyl)urea hydrochloride

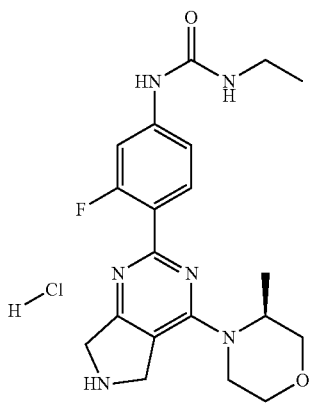 [SMILES: Cl ; CCNC(=O)Nc1ccc(-c2nc3c(c(N4CCOC[C@@H]4C)n2)CNC3)c(F)c1]

Method as described for (R)-1-cyclopropyl-3-(3-fluoro-4-(4-(3-methylmorpholino)-6,7-dihydro-5H-pyrrolo[3,4-d]pyrimidin-2-yl)phenyl)urea hydrochloride (intermediate 33) step 3 using (S)-tert-butyl 2-(4-(3-ethylureido)-2-fluorophenyl)-4-(3-methylmorpholino)-5H-pyrrolo[3,4-d]pyrimidine-6-(7H)-carboxylate (example 153)

$^1$H NMR (CD$_3$OD) 8.02 (t, 1H), 7.74 (dd, 1H), 7.26 (dd, 1H), 5.05-4.90 (m, 2H), 4.76 (s, 2H), 4.08 (d, 1H), 3.86 (t, 2H), 3.81-3.56 (m, 4H), 3.25 (q, 2H), 1.51 (d, 3H), 1.17 (t, 3H)

LCMS (method A), (M+H$^+$) 401, Rt=4.84 min

Example 159

1-(Cyclopropyl)-3-(3-fluoro-4-(6-methyl-4-morpholino-6,7-dihydro-5H-pyrrolo[3,4-d]pyrimidin-2-yl)phenyl)urea

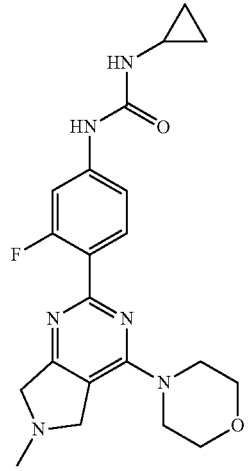 [SMILES: CN1Cc2nc(-c3ccc(NC(=O)NC4CC4)cc3F)nc(N3CCOCC3)c2C1]

Method as described for (S)-1-cyclopropyl-3-(3-fluoro-4-(6-methyl-4-(3-methylmorpholino)-6,7-dihydro-5H-pyrrolo

[3,4-d]pyrimidin-2-yl)phenyl)urea (example 147) using 4-(2-chloro-6-methyl-6,7-dihydro-5H-pyrrolo[3,4-d]pyrimidin-4-yl)morpholine (intermediate 21). Residue was then purified by preparative HPLC at high pH to afford a yellow solid (31% yield).

$^1$H NMR (d$_6$-DMSO) 8.74 (br s, 2H), 7.91 (t, 1H), 7.51 (dd, 1H), 7.11 (dd, 1H), 6.55 (d, 1H), 4.03 (br s, 2H), 3.72-3.63 (m, 10H), 2.58-2.53 (m, 1H), 0.67-0.62 (m, 2H), 0.44-0.40 (m, 2H).

LCMS (method A), (M+H$^+$) 413, Rt=4.98 min.

Example 160

(S)-1-ethyl-3-(3-fluoro-4-(6-methyl-4-(3-methylmorpholino)-6,7-dihydro-5H-pyrrolo[3,4-d]pyrimidin-2-yl)phenyl)urea

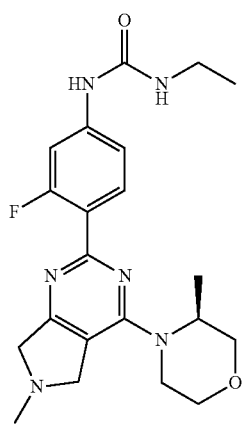

Method as described for example 147 using (S)-4-(2-chloro-6-methyl-6,7-dihydro-5H-pyrrolo[3,4-d]pyrimidin-4-yl)-3-methylmorpholine (intermediate 12) and 1-ethyl-3-(3-fluoro-4-(4,4,5,5-tetramethyl-1,3,2-dioxaborolan-2-yl)phenyl)urea (intermediate 28) as starting materials. The crude reaction mixture was partitioned between EtOAc (25 ml) and water (25 ml). The organic layer was recovered, passed through a hydrophobic frit and the solvent removed in vacuo. Residue was then purified by prep. HPLC at low pH to afford a yellow solid (8.4 mg, 0.02 mmol, 4%).

$^1$H NMR (d$_6$-DMSO) 9.05 (s, 1H), 7.91 (t, 1H), 7.51 (dd, 1H), 7.10 (dd, 1H), 6.47 (t, 1H), 4.31 (s, 1H), 4.11-3.98 (m, 3H), 3.92 (dd, 1H), 3.76-3.60 (m, 4H), 3.52-3.44 (m, 1H), 3.33-3.25 (m, 1H), 3.17-3.08 (m, 2H), 2.50 (s, 3H), 1.24 (d, 3H), 1.06 (t, 3H).

LCMS (Method A), (M+H$^+$) 415, Rt=4.94 min

Example 161

1-(4-(6-acetyl-4-morpholino-6,7-dihydro-5H-pyrrolo[3,4-d]pyrimidin-2-yl)-3-fluorophenyl)-3-ethylurea

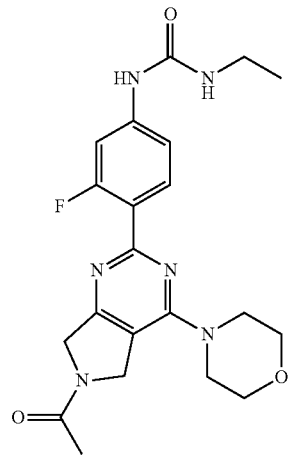 [SMILES: CCNC(=O)Nc1ccc(-c2nc3c(c(N4CCOCC4)n2)CN(C(C)=O)C3)c(F)c1]

Method as described for example 147 using 1-(2-chloro-4-morpholino-5H-pyrrolo[3,4-d]pyrimidin-6(7H)-yl)ethanone (intermediate 23) and 1-ethyl-3-(3-fluoro-4-(4,4,5,5-tetramethyl-1,3,2-dioxaborolan-2-yl)phenyl) (intermediate 28) as starting materials. The crude reaction mixture was purified by SCX-2 cartridge (loaded in MeOH eluted with 2M methanolic ammonia). Ammonia eluent was concentrated in vacuo. Residue was then purified by prep. HPLC at high pH to afford an off white solid (17.4 mg, 0.04 mmol, 8%).

$^1$H NMR (d$_6$-DMSO) 8.90 (s, 1H), 7.95 (td, 1H), 7.53 (dt, 1H), 7.15-7.06 (m, 1H), 6.32-6.25 (m, 1H), 5.00 (s, 1H), 4.73 (d, 2H), 4.43 (s, 1H), 3.70 (s, 8H), 3.17-3.08 (m, 2H), 2.08 (d, 3H), 1.07 (t, 3H).

LCMS (Method A), (M+H$^+$) 429, Rt=5.95 min

Example 162 methyl 2-(4-(3-ethylureido)-2-fluorophenyl)-4-morpholino-5H-pyrrolo[3,4-d]pyrimidine-6(7H)-carboxylate

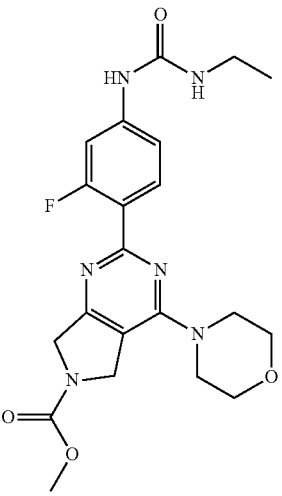 [SMILES: CCNC(=O)Nc1ccc(-c2nc3c(c(N4CCOCC4)n2)CN(C(=O)OC)C3)c(F)c1]

Method as described for example 147 using methyl 2-chloro-4-morpholino-5H-pyrrolo[3,4-d]pyrimidine-6(7H)-carboxylate (intermediate 25) and 1-ethyl-3-(3-fluoro-4-(4,4,5,5-tetramethyl-1,3,2-dioxaborolan-2-yl)phenyl) (intermediate 28) as starting materials. The crude reaction mixture was purified by SCX-2 cartridge (loaded in MeOH eluted with 2M methanolic ammonia). Ammonia eluant was concentrated in vacuo. Residue was then purified by prep. HPLC at high pH to afford an off white solid (34.6 mg, 0.08 mmol, 16%).

$^1$H NMR (d$_6$-DMSO) 8.89 (s, 1H), 7.94 (td, 1H), 7.53 (dd, 1H), 7.09 (dd, 1H), 6.28 (t, 1H), 4.81 (d, 2H), 4.47 (d, 2H), 3.68 (s, 11H), 3.16-3.08 (m, 2H), 1.06 (t, 3H).

LCMS (Method A), (M+H$^+$) 445, Rt=6.68 min

Example 163

(S)-1-cyclopropyl-3-(3-fluoro-4-(4-(3-methylmorpholino)-5,6,7,8-tetrahydropyrido[3,4-d]pyrimidin-2-yl)phenyl)urea

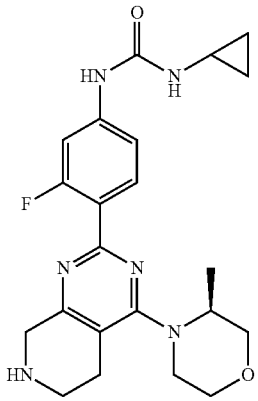 [SMILES: C[C@H]1COCCN1c1nc(-c2ccc(NC(=O)NC3CC3)cc2F)nc2c1CCNC2]

(S)-tert-butyl 2-chloro-4-(3-methylmorpholino)-5,6-dihydropyrido[3,4-d]pyrimidine-7(8H)-carboxylate (intermediate 4) (738 mg, 2.0 mmol), 1-cyclopropyl-3-(3-fluoro-4-(4,4,5,5-tetramethyl-1,3,2-dioxaborolan-2-yl)phenyl)urea (intermediate 29) (730 mg, 2.28 mmol), sodium carbonate (594 mg, 5.6 mmol) and [1,1'-Bis(diphenylphosphino)ferrocene]dichloropalladium (II), complex with dichloromethane (82 mg, 0.1 mmol) were combined and heated in a microwave for 60 minutes at 100° C. Reaction mixture was partitioned between DCM (50 ml) and water (40 ml), the organic layer passed through a hydrophobic fit and concentrated in vacuo to leave a brown solid. The solid was purified by flash chromatography using 15-100% EtOAc/petroleum ether 40-60 to afford a yellow oil (910 mg, 86%). The yellow oil was dissolved in dioxane (20 ml) and methanol (2 ml) and 4M HCl in dioxane (4 ml) was added and the mixture stirred overnight at room temperature. The reaction mixture was concentrated in vacuo and the resultant material was isolated as a free base using a 5 g SCX cartridge to yield a yellow solid (656 mg, 89%). A sample of the free base (100 mg, 0.23 mmol) was purified by prep. HPLC at high pH to afford a pale yellow solid (40 mg, 40%).

$^1$H NMR (d$_6$-DMSO) 8.78 (s, 1H), 7.94-7.82 (m, 1H), 7.53 (dd, 1H), 7.13 (dd, 1H), 6.60 (s, 1H), 4.06 (d, 1H), 3.90-3.76 (m, 3H), 3.68 (dd, 1H), 3.63-3.50 (m, 3H), 2.99-2.88 (m, 1H), 2.88-2.77 (m, 1H), 2.62-2.53 (m, 3H), 1.22 (d, 3H), 0.69-0.62 (m, 2H), 0.45-0.38 (m, 2H).

LCMS (method A), (M+H$^+$) 427, Rt=5.25 min.

Example 164

(S)-1-ethyl-3-(3-fluoro-4-(4-(3-methylmorpholino)-5,6,7,8-tetrahydropyrido[3,4-d]pyrimidin-2-yl)phenyl)urea

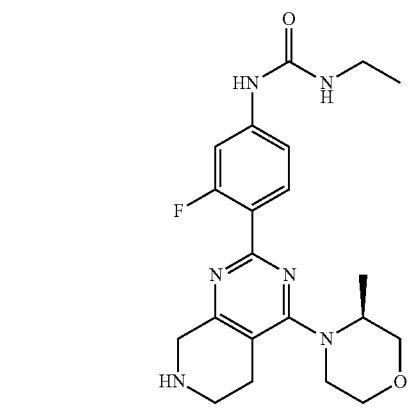

(S)-tert-butyl 2-chloro-4-(3-methylmorpholino)-5,6-dihydropyrido[3,4-d]pyrimidine-7(8H)-carboxylate (intermediate 4) (408 mg, 1.1 mmol), 1-ethyl-3-(3-fluoro-4-(4,4,5,5-tetramethyl-1,3,2-dioxaborolan-2-yl)phenyl)urea (intermediate 28) (387 mg, 1.254 mmol), sodium carbonate (327 mg, 3.08 mmol) and [1,1'-Bis(diphenylphosphino)ferrocene]dichloropalladium (II), complex with dichloromethane (45 mg, 0.055 mmol) were combined and heated in a microwave for 60 minutes at 100° C. Reaction mixture was partitioned between DCM (50 ml) and water (40 ml), the organic layer passed through a hydrophobic frit and concentrated in vacuo to leave a brown solid. The solid was purified by flash chromatography using 25-100% EtOAc/petroleum ether 40-60 to afford a yellow oil (470 mg, 83%). The yellow oil was dissolved in dioxane (10 ml) and methanol (1 ml) and 4M HCl in dioxane (2 ml) was added and the mixture stirred overnight at room temperature. Reaction mixture was concentrated in vacuo and the resultant material was isolated as a free base using a 5 g SCX cartridge to yield a yellow solid (341 mg, 90%). A sample of the free base (100 mg, 0.23 mmol) was purified by prep. HPLC at high pH to afford a pale yellow solid (40 mg, 40%).

$^1$H NMR (d$_6$-DMSO) 8.89 (s, 1H), 7.93-7.84 (m, 1H), 7.52 (d, 1H), 7.09 (d, 1H), 6.30 (t, 1H), 4.12-4.02 (m, 1H), 3.91-3.76 (m, 3H), 3.68 (d, 1H), 3.63-3.48 (m, 3H), 3.19-3.07 (m, 2H), 3.00-2.88 (m, 1H), 2.88-2.75 (m, 1H), 2.62-2.53 (m, 2H), 1.22 (d, 3H), 1.07 (t, 3H).

LCMS (method A), (M+H$^+$) 415, Rt=5.11 min.

Example 165

(S)-2-(4-(3-cyclopropylureido)-2-fluorophenyl)-N,N-dimethyl-4-(3-methylmorpholino)-5,6-dihydropyrido[3,4-d]pyrimidine-7(8H)-carboxamide

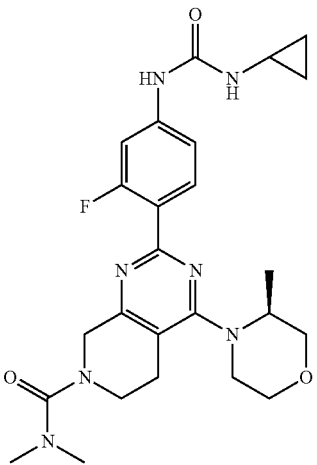 [SMILES: C[C@H]1COCCN1c1nc(-c2ccc(NC(=O)NC3CC3)cc2F)nc2c1CCN(C(=O)N(C)C)C2]

To a stirring solution of (S)-1-cyclopropyl-3-(3-fluoro-4-(4-(3-methylmorpholino)-5,6,7,8-tetrahydropyrido[3,4-d]pyrimidin-2-yl)phenyl)urea (example 163) (99 mg, 0.23 mmol) and NEt$_3$ (35 µL, 0.25 mmol) in DMF (2 ml) was added dimethylcarbamoyl chloride (29 µL, 0.25 mmol). Reaction mixture was stirred at room temperature (20° C.) overnight before being concentrated in vacuo and purified by prep. HPLC at high pH to afford a white solid (42 mg, 37%).
$^1$H NMR (d$_6$-DMSO) 8.75 (s, 1H), 7.95-7.87 (m, 1H), 7.53 (dd, 1H), 7.13 (dd, 1H), 6.56 (d, 1H), 4.29 (s, 2H), 4.17-4.08 (m, 1H), 3.90-3.82 (m, 1H), 3.72-3.52 (m, 4H), 2.82 (s, 6H), 2.76-2.69 (m, 2H), 2.59-2.53 (m, 1H), 1.25 (d, 3H), 0.69-0.62 (m, 2H), 0.46-0.40 (m, 2H).
LCMS (method A), (M+H$^+$) 498, Rt=6.06 min.

Example 166

1-(4-(6-Acetyl-4-morpholino-6,7-dihydro-5H-pyrrolo[3,4-d]pyrimidin-2-yl)-3-fluorophenyl)-3-cyclopropylurea

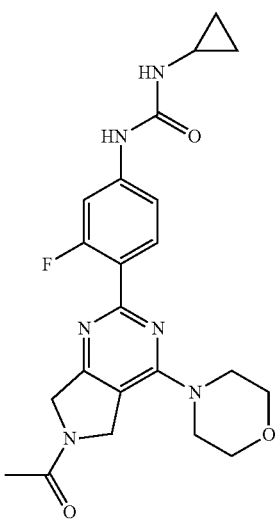 [SMILES: CC(=O)N1Cc2nc(-c3ccc(NC(=O)NC4CC4)cc3F)nc(N3CCOCC3)c2C1]

Method as described for (S)-1-cyclopropyl-3-(3-fluoro-4-(6-methyl-4-(3-methylmorpholino)-6,7-dihydro-5H-pyrrolo[3,4-d]pyrimidin-2-yl)phenyl)urea(example 147) using 1-(2-chloro-4-morpholino-5H-pyrrolo[3,4-d]pyrimidin-6(7H)-yl)ethanone (intermediate 23) and 1-cyclopropyl-3-(3-fluoro-4-(4,4,5,5-tetramethyl-1,3,2-dioxaborolan-2-yl)phenyl)urea (intermediate 29). Residue was then purified by prep. HPLC at high pH to afford a cream solid (15% yield).
$^1$H NMR (d$_6$-DMSO) 8.96 (d, 1H), 7.95 (td, 1H), 7.53 (dd, 1H), 7.13 (d, 1H), 6.76 (dd, 1H), 5.00 (br s, 1H), 4.77 (br s, 1H), 4.70 (br s, 1H), 4.43 (br s, 1H), 3.70 (d, 8H), 2.58-2.52 (m, 1H), 2.08 (d, 3H), 0.68-0.61 (m, 2H), 0.43-0.40 (m, 2H).
LCMS (method A), (M+H$^+$) 441, Rt=6.02 min.

Example 167

(S)-Ethyl 2-(2-fluoro-4-(3-(2-hydroxyethyl)ureido)phenyl)-4-(3-methylmorpholino)-5H-pyrrolo[3,4-d]pyrimidine-6(7H)-carboxylate

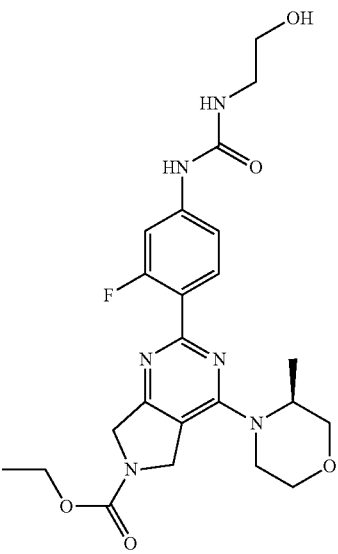 [SMILES: CCOC(=O)N1Cc2nc(-c3ccc(NC(=O)NCCO)cc3F)nc(N3CCOC[C@@H]3C)c2C1]

A solution of (S)-ethyl 2-chloro-4-(3-methylmorpholino)-5H-pyrrolo[3,4-d]pyrimidine-6(7H)-carboxylate (intermediate 11) (100 mg, 0.31 mmol), 1-(3-fluoro-4-(4,4,5,5-tetramethyl-1,3,2-dioxaborolan-2-yl)phenyl)-3-(2-hydroxyethyl)urea (intermediate 32) (149 mg, 0.46 mmol), [1,1'-Bis(diphenylphosphino)ferrocene]dichloropalladium (II), complex with dichloromethane (15 mg, 0.018 mmol) and sodium carbonate (49 mg, 0.46 mmol) in 2 ml of a 7:3:2 mixture of DME:EtOH:H$_2$O respectively was heated in the microwave at 130° C. for 1 hour. The reaction was concentrated in vacuo and the residue redissolved in a mix of MeOH/DCM. It was loaded onto an SCX cartridge and washed with two column volumes of MeOH/DCM before being eluted with 2M NH$_3$ in MeOH and concentrated in vacuo. The sample was then purified via preparative HPLC at high pH to yield the title compound (32.8 mg, 22%).

¹H NMR (d₆-DMSO) 9.03 (s, 1H), 7.93 (td, 1H), 7.52 (dd, 1H), 7.07 (dd, 1H), 6.37 (t, 1H), 4.86-4.65 (m, 3H), 4.47-4.35 (m, 3H), 4.13 (qn, 2H), 3.99 (br s, 1H), 3.93 (dd, 1H), 3.73 (d, 1H), 3.64 (dd, 1H), 3.51-3.43 (m, 3H), 3.35-3.30 (m, 1H), 3.17 (q, 2H), 1.26-1.22 (m, 6H).
LCMS (method A), (M+H⁺) 489, Rt=6.54 min.

Example 168

(S)-ethyl 2-(2-fluoro-4-(3-(2-fluoroethyl)ureido)phenyl)-4-(3-methylmorpholino)-5H-pyrrolo[3,4-d]pyrimidine-6(7H)-carboxylate

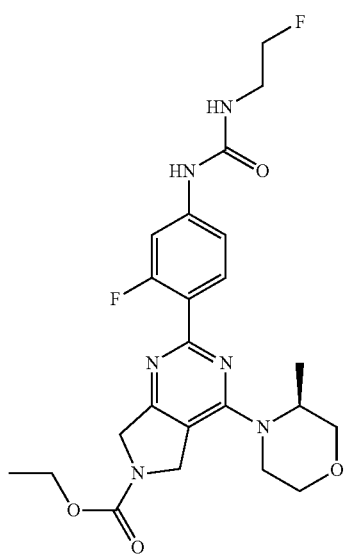 [SMILES: CCOC(=O)N1Cc2nc(-c3ccc(NC(=O)NCCF)cc3F)nc(N3CCOC[C@@H]3C)c2C1]

A solution of (S)-ethyl 2-chloro-4-(3-methylmorpholino)-5H-pyrrolo[3,4-d]pyrimidine-6(7H)-carboxylate (intermediate 11) (100 mg, 0.31 mmol), 1-(3-fluoro-4-(4,4,5,5-tetramethyl-1,3,2-dioxaborolan-2-yl)phenyl)-3-(2-fluoroethyl)urea (intermediate 31) (450 mg, 1.38 mmol), [1,1'-Bis(diphenylphosphino)ferrocene]dichloropalladium (II), complex with dichloromethane (16 mg, 0.02 mmol) and sodium carbonate (49 mg, 0.46 mmol) in 2 ml of a 7:3:2 mixture of DME:EtOH:H₂O respectively was heated in the microwave at 130° C. for 1 hour. The reaction was filtered through celite and purified via preparative HPLC at high pH then low pH to yield the title compound (15 mg, 10%).
¹H NMR (d₆-DMSO) 9.01 (br s, 1H), 7.94 (td, 1H), 7.51 (dd, 1H), 7.11 (dd, 1H), 6.53 (t, 1H), 4.88-4.74 (m, 2H), 4.53 (t, 1H), 4.50 (d, 2H), 4.41 (t, 1H), 4.36 (br s, 1H), 4.14 (qn, 2H), 4.10-4.00 (m, 1H), 3.93 (dd, 1H), 3.73 (d, 1H), 3.64 (dd, 1H), 3.52-3.43 (m, 2H), 3.40-3.35 (m, 2H), 1.26-1.22 (m, 6H).
LCMS (method A), (M+H⁺) 491, Rt=7.53 min.

Example 169

Methyl 2-(2-fluoro-4-(3-(2-fluoroethyl)ureido)phenyl)-4-morpholino-5H-pyrrolo[3,4-d]pyrimidine-6(7H)-carboxylate

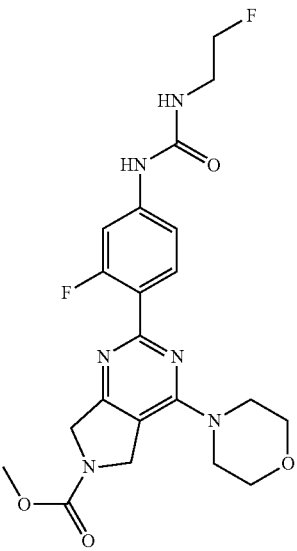 [SMILES: COC(=O)N1Cc2nc(-c3ccc(NC(=O)NCCF)cc3F)nc(N3CCOCC3)c2C1]

Method as (S)-Ethyl 2-(2-fluoro-4-(3-(2-fluoroethyl)ureido)phenyl)-4-(3-methylmorpholino)-5H-pyrrolo[3,4-d]pyrimidine-6(7H)-carboxylate (Example 168) using methyl 2-chloro-4-morpholino-5H-pyrrolo[3,4-d]pyrimidine-6(7H)-carboxylate (intermediate 25). Residue was then purified by prep. HPLC at low pH to afford a colourless solid (16%).
¹H NMR (d₆-DMSO) 9.03 (br s, 1H), 7.94 (td, 1H), 7.52 (dd, 1H), 7.10 (dd, 1H), 6.54 (t, 1H), 4.82 (d, 2H), 4.53 (t, 1H), 4.47 (d, 2H), 4.41 (t, 1H), 3.69 (br s, 11H), 3.44 (q, 1H), 3.37 (q, 1H).
LCMS (method A), (M+H⁺) 493, Rt=6.54 min.

Example 170 ethyl 2-(2-fluoro-4-(3-(2-fluoroethyl)ureido)phenyl)-4-morpholino-5H-pyrrolo[3,4-d]pyrimidine-6(7H)-carboxylate

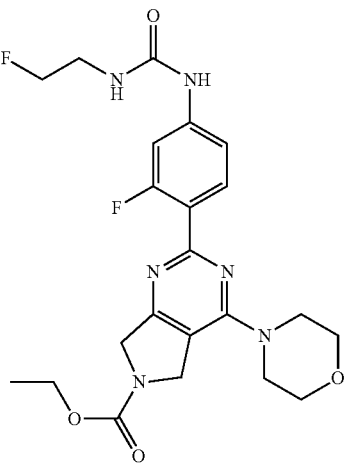 [SMILES: CCOC(=O)N1Cc2nc(-c3ccc(NC(=O)NCCF)cc3F)nc(N3CCOCC3)c2C1]

Method as described for example 47 using ethyl 2-chloro-4-morpholino-5H-pyrrolo[3,4-d]pyrimidine-6(7H)-carboxylate (intermediate 27) and 1-(3-fluoro-4-(4,4,5,5-tetramethyl-1,3,2-dioxaborolan-2-yl)phenyl)-3-(2-fluoroethyl)urea (intermediate 31) as starting materials.

[1,1'-Bis(diphenylphosphino)ferrocene]dichloropalladium (II), complex with dichloromethane was used as catalyst. The reaction mixture was heated at 130° C. in the microwave for 30 mins, then a further 45 mins at 140° C. The mixture was filtered through a celite 545 pre-packed cartridge (2.5 g), washed with MeOH and the solvent removed in vacuo. The residue was purified by prep. HPLC at low pH, yielding the title compound (27 mg, 0.06 mmol, 12%).

1H NMR (d$_6$-DMSO) 9.24 (br s, 1H), 7.98-7.89 (m, 1H), 7.55-7.49 (dd, 1H). 7.15-7.09 (dd, 1H), 6.79-6.72 (m, 1H), 4.81 (d, 2H), 4.52 (t, 1H), 4.47 (d, 2H), 4.40 (t, 1H), 4.18-4.08 (m, 2H), 3.69 (s, 8H), 3.47-3.40 (m, 1H), 3.40-3.33 (m, 1H), 1.27-1.20 (m, 3H).

LCMS (Method A), (M+H+) 477 Rt=7.08 min

Example 171 ethyl 2-(2-fluoro-4-(3-(2-hydroxyethyl)ureido)phenyl)-4-morpholino-5H-pyrrolo[3,4-d]pyrimidine-6(7H)-carboxylate

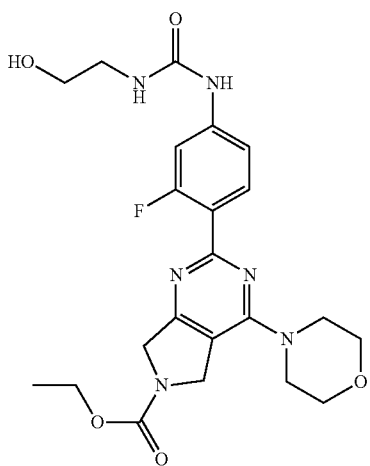 [SMILES: CCOC(=O)N1Cc2nc(-c3ccc(NC(=O)NCCO)cc3F)nc(N3CCOCC3)c2C1]

Method as described for example 47 using ethyl 2-chloro-4-morpholino-5H-pyrrolo[3,4-d]pyrimidine-6(7H)-carboxylate (intermediate 27) and 1-(3-fluoro-4-(4,4,5,5-tetramethyl-1,3,2-dioxaborolan-2-yl)phenyl)-3-(2-hydroxyethyl)urea (intermediate 32) as starting materials. [1,1'-Bis(diphenylphosphino)ferrocene]dichloropalladium (II), complex with dichloromethane was used as catalyst. The mixture was filtered through a celite 545 pre-packed cartridge (2.5 g), washed with MeOH and the solvent removed in vacuo. The residue was purified by prep. HPLC at high pH, yielding the title compound (115 mg, 0.24 mmol, 50%).

$^1$H NMR (d$_6$-DMSO) 9.00 (br s, 1H), 7.98-7.89 (m, 1H), 7.55-7.48 (dd, 1H), 7.09-7.04 (dd, 1H), 6.33 (t, 1H), 4.81 (d, 2H), 4.75 (t, 1H), 4.47 (d, 2H), 4.18-4.08 (m, 2H), 3.69 (s, 8H), 3.48-3.41 (m, 2H), 3.19-3.13 (m, 2H), 1.27-1.20 (m, 3H).

LCMS (Method A), (M+H$^+$) 475 Rt=6.28 min

Example 172

(S)-1-cyclopropyl-3-(3-fluoro-4-(6-isopropyl-4-(3-methylmorpholino)-6,7-dihydro-5H-pyrrolo[3,4-d]pyrimidin-2-yl)phenyl)urea

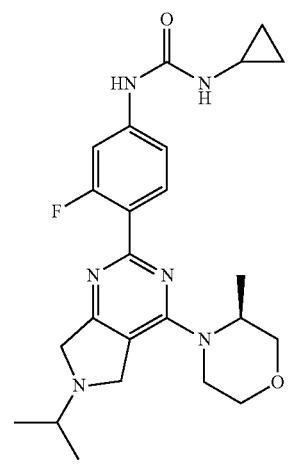 [SMILES: CC(C)N1Cc2nc(-c3ccc(NC(=O)NC4CC4)cc3F)nc(N3CCOC[C@@H]3C)c2C1]

To a stirred solution of (S)-1-cyclopropyl-3-(3-fluoro-4-(4-(3-methylmorpholino)-6,7-dihydro-5H-pyrrolo[3,4-d]pyrimidin-2-yl)phenyl)urea (example 149) (115 mg, 0.279 mmol) in anhydrous DMF (2 ml) was added triethylamine (780, 0.558 mmol) and anhydrous acetone (100 µL). The reaction was stirred at RT for 30 minutes after which time sodium triacetoxyborohydride (118 mg, 0.558 mmol) was added and the reaction was stirred for a further 2 hours at RT. The reaction was then partitioned between H$_2$O and DCM and the aqueous phase was extracted into DCM. The organic extracts were combined, dried over magnesium sulphate and concentrated in vacuo. The sample was then purified via preparative HPLC at high pH to yield the title compound (16 mg, 13%).

$^1$H NMR (CD$_3$OD) 7.83 (t, 1H), 7.48 (dd, 1H), 7.13 (dd, 1H), 4.45 (d, 1H), 4.22-4.09 (m, 3H), 3.98 (dd, 1H), 3.94-3.85 (m, 2H), 3.80-3.71 (m, 2H), 3.60 (td, 1H), 3.43 (td, 1H), 2.85 (qn, 1H), 2.64-2.56 (sept, 1H), 1.35 (d, 3H), 1.22 (d, 6H), 0.79-0.72 (m, 2H), 0.55-0.49 (m, 2H)

LCMS (method A), (M+H$^+$) 455, Rt=5.37 min

Example 173

Methyl 2-(4-(3-cyclopropylureido)-2-fluorophenyl)-4-morpholino-5H-pyrrolo[3,4-d]pyrimidine-6(7H)-carboxylate

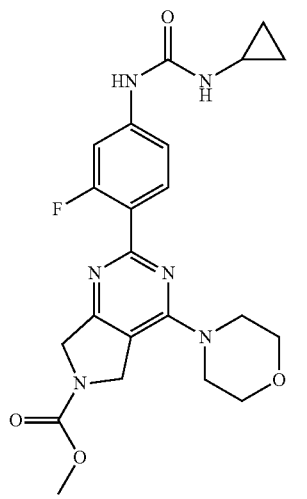 [SMILES: COC(=O)N1Cc2nc(-c3ccc(NC(=O)NC4CC4)cc3F)nc(N3CCOCC3)c2C1]

A solution of methyl 2-chloro-4-morpholino-5H-pyrrolo[3,4-d]pyrimidine-6(7H)-carboxylate (intermediate 25) (10 mg, 0.335 mol), 1-cyclopropyl-3-(3-fluoro-4-(4,4,5,5-tetramethyl-1,3,2-dioxaborolan-2-yl)phenyl)urea (intermediate 29) (122 mg, 0.382 mmol), [1,1'-Bis(diphenylphosphino)ferrocene]dichloropalladium (II), complex with dichloromethane (14 mg, 0.0168 mmol) and sodium carbonate (107 mg, 1.01 mmol) in 2 ml of a 7:3:1 mixture of DME:H$_2$O:EtOH respectively was heated in the microwave at 115° C. for 45 minutes. The reaction was concentrated in vacuo and the residue redissolved in a mix of MeOH/DCM. It was loaded onto an SCX cartridge and washed with two column volumes of MeOH/DCM before being eluted with 2M NH$_3$ in MeOH and concentrated in vacuo. The sample was then purified via preparative HPLC at low pH to yield the title compound (33 mg, 22%).

$^1$H NMR (d$_6$-DMSO) 8.74 (s, 1H), 7.94 (td, 1H), 7.53 (dd, 1H), 7.12 (dd, 1H), 6.54 (d, 1H), 4.81 (d, 2H), 4.46 (d, 2H), 3.68 (s, 11H), 2.59-2.52 (m, 1H), 0.69-0.60 (m, 2H), 0.47-0.38 (m, 2H)

LCMS (method A), (M+H$^+$) 457, Rt=6.63 min

Example 174

(S)-1-cyclopropyl-3-(3-fluoro-4-(6-isobutyryl-4-(3-methylmorpholino)-6,7-dihydro-5H-pyrrolo[3,4-d]pyrimidin-2-yl)phenyl)urea

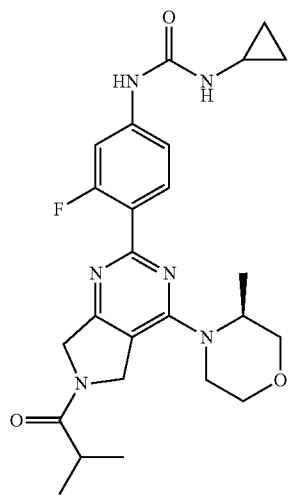 [SMILES: CC(C)C(=O)N1Cc2nc(-c3ccc(NC(=O)NC4CC4)cc3F)nc(N3CCOC[C@@H]3C)c2C1]

A solution of (S)-1-cyclopropyl-3-(3-fluoro-4-(4-(3-methylmorpholino)-6,7-dihydro-5H-pyrrolo[3,4-d]pyrimidin-2-yl)phenyl)urea hydrochloride (example 149) (115 mg, 0.279 mmol) and triethylamine 0.558 mmol) in anhydrous DMF (2 ml) was stirred at RT for 1 hour. After this time, isobutyryl chloride (35 μl, 0.335 mmol) was added and stirring was continued at RT overnight. The reaction was partitioned between water and EtOAc and the aqueous phase was extracted into EtOAc. The organic extracts were combined, dried over magnesium sulphate and concentrated in vacuo. The sample was then purified via preparative HPLC at low pH to yield the title compound (60 mg, 45%).

$^1$H NMR (CD$_3$OD) 7.88 (td, 1H), 7.48 (dd, 1H), 7.13 (dm, 1H), 5.10 (q, 1H), 4.93-4.81 (m, 1H), 4.79 (s, 1H), 4.59 (s, 1H), 4.50 (br d, 1H), 4.23-4.08 (m, 1H), 3.99 (dd, 1H), 3.82-3.73 (m, 2H), 3.66-3.57 (m, 1H), 3.54-3.40 (m, 1H), 2.92 (m, 1H), 2.60 (sept, 1H), 1.37 (d, 3H), 1.18 (d, 6H), 0.80-0.72 (m, 2H), 0.55-0.49 (m, 2H).

LCMS (method A), (M+H$^+$) 483, Rt=7.27 min

Example 175

Methyl 2-(2-fluoro-4-(3-(2-hydroxyethyl)ureido)phenyl)-4-morpholino-5H-pyrrolo[3,4-d]pyrimidine-6(7H)-carboxylate

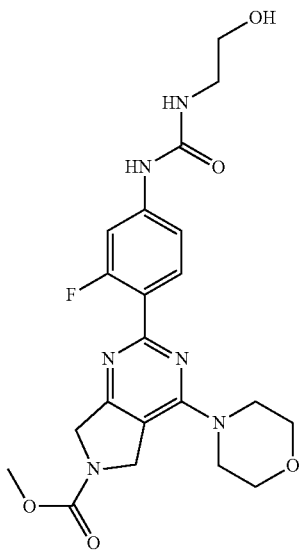 [SMILES: COC(=O)N1Cc2nc(-c3ccc(NC(=O)NCCO)cc3F)nc(N3CCOCC3)c2C1]

Method as (S)-Ethyl 2-(2-fluoro-4-(3-(2-hydroxyethyl)ureido)phenyl)-4-(3-methylmorpholino)-5H-pyrrolo[3,4-d]pyrimidine-6(7H)-carboxylate (Example 167) using methyl 2-chloro-4-morpholino-5H-pyrrolo[3,4-d]pyrimidine-6(7H)-carboxylate (intermediate 25). Residue was then purified by prep. HPLC at low pH then high pH to afford a colourless solid (16% yield).

$^1$HNMR (d$_6$-DMSO) 8.99 (br s, 1H), 7.93 (td, 1H), 7.52 (dd, 1H), 7.07 (dd, 1H), 6.32 (t, 1H), 4.82 (d, 2H), 4.76 (t, 1H), 4.46 (d, 2H), 3.69 (br s, 11H), 3.45 (q, 2H), 3.16 (q, 2H).

LCMS (method A), (M+H$^+$) 461, Rt=5.68 min.

Example 176

(S)-2-(4-(3-ethylureido)-2-fluorophenyl)-N,N-dimethyl-4-(3-methylmorpholino)-5,6-dihydropyrido[3,4-d]pyrimidine-7(8H)-carboxamide

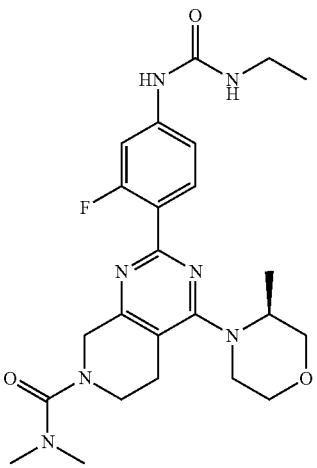 [SMILES: CCNC(=O)Nc1ccc(-c2nc3c(c(N4CCOC[C@@H]4C)n2)CCN(C(=O)N(C)C)C3)c(F)c1]

Method as example 165 using (S)-1-ethyl-3-(3-fluoro-4-(4-(3-methylmorpholino)-5,6,7,8-tetrahydropyrido[3,4-d]pyrimidin-2-yl)phenyl)urea (example 164) (132 mg, 0.32 mmol) as a starting material. Reaction mixture was purified using an SCX cartridge before being dissolved in EtOAc (10 ml). The organic layer was washed with saturated sodium bicarbonate (3×10 ml), passed through a hydrophobic frit and concentrated in vacuo to afford a white solid (16 mg, 10%).

$^1$H NMR (d$_6$-DMSO) 9.40-9.25 (m, 1H), 7.94-7.86 (m, 1H), 7.53 (dd, 1H), 7.13 (dd, 1H), 6.80-6.65 (m, 1H), 4.29 (s, 2H), 4.16-4.07 (m, 2H), 3.89-3.82 (m, 1H), 3.71-3.53 (m, 6H), 3.15-3.08 (m, 2H), 2.81 (s, 6H), 2.74-2.68 (m, 2H), 1.25 (d, 3H), 1.06 (t, 3H).

LCMS (method A), (M+H$^+$) 486, Rt=6.05 min.

Example 177

(S)-1-cyclopropyl-3-(3-fluoro-4-(4-(3-methylmorpholino)-6-(methylsulfonyl)-6,7-dihydro-5H-pyrrolo[3,4-d]pyrimidin-2-yl)phenyl)urea

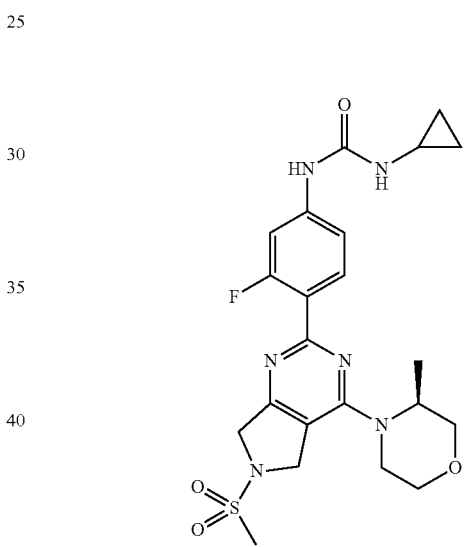

To a stirring solution of (S)-1-cyclopropyl-3-(3-fluoro-4-(4-(3-methylmorpholino)-6,7-dihydro-5H-pyrrolo[3,4-d]pyrimidin-2-yl)phenyl)urea hydrochloride (Example 149) (115 mg, 0.279 mmol) and NEt$_3$ (43 µL, 0.307 mmol) in DMF (2 ml) was added methanesulfonyl chloride (24 µL, 0.307 mmol). Reation mixture was stirred at room temperature (20° C.) overnight before being concentrated in vacuo and purified by prep. HPLC at high pH to afford a white solid (75 mg, 55%).

$^1$H NMR (d$_6$-DMSO) 8.74 (s, 1H), 7.94 (t, 1H), 7.54 (dd, 1H), 7.13 (dd, 1H), 6.54 (d, 1H), 4.89 (d, 1H), 4.78 (d, 1H), 4.49 (s, 2H), 4.40 (br s, 1H), 4.03 (br d, 1H), 3.94 (dd, 1H), 3.73 (d, 1H), 3.63 (dd, 1H), 3.49 (td, 1H), 3.40-3.33 (m, 1H), 3.06 (s, 3H), 2.60-2.53 (m, 1H), 1.27 (d, 3H), 0.67-0.62 (m, 2H), 0.44-0.40 (m, 2H).

LCMS (method A), (M+H$^+$) 491, Rt=7.37 min.

Example 178

(S)-2-(4-(3-cyclopropylureido)-2-fluorophenyl)-N,N-dimethyl-4-(3-methylmorpholino)-5H-pyrrolo[3,4-d]pyrimidine-6(7H)-carboxamide

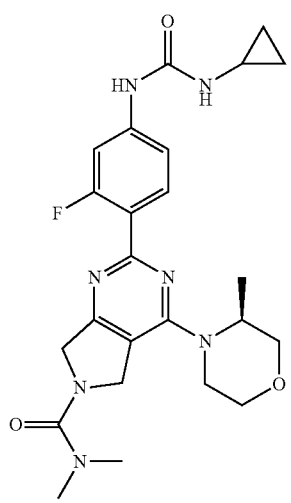 [SMILES: C[C@H]1COCCN1c1nc(-c2ccc(NC(=O)NC3CC3)cc2F)nc2c1CN(C(=O)N(C)C)C2]

To a stirring solution of (S)-1-cyclopropyl-3-(3-fluoro-4-(4-(3-methylmorpholino)-6,7-dihydro-5H-pyrrolo[3,4-d]pyrimidin-2-yl)phenyl)urea hydrochloride (Example 149) (115 mg, 0.279 mmol) and NEt₃ (43 µL, 0.307 mmol) in DMF (2 ml) was added dimethylcarbamoyl chloride (35 µL, 0.307 mmol). Reaction mixture was stirred at room temperature (20° C.) overnight before being concentrated in vacuo and purified by prep. HPLC at high pH to afford a white solid (75 mg, 56%).

$^1$H NMR (d$_6$-DMSO) 8.75 (s, 1H), 7.97-7.91 (m, 1H), 7.53 (dd, 1H), 7.13 (dd, 1H), 6.56 (d, 1H), 4.93-4.80 (m, 2H), 4.54 (s, 2H), 4.44-4.33 (m, 1H), 4.12-4.03 (m, 1H), 3.94 (dd, 1H), 3.73 (d, 1H), 3.65 (dd, 1H), 3.55-3.46 (m, 1H), 3.37 (br m, 1H), 2.86 (s, 6H), 2.60-2.54 (m, 1H), 1.26 (d, 3H), 0.69-0.62 (m, 2H), 0.46-0.40 (m, 2H).

LCMS (method A), (M+H$^+$) 484, Rt=6.45 min.

Example 179

(R)-ethyl 2-(4-(3-cyclopropylureido)-2-fluorophenyl)-4-(3-methylmorpholino)-5H-pyrrolo[3,4-d]pyrimidine-6(7H)-carboxylate

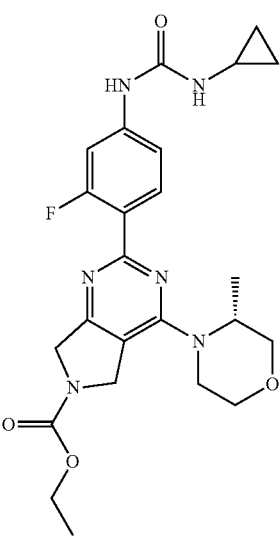 [SMILES: CCOC(=O)N1Cc2nc(-c3ccc(NC(=O)NC4CC4)cc3F)nc(N3CCOC[C@H]3C)c2C1]

A solution of (R)-1-cyclopropyl-3-(3-fluoro-4-(4-(3-methylmorpholino)-6,7-dihydro-5H-pyrrolo[3,4-d]pyrimidin-2-yl)phenyl)urea hydrochloride (intermediate 33) (121 mg, 0.270 mmol) and triethylamine (75 µL, 0.534 mmol) in anhydrous DMF (2 ml) was stirred at RT for 40 minutes. After this time, ethyl chloroformate (30 µl, 0.322 mmol) was added and stirring was continued at RT overnight. The reaction was partitioned between H₂O and EtOAc and the aqueous phase was extracted into EtOAc. The organic extracts were combined, dried over magnesium sulphate and concentrated in vacuo. The sample was then purified via preparative HPLC at low pH to yield the title compound (35 mg, 27%).

$^1$H NMR (CD$_3$OD) 7.86 (td, 1H), 7.48 (dd, 1H), 7.11 (d, 1H), 4.90-4.76 (m, 2H), 4.54 (s, 2H), 4.45 (br s, 1H), 4.22 (q, 2H), 4.13 (br t, 1H), 3.99 (dd, 1H), 3.81-3.72 (m, 2H), 3.61 (td, 1H), 3.44 (br t, 1H), 2.63-2.56 (m, 1H), 1.36 (d, 3H), 1.32 (t, 3H), 0.79-0.72 (m, 2H), 0.55-0.49 (m, 2H)

LCMS (method A), (M+H$^+$) 485, Rt=7.60 min

Example 180

(R)-methyl 2-(4-(3-cyclopropylureido)-2-fluorophenyl)-4-(3-methylmorpholino)-5H-pyrrolo[3,4-d]pyrimidine-6(7H)-carboxylate

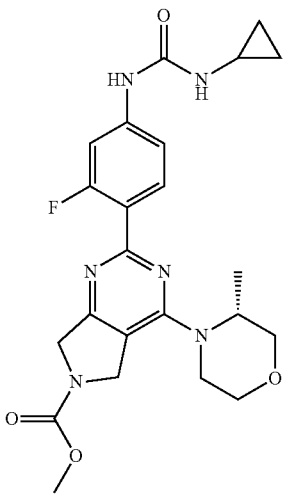 [SMILES: COC(=O)N1Cc2nc(-c3ccc(NC(=O)NC4CC4)cc3F)nc(N3CCOC[C@H]3C)c2C1]

Method as described for example 179 using methyl chloroformate.

$^1$H NMR (d$_6$-DMSO) 8.84 (s, 1H), 7.93 (td, 1H), 7.53 (dd, 1H), 7.13 (dd, 1H), 6.64 (d, 1H), 4.91-4.73 (m, 2H), 4.47 (d, 2H), 4.35 (br s, 1H), 4.06 (br s, 1H), 3.94 (d, 1H), 3.73 (d, 1H), 3.69 (s, 3H), 3.64 (d, 1H), 3.48 (t, 1H), 3.35 (br s, 1H), 2.60-2.53 (m, 1H), 1.25 (d, 3H), 0.68-0.60 (m, 2H), 0.47-0.37 (m, 2H)

LCMS (method A), (M+H$^+$) 471, Rt=7.07 min

Example 181

(S)-methyl 2-(2-fluoro-4-(3-(2-hydroxyethyl)ureido)phenyl)-4-(3-methylmorpholino)-5H-pyrrolo[3,4-d]pyrimidine-6(7H)-carboxylate

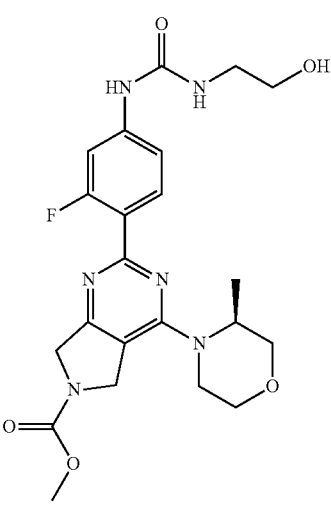 [SMILES: COC(=O)N1Cc2nc(-c3ccc(NC(=O)NCCO)cc3F)nc(N3CCOC[C@@H]3C)c2C1]

Method as described for example 147 using (S)-methyl 2-chloro-4-(3-methylmorpholino)-5H-pyrrolo[3,4-d]pyrimidine-6(7H)-carboxylate (intermediate 26) and 1-(3-fluoro-4-(4,4,5,5-tetramethyl-1,3,2-dioxaborolan-2-yl)phenyl)-3-(2-hydroxyethyl)urea (intermediate 32) as starting materials. The crude reaction mixture was purified by SCX-2 cartridge (loaded in MeOH eluted with 2M methanolic ammonia). Ammonia eluent was concentrated in vacuo. Residue was then purified by prep. HPLC at high pH to afford a light brown solid (50 mg, 0.11 mmol, 26%).

$^1$HNMR (d$_6$-DMSO) 9.00 (s, 1H), 7.94 (td, 1H), 7.52 (dd, 1H), 7.08 (dd, 1H), 6.33 (t, 1H), 4.92-4.72 (m, 3H), 4.48 (d, 2H), 4.36 (s, 1H), 4.07 (s, 1H), 3.95 (d, 1H), 3.79-3.60 (m, 5H), 3.56-3.40 (m, 3H), 3.17 (q, 2H), 1.26 (d, 3H).

LCMS (Method A), (M+H$^+$) 475, Rt=6.09 min

Example 182

(R)-tert-butyl 2-(4-(3-cyclopropylureido)-2-fluorophenyl)-4-(3-methylmorpholino)-5H-pyrrolo[3,4-d]pyrimidine-6(7H)-carboxylate

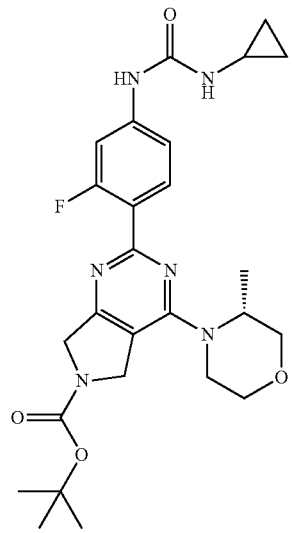 [SMILES: C[C@@H]1COCCN1c1nc(-c2ccc(NC(=O)NC3CC3)cc2F)nc2c1CN(C(=O)OC(C)(C)C)C2]

Step 1: Method as (S)-tert-butyl 2-chloro-4-(3-methylmorpholino)-5H-pyrrolo[3,4-d]pyrimidine-6(7H)-carboxylate (intermediate 1) using tert-butyl 2,4-dichloro-5H-pyrrolo[3,4-d]pyrimidine-6(7H)-carboxylate and (R)-3-methylmorpholine as starting materials to yield (R)-tert-butyl 2-chloro-4-(3-methylmorpholino)-5H-pyrrolo[3,4-d]pyrimidine-6(7H)-carboxylate a white solid (4.55 g, 12.8 mmol, 70%)

LCMS (Method B), (M+H$^+$) 355, Rt=2.72 min

Step 2: Method as described for example 147 using (R)-tert-butyl 2-chloro-4-(3-methylmorpholino)-5H-pyrrolo[3,4-d]pyrimidine-6(7H)-carboxylate (from step 1) and 1-cyclopropyl-3-(3-fluoro-4-(4,4,5,5-tetramethyl-1,3,2-dioxaborolan-2-yl)phenyl)urea (intermediate 29) as starting materials. Reaction solvent was removed in vacuo. The residue was then partitioned between DCM (100 ml) and water (80 ml). The organic layer was recovered, passed through a hydrophobic frit and the solvent removed in vacuo. The residue was purified by flash chromatography using 20-100% ethyl acetate/petroleum ether 40-60 to yield an off white solid (1.107 g, 2.16 mmol, 78%).

$^1$HNMR (d$_6$-DMSO) 8.52 (s, 1H), 7.72 (t, 1H), 7.32 (d, 1H), 6.92 (dd, 1H), 6.33 (s, 1H), 4.63-4.47 (m, 2H), 4.26-4.09 (m, 3H), 3.88 (q, 1H), 3.76-3.69 (m, 1H), 3.55-3.40 (m, 2H), 3.27 (td, 1H), 2.96 (d, 1H), 2.38-2.31 (m, 1H), 1.26 (s, 9H), 1.04 (d, 3H), 0.47-0.40 (m, 2H), 0.24-0.18 (m, 2H).
LCMS (Method A), (M+H⁺) 513, Rt=8.74 min Example 183

(S)-methyl 2-(2-fluoro-4-(3-(2-fluoroethyl)ureido)phenyl)-4-(3-methylmorpholino)-5H-pyrrolo[3,4-d]pyrimidine-6(7H)-carboxylate

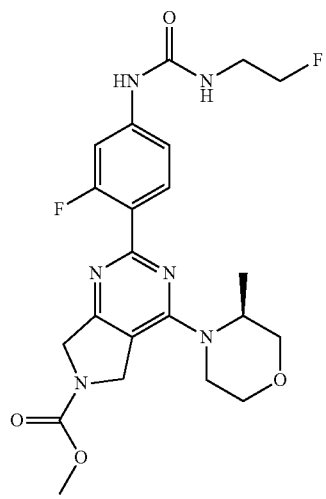 [SMILES: COC(=O)N1Cc2nc(-c3ccc(NC(=O)NCCF)cc3F)nc(N3CCOC[C@@H]3C)c2C1]

Method as described for example 147 using (S)-methyl 2-chloro-4-(3-methylmorpholino)-5H-pyrrolo[3,4-d]pyrimidine-6(7H)-carboxylate (intermediate 26) and 1-(3-fluoro-4-(4,4,5,5-tetramethyl-1,3,2-dioxaborolan-2-yl)phenyl)-3-(2-fluoroethyl)urea (intermediate 31) as starting materials. The crude reaction mixture was purified by SCX-2 cartridge (loaded in MeOH eluted with 2M methanolic ammonia). Ammonia eluent was concentrated in vacuo. Residue was then purified by prep. HPLC at low pH to afford a brown solid (10 mg, 0.02 mmol, 5%).

¹H NMR (d₆-DMSO) 9.11 (s, 1H), 7.95 (td, 1H), 7.53 (dd, 1H), 7.12 (dd, 1H), 6.63 (t, 1H), 4.83 (dt, 2H), 4.53 (t, 1H), 4.48 (d, 2H), 4.41 (t, 1H), 4.36 (s, 1H), 4.07 (s, 1H), 3.95 (d, 1H), 3.77-3.61 (m, 6H), 3.46 (dd, 3H), 1.26 (d, 3H).
LCMS (Method A), (M+H⁺) 477, Rt=6.85 min Example 184

1-(3-fluoro-4-(6-isopropyl-4-morpholino-6,7-dihydro-5H-pyrrolo[3,4-d]pyrimidin-2-yl)phenyl)-3-(2-hydroxyethyl)urea

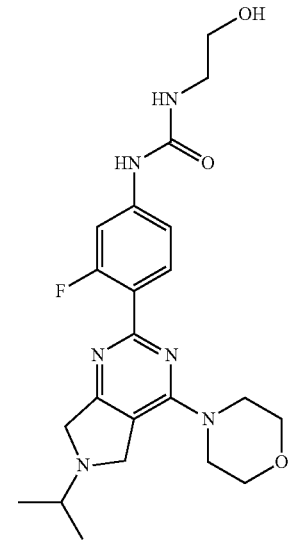 [SMILES: CC(C)N1Cc2nc(-c3ccc(NC(=O)NCCO)cc3F)nc(N3CCOCC3)c2C1]

Method as (S)-Ethyl 2-(2-fluoro-4-(3-(2-hydroxyethyl)ureido)phenyl)-4-(3-methylmorpholino)-5H-pyrrolo[3,4-d]pyrimidine-6(7H)-carboxylate (example 167) using 4-(2-chloro-6-isopropyl-6,7-dihydro-5H-pyrrolo[3,4-d]pyrimidin-4-yl)morpholine (intermediate 34)

¹H NMR (d₆-DMSO) 8.96 (br s, 1H), 7.92 (t, 1H), 7.50 (dd, 1H), 7.06 (dd, 1H), 6.31 (t, 1H), 4.75 (t, 1H), 4.06 (br s, 2H), 3.77 (br s, 2H), 3.67-3.66 (m, 6H), 3.45 (q, 2H), 3.31 (br s, 2H), 3.16 (q, 2H), 2.75 (qn, 1H), 1.11 (d, 6H).
LCMS (method A), (M+H⁺) 445, Rt=4.45 min.

Example 185

1-(3-fluoro-4-(6-isopropyl-4-morpholino-6,7-dihydro-5H-pyrrolo[3,4-d]pyrimidin-2-yl)phenyl)-3-(2-fluoroethyl)urea

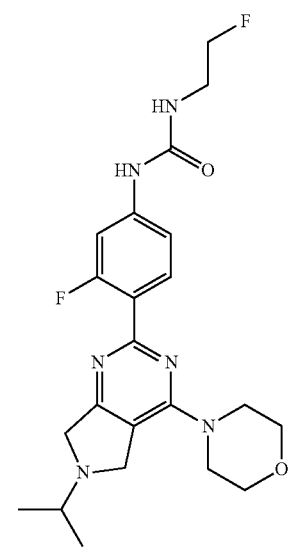 [SMILES: CC(C)N1Cc2nc(-c3ccc(NC(=O)NCCF)cc3F)nc(N3CCOCC3)c2C1]

Method as (S)-ethyl 2-(2-fluoro-4-(3-(2-fluoroethyl)ureido)phenyl)-4-(3-methylmorpholino)-5H-pyrrolo[3,4-d]pyrimidine-6(7H)-carboxylate (Example 168) using 4-(2-chloro-6-isopropyl-6,7-dihydro-5H-pyrrolo[3,4-d]pyrimidin-4-yl)morpholine (intermediate 34).

$^1$H NMR (d$_6$-DMSO) 9.16 (br s, 1H), 7.92 (t, 1H), 7.50 (dd, 1H), 7.10 (dd, 1H), 6.70 (t, 1H), 4.52 (t, 1H), 4.41 (t, 1H), 4.06 (br s, 2H), 3.78 (br s, 2H), 3.67-3.66 (m, 8H), 3.44 (q, 1H), 3.37 (q, 1H), 2.75 (qn, 1H), 1.11 (d, 6H).

LCMS (method A), (M+H$^+$) 447, Rt=4.74 min.

Example 186

(S)-1-(3-fluoro-4-(6-isopropyl-4-(3-methylmorpholino)-6,7-dihydro-5H-pyrrolo[3,4-d]pyrimidin-2-yl)phenyl)-3-(2-fluoroethyl)urea

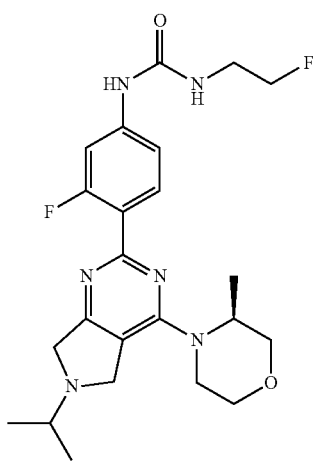 [SMILES: CC(C)N1Cc2nc(-c3ccc(NC(=O)NCCF)cc3F)nc(N3CCOC[C@@H]3C)c2C1]

A solution of (S)-4-(2-chloro-6-isopropyl-6,7-dihydro-5H-pyrrolo[3,4-d]pyrimidin-4-yl)-3-methylmorpholine (intermediate 22) (120 mg, 0.404 mmol), 1-(3-fluoro-4-(4,4,5,5-tetramethyl-1,3,2-dioxaborolan-2-yl)phenyl)-3-(2-fluoroethyl)urea (intermediate 31) (145 mg, 0.445 mmol), [1,1'-Bis(diphenylphosphino)ferrocene]dichloropalladium (II), complex with dichloromethane (16 mg, 0.02 mmol) and sodium carbonate (128 mg, 1.21 mmol) in 2 ml of a 7:3:1 mixture of DME:H$_2$O:EtOH respectively was heated in the microwave at 140° C. for 1 hour. The reaction was filtered through celite and purified via preparative HPLC at high pH to yield the title compound (15 mg, 8%).

$^1$H NMR (CD$_3$OD) 7.85 (t, 1H), 7.49 (dd, 1H), 7.12 (dd, 1H), 4.57 (t, 1H), 4.46 (br s, 1H), 4.45 (t, 1H), 4.21-4.13 (m, 3H), 3.99 (dd, 1H), 3.95-3.87 (m, 2H), 3.81-3.74 (m, 2H), 3.61 (td, 1H), 3.56 (t, 1H), 3.49 (t, 1H), 3.45 (td, 1H), 2.87 (sept, 1H), 1.37 (d, 3H), 1.24 (d, 6H)

LCMS (method A), (M+H$^+$) 461, Rt=5.07 min

Example 187

(S)-1-(3-fluoro-4-(6-isopropyl-4-(3-methylmorpholino)-6,7-dihydro-5H-pyrrolo[3,4-d]pyrimidin-2-yl)phenyl)-3-(2-hydroxyethyl)urea

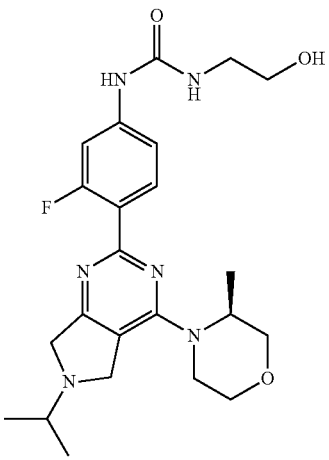 [SMILES: CC(C)N1Cc2nc(-c3ccc(NC(=O)NCCO)cc3F)nc(N3CCOC[C@@H]3C)c2C1]

A solution of (S)-4-(2-chloro-6-isopropyl-6,7-dihydro-5H-pyrrolo[3,4-d]pyrimidin-4-yl)-3-methylmorpholine (intermediate 22) (109 mg, 0.367 mmol), 1-(3-fluoro-4-(4,4,5,5-tetramethyl-1,3,2-dioxaborolan-2-yl)phenyl)-3-(2-hydroxyethyl)urea (intermediate 32) (151 mg, 0.466 mmol), [1,1'-Bis(diphenylphosphino)ferrocene]dichloropalladium (II), complex with dichloromethane (15 mg, 0.018 mmol) and sodium carbonate (117 mg, 1.10 mmol) in 2 ml of a 7:3:1 mixture of CPME:H$_2$O:EtOH respectively was heated in the microwave at 130° C. for 1 hour. The reaction was concentrated in vacuo and the residue redissolved in a mix of MeOH/DCM. It was loaded onto an SCX cartridge and washed with two column volumes of MeOH/DCM before being eluted with 2M NH$_3$ in MeOH and concentrated in vacuo. The sample was then purified via preparative HPLC at high pH to yield the title compound (8 mg, 5%).

$^1$H NMR (d$_6$-DMSO) 8.99 (s, 1H), 7.91 (t, 1H), 7.50 (dd, 1H), 7.06 (dd, 1H), 6.35 (t, 1H), 4.76 (br s, 1H), 4.37 (br s, 1H), 4.12-3.99 (m, 3H), 3.91 (dd, 1H), 3.77 (s, 2H), 3.69 (d, 1H), 3.63 (dd, 1H), 3.50-3.43 (m, 3H), 3.29 (s, 1H), 3.17 (q, 2H), 2.75 (qn, 1H), 1.23 (d, 3H), 1.11 (d, 6H)

LCMS (method A), (M+H$^+$) 459, Rt=4.54 min

Example 188

(R)-1-(4-(6-(cyclopropanecarbonyl)-4-(3-methyl-morpholino)-6,7-dihydro-5H-pyrrolo[3,4-d]pyrimidin-2-yl)-3-fluorophenyl)-3-cyclopropylurea

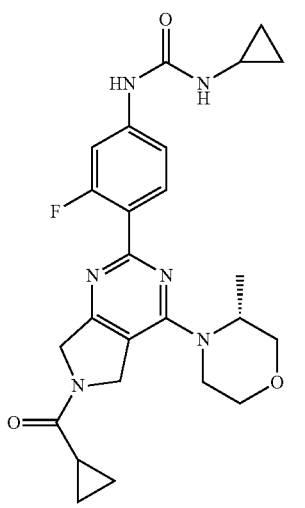 [SMILES: C[C@@H]1COCCN1c1nc(-c2ccc(NC(=O)NC3CC3)cc2F)nc2c1CN(C(=O)C1CC1)C2]

To a stirring solution of (R)-1-cyclopropyl-3-(3-fluoro-4-(4-(3-methylmorpholino)-6,7-dihydro-5H-pyrrolo[3,4-d]pyrimidin-2-yl)phenyl)urea hydrochloride (intermediate 33) (112 mg, 0.25 mmol) in DMF (2 ml), was added Et₃N (70 µL, 0.5 mmol). Reaction mixture was stirred at room temperature (20° C.) for 2 minutes followed by the addition of cyclopropanecarbonyl chloride (23 µL, 0.25 mmol) followed by stirring at room temperature for two hours. The reaction mixture was concentrated in vacuo before partitioning between water (10 ml) and DCM (10 ml). The organic layer was recovered, passed through a hydrophobic frit and the solvent removed in vacuo. Residue was then purified by prep. HPLC at high pH to afford the title compound as an off white solid (25 mg, 0.052 mmol, 21%).

$^1$H NMR (d$_6$-DMSO) 8.76 (s, 1H), 7.96 (t, 1H), 7.54 (dd, 1H), 7.16-7.11 (m, 1H), 6.57 (s, 1H), 5.27-5.11 (m, 1H), 4.91-4.73 (m, 2H), 4.51-4.30 (m, 2H), 4.11 (d, 1H), 3.95 (d, 1H), 3.77-3.60 (m, 2H), 3.56-3.45 (m, 1H), 2.61-2.53 (m, 1H), 2.09-1.88 (m, 1H), 1.27 (t, 3H), 0.85-0.78 (m, 4H), 0.68-0.62 (m, 2H), 0.46-0.40 (m, 2H).

LCMS (Method A), (M+H⁺) 481, Rt=7.02 min

Example 189

(S)-2-(4-(3-cyclopropylureido)-2-fluorophenyl)-N-isopropyl-4-(3-methylmorpholino)-5,6-dihydropyrido[3,4-d]pyrimidine-7(8H)-carboxamide

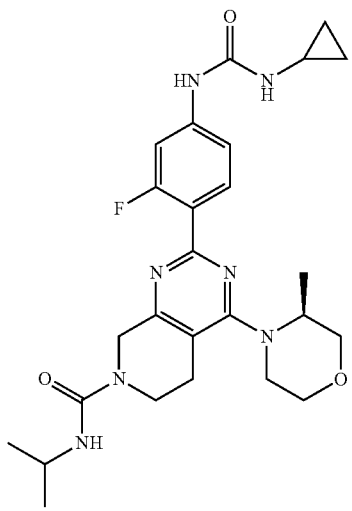 [SMILES: CC(C)NC(=O)N1CCc2c(nc(-c3ccc(NC(=O)NC4CC4)cc3F)nc2N2CCOC[C@@H]2C)C1]

To a stirred solution of (S)-1-cyclopropyl-3-(3-fluoro-4-(4-(3-methylmorpholino)-5,6,7,8-tetrahydropyrido[3,4-d]pyrimidin-2-yl)phenyl)urea (Example 163) (100 mg, 0.23 mmol) in DMF (2 ml) was added isopropyl isocyanate (35 µl, 0.35 mmol). Reaction mixture was stirred at 20° C. for 2 hours. The crude reaction mixture was then partitioned between water (10 ml) and DCM (10 ml). The organic layer was recovered, passed through a hydrophobic frit and the solvent removed in vacuo. Residue was then purified by prep. HPLC at high pH to afford the title compound as a white solid (61 mg, 0.12 mmol, 52%)

$^1$H NMR (d$_6$-DMSO) 8.72 (s, 1H), 7.91 (t, 1H), 7.53 (dd, 1H), 7.13 (dd, 1H), 6.55 (d, 1H), 6.37 (d, 1H), 4.45 (q, 2H), 4.13-4.05 (m, 1H), 3.88-3.74 (m, 2H), 3.69-3.53 (m, 5H), 3.45-3.35 (m, 2H), 2.65-2.59 (m, 2H), 2.58-2.52 (m, 1H), 1.24 (d, 3H), 1.08 (d, 6H), 0.68-0.62 (m, 2H), 0.45-0.39 (m, 2H).

LCMS (Method A), (M+H⁺) 512, Rt=6.43 min

Example 190

(R)-1-cyclopropyl-3-(3-fluoro-4-(6-formyl-4-(3-methylmorpholino)-6,7-dihydro-5H-pyrrolo[3,4-d]pyrimidin-2-yl)phenyl)urea

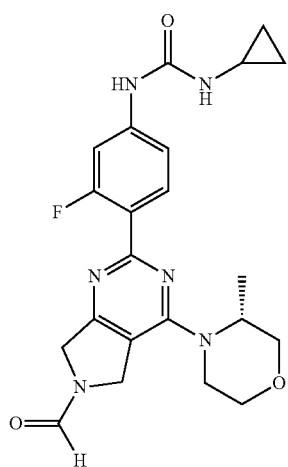 [SMILES: C[C@@H]1COCCN1c1nc(-c2ccc(NC(=O)NC3CC3)cc2F)nc2c1CN(C=O)C2]

(R)-1-cyclopropyl-3-(3-fluoro-4-(6-formyl-4-(3-methylmorpholino)-6,7-dihydro-5H-pyrrolo[3,4-d]pyrimidin-2-yl)phenyl)urea was formed as a by-product from the following reaction:

To a stirring solution of (R)-1-cyclopropyl-3-(3-fluoro-4-(4-(3-methylmorpholino)-6,7-dihydro-5H-pyrrolo[3,4-d]pyrimidin-2-yl)phenyl)urea hydrochloride (intermediate 33) (112 mg, 0.25 mmol) in DMF (2 mL) was added NEt$_3$ (70 μL, 0.5 mmol), and acetone (37 μL, 0.5 mmol). After stirring for 30 min sodium triactetoxyborohydride (106 mg, 0.5 mmol) was added and reaction stirred at room temp overnight. The reaction mixture was concentrated in vacuo before partitioned between DCM (10 ml) and water (10 ml). The organic layer was recovered, passed through a hydrophobic frit and the solvent removed in vacuo. Residue was then purified by prep. HPLC at high pH to afford the compound as a by product of the reaction as a light brown solid (15 mg, 0.03 mmol, 14%)

$^1$H NMR (d$_6$-DMSO) 8.80 (s, 1H), 8.36 (d, 1H), 7.99-7.92 (m, 1H), 7.57-7.51 (m, 1H), 7.14 (dd, 1H), 6.59 (s, 1H), 5.15-5.02 (m, 1H), 4.87-4.73 (m, 2H), 4.45 (s, 1H), 4.38 (br, s, 1H), 4.16-4.01 (m, 1H), 3.94 (dd, 1H), 3.77-3.61 (m, 2H), 3.54-3.46 (m, 1H), 2.60-2.52 (m, 1H), 1.29-1.25 (m, 3H), 1.25-1.09 (m, 1H), 0.69-0.62 (m, 2H), 0.46-0.40 (m, 2H).

LCMS (Method A), (M+H$^+$) 441, Rt=6.38 min

Example 191

(R)-1-cyclopropyl-3-(3-fluoro-4-(4-(3-methylmorpholino)-6-(methylsulfonyl)-6,7-dihydro-5H-pyrrolo[3,4-d]pyrimidin-2-yl)phenyl)urea

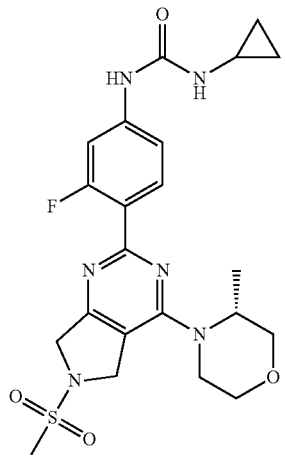 [SMILES: C[C@@H]1COCCN1c1nc(-c2ccc(NC(=O)NC3CC3)cc2F)nc2c1CN(S(C)(=O)=O)C2]

To a stirring solution of (R)-1-cyclopropyl-3-(3-fluoro-4-(4-(3-methylmorpholino)-6,7-dihydro-5H-pyrrolo[3,4-d]pyrimidin-2-yl)phenyl)urea hydrochloride (intermediate 33) (112 mg, 0.25 mmol) in DMF (2 mL) was added NEt$_3$ (70 μl, 0.5 mmol), and methanesulfonyl chloride (21 μL, 0.275 mmol). Reaction was stirred at room temp overnight. The reaction mixture was concentrated in vacuo before partitioning between DCM (10 ml) and water (10 ml). The organic layer was recovered, passed through a hydrophobic frit and the solvent removed in vacuo. Residue was then purified by prep. HPLC at high pH to afford the compound title compound as a light brown solid (30 mg, 0.06 mmol, 24%).

$^1$HNMR (d$_6$-DMSO) 8.73 (s, 1H), 7.94 (t, 1H), 7.53 (dd, 1H), 7.13 (dd, 1H), 6.54 (d, 1H), 4.83 (q, 3H), 4.49 (s, 1H), 4.39 (br, s, 1H), 4.02 (br, s, 1H), 3.94 (dd, 1H), 3.76-3.60 (m, 2H), 3.53-3.44 (m, 1H), 3.40-3.33 (m, 1H), 3.06 (s, 3H), 2.59-2.52 (m, 1H), 1.26 (d, 3H), 0.68-0.62 (m, 2H), 0.45-0.38 (m, 2H).

LCMS (Method A), (M+H$^+$) 491, Rt=7.45 min.

Biological Assays

Example 192

Determination of the Effect of the Compounds According to the Invention on mTOR The compounds of the present invention as described were tested in the mTOR kinobeads assay as described below. Briefly, test compounds (at various concentrations) and the affinity matrix with the immobilized phenylmorpholin-chromen ligand (8-(4-aminomethyl-phenyl)-2-morpholin-4-yl-chromen-4-one) were added to cell lysate aliquots and allowed to bind to the proteins in the lysate sample. After the incubation time the beads with captured proteins were separated from the lysate. Bound proteins were then eluted and the presence of mTOR, PI3K delta (PI3 Kd) and DNA-dependent protein kinase (DNA-PK) was detected and quantified using a specific antibody in a dot blot procedure and the Odyssey infrared detection system. Kinobeads assays for PI3K (WO-A 2008/015013) and for kinase selectivity profiling (WO 2006/134056) have been previously described.

Preparation of the Affinity Matrix with the Phenylmorpholin-Chromen Ligand

This protocol describes the synthesis of the phenylmorpholin-chromen ligand (8-(4-aminomethyl-phenyl)-2-morpholin-4-yl-chromen-4-one). This capture ligand was immobilized on a solid support through covalent linkage using an amino functional group and used for the capturing of proteins from cell lysates.

Synthesis of 8-(4-aminomethyl-phenyl)-2-morpholin-4-yl-chromen-4-one

Step 1

2,3-Dihydroxy-benzoic acid [A] (25 g, 0.16 mol) (Sigma-Aldrich, Cat no. 126209) was stirred in methanol (125 ml) with concentrated sulphuric acid (1 ml) and the reaction heated to gentle reflux over night. It was then concentrated and the residue partitioned between ethyl acetate and saturated aqueous sodium bicarbonate. The organic layer was washed with further saturated aqueous sodium bicarbonate, dried with magnesium sulphate, filtered and concentrated to afford 2,3-dihydroxy-benzoic acid methyl ester [B]. Yield 15.2 g, 57%.

HPLC (Method B): (M−H$^+$) 167; RT=2.3 min. $^1$H NMR: (CDCl$_3$) 10.92 (s, 1H); 7.39 (dd, 1H); 7.13 (dd, 1H); 6.82 (dt, 1H); 5.70 (s, 1H); 3.98 (s, 3H).

Step 2

2,3-Dihydroxy-benzoic acid methyl ester [B] (15.g, 89 mmol) was dissolved in dichloromethane (100 ml) with pyridine (3.6 ml, 44.6 mmol, 0.5 eq) and DMAP (272 mg, 2.2 mmol, 0.025 eq) and the reaction cooled in an ice/water bath. Trifluoromethanesulphonic anhydride (16.2 ml, 98.2 mmol, 1.1 eq) was added, the reaction was allowed to warm to room temperature and stirred over night. The reaction mixture was diluted with dichloromethane, washed with 1M hydrochloric acid (150 ml), dried with sodium sulphate, filtered and evaporated. The product was recrystallised from ethyl acetate to afford 2-hydroxy-3-trifluoromethanesulfonyloxy-benzoic acid methyl ester [α]. Yield crop 1, 6.5 g, 24%. Further recrysatllisation afforded a second crop, 6.8 g, 26%.

$^1$H NMR (CDCl$_3$): 11.11 (s, 1H); 7.80 (dd, 1H); 7.36 (dd, 1H); 6.86 (t, 1H); 3.93 (s, 3H).

Step 3

A solution of N-acetylmorpholine (1.72 g, 13.3 mmol, 2 eq) in 30 ml dry tetrahydrofuran under nitrogen was cooled in an acetone/dry ice bath (−78° C.) and treated with LDA (10 ml, 2M solution in THF, 3 eq). The reaction mixture was stirred for 60 minutes then 2-hydroxy-3-trifluoromethanesulfonyloxy-benzoic acid methyl ester [α] (2 g, 6.6 mmol, 1 eq as a solution in 10 ml dry THF) was added. The reaction mixture was allowed to warm from −78° C. to room temperature and stirred over night. The reaction was diluted with water (4 ml) followed by 2M hydrochloric acid (40 ml), then extracted three times with dichloromethane. The extracts were combined, washed with brine, dried with magnesium sulphate, filtered and evaporated. The crude product was purified by flash chromatography eluting with ethyl acetate to afford trifluoro-methanesulfonic acid 2-hydroxy-3-(3-morpholin-4-yl-3-oxo-propionyl)-phenyl ester [D]. Yield 1.06 g, 40%

$^1$H NMR (CDCl$_3$): 7.96 (dd, 1H); 7.49 (dd, 1H); 7.00 (t, 1H); 4.14 (s, 2H); 3.65-3.73 (m, 6H), 3.56 (t, 2H).

Step 4

Trifluoro-methanesulfonic acid 2-hydroxy-3-(3-morpholin-4-yl-3-oxo-propionyl)-phenyl ester [D] (1.06 g, 2.7 mmol) in dichloromethane (30 ml) was treated with trifluoromethanesulphonic anhydride and stirred over night at room temperature. The reaction mixture was then concentrated, re-dissolved in methanol and stirred for a further 2 hours. The solution was diluted with water and basified to pH8. It was then extracted three times with dichloromethane. The extracts were combined, washed with brine, dried with magnesium sulphate and evaporated to give the crude product as a brown oil. Trituration with ether gave trifluoro-methanesulfonic acid 2-morpholin-4-yl-4-oxo-4H-chromen-8-yl ester [E] as a brown solid. Yield 210 mg, 20%.

HPLC (Method B): RT=2.8 min. $^1$H NMR (CDCl$_3$): 8.16 (dd, 1H); 7.49 (dd, 1H); 7.40 (t, 1H); 5.62 (s, 1H); 3.85 (dd, 4H), 3.60 (dd, 4H).

Step 5

Trifluoro-methanesulfonic acid 2-morpholin-4-yl-4-oxo-4H-chromen-8-yl ester [E] (380 mg, 1.0 mmol), 4-(N-Boc-aminomethyl)phenylboronic acid (280 mg, 1.1 mmol, 1.1 eq), potassium carbonate (275 mg, 2.0 mmol, 2 eq) and tetrakis triphenylphosphine palladium (0) (60 mg, 0.05 mmol 0.05 eq) were stirred in dioxane (4 ml) and heated to 80° C. for 4 hours. The cooled reaction was then filtered and the filtrate concentrated in vacuo. The residue was purified by flash chromatography eluting with 0-3% methanol in dichloromethane to afford [4-(2-morpholin-4-yl-4-oxo-4H-chromen-8-yl)-benzyl]-carbamic acid tert-butyl ester [F]. Yield 238 mg, 54%.

HPLC (Method A): (MH$^+$) 437, (MNa$^+$) 459; RT 3.0 min. $^1$H NMR (CDCl$_3$) 8.17 (dd, 1H); 7.55 (dd, 1H); 7.49 (d, 2H); 7.37-7.42 (m, 3H); 5.51 (s, 1H), 5.00 (brs, 1H), 4.39 (d, 2H); 3.74 (dd, 4H); 3.35 (dd, 4H); 1.48 (s, 9H).

Step 6

[4-(2-Morpholin-4-yl-4-oxo-4H-chromen-8-yl)-benzyl]-carbamic acid tert-butyl ester [F] (230 mg, 0.53 mmol), in dichloromethane (5 ml) was treated with 4M hydrogen chloride in dioxane (2 ml). The reaction was stirred at room temperature for 3 hours during which time a precipitate forms. The solvent was removed in vacuo and the residue triturated with ether. The resulting solid was collected by filtration and dried to give 8-(4-aminomethyl-phenyl)-2-morpholin-4-yl-chromen-4-one [G]. Yield 189 mg, quantitative.

HPLC (Method 18): (MH$^+$) 337, (MNa$^+$) 359; RT 1.32 min (broad). $^1$H NMR (DMSO-d$_6$): 8.54 (brs, 2H); 7.99 (dd, 1H); 7.68-7.73 (m, 3H); 7.62 (d, 2H); 7.51 (t, 1H); 5.79 (s, 1H); 4.09 (q, 2H); 3.68 (t, 4H); 3.41 (t, 4H)

TABLE 1

Abbreviations

| | |
|---|---|
| DCM | Dichloromethane |
| DMAP | 4-(Dimethylamino)pyridine |
| LDA | Lithium diisopropylamide |
| MeOH | Methanol |
| THF | Tetrahydrofuran |

NMR spectra were obtained on a Bruker dpx400. LCMS was carried out on an Agilent 1100 using a ZORBAX® SB-C18, 4.6×75 mm, 3.5 micron column. Column flow was 1 ml/min and solvents used were water and acetonitrile (0.1% formic acid) with an injection volume of 10 ul. Wavelengths were 254 and 210 nm. Methods are described below.

TABLE 2

| Method | Easy Access Method Name | ChemStation Method Name | Flow Rate | Solvent | Run Time |
|---|---|---|---|---|---|
| A | Short column ANL Positive Medium | SANL_PGM.M | 1 ml/min | 0-1.5 min 30-95% MeCN 1.5-4.5 min 95% MeCN | 5 min |
| B | Short column ANL Negative Medium | SANL_NGM.M | 1 ml/min | 0-1.5 min 30-95% MeCN 1.5-4.5 min 95% MeCN | 5 min |

Immobilization of the Phenylmorpholin-Chromen Ligand on Beads (Affinity Matrix)

NHS-activated Sepharose 4 Fast Flow (Amersham Biosciences, 17-0906-01) was equilibrated with anhydrous DMSO (Dimethylsulfoxid, Fluka, 41648, H20<=0.005%). 1 ml of settled beads was placed in a 15 ml Falcon tube, compound stock solution (usually 100 mM in DMF or DMSO) was added (final concentration 0.2-2 µmol/ml beads) as well as 15 µl of triethylamine (Sigma, T-0886, 99% pure). Beads were incubated at room temperature in darkness on an end-over-end shaker (Roto Shake Genie, Scientific Industries Inc.) for 16-20 hours. Coupling efficiency is determined by HPLC. Non-reacted NHS-groups were blocked by incubation with aminoethanol at room temperature on the end-over-end shaker over night. Beads were washed with 10 ml of DMSO and were stored in isopropanol at −20° C. These beads were used as the affinity matrix in example 2, 3 and 4. Control beads (no ligand immobilized) were generated by blocking the NHS-groups by incubation with aminoethanol as described above.

Kinobeads Assay Using Multiplex Immunodetection

The kinobeads assay was performed as a competitive binding assay in which test compounds were added directly into a cell lysate. Test compounds (at various concentrations) and the affinity matrix (beads with immobilized phenylmorpholin-chromen ligand) were added to cell lysate aliquots and allowed to bind to the proteins contained in the lysate sample. After the incubation time the beads with captured proteins were separated from the lysate. Bound proteins were then eluted and the presence of kinases was detected and quantified using a multiplexed immunodetection format. Dose response curves for individual kinases were generated and $IC_{50}$ values calculated.

Washing of Affinity Matrix

The affinity matrix (beads with immobilized phenylmorpholin-chromen ligand) was washed two times with 15 ml of 1×DP buffer containing 0.2% NP40 (IGEPAL® CA-630, Sigma, #13021) and then resupended in 5.5 ml of 1×DP buffer containing 0.2% NP40 (10% beads slurry).

5×DP buffer: 250 mM Tris-HCl pH 7.4, 25% Glycerol, 7.5 mM $MgCl_2$, 750 mM NaCl, 5 mM $Na_3VO_4$, filter the 5×-lysis buffer through 0.22 µm filter and store in aliquots at −80° C. The 5×DP buffer is diluted to 1×DP buffer containing 1 mM DTT and 25 mM NaF.

Preparation of Test Compounds

Stock solutions of test compounds were prepared in DMSO. In a 96 well plate 30 µl solution of diluted test compounds at 5 mM in DMSO were prepared. Starting with this solution a 1:3 dilution series (9 steps) was prepared. For control experiments (no test compound) a buffer containing 2% DMSO was used. Compound CZC00018052 served as a positive control (PI-103; Calbiochem catalogue number 528100).

Cell Culture and Preparation of Cell Lysates

Jurkat cells (ATCC catalogue number TIB-152 Jurkat, clone E6-1) were grown in 1 liter Spinner flasks (Integra Biosciences, #182101) in suspension in RPMI 1640 medium (Invitrogen, #21875-034) supplemented with 10% Fetal Bovine Serum (Invitrogen) at a density between $0.15 \times 10^6$ and $1.2 \times 10^6$ cells/ml. Cells were harvested by centrifugation, washed once with 1×PBS buffer (Invitrogen, #14190-094) and cell pellets were frozen in liquid nitrogen and subsequently stored at −80° C.

Jurkat cells were homogenized in a Potter S homogenizer in lysis buffer: 50 mM Tris-HCl, 0.8% NP40, 5% glycerol, 150 mM NaCl, 1.5 mM $MgCl_2$, 25 mM NaF, 1 mM sodium vanadate, 1 mM DTT, pH 7.5. One complete EDTA-free tablet (protease inhibitor cocktail, Roche Diagnostics, 1873580) per 25 ml buffer was added. The material was dounced 10 times using a mechanized POTTER S, transferred to 50 ml falcon tubes, incubated for 30 minutes on ice and spun down for 10 min at 20,000 g at 4° C. (10,000 rpm in Sorvall SLA600, precooled). The supernatant was transferred to an ultracentrifuge (UZ)-polycarbonate tube (Beckmann, 355654) and spun for 1 hour at 100.000 g at 4° C. (33.500 rpm in Ti50.2, precooled). The supernatant was transferred again to a fresh 50 ml falcon tube, the protein concentration was determined by a Bradford assay (BioRad) and samples containing 50 mg of protein per aliquot were prepared. The samples were immediately used for experiments or frozen in liquid nitrogen and stored frozen at −80° C.

Dilution of Cell Lysate

Jurkat cell lysate (approximately 50 mg protein per plate) was thawed in a water bath at room temperature and then kept on ice. To the thawed cell lysate 1×DP 0.8% NP40 buffer containing protease inhibitors (1 tablet for 25 ml buffer; EDTA-free protease inhibitor cocktail; Roche Diagnostics 1873580) was added in order to reach a final protein concentration of 5 mg/ml total protein. The diluted cell lysate was stored on ice.

Incubation of Lysate with Test Compound and Affinity Matrix

To a 96 well filter plate (Multiscreen HTS, BV Filter Plates, Millipore #MSBVN1250) were added per well: 50 µl affinity matrix (10% beads slurry), 3 µl of compound solution, and 100 µl of cell diluted lysate. Plates were sealed and incubated for two hours in a cold room on a Thermoxer with shaking (750 rpm). Afterwards the plate was washed twice with 230 µl washing buffer (1×DP 0.4% NP40). The filter plate was placed on top of a collection plate (Greiner bio-one, PP-microplate 96 well V-shape, 65120) and the beads were then eluted with 20 µl of sample buffer (100 mM Tris, pH 7.4, 4%

SDS, 0.00025% Bromophenol blue, 20% glycerol, 50 mM DTT). The eluate was frozen quickly at −80° C. and stored at −20° C.

Detection and Quantification of Eluted Kinases

The kinases in the eluates were detected and quantified by spotting on Nitrocellulose membranes and using a first antibody directed against the kinase of interest and a fluorescently labeled secondary antibody (anti-mouse or anti-rabbit IRDye™ antibodies from Rockland). The Odyssey Infrared Imaging system from LI-COR Biosciences (Lincoln, Nebr., USA) was operated according to instructions provided by the manufacturer (Schutz-Geschwendener et al., 2004. Quantitative, two-color Western blot detection with infrared fluorescence. Published May 2004 by LI-COR Biosciences, www.licor.com).

After spotting of the eluates the nitrocellulose membrane (BioTrace NT; PALL, #BTNT30R) was first blocked by incubation with Odyssey blocking buffer (LICOR, 927-40000) for one hour at room temperature. Blocked membranes were then incubated for 16 hours at 25° C. with the first antibody diluted in Odyssey blocking buffer (LICOR #927-40000). Afterwards the membrane was washed three times for 10 minutes with PBS buffer containing 0.1% Tween 20 at room temperature. Then the membrane was incubated for 60 minutes at room temperature with the detection antibody (IRDye™ labelled antibody from Rockland) diluted in Odyssey blocking buffer (LICOR #927-40000). Afterwards the membrane was washed three times for 10 minutes each with 1×PBS buffer containing 0.1% Tween 20 at room temperature. Then the membrane was rinsed once with PBS buffer to remove residual Tween 20. The membrane was kept in PBS buffer at 4° C. and then scanned with the Odyssey instrument. Fluorescence signals were recorded and analysed according to the instructions of the manufacturer.

TABLE 3

Sources and dilutions of antibodies

| Target kinase | Primary antibody (dilution) | Temperature of Primary incubation | Secondary antibody (dilution) |
|---|---|---|---|
| mTOR | Cell signaling #2972 (1:500) | Room Temperature | Licor anti-rabbit 800 (1:5000) |
| PI3Kδ | Santa Cruz #sc-7176 (1:1000) | 4° C. | Licor anti-rabbit 800 (1:2500) |
| DNAPK | Calbiochem #NA57 (1:1000) | 4° C. | Licor anti-mouse 800 (1:5000) |

Results

TABLE 4

Inhibition values ($IC_{50}$ in µM) as determined in the kinobeads assay (Activity level: A <0.1 µM; B >0.1 µM < 1 µM; C >1 µM < 10 µM; D >10 µM).

| Example Number | mTor | PI3Kd | DNA-PK |
|---|---|---|---|
| 1 | B | D | D |
| 2 | B | D | D |
| 3 | A | D | D |
| 4 | A | C | D |
| 5 | A | C | D |
| 6 | B | C | D |
| 7 | A | D | D |
| 8 | A | D | D |
| 9 | A | D | D |
| 10 | B | D | D |
| 11 | B | D | D |

TABLE 4-continued

Inhibition values ($IC_{50}$ in µM) as determined in the kinobeads assay (Activity level: A <0.1 µM; B >0.1 µM < 1 µM; C >1 µM < 10 µM; D >10 µM).

| Example Number | mTor | PI3Kd | DNA-PK |
|---|---|---|---|
| 12 | B | D | D |
| 13 | A | D | D |
| 14 | A | C | D |
| 15 | A | D | D |
| 16 | A | D | D |
| 17 | A | D | D |
| 18 | A | C | D |
| 19 | B | D | D |
| 20 | A | D | D |
| 21 | A | C | D |
| 22 | B | D | D |
| 23 | A | C | D |
| 24 | B | D | D |
| 25 | B | D | D |
| 26 | A | D | D |
| 27 | A | D | D |
| 28 | A | D | D |
| 29 | B | D | D |
| 30 | A | D | D |
| 31 | B | D | D |
| 32 | A | D | D |
| 33 | A | D | D |
| 34 | A | D | D |
| 35 | A | D | D |
| 36 | A | D | D |
| 37 | A | D | D |
| 38 | A | D | D |
| 39 | A | D | D |
| 40 | A | D | D |
| 41 | B | D | D |
| 42 | A | D | D |
| 43 | A | D | D |
| 44 | A | D | D |
| 45 | B | D | D |
| 46 | A | D | D |
| 47 | A | C | D |
| 48 | B | C | D |
| 49 | B | D | D |
| 50 | B | D | D |
| 51 | A | D | D |
| 52 | B | D | D |
| 53 | B | D | D |
| 54 | B | B | D |
| 55 | B | D | D |
| 56 | A | D | D |
| 57 | A | D | D |
| 58 | A | D | D |
| 59 | A | D | D |
| 60 | A | D | D |
| 61 | C | D | D |
| 62 | A | D | D |
| 63 | B | C | D |

Further Determination of the Effect of the Compounds According to the Invention on mTOR and PI3 Kinases The effect of the compounds on the kinases PI3Kalpha (PI3Ka), PI3 Kbeta (PI3 Kb) and PI3 Kgamma (PI3 Kg) were tested in the kinobeads assay as described (WO-A 2009/098021).

TABLE 5

Sources and dilutions of antibodies

| Target kinase | Primary antibody (dilution) | Temperature of primary incubation | Secondary antibody (dilution) |
|---|---|---|---|
| PI3K alpha | Cell Signalling Technologies 4255 (1 in 100) | 25° C. | Anti-Rabbit (1 in 2500) |

TABLE 5-continued

Sources and dilutions of antibodies

| Target kinase | Primary antibody (dilution) | Temperature of primary incubation | Secondary antibody (dilution) |
|---|---|---|---|
| PI3K beta | Millipore 04-400 (1 in 1000) | 25° C. | Anti-Rabbit (1 in 2500) |
| PI3K delta | Santa Cruz SC7176 (1 in 1000) | 4° C. | Anti-Rabbit (1 in 2500) |
| PI3K gamma | Jena Bioscience ABD-026L (1 in 100) | 25° C. | Anti-Mouse (1 in 2500) |
| mTOR | Cell Signalling Technologies 2972 (1 in 500) | 25° C. | Anti-Rabbit (1 in 5000) |
| DNAPK | Calbiochem NA57 (1 in 1000) | 4° C. | Anti-Mouse (1 in 5000) |

Results

TABLE 6

Inhibition values ($IC_{50}$ in μM) as determined in the above assay (Activity level: A <0.1 μM; B >0.1 μM < 1 μM; C >1 μM < 10 μM; D >10 μM)

| Example No. | mTOR | DNAPK | PI3Ka | PI3Kb | PI3Kd | PI3Kg |
|---|---|---|---|---|---|---|
| 1 | B | D | — | — | D | — |
| 2 | B | D | — | — | D | — |
| 3 | A | D | — | — | D | — |
| 4 | A | D | — | — | C | — |
| 5 | A | D | B | C | C | B |
| 6 | B | D | — | — | C | — |
| 7 | A | D | — | — | D | — |
| 8 | A | D | — | — | D | — |
| 9 | A | D | — | — | D | — |
| 10 | B | D | — | — | D | — |
| 11 | B | D | — | — | D | — |
| 12 | B | D | — | — | D | — |
| 13 | A | D | — | — | D | — |
| 14 | A | D | — | — | C | — |
| 15 | A | D | — | — | D | — |
| 16 | A | D | — | — | D | — |
| 17 | A | D | — | — | D | — |
| 18 | A | D | — | — | C | — |
| 19 | B | D | D | D | D | D |
| 20 | A | D | — | — | D | — |
| 21 | A | D | C | D | C | D |
| 22 | B | D | — | — | D | — |
| 23 | A | D | C | D | C | D |
| 24 | B | D | D | D | D | D |
| 25 | B | D | D | D | D | D |
| 26 | A | D | — | — | D | — |
| 27 | A | D | C | C | D | C |
| 28 | A | D | D | D | D | D |
| 29 | B | D | D | D | D | D |
| 30 | A | D | — | — | D | — |
| 31 | C | D | — | — | D | — |
| 32 | A | D | — | — | D | — |
| 33 | A | D | — | — | D | — |
| 34 | A | D | D | D | D | D |
| 35 | A | D | D | D | D | D |
| 36 | A | D | — | — | D | — |
| 37 | A | D | D | D | D | D |
| 38 | A | D | — | — | D | — |
| 39 | A | D | — | — | D | — |
| 40 | A | D | C | C | D | C |
| 41 | B | D | D | D | D | D |
| 42 | A | D | D | D | D | D |
| 43 | A | D | C | C | D | C |
| 44 | A | D | — | — | D | — |
| 45 | B | D | D | D | D | D |
| 46 | A | D | — | — | D | — |
| 47 | A | D | — | — | C | — |
| 48 | B | D | — | — | C | — |
| 49 | B | D | — | — | D | — |
| 50 | B | D | — | — | D | — |
| 51 | A | D | — | — | D | — |
| 52 | B | D | D | D | D | D |
| 53 | B | D | — | — | D | — |
| 54 | B | D | B | B | B | C |
| 55 | B | D | — | — | D | — |
| 56 | A | D | D | D | D | D |
| 57 | A | D | D | D | D | D |
| 58 | A | D | D | D | D | D |
| 59 | A | D | — | — | D | — |
| 60 | A | D | D | D | D | D |
| 61 | A | D | D | D | D | D |
| 62 | A | D | D | D | D | D |
| 63 | B | D | — | — | C | — |
| 64 | A | D | D | D | D | D |
| 65 | A | D | D | D | D | D |
| 66 | A | D | D | D | D | D |
| 67 | B | D | D | D | D | D |
| 68 | B | D | D | D | D | D |
| 69 | A | D | C | C | D | D |
| 70 | A | C | D | D | C | D |
| 71 | A | D | C | C | C | C |
| 72 | B | D | D | D | D | D |
| 73 | A | D | C | C | C | D |
| 74 | A | D | D | D | D | D |
| 75 | A | D | D | D | D | D |
| 76 | A | D | D | D | D | D |
| 77 | A | D | D | D | D | D |
| 78 | A | D | D | D | D | D |
| 79 | A | C | C | D | C | D |
| 80 | A | D | C | C | D | C |
| 81 | A | D | D | D | D | D |
| 82 | B | D | D | D | D | D |
| 83 | A | D | D | D | D | D |
| 84 | B | D | C | D | D | D |
| 85 | B | D | D | D | D | D |
| 86 | A | D | D | D | D | D |
| 87 | A | D | D | D | D | D |
| 88 | A | D | D | D | D | D |
| 89 | A | C | D | D | D | D |
| 90 | A | D | D | D | D | D |
| 91 | A | D | D | D | D | D |
| 92 | B | D | D | D | D | D |
| 93 | B | D | D | D | D | D |
| 94 | B | D | C | D | D | D |
| 95 | B | D | D | D | D | D |
| 96 | B | D | D | D | D | D |
| 97 | A | C | C | C | C | D |
| 98 | A | D | C | D | D | D |
| 99 | A | D | C | C | C | D |
| 100 | B | D | C | D | D | D |
| 101 | B | D | — | — | D | — |
| 102 | A | D | D | D | D | D |
| 103 | B | D | D | D | D | D |
| 104 | B | D | D | D | D | D |
| 105 | B | D | D | D | D | D |
| 106 | B | D | D | D | D | D |
| 107 | B | D | D | D | D | D |
| 108 | B | D | D | D | D | D |
| 109 | B | D | D | D | D | D |
| 110 | B | D | D | D | D | D |
| 111 | B | D | D | D | D | D |
| 112 | A | D | B | C | B | C |
| 113 | B | D | D | D | D | D |
| 114 | B | D | B | C | B | C |
| 115 | B | D | D | D | D | D |
| 116 | B | D | C | D | D | D |
| 117 | B | D | D | D | D | D |
| 118 | B | D | D | D | D | D |
| 119 | B | D | D | D | D | D |
| 120 | A | D | D | D | D | D |
| 121 | A | D | D | D | D | D |
| 122 | B | D | D | D | D | D |
| 123 | B | D | D | D | D | D |
| 124 | B | D | C | D | C | D |
| 125 | B | D | B | C | B | C |

TABLE 6-continued

Inhibition values (IC$_{50}$ in μM) as determined in the above assay (Activity level: A <0.1 μM; B >0.1 μM < 1 μM; C >1 μM < 10 μM; D >10 μM)

| Example No. | mTOR | DNAPK | PI3Ka | PI3Kb | PI3Kd | PI3Kg |
|---|---|---|---|---|---|---|
| 126 | B | D | D | C | D | D |
| 127 | A | — | C | — | D | D |
| 128 | B | — | D | — | D | D |
| 129 | A | — | D | — | D | D |
| 130 | A | D | C | C | C | D |
| 131 | B | D | D | D | D | D |
| 132 | A | D | C | C | C | D |
| 133 | A | D | C | C | C | D |
| 134 | A | D | C | D | D | D |
| 135 | A | D | C | C | C | D |
| 136 | A | D | C | C | C | D |

TABLE 7

Further Kinobeads Data

| Example | mTor | DNAPK | PI3Ka | PI3Kb | PI3Kd | PI3Kg |
|---|---|---|---|---|---|---|
| 139 | C | D | D | D | D | D |
| 140 | C | D | D | D | D | D |
| 141 | C | D | D | D | D | D |
| 142 | D | D | D | D | D | D |
| 143 | A | D | D | D | D | D |
| 144 | B | D | D | D | D | D |
| 145 | B | D | D | D | D | D |
| 146 | B | D | D | D | D | D |
| 147 | A | D | D | D | D | D |
| 148 | A | D | D | D | D | D |
| 149 | B | D | C | D | D | D |
| 150 | A | D | C | D | D | D |
| 151 | B | D | C | D | D | C |
| 152 | B | D | D | D | C | D |
| 153 | A | D | D | D | D | D |
| 154 | B | D | D | D | D | D |
| 155 | A | D | D | D | D | D |
| 156 | A | D | D | D | D | D |
| 157 | A | D | D | D | C | D |
| 158 | A | D | D | D | D | D |
| 159 | B | D | C | D | D | D |
| 160 | A | D | D | D | D | D |
| 161 | A | D | D | D | D | D |
| 162 | A | D | C | C | C | D |
| 163 | A | D | D | D | D | D |
| 164 | A | D | D | D | D | D |
| 165 | A | D | D | D | D | D |
| 166 | A | D | D | D | D | D |
| 167 | A | D | D | C | C | D |
| 168 | A | D | C | D | C | D |
| 169 | A | D | D | D | D | D |
| 170 | A | C | D | D | C | D |
| 171 | A | C | D | D | D | D |
| 172 | A | C | C | D | C | C |
| 173 | A | D | D | D | D | D |
| 174 | A | D | D | D | D | D |
| 175 | B | D | D | D | D | D |
| 176 | A | C | C | C | C | C |
| 177 | A | D | D | D | D | D |
| 178 | B | D | D | D | D | D |
| 179 | A | D | D | D | D | D |
| 180 | A | C | D | D | D | D |
| 181 | A | C | D | D | D | D |
| 182 | A | C | C | D | C | D |
| 183 | B | D | D | D | D | D |
| 184 | A | D | D | D | C | D |
| 185 | A | D | C | D | C | D |
| 186 | A | D | D | D | C | D |
| 187 | A | D | D | D | D | D |
| 188 | A | D | C | D | D | D |
| 189 | A | D | D | D | D | D |
| 190 | A | D | D | D | D | D |
| 191 | B | D | D | D | D | D |

Example 193

In vitro Phospho-S6 and Phospho-Akt Cellular Assay

Activation of mTOR signaling results in phosphorylation of several downstream targets. In cells, mTOR exists in two different protein complexes. The mTOR Complex-1 (mTORC1) phosphorylates and activates S6 Kinase 1 (S6K1) and S6 Kinase 2 (S6K2) (also known as p70S6K) which then phosphorylate S6 Ribosomal Protein (S6RP) (also known as RPS6)3. S6RP is phosphorylated on serine 235, serine 236, serine 240 and serine 244 by both pS6K1 and pS6K2. The mTOR Complex-2 (mTORC2) phosphorylates AKT on serine 473 which activates the AKT signaling pathway.

The assay measures a test compound's inhibition of S6RP serine-240/244 phosphorylation and inhibition of Akt serine-473 phosphorylation in human embryonic kidney derived HEK293T/17 cells (ATCC CRL-11268).

The HEK293T/17 cell line is maintained in DMEM media (Invitrogen catalogue number 41965-039) supplemented with 10% FCS at 37° C. in a 5% CO$_2$ humidified incubator. Cells are seeded in 96-well plates at 40,000 cells/well (pS6RP S240/244 assay) or 80,000 cells/well (pAkt S473 assay) in 90 μl growth media (DMEM, 2% FCS). Plates are incubated for 1 hour in a humidified incubator to allow the cells to adhere. Cells are treated with 8 concentrations of test compounds or DMSO alone for controls (final DMSO concentration 0.1%) and incubated at 37° C. for 2 hours. Then 20 μl of 5× concentrated lysis buffer (750 mM NaCl, 100 mM Tris pH7.4, 5 mM ADTA, 5 mM EGTA, 5% Triton X-100) is added, plates are sealed and incubated for 15 minutes at 4° C. with gentle shaking. After cell lysis, 25 μl cell lysate is transferred to a MesoScale plate coated with an antibody to pS6RP Ser240/244 (MesoScale Discovery K150DGD-3) or an antibody to pAkt Ser 473 (MesoScale Discovery K151DGD-3). Plates have been blocked before by incubation with 150 μl MesoScale Discovery Blocking Solution-A for 1 hour at room temperature followed by washing with 150 μl 1× Tris wash buffer per well. After the transfer of the cell lysate to the MSD plate, the pS6RP (or pAkt) protein is captured on the coated antibody by incubation at room temperature for 1 hour with gentle shaking. After the capture step the plate is washed three times with 150 μl of 1× Tris wash buffer per well. Then 25 μl detection antibody conjugated with a Sulfo-Tag is added and incubated for 1 hour at room temperature with gentle shaking. Subsequently the antibody solution is removed and the plate is washed 3 times with 150 μl×Tris wash buffer per well and 150 μl Read buffer is added. The plates are analysed on a MSD 2400 Plate Reader (MesoScale Discovery). Data analysis is performed using nonlinear regression for a sigmoidal dose-response with a variable slope.

TABLE 8

Phospho-Akt and phospho-S6 cell assay data

| | pAKT IC50 uM | pS6 IC50 uM |
|---|---|---|
| Example 1 | | 0.052 |
| Example 2 | | 0.122 |
| Example 8 | | 0.289 |
| Example 11 | | 0.588 |
| Example 12 | | 0.839 |
| Example 13 | | 0.24 |
| Example 15 | | 0.238 |
| Example 16 | | 0.297 |
| Example 17 | | 0.142 |
| Example 18 | | 0.443 |

TABLE 8-continued

Phospho-Akt and phospho-S6 cell assay data

| | pAKT IC50 uM | pS6 IC50 uM |
|---|---|---|
| Example 19 | | 0.135 |
| Example 20 | | 0.33 |
| Example 21 | | 0.111 |
| Example 22 | 0.029 | 0.087 |
| Example 23 | | 0.115 |
| Example 24 | | 0.126 |
| Example 25 | | 0.098 |
| Example 26 | 0.068 | 0.196 |
| Example 27 | 0.016 | 0.024 |
| Example 28 | | 0.072 |
| Example 29 | | 0.13 |
| Example 30 | | 0.17 |
| Example 32 | | 0.182 |
| Example 33 | 0.16 | 0.379 |
| Example 34 | 0.021 | 0.049 |
| Example 35 | 0.014 | 0.037 |
| Example 36 | | 0.113 |
| Example 37 | 0.045 | 0.086 |
| Example 38 | | 0.17 |
| Example 39 | | 0.14 |
| Example 40 | 0.043 | 0.07 |
| Example 41 | | 0.12 |
| Example 42 | | 0.104 |
| Example 43 | 0.035 | 0.071 |
| Example 44 | | 0.205 |
| Example 45 | | 0.063 |
| Example 46 | | 0.147 |
| Example 47 | | 0.218 |
| Example 48 | | 0.698 |
| Example 49 | | 0.306 |
| Example 50 | | 0.423 |
| Example 52 | | 0.09 |
| Example 55 | | 0.435 |
| Example 56 | 0.019 | 0.032 |
| Example 57 | 0.014 | 0.032 |
| Example 58 | 0.017 | 0.034 |
| Example 59 | | 0.16 |
| Example 60 | 0.021 | 0.037 |
| Example 61 | 0.02 | 0.022 |
| Example 62 | | 0.049 |
| Example 63 | | 0.046 |
| Example 64 | 0.017 | 0.03 |
| Example 65 | | 0.149 |
| Example 66 | 0.054 | 0.074 |
| Example 67 | | 0.143 |
| Example 68 | | 0.243 |
| Example 69 | | 0.208 |
| Example 70 | | 0.133 |
| Example 71 | | 0.69 |
| Example 72 | | 0.129 |
| Example 73 | | 0.425 |
| Example 74 | | 0.11 |
| Example 75 | | 0.082 |
| Example 76 | | 0.095 |
| Example 77 | 0.028 | 0.038 |
| Example 78 | 0.021 | 0.035 |
| Example 79 | | 0.589 |
| Example 80 | 0.061 | 0.089 |
| Example 81 | 0.022 | 0.047 |
| Example 82 | | 0.991 |
| Example 83 | 0.07 | 0.14 |
| Example 84 | | 0.165 |
| Example 85 | 0.531 | 0.873 |
| Example 86 | 0.043 | 0.099 |
| Example 87 | 0.091 | 0.108 |
| Example 88 | 0.057 | 0.083 |
| Example 89 | 0.042 | 0.082 |
| Example 90 | 0.037 | 0.083 |
| Example 91 | 0.087 | 0.105 |
| Example 93 | | 0.196 |
| Example 94 | | 0.565 |
| Example 95 | | 0.218 |
| Example 96 | | 0.05 |
| Example 97 | | 0.338 |
| Example 98 | | 0.045 |
| Example 100 | | 0.202 |
| Example 101 | | 0.252 |
| Example 102 | | 0.258 |
| Example 103 | 0.088 | 0.207 |
| Example 104 | | 0.39 |
| Example 105 | | 0.414 |
| Example 106 | | 0.294 |
| Example 107 | | 0.159 |
| Example 108 | | 0.935 |
| Example 110 | 0.118 | 0.192 |
| Example 113 | 0.053 | 0.077 |
| Example 120 | | 0.025 |
| Example 121 | | 0.033 |
| Example 122 | | 0.175 |
| Example 129 | | 0.336 |
| Example 131 | 0.049 | 0.099 |
| Example 141 | | 0.838 |
| Example 146 | 0.041 | 0.096 |
| Example 147 | | 0.282 |
| Example 151 | 0.107 | 0.153 |
| Example 152 | 0.049 | 0.093 |
| Example 153 | | 0.14 |
| Example 154 | | 0.436 |
| Example 155 | | 0.815 |
| Example 156 | 0.076 | 0.135 |
| Example 159 | 0.314 | 0.271 |
| Example 160 | | 0.355 |
| Example 162 | 0.085 | 0.114 |
| Example 163 | | 0.405 |
| Example 164 | | 0.51 |
| Example 165 | 0.037 | 0.045 |
| Example 167 | | 0.615 |
| Example 168 | | 0.097 |
| Example 169 | | 0.143 |
| Example 170 | 0.054 | 0.105 |
| Example 171 | | 0.983 |
| Example 172 | 0.101 | 0.187 |
| Example 173 | 0.049 | 0.172 |
| Example 174 | | 0.545 |
| Example 176 | 0.054 | 0.076 |
| Example 177 | | 0.41 |
| Example 178 | 0.052 | 0.163 |
| Example 179 | 0.031 | 0.063 |
| Example 180 | | 0.058 |
| Example 181 | | 0.962 |
| Example 183 | | 0.06 |
| Example 185 | | 0.36 |
| Example 186 | | 0.197 |
| Example 187 | | 0.563 |
| Example 188 | | 0.218 |
| Example 189 | | 0.133 |
| Example 190 | | 0.351 |
| Example 191 | | 0.18 |

Example 194

Anti-CD3 Induced Cytokine Release in the Mouse

In this mouse model, T cells and NK cells were activated in situ by the intraperitoneal (i.p.) injection of an anti-CD3 antibody into mice that had been pre-treated for 30 minutes with certain compounds of the invention (100 mg/kg po administration). Blood samples were collected 90 minutes after anti-CD3 injection. Plasma samples were prepared and the cytokine levels (Tumor Necrosis factor alpha (TNFα), Interleukin-2 (IL-2), Interferon-gamma (IFNγ) and Interleukin-4 (IL-4)) were measured using a Cytometric Bead Array method.

Experimental Design

A single dose of test compound was administered p.o. 30 minutes before anti-CD3 injection. 90 minutes after anti-CD3 injection blood samples were collected for cytokine analysis (approximately 400 μl whole blood anti-coagulated with Na-heparin) and stored frozen until use.

The cytokine measurement was done using the mouse Cytometric Bead Array (CBA) Th1/Th2 kit (BD Biosciences, San Diego, Calif., USA; catalogue number 551287) according to the manufacturer's instruction with the following modifications: all reagents were downscaled by a factor of 2 and the mixture of plasma, beads and detection reagents was done in 96-U-bottom plates. Standards and samples were acquired on a FACSCalibur® instrument (Becton Dickinson) using an HTS plate loader. Data were analysed with the CBA Software provided by Becton Dickinson which draws standard curves and converts mean fluorescence values into concentration values (pg/ml).

Animals: male C57BL/6J mice, 9 weeks old (Janvier, Le Genest St Isle, France).

Test compounds were dosed orally (p.o.) at 100 mg/kg (vehicle: 0.5% CMC, application volume 10 ml/kg).

Anti-CD3 antibody (BD Bioscience, catalogue number 553057): 200 μl of a 10 μg/ml solution in PBS were applied i.p. (2 μg per mouse).

TABLE 9

Animal experimental groups for anti-CD3 mouse study

| Group | Compound | Dose (mg/kg) | Animals (n) | Stimulus antibody | Animals number |
|---|---|---|---|---|---|
| 1 | Control (vehicle) | 0 | 4 | — (PBS) | 1-4 |
| 2 | Control (vehicle) | 0 | 8 | anti-CD3 | 5-12 |
| 3 | Example 131 | 100 | 8 | anti-CD3 | 13-20 |
| 4 | Example 146 | 100 | 8 | anti-CD3 | 21-28 |
| 5 | Example 151 | 100 | 8 | anti-CD3 | 29-36 |
| 6 | Example 164 | 100 | 8 | anti-CD3 | 37-44 |

Results

Administration of compound example 131 (group 3) leads to a reduction of TNFα, IL-2, IFNγ and IL-4 plasma levels compared to control group 2. Further results are displayed in FIG. 1.

Example 195

Delayed Type Hypersensitivity in Mice

The Delayed type hypersensitivity (DTH) reaction is observed when subjects are immunized with an antigen, and then subsequently challenged with the same antigen to induce a localized inflammation. The model can be inhibited by drugs affecting a range of immune and inflammatory mechanisms. In this instance, a DTH reaction is induced in mice using Keyhole Limpet Hemocyanin (KLH), measuring inflammation in the ear pinna.

Immunization

Keyhole Limpet Hemocyanin (KLH; Sigma, catalogue number H7017) preparation: Lyophilized KLH (20 mg) was reconstituted with 2 ml of water for injection to give a 10 mg/ml buffered stock solution. Aliquots were stored at −20° C. For the first immunization (day 0) the KLH stock solution (10 mg/ml) was diluted to 0.5 mg/ml with PBS (1:20). Then a 1:1 mixture with Complete Freund's Adjuvant (CFA; Sigma catalogue number 5881) was prepared (final KLH concentration 0.25 mg/ml). For the second immunization (day 5) the KLH stock solution was diluted to 1 mg/ml with 0.9% NaCl (1:10).

Mice (Balb/c ~9 weeks of age) were immunized with 2×100 μl of a 1:1 emulsion of KLH in CFA (25 μg KLH/site) injected subcutaneously into the right and left flank. On day 5 post-injection, mice received a challenge of 10 μg KLH (in 10 μl physiological saline), injected intradermally into the right ear. On day 5, 6 and 7 the ear thickness was measured with a caliper. Measurements were performed one hour after compound administration in the morning.

Compound Treatment

Compound CZC1 corresponding to example 34 of the present invention was dosed once daily orally (p.o.) from day 0 to day 7 (Table 10). Vehicle: 0.5% carboxymethylcellulose (CMC).

Doses: 3, 10 and 30 mg/kg.

Cyclosporine A (Calbiochem) was dosed twice daily orally (p.o., 8 am and 4 pm from day 0 to day 7). Vehicle: 5% DMSO, 0.5 CMC. Dose: 25 mg/kg.

Control treatment: 5% DMSO, 0.5% CMC administered p.o.

TABLE 10

Animal groups and treatment (mouse DTH)

| Group | Compound | Dose | Number of animals |
|---|---|---|---|
| 1 | Vehicle control | Vehicle control | 10 |
| 2 | CZC1 (example 34) | 3 mg/kg | 10 |
| 3 | CZC1 (example 34) | 10 mg/kg | 10 |
| 4 | CZC1 (example 34) | 30 mg/kg | 10 |
| 5 | Cyclosporine A | 25 mg/kg | 10 |

Results

Figure 2:
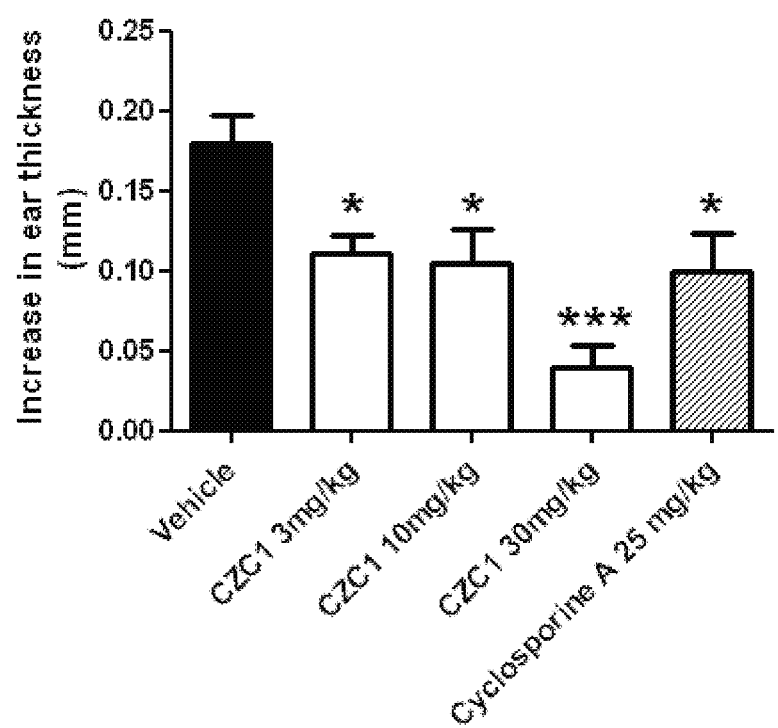
FIG. 2: Delayed type hypersensitivity in mice
The experiment was conducted as described in example 195. The increase in ear thickness after the challenge injection of Keyhole Limpet Hemocyanin (KLH) is displayed. *$p<0.05$, ***$p<0.001$, ANOVA with Bonferroni post-test, compared to Vehicle group.

A significant increase in ear thickness was observed in the vehicle control group at 24 hours post-challenge (day 6, compared with pre-challenge, day 5). The increase in ear thickness was significantly reduced at 3, 10 and 30 mg/kg compound treatment with CZC1 (FIG. 2), and with the reference compound cyclosporine A. No significant ear swelling was seen in the vehicle control group at 48 hours post-challenge (day 7 compared with pre-challenge, day 5).

Example 196

Ames Fluctuation Assay

Certain compounds of the invention were tested in a miniaturized screening version of the Ames test that requires a small amount of compound compared with the regulatory test. The Ames fluctuation assay is performed in 384-well plates using two *Salmonella* strains, TA98 and TA100. TA98 detects frameshifts and TA100 detects base substitutions leading to missense mutations. Whereas the original Ames test is carried out by plating bacteria onto selective agar plates, the Ames fluctuation assay is carried out in liquid culture using 384-well plates. The bacterial plates are incubated with the test compounds for 96 hours, after which bacterial growth is measured spectrophotometrically using a pH indicator that changes color in response to the acidification of the media due to bacterial growth.

Metabolic activation is achieved by using rat liver S9 fraction (0.2 mg/ml). To prevent false negatives due to bacteriocidal or bacteriostatic effects, a bacterial cytotoxicity assay is conducted in parallel with the Ames fluctuation assay. Compounds are typically tested in both bacterial strains with and without S9, at four concentrations (5, 10, 50 and 100 μM) with n=48 wells. A bacterial cytotoxicity test is conducted in parallel at 8 concentrations (with 100 μM as the highest concentration) and n=3 wells. Four reference compounds (quercetin, streptozotocin, aminoanthracene and mitomycin C) are included in all experiments.

Ames Test Results

Wells that displayed bacteria growth due to the reversion of the histidine mutation (as judged by the ratio of $OD_{430}/OD_{570}$ being greater than 1.0) are counted and recorded as positive counts. The significance of the positive counts between the treatment (in the presence of compound) and the control (in the absence of test compound) are calculated using the one-tailed Fisher's exact test—the significance levels are reported as follows:

Weak positive, if $0.01 \leq p \leq 0.05$, denoted as "+"
Strong positive, if $0.001 \leq p \leq 0.01$, denoted as "++"
Very strong positive, if $p<0.001$, denoted as "+++"
Hyphens (−) indicate negative results

TABLE 11

Results of Ames fluctuation assay

| Compound name | Compound structure | Conc. μM | TA98 −S9 | TA98 +S9 | TA100 −S9 | TA100 +S9 |
| --- | --- | --- | --- | --- | --- | --- |
| (S)-ethyl 2-(4-(3-cyclopropylureido)phenyl)-4-(3-methylmorpholino)-5H-pyrrolo[3,4-d]pyrimidine-6(7H)-carboxylate Example 34 | 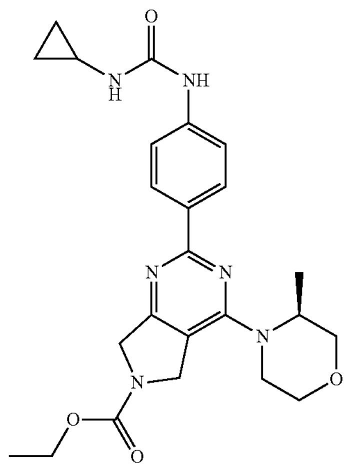 [SMILES: CCOC(=O)N1Cc2nc(-c3ccc(NC(=O)NC4CC4)cc3)nc(N3CCOC[C@@H]3C)c2C1] | 5<br>10<br>50<br>100 | −<br>−<br>−<br>− | −<br>−<br>−<br>− | −<br>−<br>−<br>− | −<br>−<br>−<br>− |
| (S)-ethyl 2-(4-aminophenyl)-4-(3-methylmorpholino)-5H-pyrrolo[3,4-d]pyrimidine-6(7H)-carboxylate Metabolite Example 137 | 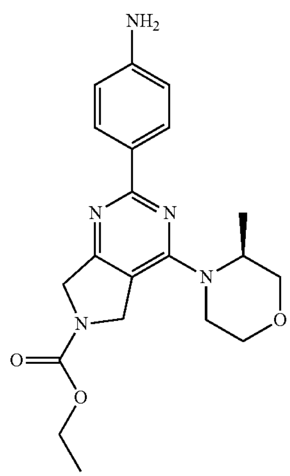 [SMILES: CCOC(=O)N1Cc2nc(-c3ccc(N)cc3)nc(N3CCOC[C@@H]3C)c2C1] | 5<br>10<br>50<br>100 | −<br>−<br>−<br>− | +++<br>+++<br>+++<br>+++ | −<br>−<br>−<br>− | −<br>−<br>++<br>− |
| (S)-ethyl 2-(4-amino-3-fluorophenyl)-4-(3-methylmorpholino)-5H-pyrrolo[3,4-d]pyrimidine-6(7H)-carboxylate Intermediate 19 | 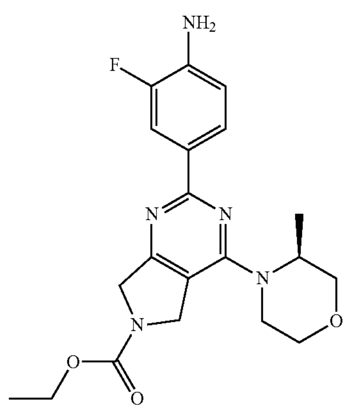 [SMILES: CCOC(=O)N1Cc2nc(-c3ccc(N)c(F)c3)nc(N3CCOC[C@@H]3C)c2C1] | 5<br>10<br>50<br>100 | −<br>−<br>−<br>− | +++<br>+++<br>+++<br>+++ | −<br>−<br>−<br>− | −<br>+++<br>+++<br>+++ |

TABLE 11-continued

Results of Ames fluctuation assay

| Compound name | Compound structure | Conc. μM | TA98 −S9 | TA98 +S9 | TA100 −S9 | TA100 +S9 |
|---|---|---|---|---|---|---|
| (S)-ethyl 2-(4-amino-2-fluorophenyl)-4-(3-methylmorpholino)-5H-pyrrolo[3,4-d]pyrimidine-6(7H)-carboxylate Metabolite Example 138 | 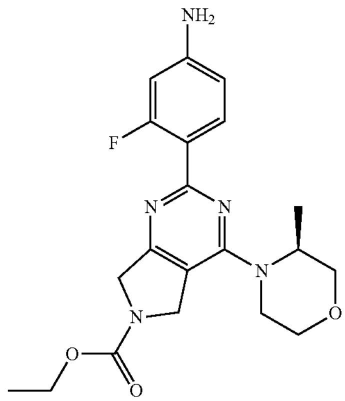 [SMILES: CCOC(=O)N1Cc2nc(-c3ccc(N)cc3F)nc(N3CCOC[C@@H]3C)c2C1] | 5 | − | − | − | − |
| | | 10 | − | − | − | − |
| | | 50 | − | − | − | − |
| | | 100 | − | − | − | − |

Example 197

Ames Plate Assay

Certain compounds of the invention were tested for their potential to induce gene mutations in bacterial strains of *Salmonella typhimurium* (strains TA1535, TA1537, TA98, TA100) and *Escherichia coli* (strain WP2uvrA(pKM101)) in a bacterial mutation assay in the absence and presence of metabolite activation (rat S9-mix). Compounds are tested at the following dose levels: 50, 150, 500, or 1500 μg/plate.

Vehicle control treatment is the vehicle used to prepare the test compound formulation diluted to the same extent as the test compound solution. Positive controls using known mutagens are included for each strain with and without rat S9 mix. Four plates are used for the vehicle control and two replicate plates per dose per strain for the treated groups and for each positive control. At the end of incubation the number of revertant colonies per plate are recorded and mean values calculated for each vehicle control, positive control and concentration of test compound used. Results are also expressed as a ratio of the mean values to the mean concurrent vehicle control value (i.e. fold increase). If the data for any treatment level shows a response ≥2 times the concurrent vehicle control value (TA98, TA100 and WP2uvrA(pKM101), or ≥3 times the concurrent vehicle control value (TA1535 and TA1537), in conjunction with a dose-related response, the result is considered positive.

TABLE 12

Results of Ames plate assay for example 34 and 138

| Exa | Conc. μg/Plate | TA98 −S9 | TA98 +S9 | TA100 −S9 | TA100 +S9 | TA1535 −S9 | TA1535 +S9 | TA1537 −S9 | TA1537 +S9 | WP2uvrA (pKM101) −S9 | WP2uvrA (pKM101) +S9 |
|---|---|---|---|---|---|---|---|---|---|---|---|
| 34 | 50 | − | − | − | − | − | − | − | − | − | − |
| | 150 | − | − | − | − | − | − | − | − | − | − |
| | 500 | − | − | − | − | − | − | − | − | − | − |
| | 1500 | − | − | − | − | − | − | − | − | − | − |
| 138 | 50 | − | − | − | − | − | − | − | − | − | − |
| | 150 | − | − | − | − | − | − | − | − | − | − |
| | 500 | − | − | − | − | − | − | − | − | − | − |
| | 1500 | − | − | − | − | − | − | − | − | − | − |

The invention claimed is:

1. A compound which is (S)-1-cyclopropyl-3-(4-(4-(3-methylmorpholino)-6,7-dihydro-5H-pyrrolo[3,4-d]pyrimidin-2-yl)phenyl)urea, or a pharmaceutically acceptable salt thereof.

2. A pharmaceutical composition comprising a compound or a pharmaceutically acceptable salt thereof of claim 1 together with a pharmaceutically acceptable carrier, optionally in combination with one or more other pharmaceutical compositions.

3. A method of treating a mammalian patient in need thereof one or more conditions selected from the group consisting of diseases and disorders associated with mTOR, wherein the method comprises administering to said patient a therapeutically effective amount of a compound of claim 1 or a pharmaceutically acceptable salt thereof.

4. The method of claim 3, wherein the disease or disorder is an immunological, inflammatory, autoimmune, or allergic disorder or disease or a transplant rejection or a Graft-versus host disease.

5. The method of claim 3, wherein the disease is a proliferative disease.

6. The method of claim 3, wherein the disease is a cardiovascular disease, a metabolic disease or a neurodegenerative disease.

7. The method of claim 3, wherein the disease is an autophagy associated disease.

8. The method of claim 5, wherein the proliferative disease is cancer.

* * * * *